United States Patent
Buttar et al.

(10) Patent No.: US 9,708,327 B2
(45) Date of Patent: Jul. 18, 2017

(54) POLYMORPHIC FORMS OF A HYDROCHLORIDE SALT OF (S)-2-(1-(9H-PURIN-6-YLAMINO)PROPYL)-5-FLUORO-3-PHENYLQUINAZOLIN-4(3H)-ONE

(71) Applicant: Gilead Calistoga LLC, Foster City, CA (US)

(72) Inventors: Suzanne Buttar, Cambridge (GB); Ernest Carra, Foster City, CA (US); Tracy Ehiwe, Cambridge (GB); Duong Tran, Edmonton (CA); Fang Wang, Foster City, CA (US); Christopher Worrall, Camridge (GB); Jerry Evarts, Seattle, WA (US)

(73) Assignee: GILEAD CALISTOGA LLC, Foster City, CA (US)

( * ) Notice: Subject to any disclaimer, the term of this patent is extended or adjusted under 35 U.S.C. 154(b) by 0 days.

(21) Appl. No.: 14/575,857

(22) Filed: Dec. 18, 2014

(65) Prior Publication Data
US 2015/0175606 A1 Jun. 25, 2015

Related U.S. Application Data

(60) Provisional application No. 61/919,558, filed on Dec. 20, 2013.

(51) Int. Cl.
*C07D 473/34* (2006.01)

(52) U.S. Cl.
CPC .................................. *C07D 473/34* (2013.01)

(58) Field of Classification Search
None
See application file for complete search history.

(56) References Cited

U.S. PATENT DOCUMENTS

| | | |
|---|---|---|
| 3,322,756 A | 5/1967 | Ruschig et al. |
| 3,691,016 A | 9/1972 | Patel |
| 3,897,432 A | 7/1975 | Shen et al. |
| 3,969,287 A | 7/1976 | Jaworek et al. |
| 3,984,555 A | 10/1976 | Amschler et al. |
| 4,179,337 A | 12/1979 | Davis et al. |
| 4,183,931 A | 1/1980 | Wolfe et al. |
| 4,195,128 A | 3/1980 | Hidebrand et al. |
| 4,225,489 A | 9/1980 | Rolf et al. |
| 4,229,537 A | 10/1980 | Hodgins et al. |
| 4,247,642 A | 1/1981 | Hirohara et al. |
| 4,289,872 A | 9/1981 | Denkewalter et al. |
| 4,301,144 A | 11/1981 | Iwashita et al. |
| 4,330,440 A | 5/1982 | Ayers et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 4,925,673 A | 5/1990 | Steiner et al. |
| 4,943,593 A | 7/1990 | Palfreyman et al. |
| 4,965,288 A | 10/1990 | Palfreyman et al. |
| 4,997,854 A | 3/1991 | Kagan et al. |
| 5,013,556 A | 5/1991 | Woodle et al. |
| 5,021,456 A | 6/1991 | Palfreyman et al. |
| 5,059,714 A | 10/1991 | Palfreyman et al. |
| 5,120,764 A | 6/1992 | McCarthy et al. |
| 5,182,297 A | 1/1993 | Palfreyman et al. |
| 5,225,347 A | 7/1993 | Goldberg et al. |
| 5,229,490 A | 7/1993 | Tam |
| 5,252,608 A | 10/1993 | Palfreyman et al. |
| 5,378,725 A | 1/1995 | Bonjouklian et al. |
| 5,480,906 A | 1/1996 | Creemer et al. |
| RE35,862 E | 7/1998 | Steiner et al. |
| 5,858,753 A | 1/1999 | Chantry et al. |
| 5,882,910 A | 3/1999 | Chantry et al. |
| 5,948,664 A | 9/1999 | Williams et al. |
| 5,985,589 A | 11/1999 | Chantry et al. |
| 6,046,049 A | 4/2000 | Monia et al. |
| 6,048,970 A | 4/2000 | Lal et al. |
| 6,277,981 B1 | 8/2001 | Tu et al. |
| 6,291,220 B1 | 9/2001 | Williams et al. |
| 6,369,038 B1 | 4/2002 | Blumenfeld et al. |
| 6,410,224 B1 | 6/2002 | Stinchcomb et al. |
| 6,426,337 B1 | 7/2002 | Cox et al. |
| 6,482,623 B1 | 11/2002 | Vanhaesebroeck et al. |
| 6,518,277 B1 | 2/2003 | Sadhu et al. |
| 6,667,300 B2 | 12/2003 | Sadhu et al. |
| 6,696,250 B1 | 2/2004 | Cech et al. |
| 6,800,620 B2 | 10/2004 | Sadhu et al. |

(Continued)

FOREIGN PATENT DOCUMENTS

CN 101031569 A 9/2007
EP 0 525 960 A1 2/1993

(Continued)

OTHER PUBLICATIONS

"Acute Congestive Heart Failure", Thomas N. Levin, Postgraduate Medicine, vol. 101, No. 1, 1997.
"Chemia Lekow", ed. E. Pawelczyk, PZWL, Warszawa 1986, see, part 1.2.2.
"Preparatyka Organiczna", ed. A.I. Vogel, WNT, Warszawa 1984, page, e.g. 83.
Abu-Duhier et al., Br. J. Haematol. (2001) 113:983-988.
Adamkiewicz, "Tumor Angiogenesis: Mechanisms" IMT Marburg—Research Group, retrieved from the internet on Apr. 13, 2004, located at: <http://www.imt.uni-marburq.de/~adamkiew/mechanism.html>, 2 pages.
Advisory Action from U.S. Appl. No. 11/596,092, mailed on Jul. 27, 2010.

(Continued)

*Primary Examiner* — Golam M M Shameem
*Assistant Examiner* — Laura Daniel
(74) *Attorney, Agent, or Firm* — Morrison & Foerster LLP

(57) ABSTRACT

Polymorphs of a hydrochloride salt of (S)-2-(1-(9H-purin-6-ylamino)propyl)-5-fluoro-3-phenylquinazolin-4(3H)-one, compositions thereof, methods for their preparation, and methods for their use are disclosed. Solvent forms of a hydrochloride salt of (S)-2-(1-(9H-purin-6-ylamino)propyl)-5-fluoro-3-phenylquinazolin-4(3H)-one, compositions thereof, methods for their preparation, and methods for their use are also disclosed.

47 Claims, 39 Drawing Sheets

(56) References Cited

U.S. PATENT DOCUMENTS

| | | |
|---|---|---|
| 6,949,535 B2 | 9/2005 | Sadhu et al. |
| 7,932,260 B2 | 4/2011 | Fowler et al. |
| 8,138,195 B2 | 3/2012 | Sadhu et al. |
| 8,207,153 B2 | 6/2012 | Fowler et al. |
| 8,492,389 B2 | 7/2013 | Sadhu et al. |
| RE44,599 E | 11/2013 | Fowler et al. |
| 8,586,597 B2 | 11/2013 | Fowler et al. |
| RE44,638 E | 12/2013 | Fowler et al. |
| 8,623,881 B2 | 1/2014 | Sadhu et al. |
| 8,637,533 B2 | 1/2014 | Sadhu et al. |
| 8,653,077 B2 | 2/2014 | Sadhu et al. |
| 8,779,131 B2 | 7/2014 | Kesicki et al. |
| 8,865,730 B2 | 10/2014 | Carra et al. |
| 8,980,901 B2 | 3/2015 | Fowler et al. |
| 8,993,583 B2 | 3/2015 | Fowler et al. |
| 9,149,477 B2 | 10/2015 | Kesicki et al. |
| 9,487,772 B2 | 11/2016 | Sadhu et al. |
| 2004/0023390 A1 | 2/2004 | Davidson et al. |
| 2004/0092561 A1 | 5/2004 | Ruckle et al. |
| 2004/0121996 A1 | 6/2004 | Barvian et al. |
| 2004/0138199 A1 | 7/2004 | Goglietti et al. |
| 2004/0242631 A1 | 12/2004 | Garlich et al. |
| 2004/0248871 A1 | 12/2004 | Farjanel et al. |
| 2004/0248953 A1 | 12/2004 | Gogliotti et al. |
| 2004/0248954 A1 | 12/2004 | Gogliotti et al. |
| 2004/0259926 A1 | 12/2004 | Bruendle et al. |
| 2005/0004195 A1 | 1/2005 | Para et al. |
| 2005/0020630 A1 | 1/2005 | Connolly et al. |
| 2005/0020631 A1 | 1/2005 | Gogliotti et al. |
| 2005/0043239 A1 | 2/2005 | Douangpanya et al. |
| 2005/0054614 A1 | 3/2005 | Diacovo et al. |
| 2005/0239809 A1 | 10/2005 | Watts et al. |
| 2006/0079538 A1 | 4/2006 | Hallahan et al. |
| 2006/0106038 A1 | 5/2006 | Bouscary et al. |
| 2008/0287469 A1 | 11/2008 | Diacovo et al. |
| 2010/0029693 A1 | 2/2010 | Douangpanya et al. |
| 2010/0202963 A1 | 8/2010 | Gallatin et al. |
| 2010/0249155 A1 | 9/2010 | Evarts et al. |
| 2010/0256167 A1 | 10/2010 | Fowler et al. |
| 2011/0044942 A1 | 2/2011 | Puri et al. |
| 2011/0230465 A1 | 9/2011 | Stammers et al. |
| 2012/0015964 A1 | 1/2012 | Fowler et al. |
| 2012/0040980 A1 | 2/2012 | Huggins et al. |
| 2013/0252976 A1* | 9/2013 | Carra .................. C07D 473/34 514/263.21 |
| 2014/0154772 A1 | 6/2014 | Sadhu et al. |
| 2014/0378479 A1 | 12/2014 | Kesicki et al. |
| 2015/0080572 A1 | 3/2015 | Carra et al. |
| 2015/0175605 A1 | 6/2015 | Bremner et al. |

FOREIGN PATENT DOCUMENTS

| | | |
|---|---|---|
| EP | 0 675 124 A2 | 10/1995 |
| EP | 0 716 857 A1 | 6/1996 |
| EP | 0 884 310 A1 | 12/1998 |
| EP | 0 900 568 A2 | 3/1999 |
| GB | 1 356 763 A | 6/1974 |
| GB | 2 017 097 A | 10/1979 |
| JP | 553-44581 A | 4/1978 |
| JP | 55-118917 A2 | 9/1980 |
| JP | 55-118918 A2 | 9/1980 |
| JP | 56-002322 A2 | 1/1981 |
| JP | 2003-519698 A | 6/2003 |
| JP | 2007-537291 A | 12/2007 |
| WO | WO-93/21259 A1 | 10/1993 |
| WO | WO-94/17090 A1 | 8/1994 |
| WO | WO-95/24379 A1 | 9/1995 |
| WO | WO-96/04923 A1 | 2/1996 |
| WO | WO-96/25488 A1 | 8/1996 |
| WO | WO-96/32478 A1 | 10/1996 |
| WO | WO-97/34631 A1 | 9/1997 |
| WO | WO-97/41097 A2 | 11/1997 |
| WO | WO-97/43276 A1 | 11/1997 |
| WO | WO-97/46688 A1 | 12/1997 |
| WO | WO-98/33802 A1 | 8/1998 |
| WO | WO-98/38173 A1 | 9/1998 |
| WO | WO-99/08501 A2 | 2/1999 |
| WO | WO-99/34804 A1 | 7/1999 |
| WO | WO-01/00881 A1 | 1/2001 |
| WO | WO-01/030768 A1 | 5/2001 |
| WO | WO-01/051919 A2 | 7/2001 |
| WO | WO-01-051919 A3 | 7/2001 |
| WO | WO-01/53266 A1 | 7/2001 |
| WO | WO-01/57034 A1 | 8/2001 |
| WO | WO-01/81346 A2 | 11/2001 |
| WO | WO-03/035075 A1 | 5/2003 |
| WO | WO-03/106622 A2 | 12/2003 |
| WO | WO-2004/007491 A1 | 1/2004 |
| WO | WO-2004/012768 A1 | 2/2004 |
| WO | WO-2004/026285 A2 | 4/2004 |
| WO | WO-2004/029055 A1 | 4/2004 |
| WO | WO-2004/052373 A1 | 6/2004 |
| WO | WO-2004/056820 A1 | 7/2004 |
| WO | WO-2004/089925 A1 | 10/2004 |
| WO | WO-2004/108708 A1 | 12/2004 |
| WO | WO-2004/108709 A1 | 12/2004 |
| WO | WO-2004/108713 A1 | 12/2004 |
| WO | WO-2004/108715 A1 | 12/2004 |
| WO | WO-2005/016348 A1 | 2/2005 |
| WO | WO-2005/016349 A1 | 2/2005 |
| WO | WO-2005/067901 A2 | 7/2005 |
| WO | WO-2005/113554 A2 | 12/2005 |
| WO | WO-2005/113556 A1 | 12/2005 |
| WO | WO-2005/120511 A1 | 12/2005 |
| WO | WO-2009/058361 A1 | 5/2009 |
| WO | WO-2010/057048 A1 | 5/2010 |
| WO | WO-2010/065923 A2 | 6/2010 |
| WO | WO-2010/123931 A1 | 10/2010 |
| WO | WO-2011/156759 | 12/2011 |
| WO | WO-2013/134288 | 9/2013 |
| WO | WO-2016/026380 A1 | 2/2016 |

OTHER PUBLICATIONS

Ager et al., J. Med. Chem. (1977) 20:379-386.
Ali et al., Nature (2004) 431:1007-1011.
Alon et al., "The molecular basis of leukocyte adhesion to and migration through vascular endothelium," Mirelman et al. (eds.), Life Sciences Open Day Book 2002, Weizmann Institute of Science, Life Sciences Department, Chapter 8, vol. 2:206-207 (2002), retrieved from the internet on Sep. 2, 2005, located at <http://www.weizmann.ac.il/Biology/open_day_2002/book/ronen_alon.pdf>, 2 pages.
Amendment from U.S. Appl. No. 09/841,341, filed Aug. 21, 2002.
Amendment from U.S. Appl. No. 10/027,591, filed Jun. 3, 2003.
Amendment in Response to Final Office Action from U.S. Appl. No. 11/596,092, filed Jul. 19, 2010.
Amendment in Response to Non-Final Office Action / Restriction Requirement from U.S. Appl. No. 11/884,566, filed Jun. 7, 2010.
Amendment in Response to Non-Final Office Action from U.S. Appl. No. 10/918,803, filed Oct. 1, 2008.
Amendment in Response to Non-Final Office Action from U.S. Appl. No. 10/918,803, filed Sep. 4, 2009.
Amendment in Response to Non-Final Office Action from U.S. Appl. No. 11/110,204, filed Dec. 31, 2008.
Amendment in Response to Non-Final Office Action from U.S. Appl. No. 11/110,204, filed Jun. 4 , 2010.
Amendment in Response to Non-Final Office Action from U.S. Appl. No. 11/110,204, filed Sep. 4, 2009.
Amendment in Response to Non-Final Office Action from U.S. Appl. No. 11/596,092, filed Mar. 24, 2010.
Amendment in Response to Non-Final Office Action from U.S. Appl. No. 11/596,092, filed Nov. 10, 2009.
Amendment Under 37 C.F.R. § 1.111 from U.S. Appl. No. 11/129,006, filed Apr. 12, 2010.
Amendment Under 37 C.F.R. § 1.111/Restriction Requirement from U.S. Appl. No. 11/110,204, filed Apr. 10, 2008.
Amendment with Request for Continued Examination from U.S. Appl. No. 11/596,092, filed Sep. 1, 2010.

(56) References Cited

OTHER PUBLICATIONS

Amin et al., Circ Res (2003) 93(4):321-329.
Amine, M.S. et al. (Nov. 1998). "Uses of Quinazolin-2-[(β-Propionoyl) Isothiocyanate]-4-One as a Building Block in Synthesis of Some Heterocyclic Compounds of Expected Biological Activity," *Indian Journal of Chemistry* 37B(11):1153-1156.
Angel, Activities of Phosphoinositide Kinase-3 (PI3K) (1999) retrieved from the Internet on May 22, 2003, URL: http://www.chem.csustan.edu/chem4400/SJBR/angel99.htm.
Angio World, "How Angiogenesis Complicates Psoriasis" (2001) retrieved from the internet on Apr. 13, 2004, located at <http://www.Angioworld.com/psoriasis.htm>, 1 page.
Annabi et al., J. Cell. Biochem. (2004) 91:1146-1158.
Anonymous (2006). "Cardiovascular Disease: Treatment for Stroke", Stanford Hospital & Clinics, located at <http://www.stanfordhospital.com/healthLib/atoz/cardiac/stktreat.html>, last visited on Sep. 19, 2006, 2 pages.
Anonymous (2006). "Heart Disease", WebMD, located at <http://www.webmd.com/content/pp./9/1675_57842.htm> as retrieved on Sep. 14, 2006, 1 page.
Anonymous (2010) "Systemic Lupus Erythematosus", located at <http://www.nlm.nih.gov/medlineplus/ency/article/000435.htm>, last visited Aug. 1, 2010, 4 pages.
Anonymous (2010). "Spinal Cord Injury", located at <http://www.medicinenet.com/spinal_cord_injury/page.htm>, last visited on Aug. 1, 2010, 3 pages.
Anonymous, (2004). "NIH Heart Disease & Stroke Research: Fact Sheet", American Heart Association, located at <http://www.americanheart.org/presenter.jhtml?identifier=3010188>, last visited Feb. 17, 2004, 1 page.
Anonymous, (2010). "Multiple Sclerosis", located at <http://www.health.nytimes.com/health/guides/disease/multiple-sclerosis/overview.html>, last visited Aug. 1, 2010, 4 pages.
Aoki et al., PNAS USA (2001) 98:136-141.
Aoudjit et al., J. Immunol. (1998) 161:2333-2338.
Arcaro et al., Biochem. J. (1994) 298:517-520.
Asti et al., Pulm. Pharmacol. Ther. (2000) 13:61-69.
Ausprunk et al., Microvasc. Res. (1977) 14:53-65.
Australian Re-Examination Report mailed Sep. 3, 2015, for Australian Patent No. 2001255667, filed Apr. 24, 2001, 7 pages.
Azenabor, A.A. et al. (2006). "Macrophage Antioxidant Enyzmes Regulate Chlamydia Pneumoniaechronicity: Evidence of the Effect of Redox Balance on Host-Pathogen Relationship," *Immunobiology* 211(5):325-339.
Bader, A.G. et al. (2005). "Oncogenic PI3K Deregulates Transcription and Translation," *Nature Reviews Cancer* 5(12):921-922 (abstract and introduction).
Barakat et al., Chemical Abstracts (1996) 124(21):1334.
Barakat, S.E-S. et al. (Dec. 1994). "Synthesis and CNS Depressant Activity of Some New Quinazoline Derivatives," *Az. J. Pharm. Sci.* 14:239-246.
Bardet et al., 9th Congress of the European Hematology Association Geneva Palexpo, Switzerland, Jun. 10-13, 2004, View Abstract data, Abstract nr.: 620.
Barker, Lancet (1991) 338:227-230.
Benekli et al., Blood (2002) 99:252-257.
Benekli et al., Blood (2003) 101:2940-2954.
Bennett et al., Ann. Intern. Med. (1985) 103:620-625.
Bennett et al., J. Pharmacol. Exp. Ther. (1997) 280:988-1000.
Bergers et al., Science (1999) 284:808-812.
Bharadwaj et al., J. Immunol. (2001) 166:6735-6741.
Binetruy-Tournaire et al., EMBO J. (2000) 19:1525-1533.
Bloemen et al., Am. J. Respir. Crit. Care Med. (1996) 153:521-529.
Boehm et al., Nature (1997) 390:404-407.
Borregaard et al., Blood (1997) 89:3503-3521.
Boudewijn et al., Nature (1995) 376:599-602.
Bouscary et al., Blood (2003) 101:3436-3443.
Bouscary et al., Oncogene (2001) 20:2197-2204.
Bowes et al., Exp. Neurol. (1993) 119:215-219.
Brennan et al., Arthritis Res. (2002) 4(Suppl. 3):S177-S182.
Brown et al., 44th Annual Meeting of the American Society of Hematology, Philadelphia, PA, Dec. 6-10, 2002, Abstract No. 3012, p. 761A.
Brown, J. et al. (2010). "Clinical Activity in a Phase 1 Study of Cal-101, an Isoform-Selective Inhibitor of Phosphatidylinositol 3-Kinase P110Delta, in Patients with B-Cell Malignancies," *Haematologica* 95(s2):466, Abstract No. 1130.
Brunn et al., EMBO J. (1996) 15:5256-5267.
Burgering et al., Nature (1995) 376:599-602.
Butcher et al., Science (1996) 272:60-66.
Cadwallader et al., J. Immunol. (2002) 169:3336-3344.
Takeuchi et al. (1989). "A new efficient of imidazolinones and quinazolinone by intramolecular aza-Wittig reaction," Tetrahedron, 45(20):6375-6386, Schemes 5-6.
Cantley et al., PNAS USA (1999) 96:4240-4245.
Cantley et al., Science (2002) 296:1655-1657.
Cardone et al., Science (1998) 282:1318-1321.
Carnero et al., FEB Letters (1998) 422:155-159.
CAS Abstract, Accession No. DN 86:83505 [1977] pp. 111-118.
Cebon et al., Cancer Immun. (2003) 3:7-25.
Chang et al., Exp. Opin. Ther. Patents (2001) 11:45-59.
Chang, BioMed. Eng. Online (2003) 2:12.
Chantry et al., J. Biol. Chem. (1997) 272:19236-19241.
Chapman-Kirkland, E.S. et al. (1991). "Superoxide Anion Production From Human Neutrophils Measured with an Improved Kinetic and Endpoint Microassay," *J Immunol Meth* 142(1):95-104.
Chen et al., Blood (2000) 96:3181-3187.
Chern et al., Chem. Pharm. Bull. (1998) 46(6):928-933.
Chern et al., Chemical Abstracts (1998) 129(16):676.
Chopp et al., Stroke (1994) 25:869-876.
Choy et al., Arthritis & Rheumatism (2002) 46:3143-3150.
Clark et al., J. Neurosurg. (1991) 75:623-627.
Clavel et al., Joint Bone Spine (2003) 70:321-326.
Clayton et al., J. Exp. Med. (2002) 196:753-763.
Cleary, J.M. et al. (2010). "Development of Phosphoinositide-3 Kinase Pathway Inhibitors for Advanced Cancer," *Curr. Oncol. Rep.* 12:87-94.
Coligan et al., Current Protocols in Protein Science (2002) 3:15-20.
Computer Search Cart Navigator, located at <http://www.chemnavigator.com/members/CartNavigator.asp#sample1>, last visited Mar. 22, 2001, 8 pages.
Constantin et al., Immunity (2000) 13:759-769.
Cosimi et al., J. Immunol. (1990) 144:4604-4612.
Coxon, Immunity (1996) 5:653-666.
Creamer et al., Angiogenesis (2002) 5:231-236.
Cross et al., Inflamm. Res. (1999) 48:255-261.
Curnock et al., Immunology (2002) 105:125-136.
Dahia et al., Hum. Mol. Genet. (1999) 8:185-193.
Dallegri et al., Inflamm. Res. (1997) 46:382-391.
Das et al., Prog. Retin. Eye Res. (2003) 22:721-748.
Datta et al., Cell (1997) 91:231-241.
Datta et al., Genes & Dev. (1999) 13:2905-2927.
Davies et al., Biochem. J. (2000) 351:95-105.
De Benedetti et al., Clin. Exper. Reheum. (1992) 10:493-498.
Deininger et al., Blood (2000) 96:3343-3356.
Demeester et al., Transplantation (1996) 62:1477-1485.
Descamps et al., J. Immunol. (2004) 173:4953-4959.
Doggett et al., Biophys. J. (2002) 83:194-205.
Domanig, R. (1981). "Chinazolinone, 2. Mitt: Synthese Und Einige Reaktionen Von 2-Azidomethy1-3-Aryl-4-Chinazolinonen," *Monatshefte fuer Chemie* 112(10):1195-1202. (English translation of abstract only).
Dorland's Illustrated Medical Dictionary (2003), retrieved Oct. 21, 2005 from Xreferplus, http://www.xreferplus.com/entry/4196914.
Downward, Nature (1995) 376:553-554.
Drakesmith et al., Immunol. Today (2000) 21:214-217.
Druker et al., New England Journal of Medicine (2001) 344:1038-1042.
Dunne et al., Blood (2002) 99:336-341.
Edwards et al., Canc. Res. (2002) 62:4671-4677.
Eichholtz et al., J. Biol. Chem. (1993) 268:1982-1986.
El-Fattah et al., Indian J Hetercyclic Chemistry (1995) 4:199-202.
El-Feky et al., Chemical Abstracts (1987) 106(13):650.

(56) References Cited

OTHER PUBLICATIONS

El-Feky et al., Chemical Abstracts (1999) 131(23):497.
El-Feky, S.A. (Aug. 1998). "Novel Quinazolinones From 2-Cyanomethyl-3-Phenyl-4(3H) Quinazolinone," *Bollettino Chimico Farmaceutico* 137(7):286-289.
El-Feky, S.A. et al. (1985). "Synthesis of Certain New Sulfur-Containing Quinazolinone Derivatives Likely to Possess CNS Depressant Action," *Egyptian Journal of Pharmaceutical Sciences* 24(1-4):39-47.
Engelman et al., Nature Reviews (2006) 7:606-619.
Environmental Protection Agency, EPA—Radiation Information (EPA's Radiation Protection Program:Information) "Ionizing Radiation Fact Sheet Series No. 1" (May 1998) Retrieved on Apr. 21, 2004: http://www.epa.gov/radiation/docs/ionize/ionize.htm.
Erbagci et al., Clin. Biochem. (2001) 34:645-650.
Estey, Cancer (2001) 92:1059-1073.
Etzioni, Pediatr. Res. (1996) 39:191-198.
European Search Report dated Jun. 6, 2013 for EP Patent Application No. 13150110.8, filed May 12, 2005, 6 pages.
European Search Report mailed Mar. 29, 2011, for EP Patent Application No. 10163434.3, filed on Apr. 24, 2001, 9 pages.
Evarts, J.B. et al. (2010). "Discovery and Synthesis of CAL-101, a Potent and Selective Inhibitor of the Phosphatidylinositol 3-Kinase P110σ Isoform," Calistoga Pharmaceuticals Poster, PacifiChem International Chemistry Conference, Dec. 15-20, 2010, 1 page.
Extended European Search Report and European Search Opinion dated Oct. 8, 2015, for EP Patent Application No. 13757230.1, filed on Mar. 5, 2013, 6 pages.
Extended European Search Report mailed Dec. 10, 2013, for EP Patent Application No. 13150110.8, filed May 12, 2005, 10 pages.
Faffe et al., Eur. Respir. J. (2000) 15:85-91.
Fantl et al., Ann. Rev. Biochem. (1993) 62:453-481.
Faust et al., Blood (2000) 96:719-726.
Final Office Action from U.S. Appl. No. 10/918,803, mailed on Jan. 8, 2009.
Final Office Action from U.S. Appl. No. 11/129,006, mailed on Oct. 5, 2010.
Final Office Action from U.S. Appl. No. 11/596,092, mailed on May 18, 2010.
Final Office Action mailed on Feb. 15, 2012, for U.S. Appl. No. 12/732,124, filed Mar. 25, 2010, 12 pages.
Final Office Action mailed on Jul. 9, 2013, for U.S. Appl. No. 13/399,828, filed Feb. 17, 2012, 6 pages.
Final Office Action mailed on Jun. 7, 2012, for U.S. Appl. No. 11/129,006, filed May 12, 2005, 14 pages.
Final Office Action mailed on Oct. 24, 2011, for U.S. Appl. No. 12/732,128, filed Mar. 25, 2010, 8 pages.
First Preliminary Amendment from U.S. Appl. No. 12/538,748, filed Apr. 1, 2010.
Flinn, I.W. et al. (2009). "Preliminary Evidence of Clinical Activity in a Phase 1 Study of CAL-101, a Selective Inhibitor of the p110δ Isoform of Phosphatidylinositol 3-Kinase (PI3K), in Patients with Select Hematologic Malignancies," Journal of Clinical Oncology 27:156s, Abstract 3543.
Flinn, I.W. et al. (Nov. 20, 2009). "Evidence of Clinical Activity in a Phase 1 Study of CAL-101, an Oral P110Δ Isoform-Selective Inhibitor of Phosphatidylinositol 3-Kinase, in Patients with Relapsed or Refractory B-Cell Malignancies," *Blood* 114(22):380, Abstract 922.
Flinn, W. et al. (Jun. 4-7, 2009). "Preliminary Evidence of Clinical Activity in a Phase 1 Study of CAL-101, A Potent Selective Inhibitor of the P110Delta Isoform of Phosphatidylinositol 3-Kinase, in Patients with B-Cell Maglignancies," Haematologica 94(s2):303, Abstract 0744.
Folkman, Curr. Mol. Med. (2003) 3:643-651.
Folkman, Nat. Med. (1995) 1:27-31.
Fraser et al., Science (1991) 251:313-316.
Frey et al., Lancet (2008) 372(9643):1088-1099 (abstract).
Freyssinier et al., Br. J. Haematol. (1999) 106:912-922.
Fruman et al., Ann. Rev. Biochem. (1998) 67:481-507.
Fruman et al., Semin. Immunol. (2002) 14:7-18.
Furman, R.R. (Jul. 2010). "New Agents in Early Clinical Trials for CLL Therapy," *Clinical Advances in Hematology & Oncology* 8(7):475-476.
Garcia-Barros et al., Science (2003) 300:1155-1159.
Genbank Accession No. AK040867, last updated Sep. 19, 2008, located at <http://www.ncbi.nlm.nih.gov.nuccore/26334014>, last visited on Apr. 16, 2010, 6 pages.
GenBank Accession No. AR255866, last updated Dec. 20, 2002, located at <http://www.ncbi.nlm.nih.gov.nuccore/27305059>, last visited on Apr. 16, 2010, 2 pages.
GenBank Accession No. BC035203, last updated Aug. 11, 2006, located at <http://www.ncbi.nlm.nih.gov/nuccore/23270986>, last visited on Apr. 16, 2010, 5 pages.
GenBank Accession No. NM_005026, last updated Apr. 11, 2010, located at <http://www.ncbi.nlm.nih.gov/nuccore/15654404>, last visited Apr. 16, 2010, 7 pages.
GenBank Accession No. NM_008840, last updated on Mar. 5, 2010, located at <http://www.ncbi.nlm.nih.gov/nuccore/255708435>, last visited on Apr. 16, 2010, 5 pages.
GenBank Accession No. U57843, last updated on May 9, 1997, located at <http://www.ncbi.nlm.nih.gov/nuccore/U57843>, last visited on Aug. 9, 2011, 2 pages.
GenBank Accession No. U86453, last updated on Jul. 7, 1998, located at <http://www.ncbi.nlm.nih.gov/nuccore/2317893>, last visited on Apr. 16, 2010, 3 pages.
GenBank Accession No. U86587, last updated Jul. 7, 1998, located at <http://www.ncbi.nlm.nih.gov/nuccore/2331237>, last visited on Apr. 16, 2010, 3 pages.
GenBank Accession No. XM_345606, last updated Jun. 22, 2006, located at <http://www.ncbi.nlm.nih.gov/nuccore/109475856?report-genbank>, last visited on Apr. 16, 2010, 3 pages.
GenBank Accession No. Y10055, last updated Oct. 7, 2008, located at <http://www.ncbi.nlm.nih.gov/nuccore/37496958>, last visited on Apr. 16, 2010, 3 pages.
Geng et al., Cancer Research (2001) 61:2413-19.
Geng et al., Cancer Research (2004) 64:4893-4899.
Geng et al., Cancer Research (2004) 64:8130-8133.
Gibson, (ed.), Antisense and Ribozyme Methodology, "Laboratory Companion" (1997) Table of Contents.
Gilliland et al., Blood (2002) 100:1532-1542.
Gilliland et al., Cancer Cell (2002) 1:417-420.
Gingras et al., Genes Dev. (2001) 15:2852-2864.
Gingras et al., Genes Dev. (2001) 15:807-826.
Glenjen et al., Int. J. Cancer (2002) 101:86-94.
Gorczynski et al., J. Immunol. (1994) 152:2011-2019.
Gorski et al., Cancer Research (1999) 59:3374-3378.
Gouilleux-Gruart et al., Blood (1996) 87:1692-1697.
Grant et al., Drugs of Today (2002) 38:783-791.
Green, S.J. et al. (1994). "Oxidative Metabolism of Murine Macrophages," 14.5 in Current Protocols in Immunology, vol. 3, John Wiley Chapter 14, Unit & Sons, Inc., pp. 14.5.1-14.5.11.
Gross et al., Science (1998) 281:703-706.
Gu et al., Mol. Cell. Biol. (2000) 20:7109-7120.
Gupta et al., Int'l J Radiation Oncology Biology Physics (2003) 56(3):846-853.
Gute et al., Mol. Cell. Biochem. (1998) 179:169-187.
Guzman et al., Blood (2001) 98:2301-2307.
Guzman et al., Proc. Natl. Acad. Sci. (USA) (2002) 99:16220-16225.
H. G. Brittain, "Polymorphism in Pharmaceutical Solids". Second Edition Informs Healthcare, NY (2009).
Hadden, Int. Immunopharmacol. (2003) 3:1061-1071.
Hallahan et al., Proc. Natl. Acad. Sci (USA) (1997) 94:6432-6437.
Halloran et al., Arthritis Rheum. (1996) 39:810-819.
Hanamoto et al., Am. J. Pathol. (2004) 164(3):997-1006.
Hannigan et al., Proc. Natl. Acad. Sci. U.S.A. (2002) 99:3603-3608.
Hardma et al. (eds.), Goodman and Gilman's The Pharmacological Basis of Therapeutics (1996) 9$^{th}$ ed., pp. 11-16.
Harlan, Haematology 96, the Education Program Book of the 26th Congress of the International Society of Haematology. Singapore, 1996.
Harning et al., Transplantation (1991) 52:842-845.

(56) References Cited

OTHER PUBLICATIONS

Hartley et al., Cell (1995) 82:849-856.
Hartman et al., Cardiovasc. Res. (1995) 30:47-54.
Hasagawa et al., Int. Immunol. (1994) 6:831-838.
Hassan et al., Chinese Journal of Chemistry (1991) 9:262-269.
Hattori, H. et al. (May/Jun. 2010). "Reactive Oxygen Species as Signaling Molecules in Neutrophil Chemotaxis," *Communicative and Integrative Biology* 3(3):278-281.
He et al., Opthalmol. Vis. Sci. (1994) 35:3218-3225.
Healy et al., Hum. Reprod. Update (1998) 4:736-740.
Healy et al., Pharma. Res. (Dec. 2004) 21:2234-2246.
Heit et al., J. Cell Biol. (2002) 159:91-102.
Hellman, Cancer: Principles and Practice of Oncology (1993) 4th ed., vol. 1:248-275.
Herman, S.E.M. et al. (Sep. 23, 2010). "Phosphatidylinositol 3-Kinase-σ Inhibitor CAL-101 Shows Promising Preclinical Activity in Chronic Lymphocytic Leukemia by Antagonizing Intrinsic and Extrinsic Cellular Survival Signals," *Blood* 116(12):2078-2088.
Herold et al., Cell Immunol. (1994) 157:489-500.
Higuchi, Prodrugs as Novel Delivery Systems, vol. 14, ASCD Symposium Series, and in Roche (ed.), Bioreversible Carriers in Drug Design, American Pharmaceutical Association and Pergamon Press (1987) Chapter 1, pp. 1-12.
Hilbert et al., J. Exper. Med. (1995) 182:243-248.
Hiles et al., Cell (1992) 70:419-429.
Hilmas et al., Rad. Res. (1975) 61:128-143.
Hirsch et al., Science (2000) 287:1049-1053.
Horgan et al., Am. J. Physiol. (1991) 261:H1578-H1584.
Hsieh, S.N. (2003). "Identification of PI3Kγ in Endothelial Cells and Its Involvement in Sphingosine 1-Phosphate Mediated Endothelial Cell Migration," Dissertation, Friedrick Schiller University, Jena, Germany, 104 pages.
Hu et al., Mol. Cell. Biol. (1993) 13:7677-7688.
Hu et al., Science (1995) 268:100-102.
Hunter, Cell (1995) 83:1-4.
Hussong et al., Blood (2000) 95:309-313.
Ikeda, H. et al. (Feb. 2009). "CAL-101: A Selective Inhibitor of P13K p110σ for the Treatment of multiple Myeloma," *Clinical Lymphoma and Myeloma* 9(Supp. 1):S98-S99.
Ikeda, H. et al. (Nov. 16, 2008). "CAL-101, a Specific Inhibitor of the p110σ Isoform of Phosphatidylinositide 3-Kinase Induces Cytotoxicity in Multiple Myeloma (MM)," *Blood* 112(11):950, Abstract No. 2753.
Ikeda, H. et al. (Sep. 2, 2010). "PI3K/p110σ is a Novel Therapeutic Target in Multiple Myeloma," *Blood* 116(9):1460-1468.
International Preliminary Report on Patentability for PCT/US2006/005621, issued on Aug. 21, 2007, 8 pages.
International Search Report for International (PCT) Patent Application Serial No. PCT/US2004/026436, dated Dec. 2, 2004.
International Search Report for International (PCT) Patent Application Serial No. PCT/US2004/026834, dated Nov. 29, 2004.
International Search Report for International (PCT) Patent Application Serial No. PCT/US2004/029561, dated May 25, 2005.
International Search Report for International (PCT) Patent Application Serial No. PCT/US2004/037860, dated May 6, 2005.
International Search Report mailed Apr. 6, 2006, for PCT/US2005/016661, 5 pages.
International Search Report mailed on Aug. 29, 2005, for PCT Application No. PCT/US2005/016778, filed on May 12, 2005, 4 pages.
International Search Report mailed on Jun. 27, 2013, for PCT Patent Application No. PCT/US2013/029157, filed on Mar. 5, 2013, 4 pages.
International Search Report mailed on Sep. 15, 2006 for PCT Application No. PCT/US2006/005621, filed on Feb. 16, 2006, 4 pages.
Interview Summary from U.S. Appl. No. 10/918,825, mailed on Jun. 14, 2006.
Ishida-Okawara, A. et al. (Dec. 12, 1996). "Modulation of Degranulation and Superoxide Generation in Human Neutrophils by Unsaturated Fatty Acids of Odd Carbon Numbers," *BioChimica et Biophysica Acta* 1314(3):239-246.
Ismail and Sayed, Indian Journal of Chemistry (1982) 21B(5):461-462.
Ismail et al., Chemical Abstracts (1983) vol. 98, No. 1, p. 406.
Isobe et al., Science (1992) 255:1125-1127.
Johnson et al., Intl. J. Rad. One. Biol. Phys. (1976) 1:659-670.
Johnson et al., J. Endourol. (2003) 17:557-562.
Jordan, Nature Reviews: Drug Discovery (2003) 2:205.
Jou et al., Mol. Cell. Biol. (2002) 22:8580-8591.
Kahl, B.S. (May 2010). "Novel Agents for Non-Hodgkin Lymphoma," *Clinical Advances in Hematology & Oncology* 8(5)(Suppl. 10):10-15.
Kakimoto et al., Cell. Immunol. (1992) 142:326-337.
Kallman et al., Canc. Res. (1972) 32:483-490.
Kandel et al., Exp. Cell Res. (1999) 253:210-229.
Kawasaki et al., J. Immunol. (1993) 150:1074-1083.
Kim et al., Endocrin. (2000) 141:1846-1853.
Kim, Retrieved from the Internet on Apr. 13, 2004: URL: http://www.math.umn.edu/~yjkim/biopaper/timy,html.
Kishimoto et al., Cell (1987) 50:193-202.
Klein et al., Cell. Signal. (2001) 13:335-343.
Klippel et al., Mol. Cell. Biol. (1994) 14:2675-2685.
Knall et al., Proc. Natl. Acad. Sci. (USA) (1997) 94:3052-3057.
Knight and Shokat, Chemistry and Biology (2005) 12:621-637.
Knight et al., Bioorganic & Medicinal Chemistry (Jul. 2004) 12:4749-4759.
Knoerzer et al., Toxicol. Pathol. (1997) 25:13-19.
Kolonin et al., Nature Medicine (2004) 10:625-632.
Kong et al., J. Biol. Chem. (2000) 275:36035-36042.
Kopf et al., Nature (1994) 368:339-342.
Krugmann et al., J. Biol. Chem. (1999) 274:17152-17158.
Kumar et al., Blood (2003) 101(10):3960-3968.
Kunkel et al., Circ. Res. (1996) 79:1196-1204.
Lannutti, B.J. et al. (Apr. 2009). "CAL-101, a Specific PI3K p110σ Inhibitor for the Treatment of Hematological Maglinancies," *Proceedings of the American Association for Cancer Research* 50:1400, Abstract No. #SY32-2.
Lannutti, B.J. et al. (Nov. 16, 2008). "CAL-101, a Potent Selective Inhibitor of the p110d Isoform of Phosphatidylinositol 3-Kinase, Attenuates PI3K Signaling and Inhibitos Proliferation and Survival of Acure Lumpoblastic Leukemia in Addition to a Range of Other Hematological Malignancies," *Blood* 112(11):12, Abstract No. 16.
Lannutti, B.J. et al. (Nov. 20, 2009). "CAL-101, An Oral P110σ Selective Phosphatidylinositol-3-Kinase (PI3K) Inhibitor for the Treatment of B Cell Malignancies Inhibits PI3K Signaling, Cellular Viability and Protective Signals of the Microenvironment," *Blood* 114(22):120-121, Abstract No. 286.
Lannutti, J. et al. (2010). "Demonstration of Pharmacodynamic Target Inhibition and Chemokine Modulation in Patients with CLL Following Treatment with CAL-101, a Selective Inhibitor of the P110 Delta Isoform of PI3K," *Haematologica* 95(52):45-46, Abstract No. 0113.
Lannutti, J. et al. (Jun. 4-7, 2009). "CAL-101, A Specific Inhibitor of the P11-Delta Isoform of Phosphatidylinositide 3-Kinase, for the Treatment of Non-Hodgkins Lymphomas," *Haematologica* 94(S2):272-273, Abstract No. 0668.
Lecoq-Lafon et al., Blood (1999) 93:2578-2585.
Lemmon et al., Trends Cell. Biol. (1997) 7:237-242.
Letter from Polish Patent Law Firm "Patpol" translating Office Action from Polish Patent Application No. P-358590, dated Feb. 27, 2008.
Li et al., Trends Biochem. Sci. (Jan. 2004) 29:32-38.
Liang et al., Molecular Cancer Therapeutics (2003) 2(4):353-360.
Liekens et al., Biochem. Pharmacol. (2001) 61:253-270.
Liu et al., J. Immunol. (Jan. 2004) 172 :7-13.
Lowell et al., J. Cell Biol. (1996) 133:895-910.
Luo et al., Cancer Cell (2003) 4:257-262.
Luo et al., Leukemia (2003) 17:1-8.
Luster, N. Engl. J. Med. (1998) 338:436-445.
Madge et al., J. Biol. Chem. (2000) 275:15458-15465.
Manning et al., Mol. Cell (2002) 10:151-162.

(56) References Cited

OTHER PUBLICATIONS

Marchione et al. (2006). "Drugs hold promise in kidney cancer fight", located at <http://www.ledger-enquirer.com/mld/ledgerenquirer/living/health/14744763.htm>, last visited on Sep. 2, 2006, 3 pages.
Marley et al., Br. J. Haematol. (May 2004) 125:500-511.
May, S.E. et al. (Nov. 16, 2008). "CAL-101, a Selective Inhibitor of the p110σ Isoform of Phosphatidylinositol 3-Kinase, Effectively Induces Apoptosis in Primary Chronic Lumphocytic Leukemia Cells Providing a Novel Therapeutic Strategy for the Treatment of this Disease," *Blood* 112(11):1085-1086, Abstract No. 3165.
Meneses et al., Gene Ther. (2001) 8:646-648.
Milella et al., J. Clin. Invest. (2001) 108:851-859.
Miller et al., Nucleic Acids Res. (1988) 16:1215.
Moehler et al., Ann. Hematol. (2001) 80:695-705.
Moore, J. Clin. Invest. (2002) 109:313-315.
Moulton et al., Circ. (1999) 99:1726-1732.
Mulligan et al., J. Immunol. (1995) 154:1350-1363.
Mulligan et al., Proc. Natl. Acad. Sci. (USA) (1993) 90:11523-11527.
Nagase et al., Am. J. Respir. Crit. Care Med. (1996) 154:504-510.
Nakao et al., Leukemia (1996) 10:1911-1918.
Nakao et al., Muscle Nerve (1995) 18:93-102.
Neshat et al., Proc. Natl. Acad. Sci. (USA) (2001) 98:10314-10319.
Ninomiya et al., J. Biol. Chem. (1994) 269:22732-22737.
Non Final Office Action from U.S. Appl. No. 11/596,092, mailed on Dec. 24, 2009.
Non-Final Office Action from U.S. Appl. No. 09/841,341, mailed on Apr. 25, 2002.
Non-Final Office Action from U.S. Appl. No. 10/027,591, mailed on Feb. 26, 2003.
Non-Final Office Action from U.S. Appl. No. 10/918,803, mailed on Apr. 1, 2008.
Non-Final Office Action from U.S. Appl. No. 10/918,803, mailed on Mar. 16, 2010.
Non-Final Office Action from U.S. Appl. No. 10/918,825, mailed on Nov. 7, 2005.
Non-Final Office Action from U.S. Appl. No. 11/110,204, mailed on Aug. 5, 2008.
Non-Final Office Action from U.S. Appl. No. 11/110,204, mailed on Feb. 4, 2010.
Non-Final Office Action from U.S. Appl. No. 11/110,204, mailed on Jun. 17, 2009.
Non-Final Office Action from U.S. Appl. No. 11/129,006, mailed on Dec. 15, 2009.
Non-Final Office Action from U.S. Appl. No. 11/596,092, mailed on Jun. 10, 2009.
Non-Final Office Action from U.S. Appl. No. 11/884,566, mailed on Aug. 3, 2010.
Non-Final Office Action mailed Oct. 8, 2015, for U.S. Appl. No. 14/323,925, filed Jul. 3, 2014, 8 pages.
Non-Final Office Action mailed on Aug. 2, 2012, for U.S. Appl. No. 12/575,277, filed Oct. 7, 2009, 8 pages.
Non-Final Office Action mailed on Aug. 7, 2012, for U.S. Appl. No. 12/575,367, filed Oct. 7, 2009, 9 pages.
Non-Final Office Action mailed on Feb. 13, 2013 for U.S. Appl. No. 13/247,962, filed Sep. 28, 2011, 21 pages.
Non-Final Office Action mailed on Feb. 3, 2015, for U.S. Appl. No. 14/284,331, filed May 21, 2014, 16 pages.
Non-Final Office Action mailed on Jan. 20, 2012 for U.S. Appl. No. 13/163,597, filed Jun. 17, 2011, 14 pages.
Non-Final Office Action mailed on Jun. 25, 2014, for U.S. Appl. No. 14/049,154, filed Oct. 8, 2013, 15 pages.
Non-Final Office Action mailed on Jun. 25, 2014, for U.S. Appl. No. 14/049,163, filed Oct. 8, 2013, 15 pages.
Non-Final Office Action mailed on Jun. 26, 2013 for U.S. Appl. No. 13/765,610, filed Feb. 12, 2013, 9 pages.
Non-Final Office Action mailed on Jun. 28, 2011, for U.S. Appl. No. 12/732,124, filed on Mar. 25, 2010, 11 pages.
Non-Final Office Action mailed on Mar. 1, 2013 for U.S. Appl. No. 13/399,828, filed Feb. 17, 2012, 6 pages.
Non-Final Office Action mailed on Mar. 25, 2013 for U.S. Appl. No. 13/728,807, filed Dec. 27, 2012, 13 pages.
Non-Final Office Action mailed on Nov. 16, 2015, for U.S. Appl. No. 14/092,287, filed Nov. 27, 2013, 11 pages.
Non-Final Office Action mailed on Oct. 17, 2011 for U.S. Appl. No. 12/732,124, filed Mar. 25, 2010, 8 pages.
Notice of Allowance from U.S. Appl. No. 09/841,341, mailed on Oct. 7, 2002.
Notice of Allowance from U.S. Appl. No. 10/027,591, mailed on Jul. 29, 2003.
Notice of Allowance from U.S. Appl. No. 10/337,192, mailed on Mar. 11, 2004.
Notice of Allowance from U.S. Appl. No. 10/697,912, mailed on Dec. 30, 2004.
Notice of Allowance mailed on Aug. 28, 2013, for U.S. Appl. No. 12/575,277, filed Oct. 7, 2009, 6 pages.
Notice of Allowance mailed on Feb. 21, 2013, for U.S. Appl. No. 12/575,367, filed Oct. 7, 2009, 5 pages.
Notice of Allowance mailed on Feb. 21, 2014, for U.S. Appl. No. 13/765,610, filed Feb. 12, 2013, 9 pages.
Notice of Allowance mailed on Jul. 8, 2013 for U.S. Appl. No. 13/728,807, filed Dec. 27, 2012, 9 pages.
Notice of Allowance mailed on Jul. 8, 2013, for U.S. Appl. No. 13/730,256, filed Dec. 28, 2012, 9 pages.
Notice of Allowance mailed on Jun. 16, 2014, for U.S. Appl. No. 13/786,222, filed Mar. 5, 2013, 12 pages.
Notice of Allowance mailed on Jun. 26, 2012, for U.S. Appl. No. 12/732,124, filed Mar. 25, 2010, 11 pages.
Notice of Allowance mailed on May 14, 2015, for U.S. Appl. No. 14/284,331, filed May 21, 2014, 9 pages.
Notice of Allowance mailed on May 20, 2013, for U.S. Appl. No. 13/730,276, filed Dec. 28, 2012, 7 pages.
Notice of Allowance mailed on Nov. 13, 2012, for U.S. Appl. No. 12/732,124, filed Mar. 25, 2010, 11 pages.
Notice of Allowance mailed on Nov. 8, 2010, for U.S. Appl. No. 11/110,204, filed Apr. 20, 2005, 6 pages.
Notice of Allowance mailed on Oct. 10, 2014, for U.S. Appl. No. 14/049,163, filed Oct. 8, 2013, 8 pages.
Notice of Allowance mailed on Oct. 18, 2013, for U.S. Appl. No. 13/765,610, filed Feb. 12, 2013, 10 pages.
Notice of Allowance mailed on Oct. 3 2013, for U.S. Appl. No. 13/247,962, filed Sep. 28, 2011, 9 pages.
Notice of Allowance mailed on Oct. 9, 2014, for U.S. Appl. No. 14/049,154, filed Oct. 8, 2013, 8 pages.
Notice of Allowance mailed on Sep. 19, 2013, for U.S. Appl. No. 13/399,828, filed Feb. 17, 2012, 6 pages.
Notice of Reexamination for Chinese Patent Application No. 0811654.X, mailed Nov. 5, 2009; 7 pages.
Notice Regarding Non-Compliant Amendment from U.S. Appl. No. 10/918,803, mailed on Nov. 19, 2009.
Notification of Reasons for Rejection for Japanese Patent Application No. 2003-537642, mailed on May 26, 2009, 4 pages.
Office Action for European Patent Application No. 01 928 855.4, mailed on Feb. 26, 2009, 3 pages.
Office Action for European Patent Application No. 01 928 855.4, mailed on Jul. 13, 2004, 5 pages.
Office Action for European Patent Application No. 01 928 855.4, mailed on Mar. 29, 2006, 6 pages.
Office Action for European Patent Application No. 01 928 855.4, mailed on Nov. 15, 2007, 4 pages.
Office Action for European Patent Application No. 02 757 407.8, mailed on Jan. 24, 2006, 3 pages.
Office Action for European Patent Application No. 02 757 407.8, mailed on Jul. 1, 2009, 2 pages.
Office Action for European Patent Application No. 02 757 407.8, mailed on Jun. 6, 2007, 2 pages.
Office Action for European Patent Application No. 02 757 407.8, mailed on Oct. 21, 2008, 3 pages.
Office Action for European Patent Application No. 02 757 407.8, mailed on Oct. 6, 2009, 3 pages.

(56) References Cited

OTHER PUBLICATIONS

Office Action for European Patent Application No. 04 810 878.1, mailed on Sep. 10, 2010, 4 pages.
Office Action for European Patent Application No. 04 816 855.3, mailed on Feb. 2, 2011, 4 pages.
Office Action for European Patent Application No. 04 816 855.3, mailed on Oct. 21, 2008, 4 pages.
Office Action for European Patent Application No. 05 752 122.1, mailed on Dec. 28, 2010, 4 pages.
Office Action for European Patent Application No. 05 752 122.1, mailed on Mar. 25, 2013, 4 pages.
Office Action for European Patent Application No. 05752122.1, mailed on Nov. 5, 2014, 3 pages.
Ohno-Matsui et al., Invest. Ophthalmol. Vis: Sci. (2003) 44:5370-5375.
Okkenhaug et al., Science (2002) 297:1031-1034.
Oppenheimer-Marks et al., J. Clin. Invest. (1998) 101:1261-1272.
Oshiro et al., Stroke (1997) 28:2031-2038.
Otsu et al., Cell (1991) 65:91-104.
Paez et al., Frank (ed.), Cancer Treatment and Research (2003) 115:146 Kluwer Academic Publishers.
Pages et al., Nature (1994) 369:327-329.
Palanki, Curr. Med. Chem. (2002) 9:219-227.
Paleolog et al., Angiogenesis (1998/1999) 2:295-307.
Panayotou et al., Trends in Cell Biol. (1992) 2:358-360.
Panes et al., Gastroenterology (1995) 108:1761-1769.
Parasharya and Parikh, J. Inst. Chemists (1992) 64(5):184-185.
Parasharya et al., Chemical Abstracts (1994) vol. 121, No. 9, p. 1065.
Park, S. et al. (2010). "Role of the PI3K/AKT and mTOR Signaling Pathways in Acute Myeloid Leukemia," *Haematologica* 95(5):819-829.
Parker et al., "PI 3-kinase puts GTP on the Rac" Curr. Biol., 5:577-79 (1995).
Passegue et al., Proc. Natl. Acad. Sci., (USA) (2003) 100 Supp. 1:11842-11849.
Patani, G.A. et al. (1996), "Bioisosterism: A Rational Approach in Drug Design," Chem Rev. 96(8):3147-3176.
Pierce et al., J. Biol. Chem. (1997) 272:21096-21103.
Plows et al., J. Immunol. (1999) 162(2):1018-1023.
Podsypanina et al., Proc. Natl. Acad. Sci. (USA) (2001) 98:10320-10325.
Psychoyos et al., J. Immunol. Methods (1991) 137:37-46.
Puri et al., Blood (2005) 106(1):150-157, 144.
Puri et al., Blood (May 2004) 103:3448-3456.
Puri, K. et al. (Jul. 18-23, 2004). "A Role for Phosphoinositide 3-Kinase σ in Neutrophil Trafficking," Immunology 2004: Cytokine Network, Regulatory Cells, Signaling, and Apoptosis Collection of Free Papers Presented at the 12th International Congress of Immunology and 4th Annual Conference of FOCIS Medimond International Proceedings in Montreal, Canada on Jul. 18, 23, 2004, pp. 303-307.
Quirici et al., Br. J. Haematol. (2001) 115:186-194.
Rada, B.K. et al. (Nov. 1, 2004, e-published Jul. 13, 2004). "Dual Role of Phagocytic NADPH Oxidase in Bacterial Killing," *Blood* 104(9):2947-2953.
Rameh et al. "The role of phosphoinositide 3-kinase lipid products in cell function." J. BioL Chem., 274:8347-8350 (1999).
Rameh et al., Cell (1995) 83:821-830.
Rathman et al., J. Org. Chem. (1980) 45:2169-2176.
Remington's Pharmaceutical Sciences (1990) 18th Ed., Chapter 89, pp. 1435-1712 Table of Contents Only.
Ren et al., Curr. Drug Targets Inflamm. Allergy (2003) 2(3):242-256.
Request for Continued Examination and Amendment Under 37 C.F.R. § 1.116 from U.S. Appl. No. 10/918,803, filed May 7, 2009.
Response to Election of Species Requirement from U.S. Appl. No. 10/918,803, filed Jun. 27, 2007.
Response to Non-Final Office Action filed on Sep. 16, 2010, for U.S. Appl. No. 10/918,803, filed Aug. 13, 2004, 25 pages.
Response to Non-Final Office Action from U.S. Appl. No. 10/918,803, filed Dec. 18, 2009.
Response to Restriction Requirement from U.S. Appl. No. 10/918,803, filed Jan. 4, 2008.
Response to Restriction Requirement from U.S. Appl. No. 11/129,006, filed May 12, 2009.
Response to Restriction Requirement from U.S. Appl. No. 11/137,901, filed Feb. 6, 2008.
Response to Restriction Requirement from U.S. Appl. No. 11/596,092, filed May 27, 2009.
Response to Rule 312 Communication mailed on Oct. 4, 2012, for U.S. Appl. No. 12/732,124, filed Mar. 25, 2010, 7 pages.
Restriction Requirement from U.S. Appl. No. 10/918,803, mailed on Jun. 12, 2009.
Restriction Requirement from U.S. Appl. No. 10/918,803, mailed on Mar. 13, 2007.
Restriction Requirement from U.S. Appl. No. 10/918,803, mailed on Sep. 7, 2007.
Restriction Requirement from U.S. Appl. No. 11/110,204, mailed on Mar. 10, 2008.
Restriction Requirement from U.S. Appl. No. 11/129,006, mailed on Nov. 12, 2008.
Restriction Requirement from U.S. Appl. No. 11/137,901, mailed on Aug. 6, 2007.
Restriction Requirement from U.S. Appl. No. 11/137,901, mailed on May 23, 2008.
Restriction Requirement from U.S. Appl. No. 11/596,092, mailed on Jan. 28, 2009.
Restriction Requirement from U.S. Appl. No. 11/884,566, mailed on Apr. 5, 2010.
Restriction Requirement mailed on Dec. 1, 2011, for U.S. Appl. No. 13/163,597, filed Jun. 17, 2011, 7 pages.
Restriction Requirement mailed on Feb. 3, 2014, for U.S. Appl. No. 13/786,222, filed Mar. 5, 2013, 17 pages.
Restriction Requirement mailed on Jul. 17, 2012, for U.S. Appl. No. 13/247,962, filed Sep. 28, 2011, 27 pages.
Restriction Requirement mailed on Jun. 7, 2012, for U.S. Appl. No. 13/399,828, filed Feb. 17, 2012, 5 pages.
Restriction Requirement mailed on May 8, 2015, for U.S. Appl. No. 14/092,287, filed Nov. 27, 2013, 8 pages.
Restriction Requirement mailed on Oct. 14, 2010, for U.S. Appl. No. 12/732,124, filed Mar. 25, 2010, 9 pages.
Restriction Requirement mailed on Sep. 11, 2012, for U.S. Appl. No. 13/399,828, filed Feb. 17, 2012, 7 pages.
Reyes et al., J. Clin. Invest. (2002) 109:337-346.
Rickert et al., Trends Cell Biol. (2000) 10:466-473.
Riesterer, Int'l J Radiation Oncology Biology Physics (2004) 361-368.
Roberts et al., Immunity (1999) 10:183-196.
Rodrigues et al., Mol. Cell. Biol. (2000) 20:1448-1459.
Rodriguez-Viciana et al., EMBO J. (1996) 15:2442-2451.
Roth et al., J. Immunol. Methods (1995) 188:97-116.
Rudd, "Upstream-downstream: CD28 cosignaling pathways and T cell function." Immunity, 4:527-34 (1996).
Rupnick et al., Proc. Nat'l. Acad. Sci. (USA) (2002) 99:10730-35.
Sadhu et al., J. Immunol. (2003) 170:2647-2654.
Salven et al., Blood (1999) 94:3334-3339.
Salvesen et al., Cell (1997) 91:443-446.
Sasaki et al., Science (2000) 287:1040-1046.
Sauder et al., J. Am. Acad. Dermatol. (2002) 47:535-541.
Schimmer et al., J. Immunol. (1998) 160:1466-1471.
Schuch et al., Blood (2002) 100:4622-4628.
Schueneman et al., Canc. Res. (2003) 63:4009-4016.
Second Preliminary Amendment and Response to Notice to File Missing Parts of Nonprovisional Application from U.S. Appl. No. 12/575,277, filed Jan. 20, 2010.
Second Preliminary Amendment and Response to Notice to File Missing Parts of Nonprovisional Application from U.S. Appl. No. 12/575,367, filed Jan. 20, 2010.
Second Preliminary Amendment from U.S. Appl. No. 11/110,204, filed Aug. 24, 2007.
Second Preliminary Amendment from U.S. Appl. No. 11/884,566, filed May 13, 2008.

(56) References Cited

OTHER PUBLICATIONS

Sengupta et al., Circulation (2003) 107:2955-2961.
Shimamoto et al., Leukemia Res. (2003) 27:783-788.
Shiojima et al., Circ. Res. (2002) 90:1243-1250.
Shvidel et al., Hematol. J. (2002) 3:32-37.
Smith et al., Am. J. Respir. Cell Mol. Biol. (1996) 15(6):693-702.
Song et al., Canc. Res. (1974) 34:2344-2350.
Springer, Cell (1994) 76:301-314.
Stein et al., Mol. Med. Today (2000) 6:347-357.
Stenmark et al., J. Cell. Sci. (1999) 112:4175-4183.
Stennicke et al., Biochim. Biophys. Acta. (2000) 1477:299-306.
Stephens et al., Current Biology (1994) 4:203-214.
Stirewalt et al., Nat. Rev. Cancer (2003) 3:650-665.
Stoyanov et al., Science (1995) 269:690-693.
Su et al., Cancer Research (2003) 63:3585-3592.
Sumariwalla et al., Arthritis Res. Ther. (2002) 5:R32-R39.
Sunil et al., Respir. Res. (2002) 3:21.
Supplemental Amendment from U.S. Appl. No. 11/110,204, filed Oct. 27, 2009.
Supplemental Notice of Allowance from U.S. Appl. No. 10/337,192, mailed on Jun. 29, 2004.
Sutton, A. (Jun. 9, 2006). "Baylor, St. Luke's study uses gene therapy as pancreatic cancer", located at <http://www.bcm.edu/news/item.cfm?newsID=640>, last visited on Sep. 2, 2006, 2 pages.
Tager et al., J. Exp. Med. (2000) 192:439-446.
Talento et al., Transplantation (1993) 55:418-422.
Tamiya et al., Immunopharmacology (1995) 29:53-63.
Tan et al., Cancer Research (2003) 63:7663-7667.
Tan et al., J. Immunol. Meths. (2000), 238:59-68.
Tan, J. et al. (Sep. 1, 2004). "A Specific Antagonist of the p110-Delta Catalytic Component of P13 Kinase, IC486068, Enhances Radiation-Induced Tumor Vascular Destruction," *International Journal of Radiation: Oncology Biology Physics* 60(1):S195.
Tanaka et al., J. Immunol. (1993) 151:5088-5095.
Tang et al., J. Biol. Chem. (1999) 274:16741-16746.
Taylor et al., Curr. Opin. Rheumatol. (2005) 17(3):293-298.
Tesar et al., Med. Sc. Monit. (2002) 8:BR24-BR29.
The Merck Manual on "arthritis" (2008).
The Merck Manual on "rheumatoid arthritis" (2008).
The Merck Manual, 17$^{th}$ ed, (1999) p. 1001.
Thelan et al., Proc. Natl. Acad. Sci. (USA) (1994) 91:4960-4964.
Ting et al., Int. J. Rad. Biol. (1991) 60:335-339.
Vacca et al., Blood (1999) 9:3064-3073.
Van Dijk et al., Blood (2000) 96:3406-3413.
Van Eeden, S.F. et al. (Dec. 17, 1999). "The Use of Flow Cytometry to Measure Neutrophil Function," *Journal Immunol Meth* 232:23-43.
Vanhaesebroeck et al., FASEB J. (1996) 10:A1395, Abst. No. 2280.
Vanhaesebroeck et al., Proc. Natl. Acad. Sci., (USA) (1997) 94:4330-4335.
Vanhaesebroeck et al., TIBS (1997) 22:267-272.
Vermes et al., J. Immunol. Meth. (1995) 184:39-51.
Vippagunta, S.R. et al. (2001). "Crystalline Solids," *Advanced Drug Delivery* 48:3-26.
Vivanco et al., Nat. Rev. Cancer (2002) 2:489-501.
Vlahos et al., J. Immunol. (1995) 154:2413-2422.
Volinia et al., EMBO J. (1995) 14:3339-3348.
Volinia et al., Genomics (1994) 24:472-477.
Volinia et al., Oncogene (1992) 7:789-793.
Webb, H.K. et al. (Apr. 2009). "CAL-101, a Potent and Selective Inhibitor of the Class 1 Phosphatidylinositol 3 Kinase (PI3K) p110σ: Preclinical Summary," *Proceedings of the American Association for Cancer Research* 50:894-895, Abstract No. #3703.
Wegner et al., Lung (1992) 170:267-279.
Wegner et al., Science (1990) 247:456-459.
Weiner et al., Nat. Cell Biol. (1999) 1:75-81.
Weyand et al., Arthritis & Rheumatism (2000) 43:1041-1048.
Williams et al., Chem. Biol. (2010) 17:123-134.

Williams, D.A. Wilkins, Baltimore et al. (2002). *Foye's Principles of Medicinal Chemistry* Lippincott, Williams & Wilkins, Baltimore MD, Fifth Edition, pp. 50 and 59-61.
Williams, Methods Mol. Med. (2004) 98:207-216.
Wolff, ed., Burger's Medicinal Chemistry and Drug Discovery, 5$^{th}$ edition (1996) vol. 1, New York: John Wiley & Sons, pp. 975-976.
Written Opinion mailed on Jun. 27, 2013 for PCT Patent Application No. PCT/US2013/029157, filed on Mar. 5, 2013, 6 pages.
Wymann et al., Biochem. Biophys. Acta. (1998) 1436:127-150.
Wymann et al., Biochem. J. (1994) 298:517-520.
Wymann et al., Trends Immunol. Today (2000) 21:260-264.
Xing et al., Am. J. Pathol. (1993) 143:1009-1015.
Xu et al., Blood (2003) 102:972-980.
Yamasawa et al., Inflammation (1999) 23:263-274.
Yamaura et al., Int. J. Rad. Biol. (1976) 30:179-187.
Yao et al., Science (1995) 267:2003-2006.
Yum et al., J. Immunol. (2001) 167:6601-6608.
Zeng et al., Transplantation (1994) 58:681-689.
Zhao et al., Leukemia (2004) 18:267-75.
Fuwa et al. (2005) "Synthetic studies on 3-arylquinazolin-4-ones: intramolecular nucleophilic aromatic substitution reaction of 2-carboxamido-3-arylquinazolin-4-ones and its application to the synthesis of secondary aryl amines," Tetrahedron, 61:4297-4312.
O'Mahony et al., (2002) "Traceless synthesis of 3H-quinazolin-4-ones yia a combination of solid-phase and solution methodologies," Tetrahedron Letters, 43:939-942.
Zhichkin et al., (2007) "A Novel Highly Stereoselective Synthesis of 2,3-Disubstituted 3H-Quinazoline-4-one Derivatives," Organic Letters, 9(7)1415-1418.
Non-Final Office Action mailed on Feb. 12, 2016 for U.S. Appl. No. 14/575,670, filed Dec. 18, 2014, 8 pages.
Caira: "Crystalline Polymorphism of Organic Compounds", Topics in Current Chemistry, Springer, Berlin, DE, vol. 198, Jan. 1, 1998, pp. 163-208.
Panayotou et al., "Phosphatidyl-inositol 3-kinase: a key enzyme in diverse signalling processes." Trends Cell BioL 2:358-60 (1992).
Pietersz et al, "Antibody conjugates for the treatment of cancer." Immunol. Rev., 129:57-80 (1992).
Trail et al., "Cure of xenografted human carcinomas by BR96-doxorubicin immunoconjugates." Science, 261:212 (1993).
Rowlinson-Busza et al, "Targeted delivery of biologic and other antineoplastic agents." Curr. Opin. Oncol, 4:1142 (1992).
Nicolaou et al. "Calicheamicin θ: A Rationally Designed Molecule with Extremely Potent and Selective DNA Cleaving Properties and Apoptosis Inducing Activity" Angew. Chem. Intl Ed. Engl, 33:183-186 (1994).
Ferrara N. and Alitalo, K. "Clinical application of angiogenic growth factors and their inhibitors," (1999) Nature Medicine 5:1359-1364.
Cheson, Rd., Leonard, J.P., "Monoclonal Antibody Therapy for B-Cell Non-Hodgkin's Lymphoma" The New England Journal of Medicine 2008, 359(6), p. 613-626.
Wierda, W.G., "Current and Investigational Therapies for Patients with CLL" Hematology 2006, p. 285-294.
Morton, LM., et al. "Lymphoma Incidence Patterns by WHO Subtype in the United States, 1992-2001" Blood 2006, 107(1), p. 265-276.
Wuts, P.G.M and Greene, T.W. (2006). Greene's Protective Groups in Organic Synthesis, 4th Edition, Wiley. Table of Contents.
Stahl, P. H. and Wermuth, C. G. (2011) Pharmaceutical Salts: Properties, Selection, and Use (International Union of Pure and Applied Chemistry), Wiley-VCH; 2nd revise Edition. Table of Contents.
Berge, S.M. et al. (1977). "Pharmaceutical Salts," J. Pharma Sci. 66(1): 1-19.
Hendrickson. (2005). Remington: The Science and Practice of Pharmacy, 21st edition, Lippincott, Williams & Wilkins, Philadelphia, PA. p. 732, Table 38-5.
Final Office Action mailed on Feb. 26, 2016, for U.S. Appl. No. 14/092,287, filed Nov. 27, 2013, 6 pages.
First Examination Report mailed Jun. 4, 2015, for New Zealand Patent Application No. 695440, Internationally filed on Mar. 5, 2013, 2 pages.

(56) References Cited

OTHER PUBLICATIONS

First Office Action mailed Jul. 2, 2015, for Chinese Patent Application No. 201380011784.1, Internationally filed on May 3, 2015, 12 pages.
First Office Action mailed Sep. 17, 2015, for Eurasian Patent Application No. 201491473/28, filed on Mar. 5, 2013, 2 pages, 2 pages English translation, (4 pages total).
Foster, A.B. (1984). "Deuterium isotope effects in studies of drug metabolism," *Trends Pharmacol Sci* 5(12):524-527.
Hatsu, I.S. (May 1, 2001) No. 568, 45 pages, English translation 1 page, 46 pages total.
Office Action dated Jan. 27, 2015, for Vietnam Patent Application No. 1-2014-02846, Internationally filed on Mar. 5, 2013, 1 page.
Office Action dated Aug. 12, 2015, for Pakistan Patent Application No. 1312013, Internationally filed on Mar. 5, 2013, 2 pages.
Office Action mailed Nov. 26, 2015, for Eurasian Patent Application No. 201491473/28, Internationally filed on Mar. 5, 2013, 1 page.
Office Action mailed Mar. 9, 2016, for Chinese Patent Application No. 201380011784.1, Internationally filed on Mar. 5, 2013, 12 pages.
Office Action mailed Apr. 12, 2016, for Japanese Patent Application No. 2014-561048, Internationally filed on Mar. 5, 2013, 7 pages.
Oshima, H. (2007) "Crystallization of Polymorphs and Pseudo-Polymorphs and Its Control," *Pharm Stage* 6(10)48-53, English translation of the introduction with certification.
Notice Prior to Examination mailed on Sep. 7, 2015, for Israeli Patent Application No. 237644, Internationally filed on Mar. 5, 2013, 3 pages.
Supplementary European Search Report dated Oct. 27, 2015, for European Patent Application No. 13757230.1, Internationally filed on Mar. 5, 2013, 1 page.
Takata, N. (2007) "API Form Screening and Selection in Drug Discovery Stage," *Pharm Stage* 6(10)20-25, English translation of the introduction with certification.
Wierda, W.G., (2006) "Current and Investigational Therapies for Patients with CLL" *Hematology* pp. 285-294.
Written Opinion dated May 27, 2015, for Singapore Patent Application No. 11201405446P, internationally filed on Mar. 5, 2013, 6 pages.
Written Opinion dated Aug. 12, 2015, for Singapore Patent Application No. 11201405446P, internationally filed on Mar. 5, 2013, 5 pages.
Yamano, M. (2007) "Approach to Crystal Polymorph in Process Research of New Drug," *Journal of the Society of Synthetic Organic Chemistry* 65(9)907-944, English translation of the introduction with certification.
Communication pursuant to Rules 161(1) and 162 EPC issued on Sep. 2, 2016, for European Patent Application No. 14827951.6, internationally filed on Dec. 18, 2014. 2 pages.
Final Office Action mailed Dec. 18, 2015, for Colombian Patent Application No. 14-202.424, Internationally filed on Mar. 5, 2013, 11 pages (23 pages with translation).
Final Office Action mailed Dec. 18, 2015, for Colombian Patent Application No. 15-129862, Internationally filed on Mar. 5, 2013, 11 pages (24 pages with translation).
International Preliminary Report on Patentability mailed on Jun. 21, 2016 for PCT/US2014/071297, filed on Dec. 18, 2014, 7 pages.
International Preliminary Report on Patentability for PCT/US2014/071286, issued on Jun. 21, 2016, internationally filed on Dec. 18, 2014, 5 pages.
International Search Report mailed on Mar. 20, 2015, for PCT/US2014/071286, internationally filed on Dec. 18, 2014, 4 pages.
International Search Report mailed on Feb. 13, 2015 for PCT Application No. PCT/US2014/071297, filed on Dec. 18, 2014, 4 pages.
Kalusa, A. et al. (Oct. 6, 2008, e-published on Jul. 22, 2008). "An Efficient Synthesis of 2,3-Diaryl (3H)-Quinazolin-4-Ones Via Imidoyl Chlorides," *Tetrahedron Letters* 49(41):5840-5842.
Notice of Acceptance mailed on Oct. 7, 2016, for New Zealand Patent Application No. 629684, internationally filed on Mar. 5, 2013, 1 page.
Notice of Allowance mailed on Sep. 28, 2016, for U.S. Appl. No. 14/575,670, filed Dec. 18, 2014, 7 pages.
Office Action mailed Jul. 14, 2015, for Colombian Patent Application No. 14-202 424, Internationally filed on Mar. 5, 2015, 10 pp. (22 pages with translation).
Office Action mailed Jul. 14, 2015, for Colombia Patent Application No. 15-129-862, filed on Jun. 5, 2015, 9 pages, (23 pages with translation).
Saleh, R.M. et al. (1994). "Synthesis and Reactions of 2-(α-Phenylimido-β-O-Chlorophenyl)Vinyl-4(H)-3,1-Benzoxazin-4-One," *Revue Roumaine De Chimie*, 39(5):567-576.
Soliman, F.M.A. et al. (1992). "Synthesis and Reactions of Substituted Benzoxazinones Bearing a Bulky Group at Position 2," *Revue Roumaine De Chimie*, 37(10):1153-1158.
Vanparia, S.F. et al. (Feb. 12, 2013). "Synthesis and in Vitro Antimicrobial Activity of Some Newer Quinazoline-Sulfonamide Linked Hybrid Heterocyclic Entities Derived from Glycine," *Med. Chem. Res.* 22(12):5184-5196.
Watanabe, T. et al. (Jan. 1, 2009, e-published on Nov. 17, 2008). "Alantrypinone and its Derivatives: Synthesis and Antagonist Activity Toward Insect GABA Receptors," *Bioorganic & Medicinal Chemistry*, 17(1):94-110.
Written Opinion mailed on Feb. 13, 2015, for PCT/US2014/071297, filed on Dec. 18, 2014. 6 pages.
Written Opinion mailed on Mar. 20, 2015, for PCT/US2014/071286, filed on Dec. 18, 2014, 4 pages.
Australian Examination Report mailed on Nov. 29, 2016, for Australian Patent No. 2014364414 filed on Jun. 10, 2016, 5 pages.

\* cited by examiner

POLYMORPHIC FORMS OF A HYDROCHLORIDE SALT OF (S)-2-(1-(9H-PURIN-6-YLAMINO)PROPYL)-5-FLUORO-3-PHENYLQUINAZOLIN-4(3H)-ONE

CROSS REFERENCE TO RELATED APPLICATION

This application claims the benefit of and priority to U.S. Provisional Application Ser. No. 61/919,558, filed Dec. 20, 2013, the disclosure of which is hereby incorporated by reference in its entirety.

FIELD

Provided are polymorphs of a hydrochloride salt of (S)-2-(1-(9H-purin-6-ylamino)propyl)-5-fluoro-3-phenylquinazolin-4(3H)-one, compositions thereof, methods for their preparation, and methods for their use. Also provided are solvate forms of a hydrochloride salt of (S)-2-(1-(9H-purin-6-ylamino)propyl)-5-fluoro-3-phenylquinazolin-4(3H)-one, compositions thereof; methods for their preparation, and methods for their use.

BACKGROUND

Cell signaling via 3'-phosphorylated phosphoinositides has been implicated in a variety of cellular processes, e.g., malignant transformation, growth factor signaling, inflammation, and immunity. See Rameh et al., J. Biol. Chem., 274:8347-8350 (1999) for a review. The enzyme responsible for generating these phosphorylated signaling products is phosphatidylinositol 3-kinase (PI 3-kinase; PI3K). PI3K originally was identified as an activity associated with viral oncoproteins and growth factor receptor tyrosine kinases that phosphorylates phosphatidylinositol (PI) and its phosphorylated derivatives at the 3'-hydroxyl of the inositol ring. See Panayotou et al., Trends Cell Biol. 2:358-60 (1992).

Studies suggest that PI3K is involved in a range of cellular responses including cell growth, differentiation, and apoptosis. See Parker et al., Curr. Biol., 5:577-99 (1995); Yao et al., Science, 267:2003-05 (1995). PI3K also appears to be involved in a number of aspects of leukocyte activation. See e.g., Pages et al., Nature, 369:327-29 (1994); Rudd, Immunity, 4:527-34 (1996); Fraser et al., Science, 251:313-16 (1991).

Several compounds have been identified as PI3K inhibitors. For example, compounds capable of inhibiting the biological activity of human PI3K, including (S)-2-(1-(9H-purin-6-ylamino)propyl)-5-fluoro-3-phenylquinazolin-4(3H)-one, and their uses are disclosed in U.S. Pat. No. 6,518,277, U.S. Pat. No. 6,667,300, and U.S. Pat. No. 7,932,260. Each of these references is hereby incorporated herein by reference in its entirety. In July 2014, ZYDELIG® (idelalisib), a first-in-class inhibitor of PI3K delta, was approved by the U.S. Food and Drug Administration for the treatment of three B-cell blood cancers. ZYDELIG® has also been approved by the European Commission for two blood cancers, chronic lymphocytic leukemia (CLL) and follicular lymphoma (FL).

BRIEF SUMMARY

The present application provides a hydrochloride salt of (S)-2-(1-(9H-purin-6-ylamino)propyl)-5-fluoro-3-phenylquinazolin-4(3H)-one. In certain embodiments, the hydrochloride salt of(S)-2-(1-(9H-purin-6-ylamino)propyl)-5-fluoro-3-phenylquinazolin-4(3H)-one is substantially crystalline. In certain embodiments, the hydrochloride salt of (S)-2-(1-(9H-purin-6-ylamino)propyl)-5-fluoro-3-phenylquinazolin-4(3H)-one is crystalline. In certain embodiments, solvates of the hydrochloride salt of (S)-2-(1-(9H-purin-6-ylamino)propyl)-5-fluoro-3-phenylquinazolin-4(3H)-one are provided.

In one aspect, provided herein are polymorphs of a hydrochloride salt of (S)-2-(1-(9H-purin-6-ylamino)propyl)-5-fluoro-3-phenylquinazolin-4(3H)-one, and this compound has the following structure:

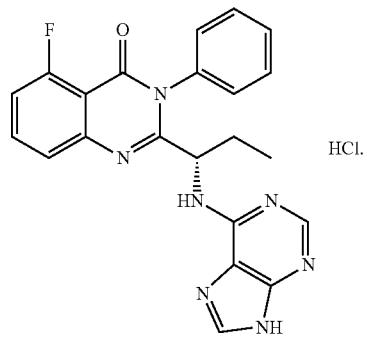 [SMILES: CC[C@H](Nc1ncnc2[nH]cnc12)c1nc2cccc(F)c2c(=O)n1-c1ccccc1]

One or more of polymorphic Forms I, II, III, IV, V, VI, VII, VIII, IX, X, XI, XII and XIII of a hydrochloride salt of (S)-2-(1-(9H-purin-6-ylamino)propyl)-5-fluoro-3-phenylquinazolin-4(3H)-one are provided. In certain embodiments of the polymorphs provided herein, the hydrochloride salt of (S)-2-(1-(9H-purin-6-ylamino)propyl)-5-fluoro-3-phenylquinazolin-4(3H)-one is a monohydrochloride salt.

These polymorphs can be characterized by a variety of solid state analytical data, including for example X-ray powder diffraction pattern (XRPD), differential scanning calorimetry (DSC), thermographic analysis (TGA), and Single Crystal X-Ray Crystallography. One of skill in the art would recognize various techniques or methods that may be used to generate such characterization data. Unless otherwise stated, the XRPD patterns provided herein are generated by a powder X-ray diffractometer at room temperature. In certain instances, an XRPD pattern may also be calculated from the single crystal data acquired at 100K for that polymorphic form.

In another aspect, provided are compositions or pharmaceutical compositions comprising one or more polymorphic forms of a hydrochloride salt of (S)-2-(1-(9H-purin-6-ylamino)propyl)-5-fluoro-3-phenylquinazolin-4(3H)-one (including any one or more of polymorphic Forms I, II, III, IV, V, VI, VII, VIII, IX, X, XI, XII and XIII) and one or more pharmaceutically acceptable carriers or excipients. Provided are also articles of manufacture and unit dosage forms comprising any one or more of the polymorphic forms of a hydrochloride salt of (S)-2-(1-(9H-purin-6-ylamino)propyl)-5-fluoro-3-phenylquinazolin-4(3H)-one (e.g., any one or more of polymorphic Forms I, II, III, IV, V, VI, VII, VIII, IX, X, XI, XII and XIII). Provided are also kits comprising any one or more of the polymorphic forms (e.g., any one or more of polymorphic Forms I, II, III, IV, V, VI, VII, VIII, IX, X, XI, XII and XIII of a hydrochloride salt of (S)-2-(1-(9H-purin-6-ylamino)propyl)-5-fluoro-3-phenylquinazolin-4(3H)-one), and instructions for use (e.g., instructions for use in PI3K-mediated disorder, such as cancer). In one embodiment of the pharmaceutical compositions, articles of manufacture, unit dosage forms, and kits, the hydrochloride salt of (S)-2-(1-(9H-purin-6-ylamino)propyl)-5-fluoro-3-phenylquinazolin-4(3H)-one is a monohydrochloride salt.

Methods of using these polymorphic forms are provided. In another aspect, provided is a method of treating a human in need thereof, comprising administering to the human a polymorph of a hydrochloride salt of (S)-2-(1-(9H-purin-6-ylamino)propyl)-5-fluoro-3-phenylquinazolin-4(3H)-one) (e.g., any one or more of polymorphic Forms I, II, III, IV, V, VI, VII, VIII, IX, X, XI, XII and XIII), or a composition (including a pharmaceutical composition) comprising one or more such polymorphs. The human may be in need of a treatment for cancer or an autoimmune disease.

In one variation, provided is a method of treating a PI3K-mediated disorder in a human in need thereof, comprising administering to the human a polymorph of a hydrochloride salt of (S)-2-(1-(9H-purin-6-ylamino)propyl)-5-fluoro-3-phenylquinazolin-4(3H)-one) (e.g., any one or more of polymorphic Forms I, II, III, IV, V, VI, VII, VIII, IX, X, XI, XII and XIII), or a composition (including a pharmaceutical composition) comprising one or more such polymorphs. The PI3K-mediated disorder, in some embodiments, is cancer (e.g., leukemia or lymphoma) or an autoimmune disease.

Also provided is a method for increasing sensitivity of cancer cells to chemotherapy, comprising administering to a human undergoing chemotherapy with a chemotherapeutic agent an amount of a polymorph of a hydrochloride salt of (S)-2-(1-(9H-purin-6-ylamino)propyl)-5-fluoro-3-phenylquinazolin-4(3H)-one) (e.g., any one or more of polymorphic Forms I, II, III, IV, V, VI, VII, VIII, IX, XI, XII and XIII), or a composition (including a pharmaceutical composition) comprising one or more such polymorphs, sufficient to increase the sensitivity of cancer cells to the chemotherapeutic agent.

Also provided is a use of a polymorph of a hydrochloride salt of (S)-2-(1-(9H-purin-6-ylamino)propyl)-5-fluoro-3-phenylquinazolin-4(3H)-one) (e.g., any one or more of polymorphic Forms I, II, III, IV, V, VI, VII, VIII, IX, X, XI, XII and XIII), or a composition (including a pharmaceutical composition) comprising one or more such polymorphs, in the manufacture of a medicament for the treatment of a disease responsive to inhibition of PI3K activity, such as cancer (e.g., leukemia or lymphoma) or an autoimmune disease.

In one embodiment of the methods of using, and the use of the polymorphic forms described herein, the hydrochloride salt of (S)-2-(1-(9H-purin-6-ylamino)propyl)-5-fluoro-3-phenylquinazolin-4(3H)-one is a monohydrochloride salt.

Methods of making these polymorphic forms are provided. In yet other aspects, provided are methods of producing a composition comprising one or more polymorphs of a hydrochloride salt of (S)-2-(1-(9H-purin-6-ylamino)propyl)-5-fluoro-3-phenylquinazolin-4(3H)-one) (e.g., any one or more of polymorphic Forms I, II, III, IV, V, VI, VII, VIII, IX, X, XI, XII and XIII). The methods comprise combining a hydrochloride salt of (S)-2-(1-(9H-purin-6-ylamino)propyl)-5-fluoro-3-phenylquinazolin-4(3H)-one) with a suitable solvent or a suitable mixture of solvents. In one embodiment, the hydrochloride salt of (S)-2-(1-(9H-purin-6-ylamino)propyl)-5-fluoro-3-phenylquinazolin-4(3H)-one is a monohydrochloride salt. The solvent(S) may be selected from the group consisting of methanol, ethanol, water, isopropyl acetate, ethyl acetate, methyl tert-butyl ether, n-heptane, acetonitrile, acetone, 2-methyltetrahydrofuran, tetrahydrofuran, methyl isobutyl ketone, methyl ethyl ketone, dichloromethane, 2-propanol, 1-propanol, 1-butanol, and any mixtures thereof. Also provided are polymorphic products obtained by the processes (e.g. methods of making) detailed herein.

In some embodiments, a solvate of a hydrochloride salt of a compound of Formula (I) is provided:

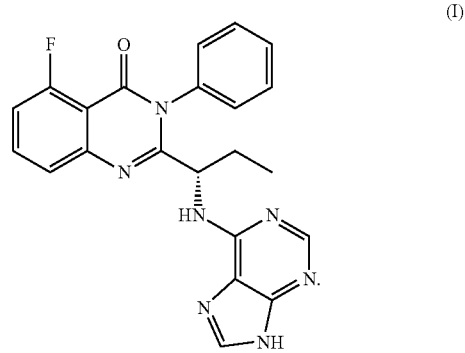 [SMILES: CC[C@H](Nc1ncnc2[nH]cnc12)c1nc2cccc(F)c2c(=O)n1-c1ccccc1]

(I)

In some embodiments, the solvate is selected from the group consisting of ethyl acetate, propyl acetate, 1-methyl-1-propanol, isopropyl acetate, 1,2-dimethyoxyethane, 1,4-dioxane, acetone, acetone:water, acetonitrile, chloroform, dichloromethane, diethyl ether, ethyl acetate, MEK, MIBK, nitromethane, propyl acetate, tetrahydrofuran, toluene, 1-propanol, 2-propanol, IPA:water (5%), and 2-methyl-1-propanol. In some embodiments, the solvate is selected from the group consisting of propyl acetate, isopropyl acetate, 1,2-dimethyoxyethane, isopropyl alcohol, 2-methyl-1-propanol, 1,4-dioxane, and toluene.

In some embodiments, the polymorph is selected from the group consisting of Pattern 1, Pattern 2, Pattern 3, Pattern 4, 2-Methyl-1-propanol solvate, 1,4-Dioxane solvate, and Toluene solvate; and wherein:
Pattern 1 has an X-ray diffraction pattern comprising degree 2θ-reflections (±0.2 degrees 2θ) at 9.2, 23.4, 16.8, 18.5, and 25.8;
Pattern 2 has an X-ray diffraction pattern comprising degree 2θ-reflections (±0.2 degrees 2θ) at 7.8, 23.4, 9.2, 25.8, and 16.7;
Pattern 3 has an X-ray diffraction pattern comprising degree 2θ-reflections (±0.2 degrees 2θ) at 9.8, 21.5, 24.0, 11.7, and 19.7;
Pattern 4 has an X-ray diffraction pattern comprising degree 2θ-reflections (±0.2 degrees 2θ) at 12.3, 24.9, 16.8, 25.3, and 20.2;
2-Methyl-1-propanol solvate has an X-ray diffraction pattern comprising degree 2θ-reflections (±0.2 degrees 2θ) at 8.6, 26.0, 17.3, 20.7, and 24.5;
1,4-Dioxane solvate has an X-ray diffraction pattern comprising degree 2θ-reflections (±0.2 degrees 2θ) at 23.2, 18.8, 11.5, 19.4, and 21.1; and
Toluene solvate has an X-ray diffraction pattern comprising degree 2θ-reflections (±0.2 degrees 2θ) at 25.5, 8.4, 23.3, 23.1, and 24.0.

DESCRIPTION OF THE FIGURES

The present disclosure can be best understood by references to the following description taken in conjunction with the accompanying figures.

DETAILED DESCRIPTION

Figure 1A:
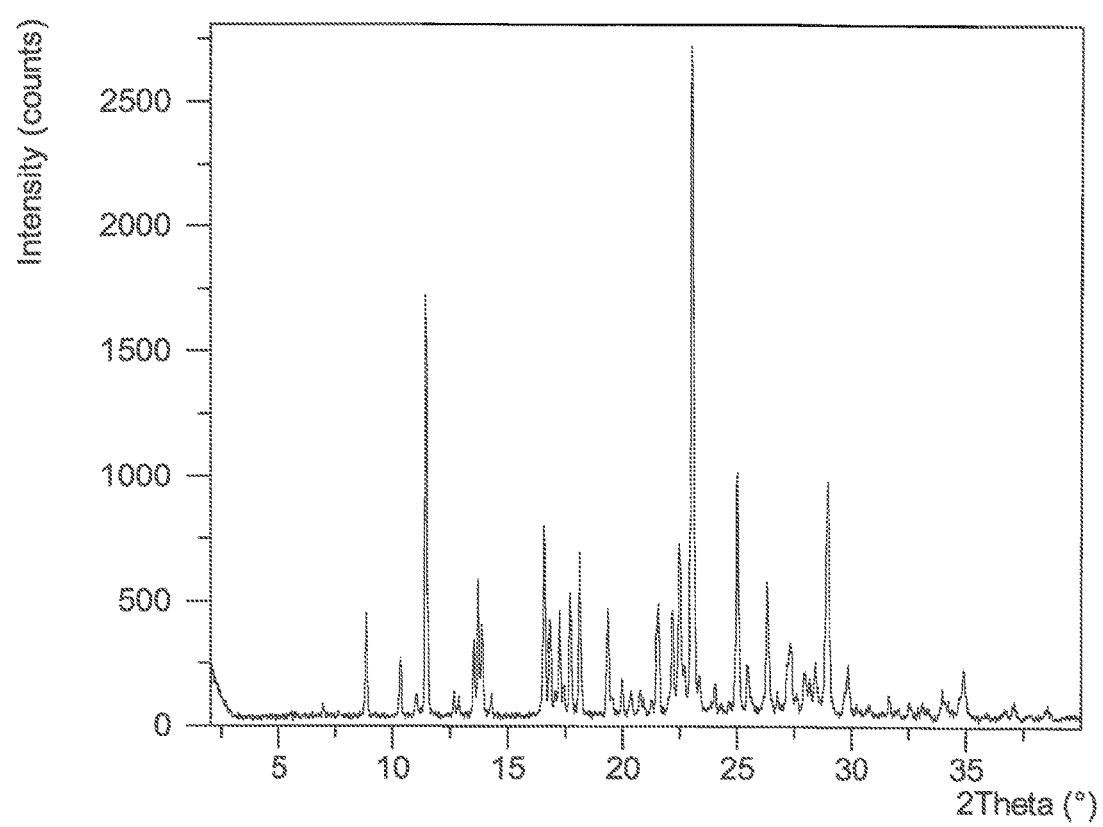
FIGS. 1A-1E show an X-ray powder diffraction pattern (XRPD) pattern, a differential scanning calorimetry (DSC) graph, a thermographic analysis (TGA) graph, and two dynamic vapour sorption (DVS) graphs, respectively, of polymorphic Form I of a hydrochloride salt of (S)-2-(1-(9H-purin-6-ylamino)propyl)-5-fluoro-3-phenylquinazolin-4(3H)-one.

The following description is presented to enable a person of ordinary skill in the art to make and use the various embodiments. Descriptions of specific compounds, methods, techniques, and applications are provided only as examples. Various modifications to the examples described herein will be readily apparent to those of ordinary skill in the art, and the general principles described herein may be applied to other examples and applications without departing from the spirit and scope of the various embodiments. Thus, the various embodiments are not intended to be limited to the examples described herein and shown, but are to be accorded the scope consistent with the claims.

Terms used in the singular will also include the plural and vice versa. The use of the term "about" includes and describes the value or parameter per se. For example, "about x" includes and describes "x" per se. In some embodiments, the term "about" when used in association with a measurement, or used to modify a value, a unit, a constant, or a range of values, refers to variations of +/−5%.

Polymorphs of a Hydrochloride Salt of (S)-2-(1-(9H-purin-6-ylamino)propyl)-5-fluoro-3-phenylquinazolin-4(3H)-one A form of a hydrochloride salt of (S)-2-(1-(9H-purin-6-ylamino)propyl)-5-fluoro-3-phenylquinazolin-4(3H)-one may be present as an intermediate to the hydrochloride salt of (S)-2-(1-(9H-purin-6-ylamino)propyl)-5-fluoro-3-phenylquinazolin-4(3H)-one, where a different polymorphic form or polymorphs may be beneficial for certain purposes, such as medical or pharmaceutical uses.

It is desirable to develop a crystalline form of (S)-2-(1-(9H-purin-6-ylamino)propyl)-5-fluoro-3-phenylquinazolin-4(3H)-one, or a pharmaceutically acceptable salt thereof that is useful in the synthesis of (S)-2-(1-(9H-purin-6-ylamino)propyl)-5-fluoro-3-phenylquinazolin-4(3H)-one. A form of a hydrochloride salt of (S)-2-(1-(9H-purin-6-ylamino)propyl)-5-fluoro-3-phenylquinazolin-4(3H)-one may be an intermediate to the hydrochloride salt of (S)-2-(1-(9H-purin-6-ylamino)propyl)-5-fluoro-3-phenylquinazolin-4(3H)-one. A polymorphic form or polymorph has properties such as bioavailability and stability at certain conditions that are suitable for medical or pharmaceutical uses. By way of example, a crystalline form of a hydrochloride salt of (S)-2-(1-(9H-purin-6-ylamino)propyl)-5-fluoro-3-phenylquinazolin-4(3H)-one is an intermediate to an active agent or ingredient in a pharmaceutical composition.

A crystalline form of (S)-2-(1-(9H-purin-6-ylamino)propyl)-5-fluoro-3-phenylquinazolin-4(3H)-one, or a pharmaceutically acceptable salt thereof, may provide the advantage of bioavailability and stability, suitable for use as an active ingredient in a pharmaceutical composition. Variations in the crystal structure of a pharmaceutical drug substance or active ingredient may affect the dissolution rate (which may affect bioavailability, etc.), manufacturability (e.g., ease of handling, ability to consistently prepare doses of known strength) and stability (e.g., thermal stability, shelf life, etc.) of a pharmaceutical drug product or active ingredient. Such variations may affect the preparation or formulation of pharmaceutical compositions in different dosage or delivery forms, such as solid oral dosage form including tablets and capsules. Compared to other forms such as non-crystalline or amorphous forms, crystalline forms may provide desired or suitable hygroscopicity, particle size controls, dissolution rate, solubility, purity, physical and chemical stability, manufacturability, yield, and/or process control. Thus, crystalline forms of (S)-2-(1-(9H-purin-6-ylamino)propyl)-5-fluoro-3-phenylquinazolin-4(3H)-one, or a pharmaceutically acceptable salt thereof, provides advantage of improving the manufacturing process of an active agent or the stability or storability of a drug product form of the compound or an active ingredient, or having suitable bioavailability and/or stability as an active agent.

The use of certain solvents has been found to produce different polymorphic forms of a hydrochloride salt of (S)-2-(1-(9H-purin-6-ylamino)propyl)-5-fluoro-3-phenylquinazolin-4(3H)-one, including any one or more of polymorphic Forms I to XIII, which may exhibit one or more favorable characteristics described above. The processes for the preparation of the polymorphs described herein, and characterization of these polymorphs are described in greater detail below.

One aspect of the application provides polymorphic forms of a hydrochloride salt of (S)-2-(1-(9H-purin-6-ylamino) propyl)-5-fluoro-3-phenylquinazolin-4(3H)-one, a compound having the molecular structure shown below:

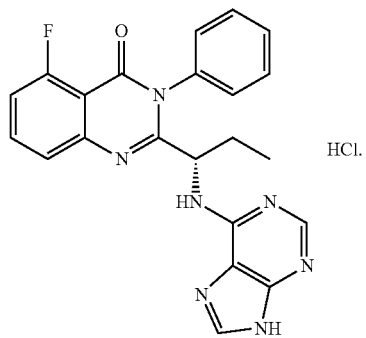 [SMILES: CC[C@H](Nc1ncnc2[nH]cnc12)c1nc2cccc(F)c2c(=O)n1-c1ccccc1]

In certain embodiments, the hydrochloride salt of (S)-2-(1-(9H-purin-6-ylamino)propyl)-5-fluoro-3-phenylquinazolin-4(3H)-one is a monohydrochloride salt of (S)-2-(1-(9H-purin-6-ylamino)propyl)-5-fluoro-3-phenylquinazolin-4 (3H)-one. In certain embodiments, one or more of the polymorphic forms provided may be a channel solvate. The crystal lattice of such polymorphic forms may contain tunnels that penetrate the lattice, and the tunnels can be occupied by one or more molecules (e.g., solvent molecules) and ions (e.g., chloride ions).

The compound name provided above is named using ChemBioDraw Ultra and one skilled in the art understands that the compound structure may be named or identified using other commonly recognized nomenclature systems and symbols. By way of example, the compound may be named or identified with common names, systematic or non-systematic names. The nomenclature systems and symbols that are commonly recognized in the art of chemistry including but not limited to Chemical Abstract Service (CAS) and International Union of Pure and Applied Chemistry (IUPAC). Accordingly, the compound structure provided above may also be named or identified as 5-fluoro-3-phenyl-2-[(1S)-1-(9H-purin-6-ylamino)propyl] quinazolin-4(3H)-one under IUPAC and 5-fluoro-3-phenyl-2-[(1S)-1-(9H-purin-6-ylamino) propyl]-4(3H)-quinazolinone under CAS.

Form I

Figure 1B:
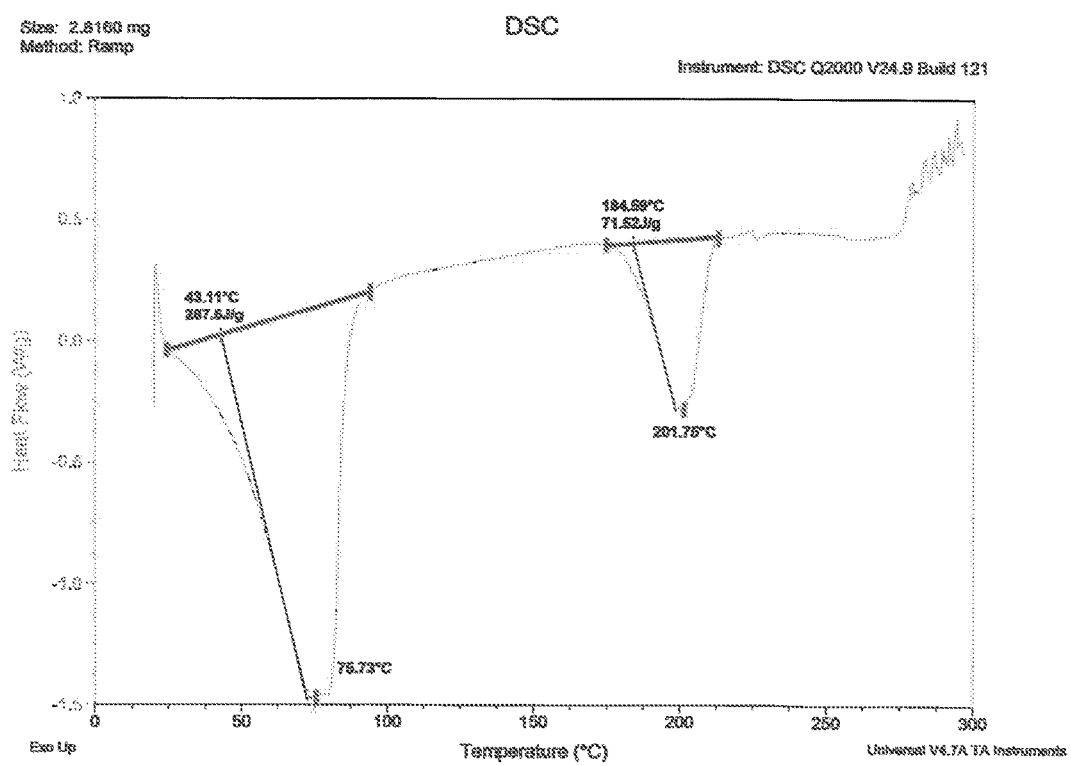
Figure 1C:
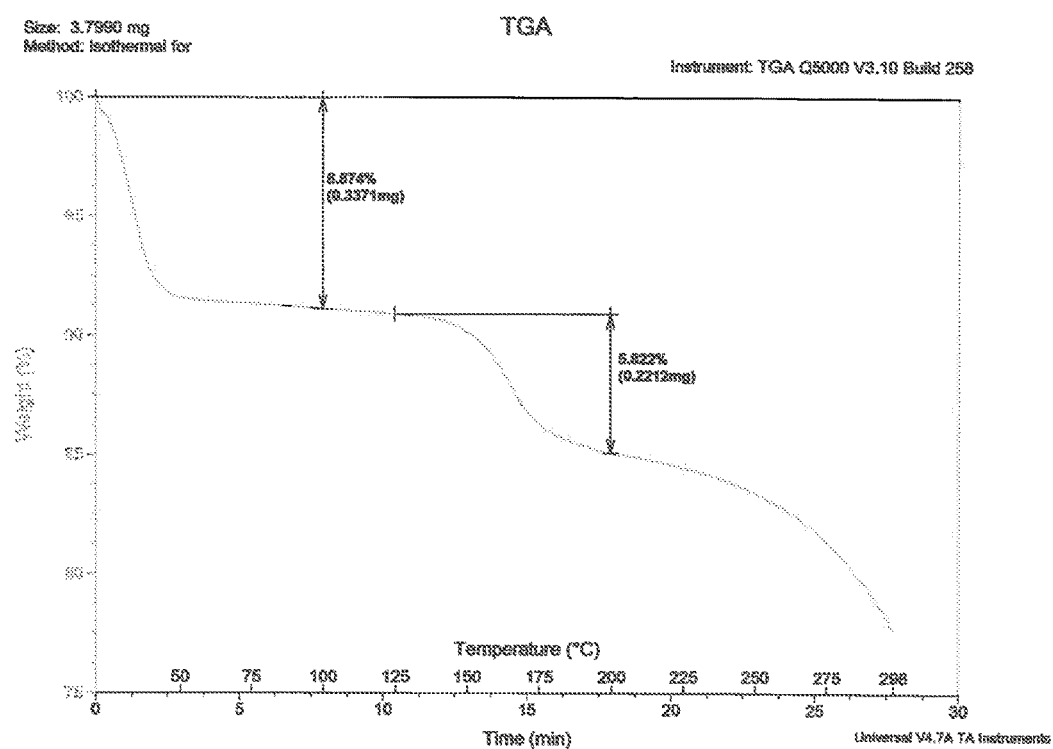
Figure 1D:
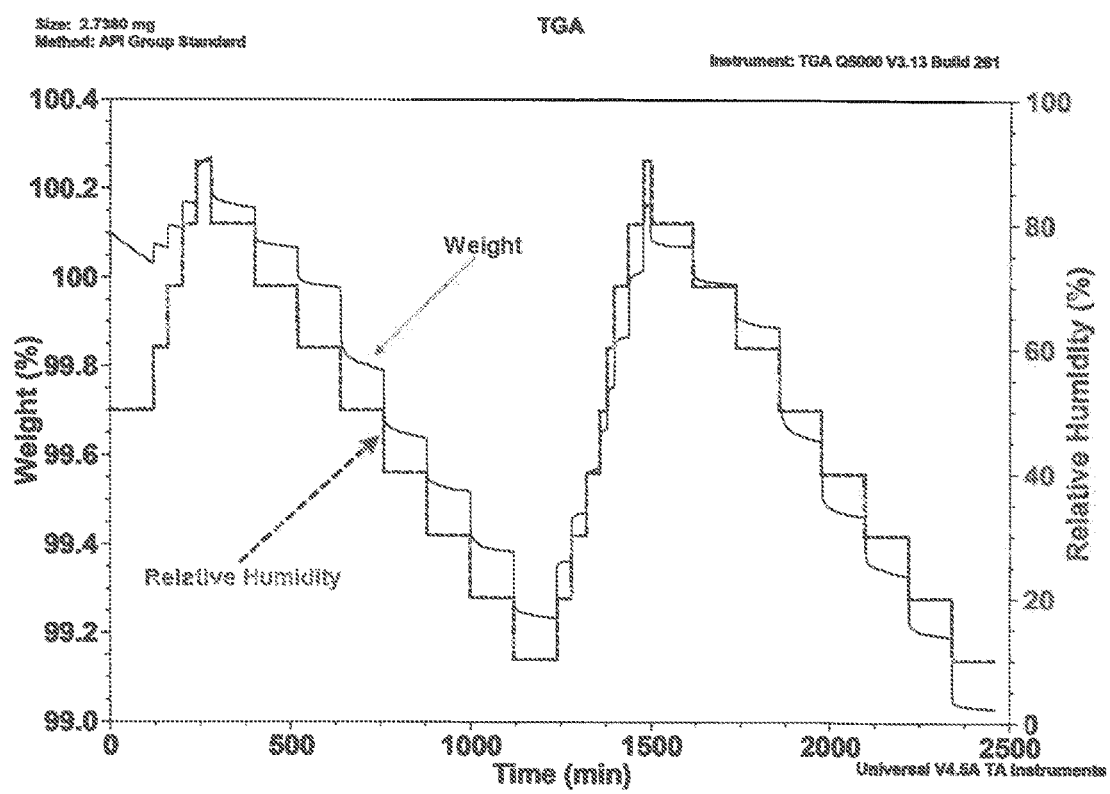
Figure 1E:
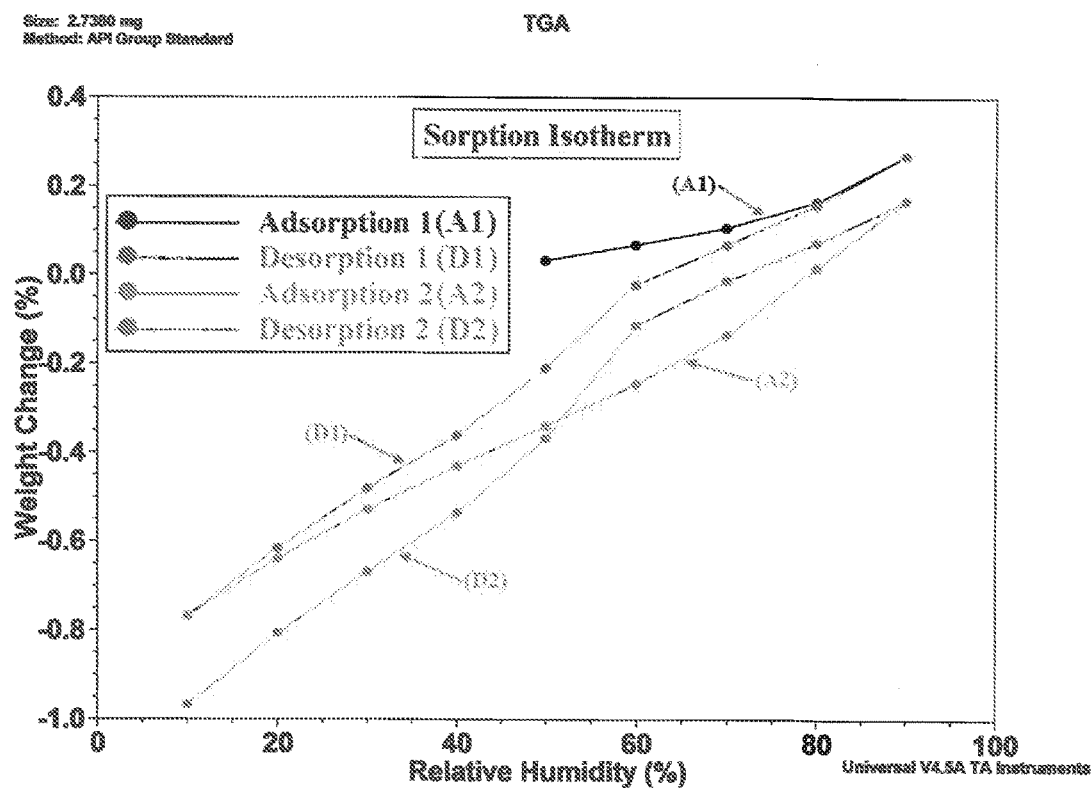

In one aspect, provided is polymorphic Form I of a hydrochloride salt of (S)-2-(1-(9H-purin-6-ylamino)propyl)-5-fluoro-3-phenylquinazolin-4(3H)-one, wherein the polymorph exhibits an X-ray powder diffraction (XRPD) pattern substantially as shown in FIG. 1A. Polymorphic Form I may exhibit a differential scanning calorimetry (DSC) thermogram substantially as shown in FIG. 1B. Polymorphic Form I may exhibit a thermographic analysis (TGA) graph substantially as shown in FIG. 1C. Polymorphic Form I may exhibit dynamic vapour sorption (DVS) graphs substantially as shown in FIGS. 1D and 1E.

The term "substantially as shown in" when referring, for example, to an XRPD pattern, a DSC thermogram, or a TGA graph includes a pattern, thermogram or graph that is not necessarily identical to those depicted herein, but that falls within the limits of experimental error or deviations when considered by one of ordinary skill in the art.

Polymorphic Form I may have a unit cell as determined by crystal X-ray crystallography of the following dimensions: a=31.102 (15) Å; b=9.166 (5) Å; c=19.738 (10) Å; α=90°; β=125.948 (17)°; and γ=90°.

In some embodiments of polymorphic Form I, at least one, at least two, at least three, at least four, at least five, at least six, at least seven, at least eight, at least nine, at least ten, or all of the following (a)-(k) apply: (a) polymorphic Form I has an XRPD pattern substantially as shown in FIG. 1A; (b) polymorphic Form I has a DSC thermogram substantially as shown in FIG. 1B; (c) polymorphic Form I has a TGA graph substantially as shown in FIG. IC; (d) polymorphic Form I has DVS graphs substantially as shown in FIGS. 1D and 1E; (e) polymorphic Form I has a unit cell, as determined by crystal X-ray crystallography, of the following dimensions: a=31.102 (15) Å; b=9.166 (5) Å; c=19.738 (10) Å; α=90°; β=125.948 (17)°; and γ=90°; (f) polymorphic Form I has a melting temperature onset as determined by DSC at about 202° C.; (g) polymorphic Form I has a monoclinic crystal system; (h) polymorphic Form I has a C2 space group; (i) polymorphic Form I has a volume of 4555 (4) Å$^3$; (j) polymorphic Form I has a Z value of 8; and (k) polymorphic Form I has a density of 1.356 g/cm$^3$.

In some embodiments, polymorphic Form I has at least one, at least two, at least three, or all of the following properties:
  (a) an XRPD pattern substantially as shown in FIG. 1A;
  (b) a DSC thermogram substantially as shown in FIG. 1B;
  (c) DVS graphs substantially as shown in FIGS. 1D and/or 1E; and (d) a unit cell, as determined by crystal X-ray crystallography, of the following dimensions: a=31.102 (15) Å; b=9.166 (5) Å; c=19.738 (10) Å; α=90°; β=125.948 (17)°; and γ=90°.

In some embodiments, polymorphic Form I has an XRPD pattern displaying at least two, at least three, at least four, at least five, or at least six of the degree 2θ-reflections with the greatest intensity as the XRPD pattern substantially as shown in FIG. 1A. It should be understood that relative intensities can vary depending on a number of factors, including sample preparation, mounting, and the instrument and analytical procedure and settings used to obtain the spectrum. As such, the peak assignments listed herein, including for polymorphic Form I, are intended to encompass variations of +/−0.2 degrees 2θ.

In certain embodiments, polymorphic Form I has an XRPD pattern comprising degree 2θ-reflections (+/−0.2 degrees 2θ) at 11.6, 16.6, 18.2, 23.2 and 25.1. In one embodiment, polymorphic Form I has an XRPD pattern comprising degree 2θ-reflections (+/−0.2 degrees 2θ) at 11.6, 16.6, 18.2, 23.2 and 25.1 and one or more of the degree 2θ-reflections (+/−0.2 degrees 2θ) at 8.9, 13.8, 19.4, and 22.5. In one embodiment, polymorphic Form I has an XRPD pattern comprising degree 2θ-reflections (+/−0.2 degrees 2θ) at 11.6, 16.6, 18.2, 23.2 and 25.1 and one of the degree 2θ-reflections (+/−0.2 degrees 2θ) at 8.9, 13.8, 19.4, and 22.5. In one embodiment, polymorphic Form I has an XRPD pattern comprising degree 2θ-reflections (+/−0.2 degrees 2θ) at 11.6, 16.6, 18.2, 23.2 and 25.1 and two of the degree 2θ-reflections (+/−0.2 degrees 2θ) at 8.9, 13.8, 19.4, and 22.5. In one embodiment, polymorphic Form I has an XRPD pattern comprising degree 2θ-reflections (+/−0.2 degrees 2θ) at 11.6, 16.6, 18.2, 23.2 and 25.1 and three of the degree 2θ-reflections (+/−0.2 degrees 2θ) at 8.9, 13.8, 19.4, and 22.5. In one embodiment, polymorphic Form I has an XRPD pattern comprising degree 2θ-reflections (+/−0.2 degrees 2θ) at 8.9, 11.6, 13.8, 16.6, 18.2, 19.4, 22.5, 23.2 and 25.1.

In certain embodiments, the hydrochloride salt of polymorphic Form I is a monohydrochloride salt of (S)-2-(1-(9H-purin-6-ylamino)propyl)-5-fluoro-3-phenylquinazolin-4(3H)-one. In one embodiment, polymorphic Form I may be a channel solvate. As commonly referred to by a person skilled in the art, the term "channel solvate", or a variant thereof, refers to a crystal lattice containing tunnels that can be occupied by solvent molecules (e.g., channel solvents), and other molecules and ions. Examples of other molecules and ions that may be present in the channels of polymorphic Form I include water, ethanol and/or chloride ions.

Form II

In another aspect, provided is polymorphic Form II of a hydrochloride salt of (S)-2-(1-(9H-purin-6-ylamino)propyl)-5-fluoro-3-phenylquinazolin-4(3H)-one, wherein the polymorph has a unit cell, as determined by Single Crystal X-Ray Crystallography, of the following dimensions: a=13.266 (3) Å; b=13.858 (3) Å; c=31.012 (6) Å; α=90°; β=90°; and γ=90°.

Figure 2:
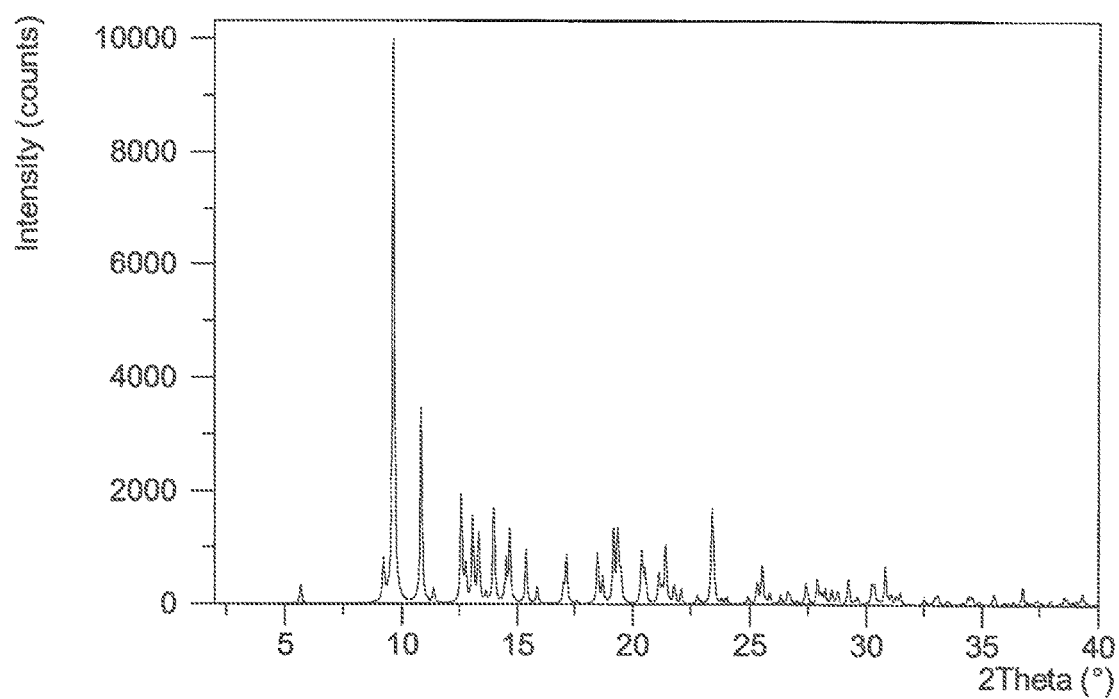
FIG. 2 shows XRPD patterns of polymorphic Form II of a hydrochloride salt of (S)-2-(1-(9H-purin-6-ylamino)propyl)-5-fluoro-3-phenylquinazolin-4(3H)-one.

Polymorphic Form II may have a calculated XRPD pattern substantially as shown in FIG. 2. It should be understood that the XRPD provided in FIG. 2 is a calculated XRPD from the single crystal data acquired at 100K for polymorphic Form II.

In some embodiments of polymorphic Form II, at least one, at least two, at least three, at least four, at least five, at least six, or all of the following (a)-(g) apply: (a) polymorphic Form II has an XRPD pattern, calculated from the single crystal data acquired at 100K for polymorphic Form II, substantially as shown in FIG. 2; (b) polymorphic Form II has a unit cell, as determined by Single Crystal X-Ray Crystallography, of the following dimensions: a=13.266 (3) Å; b=13.858 (3) Å; c=31.012 (6) Å; α=90°; β=90β; and γ=90°; (c) polymorphic Form II has an orthorhombic crystal system; (d) polymorphic Form II has a C222 (1) space group; (e) polymorphic Form II has a volume of 5702 (2) Å³; (f) polymorphic Form II has a Z value of 8; and (g) polymorphic Form I has a density of 1.254 g/cm³.

In some embodiments, polymorphic Form II has at least one, or both of the following properties:
  (a) an XRPD pattern, calculated from the single crystal data acquired at 100K for polymorphic Form II, substantially as shown in FIG. 2; and
  (b) a unit cell, as determined by Single Crystal X-ray Crystallography, of the following dimensions: a=13.266 (3) Å; b=13.858 (3) Å; c=31.012 (6) Å; α=90°; β=90°; and γ=90°.

In some embodiments, polymorphic Form II has an XRPD pattern, calculated from the single crystal data acquired at 100K for polymorphic Form II, displaying at least two, at least three, at least four, at least five, or at least six of the degree 2θ-reflections with the greatest intensity as the XRPD pattern substantially as shown in FIG. 2. It should be understood that relative intensities can vary depending on a number of factors, including sample preparation, mounting, and the instrument and analytical procedure and settings used to obtain the spectrum. As such, the peak assignments disclosed herein, including for polymorphic Form II, are intended to encompass variations of +/−0.2 degrees 2θ.

In certain embodiments, the hydrochloride salt of polymorphic Form II is a monohydrochloride salt of (S)-2-(1-(9H-purin-6-ylamino)propyl)-5-fluoro-3-phenylquinazolin-4(3H)-one.

Form III

In another aspect, provided is polymorphic Form II of a hydrochloride salt of(S)-2-(1-(9H-purin-6-ylamino)propyl)-5-fluoro-3-phenylquinazolin-4(3H)-one, wherein the polymorph has a unit cell, as determined by Single Crystal X-Ray Crystallography, of the following dimensions: a=25.077 (3) Å; b=9.149 (10) Å; c=14.248 (14) Å; α=90°; β=110.967 (3)°; and γ=90°.

Figure 3:
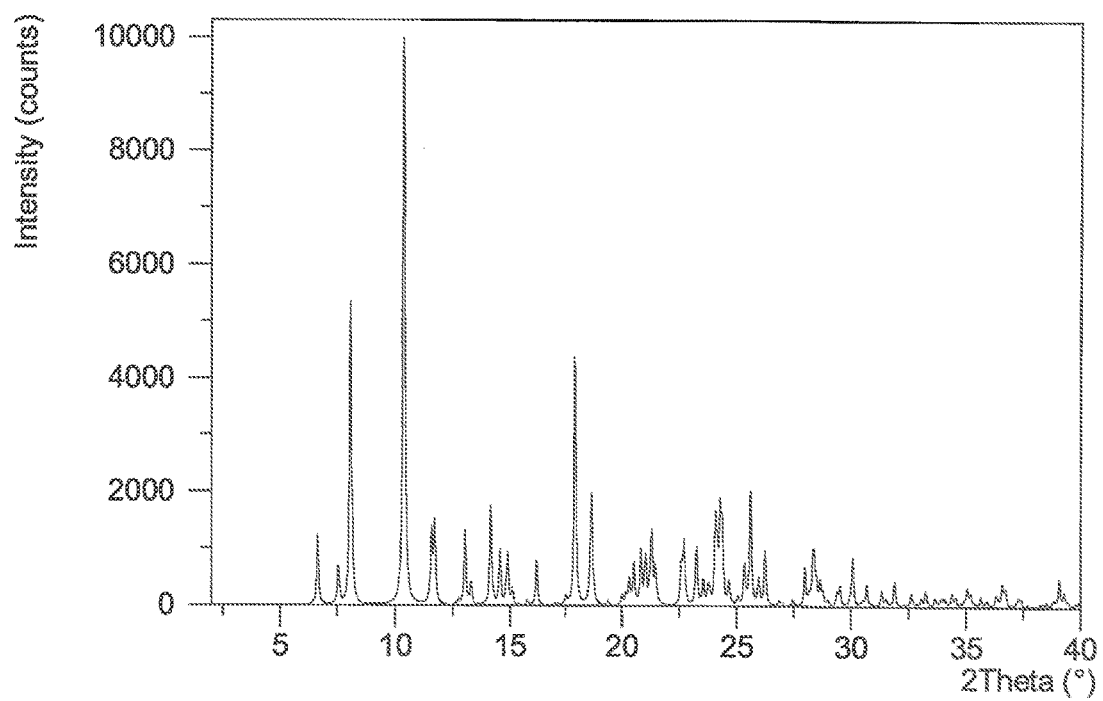
FIG. 3 shows XRPD patterns of polymorphic Form III of a hydrochloride salt of (S)-2-(1-(9H-purin-6-ylamino)propyl)-5-fluoro-3-phenylquinazolin-4(3H)-one.

Polymorphic Form m may have a calculated XRPD pattern substantially as shown in FIG. 3. It should be understood that the XRPD provided in FIG. 3 is a calculated XRPD from the single crystal data acquired at 100K for polymorphic Form II.

In some embodiments of polymorphic Form III, at least one, at least two, at least three, at least four, or all of the following (a)-(e) apply: (a) polymorphic Form II has an XRPD pattern, calculated from the single crystal data acquired at 100K for polymorphic Form III, substantially as shown in FIG. 3; (b) polymorphic Form III has a unit cell, as determined by Single Crystal X-Ray Crystallography, of the following dimensions: a=25.077 (3) Å; b=9.149 (10) Å; c=14.248 (14) Å; α=90°; β=110.967 (3)°; and γ=90°; (c) polymorphic Form III has an monoclinic crystal system; (d) polymorphic Form III has a C2 space group; and (e) polymorphic Form III has a volume of 3052.2 (5) Å³.

In some embodiments, polymorphic Form III has at least one, or both of the following properties:
  (a) an XRPD pattern, calculated from the single crystal data acquired at 100K for polymorphic Form III, substantially as shown in FIG. 3; and
  (b) a unit cell, as determined by Single Crystal X-Ray Crystallography, of the following dimensions: a=25.077 (3) Å; b=9.149 (10) Å; c=14.248 (14) Å; α=90°; β=110.967 (3)°; and γ=90°.

In some embodiments, polymorphic Form III has an XRPD pattern displaying at least two, at least three, at least four, at least five, or at least six of the degree 2θ-reflections with the greatest intensity as the XRPD pattern substantially as shown in FIG. 3. It should be understood that relative intensities can vary depending on a number of factors, including sample preparation, mounting, and the instrument and analytical procedure and settings used to obtain the spectrum. As such, the peak assignments disclosed herein, including for polymorphic Form III, are intended to encompass variations of +/−0.2 degrees 2θ.

In certain embodiments, the hydrochloride salt of polymorphic Form II is a monohydrochloride salt of (S)-2-(1-(9H-purin-6-ylamino)propyl)-5-fluoro-3-phenylquinazolin-4(3H)-one. In one embodiment, polymorphic Form III may have one or more channels. Such channels may be occupied by certain molecules and/or ions, such as water and/or chloride ions.

Form IV

In another aspect, provided is polymorphic Form IV of a hydrochloride salt of (S)-2-(1-(9H-purin-6-ylamino)propyl)-5-fluoro-3-phenylquinazolin-4(3H)-one, wherein the polymorph has a unit cell, as determined by Single Crystal X-Ray Crystallography, of the following dimensions: a=13.469 (6) Å; b=13.842 (6) Å; c=31.754 (14) Å; α=90°; β=90°; and γ=90°.

Figure 4:
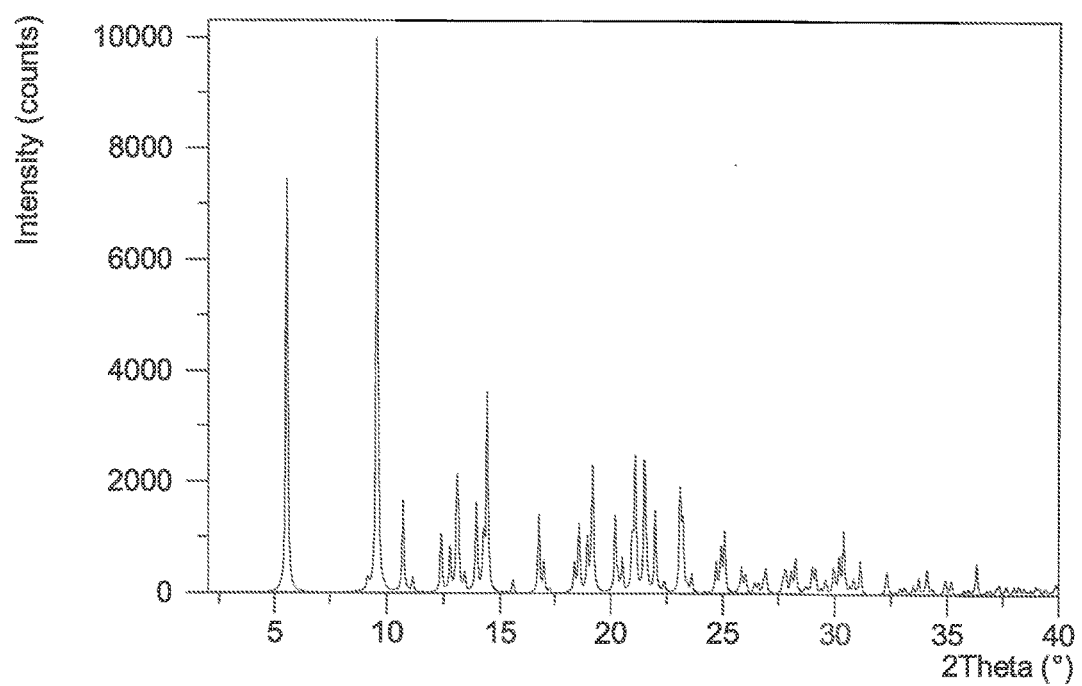
FIG. 4 shows XRPD patterns of polymorphic Form IV of a hydrochloride salt of (S)-2-(1-(9H-purin-6-ylamino)propyl)-5-fluoro-3-phenylquinazolin-4(3H)-one.

Polymorphic Form IV may have a calculated XRPD pattern substantially as shown in FIG. 4. It should be understood that the XRPD provided in FIG. 4 is a calculated XRPD from the single crystal data acquired at 100K for polymorphic Form IV.

In some embodiments of polymorphic Form IV, at least one, at least two, at least three, at least four, at least five, at least six, at least seven, or all of the following (a)-(h) apply: (a) polymorphic Form IV has an XRPD pattern, calculated from the single crystal data acquired at 100K for polymorphic Form IV, substantially as shown in FIG. 4; (b) polymorphic Form IV has a unit cell, as determined by Single Crystal X-Ray Crystallography, of the following dimensions: a=13.469 (6) Å; b=13.842 (6) Å; c=31.754 (14) Å; α=90°; β=90°; and γ=90°; (c) polymorphic Form IV has an orthorhombic crystal system; (d) polymorphic Form IV has a C222 (1) space group; (e) polymorphic Form IV has a volume of 5919.8 (5) Å$^3$; (f) polymorphic Form IV has a Z value of 8; (g) polymorphic Form IV has a density of 1.405 g/cm$^3$; and (h) polymorphic Form IV has an absorption coefficient of 0.184 mm$^{-1}$.

In some embodiments, polymorphic Form IV has at least one, or both of the following properties:
  (a) an XRPD pattern, calculated from the single crystal data acquired at 100K for polymorphic Form IV, substantially as shown in FIG. 4; and
  (b) a unit cell, as determined by Single Crystal X-Ray Crystallography, of the following dimensions: a=13.469 (6) Å; b=13.842 (6) Å; c=31.754 (14) Å; α=90°; β=90°; and γ=90°.

In some embodiments, polymorphic Form IV has an XRPD pattern displaying at least two, at least three, at least four, at least five, or at least six of the degree 2θ-reflections with the greatest intensity as the XRPD pattern substantially as shown in FIG. 4. It should be understood that relative intensities can vary depending on a number of factors, including sample preparation, mounting, and the instrument and analytical procedure and settings used to obtain the spectrum. As such, the peak assignments disclosed herein, including for polymorphic Form IV, are intended to encompass variations of +/−0.2 degrees 2θ.

In certain embodiments, the hydrochloride salt of polymorphic Form IV is a monohydrochloride salt of (S)-2-(1-(9H-purin-6-ylamino)propyl)-5-fluoro-3-phenylquinazolin-4(3H)-one. In one embodiment, polymorphic Form IV may have one or more channels. Such channels may be occupied by certain ions, such as chloride ions.

Form V

Figure 5:
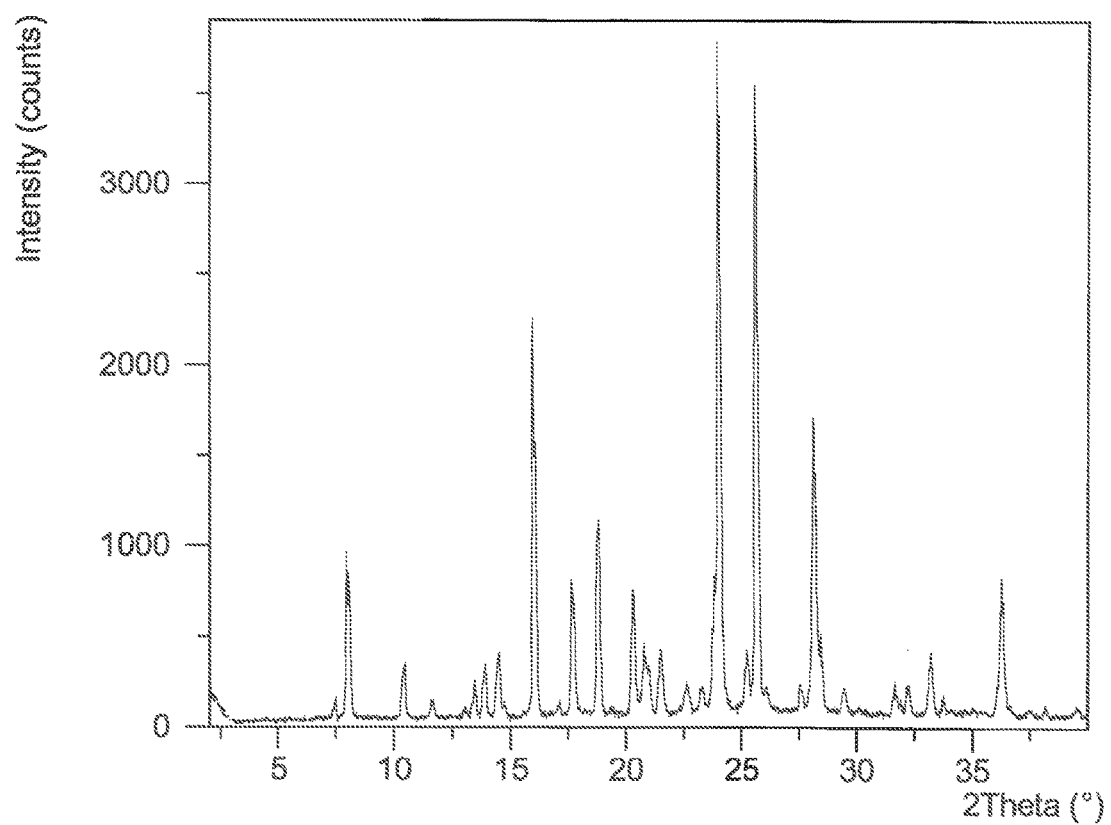
FIG. 5 shows XRPD patterns of polymorphic Form V of a hydrochloride salt of (S)-2-(1-(9H-purin-6-ylamino)propyl)-5-fluoro-3-phenylquinazolin-4(3H)-one.

In another aspect, provided is polymorphic Form V of a hydrochloride salt of (S)-2-(1-(9H-purin-6-ylamino)propyl)-5-fluoro-3-phenylquinazolin-4(3H)-one, wherein the polymorph exhibits an XRPD pattern substantially as shown in FIG. 5.

In some embodiments, polymorphic Form V has an XRPD pattern displaying at least two, at least three, at least four, at least five, or at least six of the degree 2θ-reflections with the greatest intensity as the XRPD pattern substantially as shown in FIG. 5. It should be understood that relative intensities can vary depending on a number of factors, including sample preparation, mounting, and the instrument and analytical procedure and settings used to obtain the spectrum. As such, the peak assignments listed herein, including for polymorphic Form V, are intended to encompass variations of +/−0.2 degrees 2θ.

In certain embodiments, polymorphic Form V has an XRPD pattern comprising degree 2θ-reflections (+/−0.2 degrees 2θ) at 15.9, 24.0, 25.6 and 28.1. In one embodiment, polymorphic Form V has an XRPD pattern comprising degree 2θ-reflections (+/−0.2 degrees 2θ) at 15.9, 24.0, 25.6, and 28.1 and one or more degree 2θ-reflections (+/−0.2 degrees 2θ) at 8.0, 18.9, 20.3, and 36.3. In one embodiment, polymorphic Form V has an XRPD pattern comprising degree 2θ-reflections (+/−0.2 degrees 2θ) at 15.9, 24.0, 25.6, and 28.1 and one degree 2θ-reflections (+/−0.2 degrees 2θ) at 8.0, 18.9, 20.3, and 36.3. In one embodiment, polymorphic Form V has an XRPD pattern comprising degree 2θ-reflections (+/−0.2 degrees 2θ) at 15.9, 24.0, 25.6, and 28.1 and two degree 2θ-reflections (+/−0.2 degrees 2θ) at 8.0, 18.9, 20.3, and 36.3. In one embodiment, polymorphic Form V has an XRPD pattern comprising degree 2θ-reflections (+/−0.2 degrees 2θ) at 15.9, 24.0, 25.6, and 28.1 and three degree 2θ-reflections (+/−0.2 degrees 2θ) at 8.0, 18.9, 20.3, and 36.3. In one embodiment, polymorphic Form V has an XRPD pattern comprising degree 2θ-reflections (+/−0.2 degrees 2θ) at 8.0, 15.9, 18.9, 20.3, 24.0, 25.6, 28.1 and 36.3.

Form VI

Figure 6:
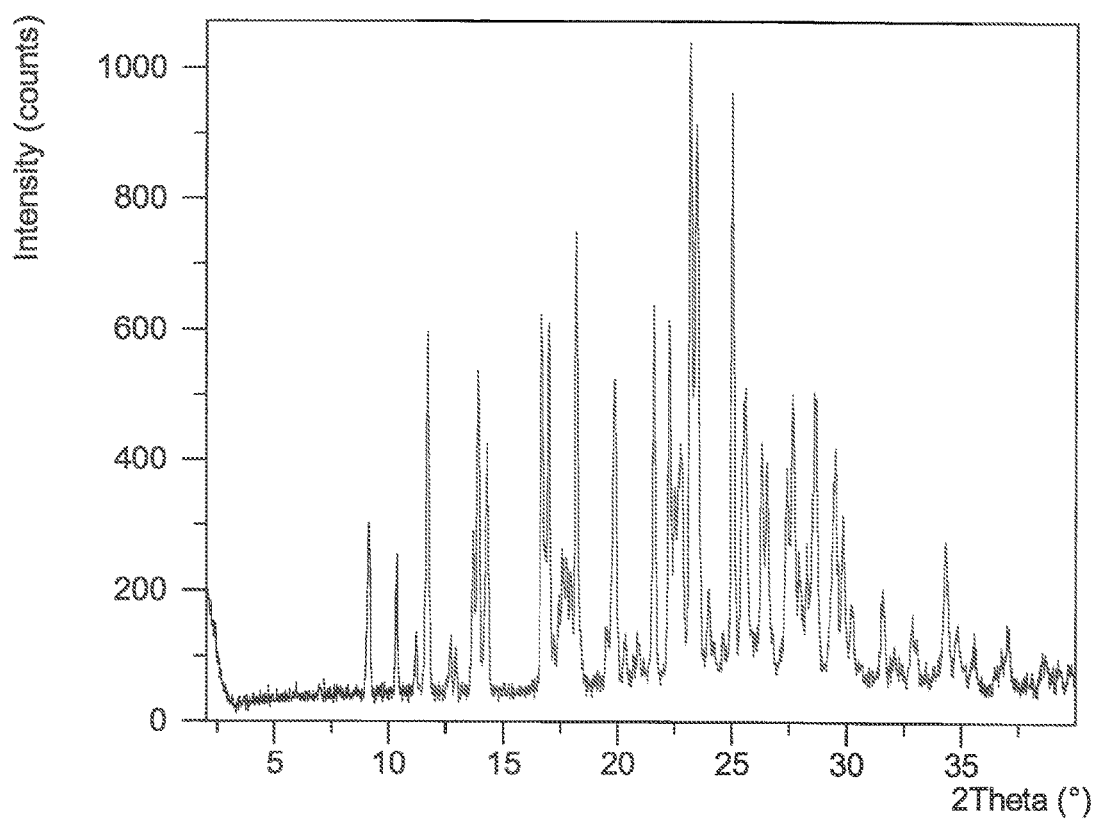
FIG. 6 shows XRPD patterns of polymorphic Form VI of a hydrochloride salt of (S)-2-(1-(9H-purin-6-ylamino)propyl)-5-fluoro-3-phenylquinazolin-4(3H)-one.

In another aspect, provided is polymorphic Form VI of a hydrochloride salt of (S)-2-(1-(9H-purin-6-ylamino)propyl)-5-fluoro-3-phenylquinazolin-4(3H)-one, wherein the polymorph exhibits an XRPD pattern substantially as shown in FIG. 6.

In some embodiments, polymorphic Form VI has an XRPD pattern displaying at least two, at least three, at least four, at least five, or at least six of the degree 2θ-reflections with the greatest intensity as the XRPD pattern substantially as shown in FIG. 6. It should be understood that relative intensities can vary depending on a number of factors, including sample preparation, mounting, and the instrument and analytical procedure and settings used to obtain the spectrum. As such, the peak assignments listed herein, including for polymorphic Form VI, are intended to encompass variations of +/−0.2 degrees 2θ.

In certain embodiments, polymorphic Form VI has an XRPD pattern comprising degree 2θ-reflections (+/−0.2 degrees 2θ) at 11.8, 17.0, 23.2 and 25.1. In one embodiment, polymorphic Form VI has an XRPD pattern comprising degree 2θ-reflections (+/−0.2 degrees 29) at 11.8, 13.9, 16.7, 17.0, 19.9, 22.3, 22.5, 23.2 and 25.1 and one or more degree 2θ-reflections (+/−0.2 degrees 2θ) at 13.9, 16.7, 19.9, 22.3, and 22.5. In one embodiment, polymorphic Form VI has an XRPD pattern comprising degree 2θ-reflections (+/−0.2 degrees 2θ) at 11.8, 13.9, 16.7, 17.0, 19.9, 22.3, 22.5, 23.2 and 25.1 and one degree 2θ-reflections (+/−0.2 degrees 2θ) at 13.9, 16.7, 19.9, 22.3, and 22.5. In one embodiment, polymorphic Form VI has an XRPD pattern comprising degree 2θ-reflections (+/−0.2 degrees 2θ) at 11.8, 13.9, 16.7, 17.0, 19.9, 22.3, 22.5, 23.2 and 25.1 and two degree 2θ-reflections (+/−0.2 degrees 2θ) at 13.9, 16.7, 19.9, 22.3, and 22.5. In one embodiment, polymorphic Form VI has an XRPD pattern comprising degree 2θ-reflections (+/−0.2 degrees 2θ) at 11.8, 13.9, 16.7, 17.0, 19.9, 22.3, 22.5, 23.2 and 25.1 and three degree 2θ-reflections (+/−0.2 degrees 2θ) at 13.9, 16.7, 19.9, 22.3, and 22.5. In one embodiment, polymorphic Form VI has an XRPD pattern comprising degree 2θ-reflections (+/−0.2 degrees 2θ) at 11.8, 13.9, 16.7, 17.0, 19.9, 22.3, 22.5, 232 and 25.1 and four degree 2θ-reflections (+/−0.2 degrees 2θ) at 13.9, 16.7, 19.9, 22.3, and 22.5. In one embodiment, polymorphic Form VI has an XRPD pattern comprising degree 2θ-reflections (+/−0.2 degrees 2θ) at 11.8, 13.9, 16.7, 17.0, 19.9, 22.3, 22.5, 23.2 and 25.1.

Form VII

Figure 7:
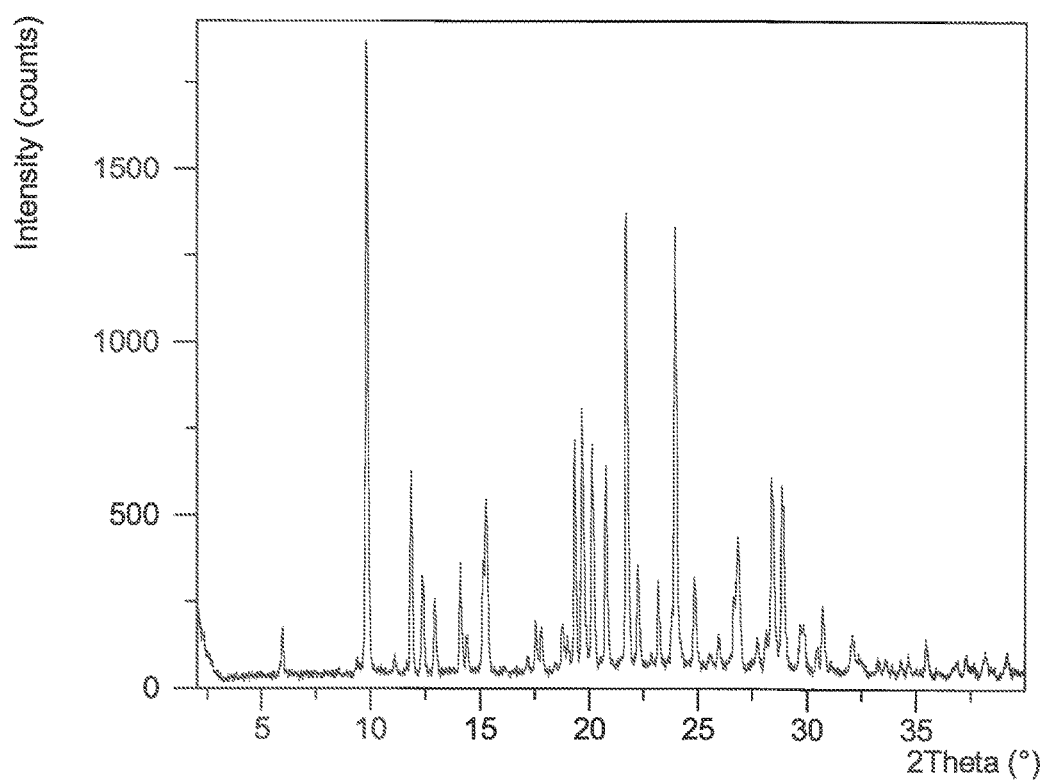
FIG. 7 shows XRPD patterns of polymorphic Form VII of a hydrochloride salt of (S)-2-(1-(9H-purin-6-ylamino)propyl)-5-fluoro-3-phenylquinazolin-4(3H)-one.

In another aspect, provided is polymorphic Form VII of a hydrochloride salt of (S)-2-(1-(9H-purin-6-ylamino)propyl)-5-fluoro-3-phenylquinazolin-4(3H)-one, wherein the polymorph exhibits an XRPD pattern substantially as shown in FIG. 7.

In some embodiments, polymorphic Form VII has an XRPD pattern displaying at least two, at least three, at least four, at least five, or at least six of the degree 2θ-reflections with the greatest intensity as the XRPD pattern substantially as shown in FIG. 7. It should be understood that relative intensities can vary depending on a number of factors, including sample preparation, mounting, and the instrument and analytical procedure and settings used to obtain the spectrum. As such, the peak assignments listed herein, including for polymorphic Form VII, are intended to encompass variations of +/−0.2 degrees 2θ.

In certain embodiments, polymorphic Form VII has an XRPD pattern comprising degree 2θ-reflections (+/−0.2 degrees 2θ) at 9.8, 17.8, 21.7 and 24.0. In certain embodiments, polymorphic Form VII has an XRPD pattern comprising degree 2θ-reflections (+/−0.2 degrees 2θ) at 9.8, 11.9, 15.3, 19.7, 20.1, 21.7 and 24.0. In one embodiment, polymorphic Form VII has an XRPD pattern comprising degree 2θ-reflections (+/−0.2 degrees 2θ) at 9.8, 17.8, 21.7, and 24.0 and one or more degree 2θ-reflections (+/−0.2 degrees 2θ) at 6.0, 11.9, 15.3, 19.7, 20.1, 28.4 and 28.9. In one embodiment, polymorphic Form VII has an XRPD pattern comprising degree 2θ-reflections (+/−0.2 degrees 2θ) at 9.8, 17.8, 21.7 and 24.0 and one degree 2θ-reflections (+/−0.2 degrees 2θ) at 6.0, 11.9, 15.3, 19.7, 20.1, 28.4 and 28.9. In one embodiment, polymorphic Form VII has an XRPD pattern comprising degree 2θ-reflections (+/−0.2 degrees 2θ) at 9.8, 17.8, 21.7 and 24.0 and two degree 2θ-reflections (+/−0.2 degrees 2θ) at 6.0, 11.9, 15.3, 19.7, 20.1, 28.4 and 28.9. In one embodiment, polymorphic Form VII has an XRPD pattern comprising degree 2θ-reflections (+/−0.2 degrees 2θ) at 9.8, 17.8, 21.7 and 24.0 and three degree 2θ-reflections (+/−0.2 degrees 2θ) at 6.0, 11.9, 15.3, 19.7, 20.1, 28.4 and 28.9. In one embodiment, polymorphic Form VII has an XRPD pattern comprising degree 2θ-reflections (+/−0.2 degrees 2θ) at 9.8, 17.8, 21.7 and 24.0 and four degree 2θ-reflections (+/−0.2 degrees 2θ) at 6.0, 11.9, 15.3, 19.7, 20.1, 28.4 and 28.9. In one embodiment, polymorphic Form VII has an XRPD pattern comprising degree 2θ-reflections (+/−0.2 degrees 2θ) at 9.8, 17.8, 21.7 and 24.0 and five degree 2θ-reflections (+/−0.2 degrees 2θ) at 6.0, 11.9, 153, 19.7, 20.1, 28.4 and 28.9. In one embodiment, polymorphic Form VII has an XRPD pattern comprising degree 2θ-reflections (+/−0.2 degrees 2θ) at 9.8, 17.8, 21.7 and 24.0 and six degree 2θ-reflections (+/−0.2 degrees 2θ) at 6.0, 11.9, 15.3, 19.7, 20.1, 28.4 and 28.9. In one embodiment, polymorphic Form VII has an XRPD pattern comprising degree 2θ-reflections (+/−0.2 degrees 2θ) at 6.0, 9.8, 11.9, 15.3, 19.7, 20.1, 21.7, 24.0, 28.4 and 28.9.

Form VIII

Figure 8:
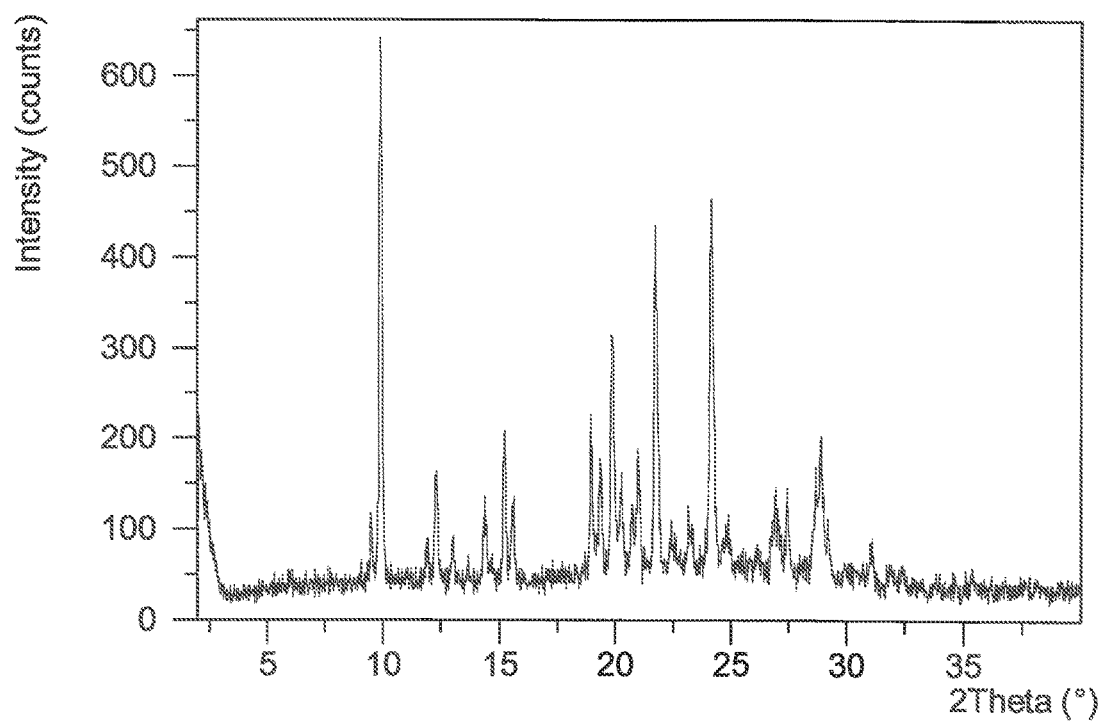
FIG. 8 shows XRPD patterns of polymorphic Form VIII of a hydrochloride salt of (S)-2-(1-(9H-purin-6-ylamino)propyl)-5-fluoro-3-phenylquinazolin-4(3H)-one.

In another aspect, provided is polymorphic Form VIII of a hydrochloride salt of (S)-2-(1-(9H-purin-6-ylamino)propyl)-5-fluoro-3-phenylquinazolin-4(3H)-one, wherein the polymorph exhibits an XRPD pattern substantially as shown in FIG. 8.

In some embodiments, polymorphic Form VIII has an XRPD pattern displaying at least two, at least three, at least four, at least five, or at least six of the degree 2θ-reflections with the greatest intensity as the XRPD pattern substantially as shown in FIG. 8. It should be understood that relative intensities can vary depending on a number of factors, including sample preparation, mounting, and the instrument and analytical procedure and settings used to obtain the spectrum. As such, the peak assignments listed herein, including for polymorphic Form VIII, are intended to encompass variations of +/−0.2 degrees 2θ.

In certain embodiments, polymorphic Form VIII has an XRPD pattern comprising degree 2θ-reflections (+/−0.2 degrees 2θ) at 10.0, 19.9, 21.7 and 24.1. In certain embodiments, polymorphic Form VIII has an XRPD pattern comprising degree 2θ-reflections (+/−0.2 degrees 2θ) at 10.0, 12.4, 15.3, 20.3, 21.7 and 28.9. In one embodiment, polymorphic Form VIII has an XRPD pattern comprising degree 2θ-reflections (+/−0.2 degrees 2θ) at 10.0, 19.9, 21.7 and 24.1 and one or more 2θ-reflections (+/−0.2 degrees 2θ) at 12.4, 15.3, 19.0, 20.3, and 28.9. In one embodiment, polymorphic Form VIII has an XRPD pattern comprising degree 2θ-reflections (+/−0.2 degrees 2θ) at 10.0, 19.9, 21.7 and 24.1 and one 2θ-reflections (+/−0.2 degrees 2θ) at 12.4, 15.3, 19.0, 20.3, and 28.9. In one embodiment, polymorphic Form VIII has an XRPD pattern comprising degree 2θ-reflections (+/−0.2 degrees 2θ) at 10.0, 19.9, 21.7 and 24.1 and two 2θ-reflections (+/−0.2 degrees 2θ) at 12.4, 15.3, 19.0, 20.3, and 28.9. In one embodiment, polymorphic Form VIII has an XRPD pattern comprising degree 2θ-reflections (+/−0.2 degrees 2θ) at 10.0, 19.9, 21.7 and 24.1 and three 2θ-reflections (+/−0.2 degrees 2θ) at 12.4, 15.3, 19.0, 20.3, and 28.9. In one embodiment, polymorphic Form VIII has an XRPD pattern comprising degree 2θ-reflections (+/−0.2 degrees 2θ) at 10.0, 19.9, 21.7 and 24.1 and four 2θ-reflections (+/−0.2 degrees 2θ) at 12.4, 15.3, 19.0, 20.3, and 28.9. In one embodiment, polymorphic Form VIII has an XRPD pattern comprising degree 2θ-reflections (+/−0.2 degrees 2θ) at 10.0, 12.4, 15.3, 19.0, 19.9, 20.3, 21.7, 24.1 and 28.9.

Form IX

Figure 9:
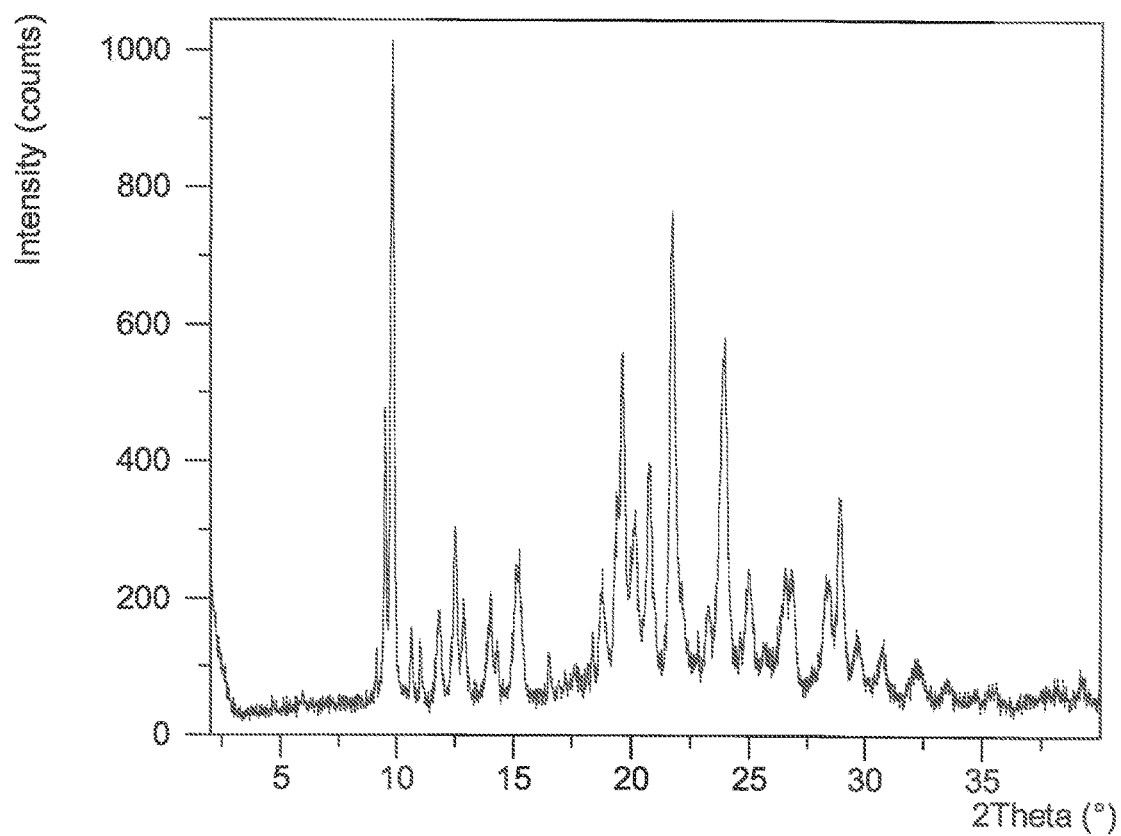
FIG. 9 shows XRPD patterns of polymorphic Form IX of a hydrochloride salt of(S)-2-(1-(9H-purin-6-ylamino)propyl)-5-fluoro-3-phenylquinazolin-4(3H)-one.

In another aspect, provided is polymorphic Form IX of a hydrochloride salt of (S)-2-(1-(9H-purin-6-ylamino)propyl)-5-fluoro-3-phenylquinazolin-4(3H)-one, wherein the polymorph exhibits an XRPD pattern substantially as shown in FIG. 9.

In some embodiments, polymorphic Form IX has an XRPD pattern displaying at least two, at least three, at least four, at least five, or at least six of the degree 2θ-reflections with the greatest intensity as the XRPD pattern substantially as shown in FIG. 9. It should be understood that relative intensities can vary depending on a number of factors, including sample preparation, mounting, and the instrument and analytical procedure and settings used to obtain the spectrum. As such, the peak assignments listed herein, including for polymorphic Form IX, are intended to encompass variations of +/−0.2 degrees 2θ.

In certain embodiments, polymorphic Form IX has an XRPD pattern comprising degree 2θ-reflections (+/−0.2 degrees 2θ) at 9.8, 19.6, 21.8 and 24.0. In certain embodiments, polymorphic Form IX has an XRPD pattern comprising degree 2θ-reflections (+/−0.2 degrees 2θ) at 9.8, 19.6, 21.8, 24.0 and 29.0. In one embodiment, polymorphic Form IX has an XRPD pattern comprising degree 2θ-reflections (+/−0.2 degrees 2θ) at 9.8, 19.6, 21.8 and 24.0 and one or more 2θ-reflections (+/−0.2 degrees 2θ) at 9.5, 12.5, 20.8, and 29.0. In one embodiment, polymorphic Form IX has an XRPD pattern comprising degree 2θ-reflections (+/−0.2 degrees 2θ) at 9.8, 19.6, 21.8 and 24.0 and one 2θ-reflections (+/−0.2 degrees 2θ) at 9.5, 12.5, 20.8, and 29.0. In one embodiment, polymorphic Form IX has an XRPD pattern comprising degree 2θ-reflections (+/−0.2 degrees 2θ) at 9.8, 19.6, 21.8 and 24.0 and two 2θ-reflections (+/−0.2 degrees 2θ) at 9.5, 12.5, 20.8, and 29.0. In one embodiment, polymorphic Form IX has an XRPD pattern comprising degree 2θ-reflections (+/−0.2 degrees 2θ) at 9.8, 19.6, 21.8 and 24.0 and three 2θ-reflections (+/−0.2 degrees 2θ) at 9.5, 12.5, 20.8, and 29.0. In one embodiment, polymorphic Form IX has an XRPD pattern comprising degree 2θ-reflections (+/−0.2 degrees 2θ) at 9.5, 9.8, 12.5, 19.6, 20.8, 21.8, 24.0 and 29.0.

Form X

Figure 10:
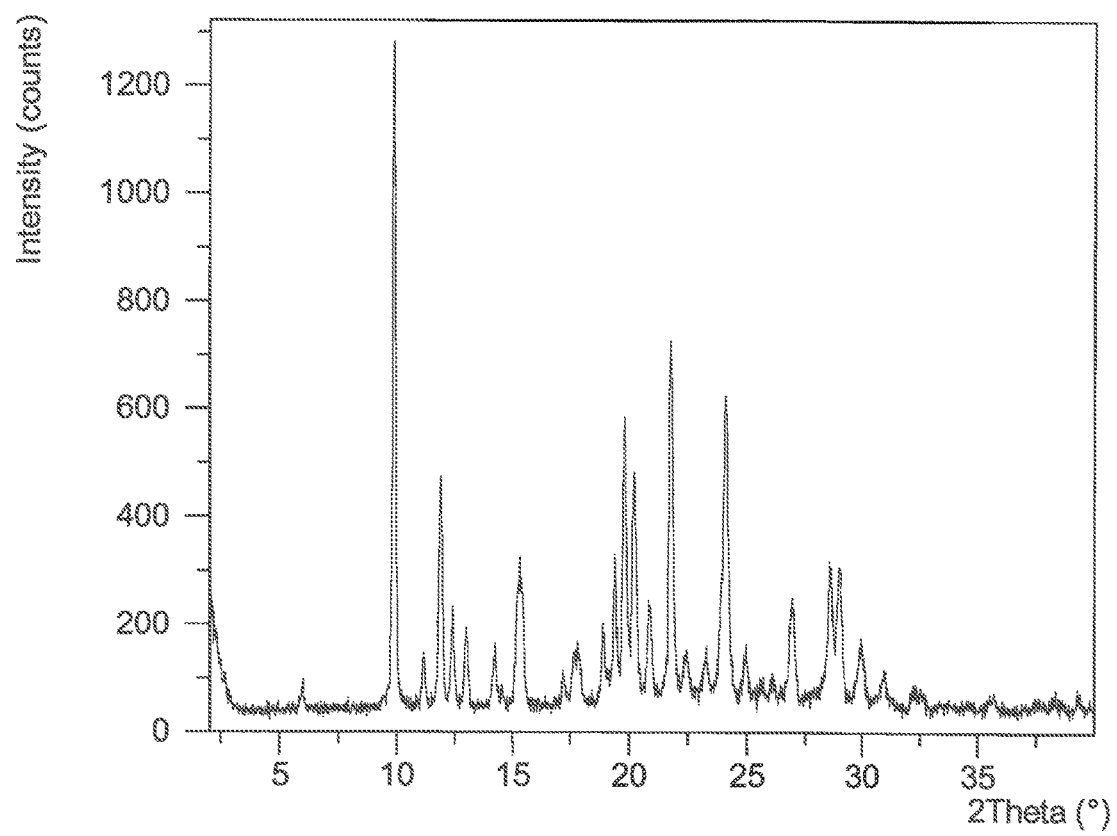
FIG. 10 shows XRPD patterns of polymorphic Form X of a hydrochloride salt of (S)-2-(1-(9H-purin-6-ylamino)propyl)-5-fluoro-3-phenylquinazolin-4(3H)-one.

In another aspect, provided is polymorphic Form X of a hydrochloride salt of (S)-2-(1-(9H-purin-6-ylamino)propyl)-5-fluoro-3-phenylquinazolin-4(3H)-one, wherein the polymorph exhibits an XRPD pattern substantially as shown in FIG. 10.

In some embodiments, polymorphic Form X has an XRPD pattern displaying at least two, at least three, at least four, at least five, or at least six of the degree 2θ-reflections with the greatest intensity as the XRPD pattern substantially as shown in FIG. 10. It should be understood that relative intensities can vary depending on a number of factors, including sample preparation, mounting, and the instrument and analytical procedure and settings used to obtain the spectrum. As such, the peak assignments listed herein, including for polymorphic Form X, are intended to encompass variations of +/−0.2 degrees 2θ.

In certain embodiments, polymorphic Form X has an XRPD pattern comprising degree 2θ-reflections (+/−0.2 degrees 2θ) at 9.9, 21.8, and 24.2. In certain embodiments, polymorphic Form X has an XRPD pattern comprising degree 2θ-reflections (+/−0.2 degrees 2θ) at 9.9, 11.9, 15.5, 21.8, 24.2, 28.6 and 29.0. In one embodiment, polymorphic Form X has an XRPD pattern comprising degree 2θ-reflections (+/−0.2 degrees 2θ) at 9.9, 21.8, and 24.2 and one or more degree 2θ-reflections (+/−0.2 degrees 2θ) at 11.9, 15.5, 19.4, 19.8, 20.3, 28.6 and 29.0. In one embodiment, polymorphic Form X has an XRPD pattern comprising degree 2θ-reflections (+/−0.2 degrees 2θ) at 9.9, 21.8, and 24.2 and one degree 2θ-reflections (+/−0.2 degrees 2θ) at 11.9, 15.5, 19.4, 19.8, 20.3, 28.6 and 29.0. In one embodiment, polymorphic Form X has an XRPD pattern comprising degree 2θ-reflections (+/−0.2 degrees 2θ) at 9.9, 21.8, and 24.2 and two degree 2θ-reflections (+/−0.2 degrees 2θ) at 11.9, 15.5, 19.4, 19.8, 20.3, 28.6 and 29.0. In one embodiment, polymorphic Form X has an XRPD pattern comprising degree 2θ-reflections (+/−0.2 degrees 2θ) at 9.9, 21.8, and 24.2 and three degree 2θ-reflections (+/−0.2 degrees 2θ) at 11.9, 15.5, 19.4, 19.8, 20.3, 28.6 and 29.0. In one embodiment, polymorphic Form X has an XRPD pattern comprising degree 2θ-reflections (+/−0.2 degrees 2θ) at 9.9, 21.8, and 24.2 and four degree 2θ-reflections (+/−0.2 degrees 2θ) at 11.9, 15.5, 19.4, 19.8, 20.3, 28.6 and 29.0. In one embodiment, polymorphic Form X has an XRPD pattern comprising degree 2θ-reflections (+/−0.2 degrees 2θ) at 9.9, 21.8, and 24.2 and five degree 2θ-reflections (+/−0.2 degrees 2θ) at 11.9, 15.5, 19.4, 19.8, 20.3, 28.6 and 29.0. In one embodiment, polymorphic Form X has an XRPD pattern comprising degree 2θ-reflections (+/−0.2 degrees 2θ) at 9.9, 21.8, and 24.2 and six degree 2θ-reflections (+/−0.2 degrees 2θ) at 11.9, 15.5, 19.4, 19.8, 20.3, 28.6 and 29.0. In one embodiment, polymorphic Form X has an XRPD pattern comprising degree 2θ-reflections (+/−0.2 degrees 2θ) at 9.9, 11.9, 15.5, 19.4, 19.8, 20.3, 21.8, 24.2, 28.6 and 29.0.

Form XI

Figure 11:
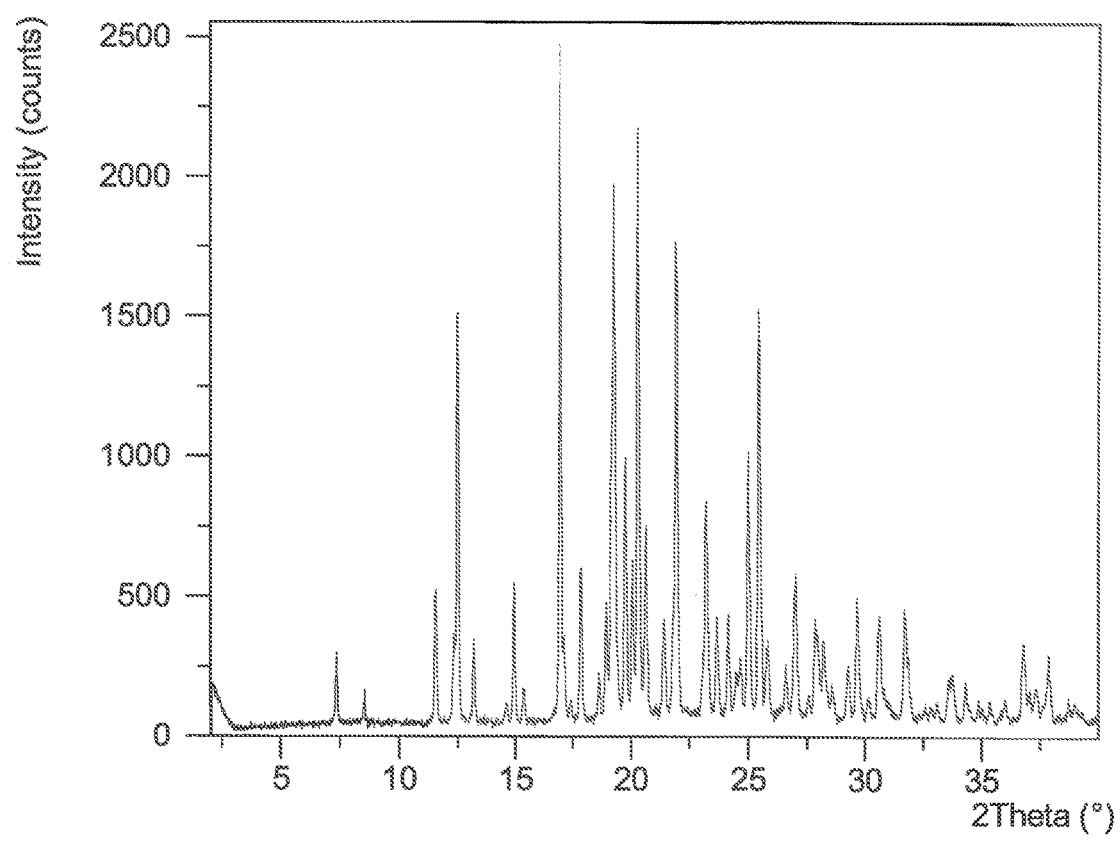
FIG. 11 shows XRPD patterns of polymorphic Form XI of a hydrochloride salt of (S)-2-(1-(9H-purin-6-ylamino)propyl)-5-fluoro-3-phenylquinazolin-4(3H)-one.

In another aspect, provided is polymorphic Form XI of a hydrochloride salt of (S)-2-(1-(9H-purin-6-ylamino)propyl)-5-fluoro-3-phenylquinazolin-4(3H)-one, wherein the polymorph exhibits an XRPD pattern substantially as shown in FIG. 11.

In some embodiments, polymorphic Form XI has an XRPD pattern displaying at least two, at least three, at least four, at least five, or at least six of the degree 2θ-reflections with the greatest intensity as the XRPD pattern substantially as shown in FIG. 11. It should be understood that relative intensities can vary depending on a number of factors, including sample preparation, mounting, and the instrument and analytical procedure and settings used to obtain the spectrum. As such, the peak assignments listed herein, including for polymorphic Form XI, are intended to encompass variations of +/−0.2 degrees 2θ.

In certain embodiments, polymorphic Form XI has an XRPD pattern comprising degree 2θ-reflections (+/−0.2 degrees 2θ) at 12.5, 17.0, 19.3, 20.3, 22.0 and 25.5. In one embodiment, polymorphic Form XI has an XRPD pattern comprising degree 2θ-reflections (+/−0.2 degrees 2θ) at 12.5, 17.0, 19.3, 20.3, 22.0 and 25.5 and one or more degree 2θ-reflections (+/−0.2 degrees 2θ) at 7.4, 15.0, and 31.7. In one embodiment, polymorphic Form XI has an XRPD pattern comprising degree 2θ-reflections (+/−0.2 degrees 2θ) at 12.5, 17.0, 19.3, 20.3, 22.0 and 25.5 and one degree 2θ-reflections (+/−0.2 degrees 2θ) at 7.4, 15.0, and 31.7. In one embodiment, polymorphic Form XI has an XRPD pattern comprising degree 2θ-reflections (+/−0.2 degrees 2θ) at 12.5, 17.0, 19.3, 20.3, 22.0 and 25.5 and two degree 2θ-reflections (+/−0.2 degrees 2θ) at 7.4, 15.0, and 31.7. In one embodiment, polymorphic Form XI has an XRPD pattern comprising degree 2θ-reflections (+/−0.2 degrees 2θ) at 7.4, 12.5, 15.0, 17.0, 19.3, 20.3, 22.0, 25.5 and 31.7.

Form XII

Figure 12:
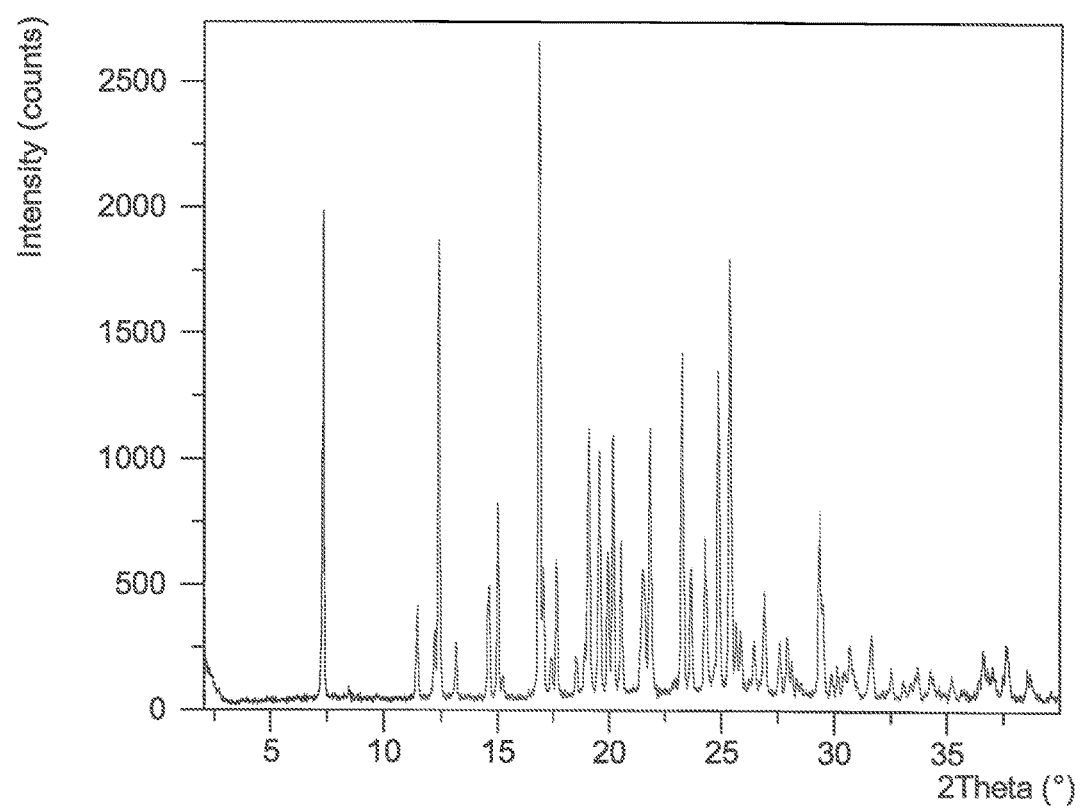
FIG. 12 shows XRPD patterns of polymorphic Form XII of a hydrochloride salt of (S)-2-(1-(9H-purin-6-ylamino)propyl)-5-fluoro-3-phenylquinazolin-4(3H)-one.

In another aspect, provided is polymorphic Form XII of a hydrochloride salt of (S)-2-(1-(9H-purin-6-ylamino)propyl)-5-fluoro-3-phenylquinazolin-4(3H)-one, wherein the polymorph exhibits an XRPD pattern substantially as shown in FIG. 12.

Polymorphic Form XII may have a unit cell as determined by crystal X-ray crystallography of the following dimensions: a=10.717 Å (3); b=10.161 Å (3); c=12.409 Å (4); α=90°; β=104.021° (4); and γ=90°.

In some embodiments, polymorphic Form XII has at least one, or both of the following properties:
 (a) an XRPD pattern substantially as shown in FIG. 12; and (b) a unit cell, as determined by Single Crystal X-Ray Crystallography, of the following dimensions: a=10.717 Å (3); b=10.161 Å (3); c=12.409 Å (4); α=90°; β=104.021° (4); and γ=90°.

In some embodiments, polymorphic Form XII has an XRPD pattern displaying at least two, at least three, at least four, at least five, or at least six of the degree 2θ-reflections with the greatest intensity as the XRPD pattern substantially as shown in FIG. 12. It should be understood that relative intensities can vary depending on a number of factors, including sample preparation, mounting, and the instrument and analytical procedure and settings used to obtain the spectrum. As such, the peak assignments listed herein, including for polymorphic Form XII, are intended to encompass variations of +/−0.2 degrees 2θ.

In certain embodiments, polymorphic Form XII has an XRPD pattern comprising degree 2θ-reflections (+/−0.2 degrees 2θ) at 7.4, 12.4, 16.9 and 25.4. In one embodiment, polymorphic Form XII has an XRPD pattern comprising degree 2θ-reflections (+/−0.2 degrees 2θ) at 7.4, 12.4, 16.9 and 25.4 and one or more degree 2θ-reflections (+/−0.2 degrees 2θ) at 19.1, 19.6, 23.3, 24.9, and 29.4. In one embodiment, polymorphic Form XII has an XRPD pattern comprising degree 2θ-reflections (+/−0.2 degrees 2θ) at 7.4, 12.4, 16.9 and 25.4 and one degree 2θ-reflections (+/−0.2 degrees 2θ) at 19.1, 19.6, 23.3, 24.9, and 29.4. In one embodiment, polymorphic Form XII has an XRPD pattern comprising degree 2θ-reflections (+/−0.2 degrees 2θ) at 7.4, 12.4, 16.9 and 25.4 and two degree 2θ-reflections (+/−0.2 degrees 2θ) at 19.1, 19.6, 23.3, 24.9, and 29.4. In one embodiment, polymorphic Form XII has an XRPD pattern comprising degree 2θ-reflections (+/−0.2 degrees 2θ) at 7.4, 12.4, 16.9 and 25.4 and three degree 2θ-reflections (+/−0.2 degrees 2θ) at 19.1, 19.6, 23.3, 24.9, and 29.4. In one embodiment, polymorphic Form XII has an XRPD pattern comprising degree 2θ-reflections (+/−0.2 degrees 2θ) at 7.4, 12.4, 16.9 and 25.4 and four degree 2θ-reflections (+/−0.2 degrees 2θ) at 19.1, 19.6, 23.3, 24.9, and 29.4. In one embodiment, polymorphic Form XII has an XRPD pattern comprising degree 2θ-reflections (+/−0.2 degrees 2θ) at 7.4, 12.4, 16.9, 19.1, 19.6, 23.3, 24.9, 25.4 and 29.4.

In certain embodiments, the hydrochloride salt of polymorphic Form XII is a monohydrochloride salt of (S)-2-(1-(9H-purin-6-ylamino)propyl)-5-fluoro-3-phenylquinazolin-4(3H)-one. In one embodiment, polymorphic Form XII may have one or more channels.

Form XIII

Figure 13:
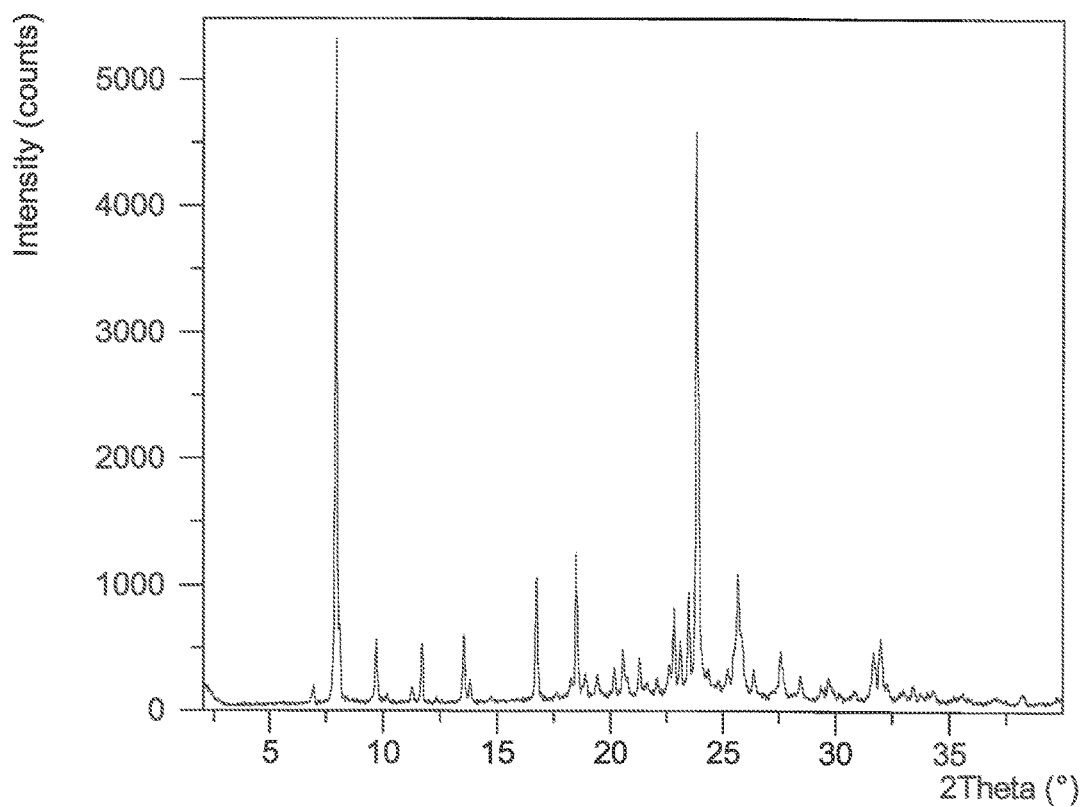
FIG. 13 shows XRPD patterns of polymorphic Form XIII of a hydrochloride salt of (S)-2-(1-(9H-purin-6-ylamino)propyl)-5-fluoro-3-phenylquinazolin-4(3H)-one.

In another aspect, provided is polymorphic Form XIII of a hydrochloride salt of (S)-2-(1-(9H-purin-6-ylamino)propyl)-5-fluoro-3-phenylquinazolin-4(3H)-one, wherein the polymorph exhibits an XRPD pattern substantially as shown in FIG. 13.

In some embodiments, polymorphic Form XIII has an XRPD pattern displaying at least two, at least three, at least four, at least five, or at least six of the degree 2θ-reflections with the greatest intensity as the XRPD pattern substantially as shown in FIG. 13. It should be understood that relative intensities can vary depending on a number of factors, including sample preparation, mounting, and the instrument and analytical procedure and settings used to obtain the spectrum. As such, the peak assignments listed herein, including for polymorphic Form XIII, are intended to encompass variations of +/−0.2 degrees 2θ.

In certain embodiments, polymorphic Form XIII has an XRPD pattern comprising degree 2θ-reflections (+/−0.2 degrees 2θ) at 6.9, 16.8, 18.5 and 23.9. In one embodiment, polymorphic Form XIII has an XRPD pattern comprising degree 2θ-reflections (+/−0.2 degrees 2θ) at 6.9, 16.8, 18.5 and 23.9 and one or more degree 2θ-reflections (+/−0.2 degrees 2θ) at 8.0, 8.1, 9.7, 11.7, 13.6, 23.5, and 25.7. In one embodiment, polymorphic Form XIII has an XRPD pattern comprising degree 2θ-reflections (+/−0.2 degrees 2θ) at 6.9, 16.8, 18.5 and 23.9 and one degree 2θ-reflections (+/−0.2 degrees 2θ) at 8.0, 8.1, 9.7, 11.7, 13.6, 23.5, and 25.7. In one embodiment, polymorphic Form XIII has an XRPD pattern comprising degree 2θ-reflections (+/−0.2 degrees 2θ) at 6.9, 16.8, 18.5 and 23.9 and two degree 2θ-reflections (+/−0.2 degrees 2θ) at 8.0, 8.1, 9.7, 11.7, 13.6, 23.5, and 25.7. In one embodiment, polymorphic Form XIII has an XRPD pattern comprising degree 2θ-reflections (+/−0.2 degrees 2θ) at 6.9, 16.8, 18.5 and 23.9 and three degree 2θ-reflections (+/−0.2 degrees 2θ) at 8.0, 8.1, 9.7, 11.7, 13.6, 23.5, and 25.7. In one embodiment, polymorphic Form XIII has an XRPD pattern comprising degree 2θ-reflections (+/−0.2 degrees 2θ) at 6.9, 16.8, 18.5 and 23.9 and four degree 2θ-reflections (+/−0.2 degrees 2θ) at 8.0, 8.1, 9.7, 11.7, 13.6, 23.5, and 25.7. In one embodiment, polymorphic Form XIII has an XRPD pattern comprising degree 2θ-reflections (+/−0.2 degrees 2θ) at 6.9, 16.8, 18.5 and 23.9 and five degree 2θ-reflections (+/−0.2 degrees 2θ) at 8.0, 8.1, 9.7, 11.7, 13.6, 23.5, and 25.7. In one embodiment, polymorphic Form XI has an XRPD pattern comprising degree 2θ-reflections (+/−0.2 degrees 2θ) at 6.9, 16.8, 18.5 and 23.9 and six degree 2θ-reflections (+/−0.2 degrees 2θ) at 8.0, 8.1, 9.7, 11.7, 13.6, 23.5, and 25.7. In one embodiment, polymorphic Form XIII has an XRPD pattern comprising degree 2θ-reflections (+/−0.2 degrees 2θ) at 6.9, 8.0, 8.1, 9.7, 11.7, 13.6, 16.8, 18.5, 23.5, 23.9 and 25.7.

In further embodiments, additional patterns of solvate forms of the hydrochloride salt of (S)-2-(1-(9H-purin-6-ylamino)propyl)-5-fluoro-3-phenylquinazolin-4(3H)-one are provided.

Pattern 1

Figure 14A:
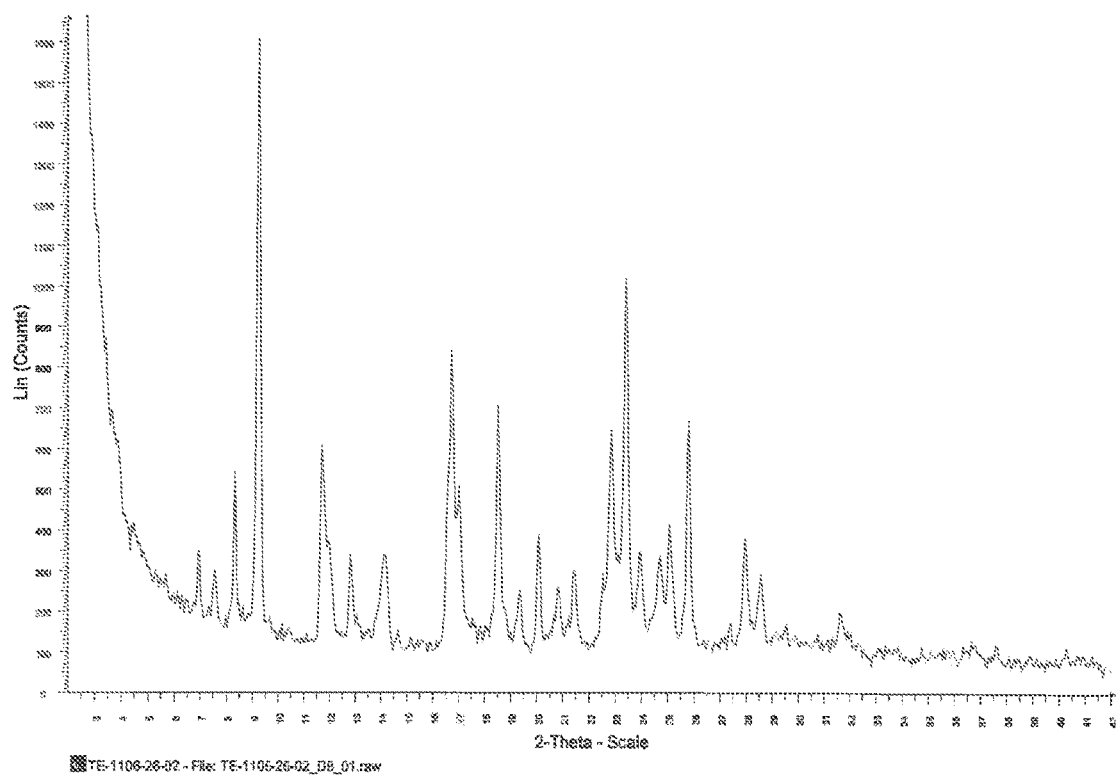
FIG. 14A shows XRPD Pattern 1 of a solvate form of a hydrochloride salt of (S)-2-(1-(9H-purin-6-ylamino)propyl)-5-fluoro-3-phenylquinazolin-4(3H)-one (damp).

In one aspect, provided is Pattern 1 of the hydrochloride salt of (S)-2-(1-(9H-purin-6-ylamino)propyl)-5-fluoro-3-phenylquinazolin-4(3H)-one, wherein Pattern 1 an X-ray powder diffraction (XRPD) pattern substantially as shown in FIG. 14A.

In some embodiments, Pattern 1 has an XRPD pattern substantially as shown in FIG. 14A.

In some embodiments, Pattern 1 is a prepared in the presence of propylacetate. In some embodiments, Pattern 1 corresponds to a propylacetate solvate of the hydrochloride salt of (S)-2-(1-(9H-purin-6-ylamino)propyl)-5-fluoro-3-phenylquinazolin-4(3H)-one.

In some embodiments, Pattern 1 has an XRPD pattern displaying at least two, at least three, at least four, at least five, or at least six of the degree 2θ-reflections with the greatest intensity as the XRPD pattern substantially as shown in FIG. 14A. It should be understood that relative intensities can vary depending on a number of factors, including sample preparation, mounting, and the instrument and analytical procedure and settings used to obtain the spectrum. As such, the peak assignments listed herein, including for Pattern 1, are intended to encompass variations of +/−0.2 degrees 2θ.

In certain embodiments, Pattern 1 has an XRPD pattern comprising degree 2θ-reflections (+/−0.2 degrees 2θ) at 9.2, 23.4, 16.8, 18.5, and 25.8. In one embodiment, Pattern 1 has an XRPD pattern comprising degree 2θ-reflections (+/−0.2 degrees 2θ) at 9.2, 23.4, 16.8, 18.5, and 25.8 and one or more of the degree 2θ-reflections (+/−0.2 degrees 2θ) at 22.9, 11.7, 8.3, and 17.0. In one embodiment, Pattern 1 has an XRPD pattern comprising degree 2θ-reflections (+/−0.2 degrees 2θ) at 9.2, 23.4, 16.8, 18.5, and 25.8 and one of the degree 2θ-reflections (+/−0.2 degrees 2θ) at 22.9, 11.7, 8.3, and 17.0. In one embodiment, Pattern 1 has an XRPD pattern comprising degree 2θ-reflections (+/−0.2 degrees 2θ) at 9.2, 23.4, 16.8, 18.5, and 25.8 and two of the degree 2θ-reflections (+/−0.2 degrees 2θ) at 22.9, 11.7, 8.3, and 17.0. In one embodiment, Pattern 1 has an XRPD pattern comprising degree 2θ-reflections (+/−0.2 degrees 2θ) at 9.2, 23.4, 16.8, 18.5, and 25.8 and three of the degree 2θ-reflections (+/−0.2 degrees 2θ) at 22.9, 11.7, 8.3, and 17.0. In one embodiment, Pattern 1 has an XRPD pattern comprising degree 2θ-reflections (+/−0.2 degrees 2θ) at 9.2, 23.4, 16.8, 18.5, 25.8, 22.9, 11.7, 8.3, and 17.0. Table 1 shows the full XRPD peak list for Pattern 1.

TABLE 1

XRPD Peak List for Pattern 1

| Angle (2-Theta °) | Intensity (%) |
|---|---|
| 7.0 | 21.5 |
| 7.5 | 18.6 |
| 8.3 | 33.6 |
| 9.2 | 100.0 |
| 11.7 | 37.6 |
| 12.0 | 26.7 |
| 12.8 | 22.1 |
| 14.1 | 21.2 |
| 16.8 | 52.1 |
| 17.0 | 31.4 |
| 18.5 | 43.9 |
| 19.3 | 15.5 |
| 20.1 | 24.0 |
| 20.8 | 16.1 |
| 21.5 | 18.6 |
| 22.5 | 19.7 |
| 22.9 | 40.1 |
| 23.1 | 23.5 |
| 23.4 | 63.3 |
| 24.0 | 21.6 |
| 24.7 | 20.8 |
| 25.1 | 25.9 |
| 25.8 | 41.5 |
| 28.0 | 23.4 |
| 28.6 | 18.0 |

Pattern 9

Figure 14B:
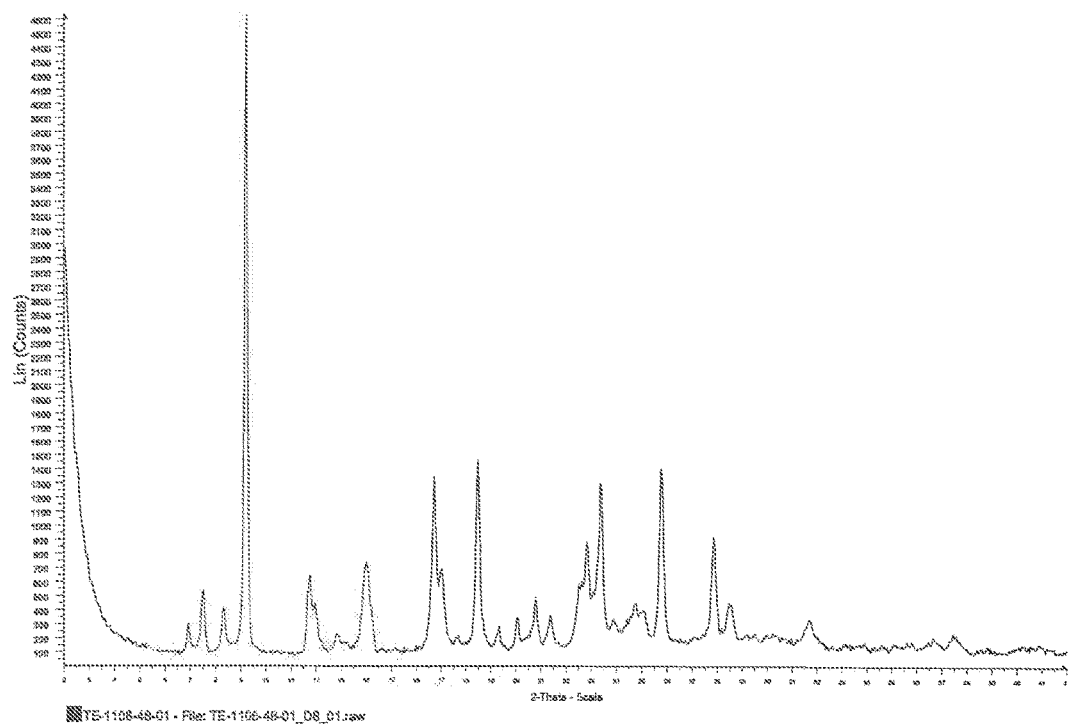
FIG. 14B shows XRPD Pattern 9 of a solvate form of a hydrochloride salt of(S)-2-(1-(9H-purin-6-ylamino)propyl)-5-fluoro-3-phenylquinazolin-4(3H)-one.

In one aspect, provided is Pattern 9 of the hydrochloride salt of (S)-2-(1-(9H-purin-6-ylamino)propyl)-5-fluoro-3-phenylquinazolin-4(3H)-one, wherein Pattern 9 an X-ray powder diffraction (XRPD) pattern substantially as shown in FIG. 14B.

In some embodiments, Pattern 9 has an XRPD pattern substantially as shown in FIG. 14B.

In some embodiments, Pattern 9 is a prepared in the presence of propylacetate. In some embodiments, Pattern 9 corresponds to a propylacetate solvate of the hydrochloride salt of (S)-2-(1-(9H-purin-6-ylamino)propyl)-5-fluoro-3-phenylquinazolin-4(3H)-one.

In some embodiments, Pattern 9 has an XRPD pattern displaying at least two, at least three, at least four, at least five, or at least six of the degree 2θ-reflections with the greatest intensity as the XRPD pattern substantially as shown in FIG. 14B. It should be understood that relative intensities can vary depending on a number of factors, including sample preparation, mounting, and the instrument and analytical procedure and settings used to obtain the spectrum. As such, the peak assignments listed herein, including for Pattern 1, are intended to encompass variations of +/−0.2 degrees 2θ.

In certain embodiments, Pattern 9 has an XRPD pattern comprising degree 2θ-reflections (+/−0.2 degrees 2θ) at 9.2, 18.5, 25.8, 16.7, and 23.4. In one embodiment, Pattern 1 has an XRPD pattern comprising degree 2θ-reflections (+/−0.2 degrees 2θ) at 9.2, 18.5, 25.8, 16.7, and 23.4 and one or more of the degree 2θ-reflections (+/−0.2 degrees 2θ) at 27.9, 22.9, 14.0, and 17.0. In one embodiment, Pattern 9 has an XRPD pattern comprising degree 2θ-reflections (+/−0.2 degrees 2θ) at 9.2, 18.5, 25.8, 16.7, and 23.4 and one of the degree 2θ-reflections (+/−0.2 degrees 2θ) at 27.9, 22.9, 14.0, and 17.0. In one embodiment, Pattern 9 has an XRPD pattern comprising degree 2θ-reflections (+/−0.2 degrees 2θ) at 9.2, 23.4, 16.8, 18.5, and 25.8 and two of the degree 2θ-reflections (+/−0.2 degrees 2θ) at 27.9, 22.9, 14.0, and 17.0. In one embodiment, Pattern 9 has an XRPD pattern comprising degree 2θ-reflections (+/−0.2 degrees 2θ) at 9.2, 18.5, 25.8, 16.7, and 23.4 and three of the degree 2θ-reflections (+/−0.2 degrees 2θ) at 27.9, 22.9, 14.0, and 17.0. In one embodiment, Pattern 9 has an XRPD pattern comprising degree 2θ-reflections (+/−0.2 degrees 2θ) at 9.2, 18.5, 25.8, 16.7, 23.4, 27.9, 22.9, 14.0, and 17.0. Table 2 shows the full XRPD peak list for Pattern 9.

TABLE 2

XRPD Peak List for Pattern 9

| Angle (2-Theta °) | Intensity (%) |
|---|---|
| 6.9 | 6.3 |
| 7.5 | 11.4 |
| 8.3 | 8.9 |
| 9.2 | 100.0 |
| 11.7 | 13.8 |
| 12.0 | 9.4 |
| 12.8 | 4.7 |
| 14.0 | 15.8 |
| 16.7 | 29.0 |
| 17.0 | 14.7 |
| 17.7 | 4.5 |
| 18.5 | 31.5 |
| 19.3 | 6.0 |
| 20.1 | 7.3 |
| 20.8 | 10.4 |
| 21.4 | 7.6 |
| 22.6 | 12.9 |
| 22.9 | 18.9 |
| 23.4 | 27.9 |
| 23.9 | 7.1 |
| 24.8 | 9.5 |
| 25.1 | 8.5 |
| 25.8 | 30.1 |
| 27.9 | 19.7 |
| 28.5 | 9.6 |

Pattern 2

Figure 15A:
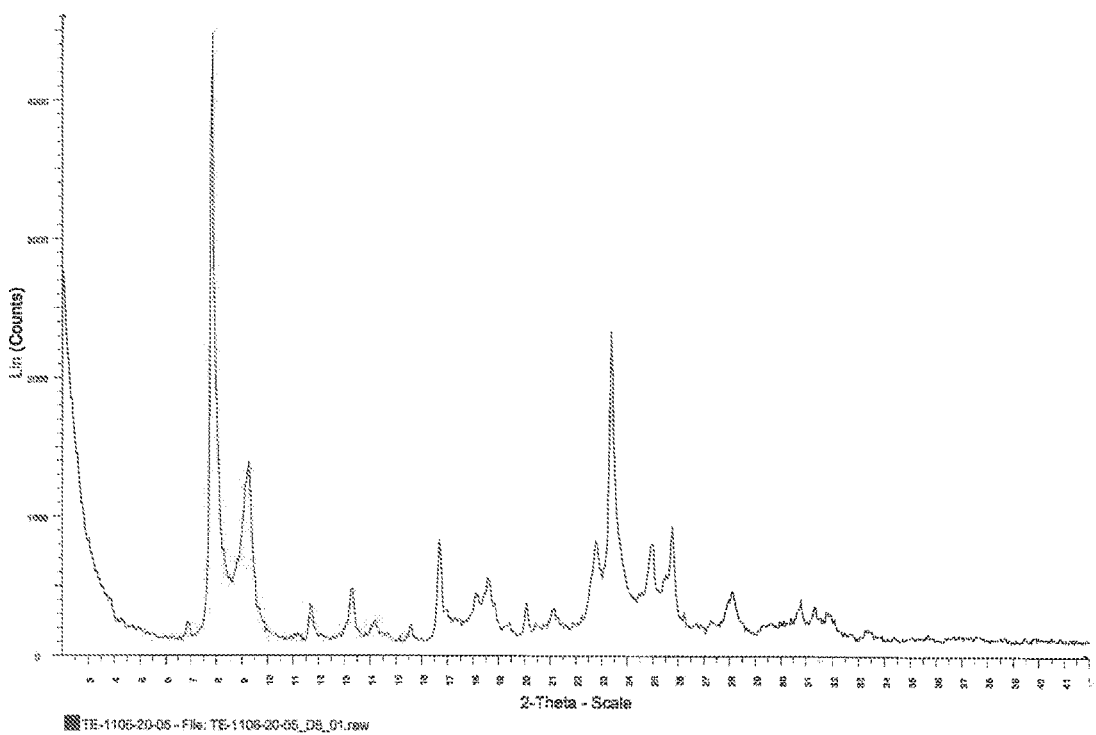
FIGS. 15A-15C show an X-ray powder diffraction pattern (XRPD) pattern, a differential scanning calorimetry (DSC) graph, and a thermographic analysis (TGA) graph of Pattern 2, a solvate of a hydrochloride salt of (S)-2-(1-(9H-purin-6-ylamino)propyl)-5-fluoro-3-phenylquinazolin-4(3H)-one.
Figure 15B:
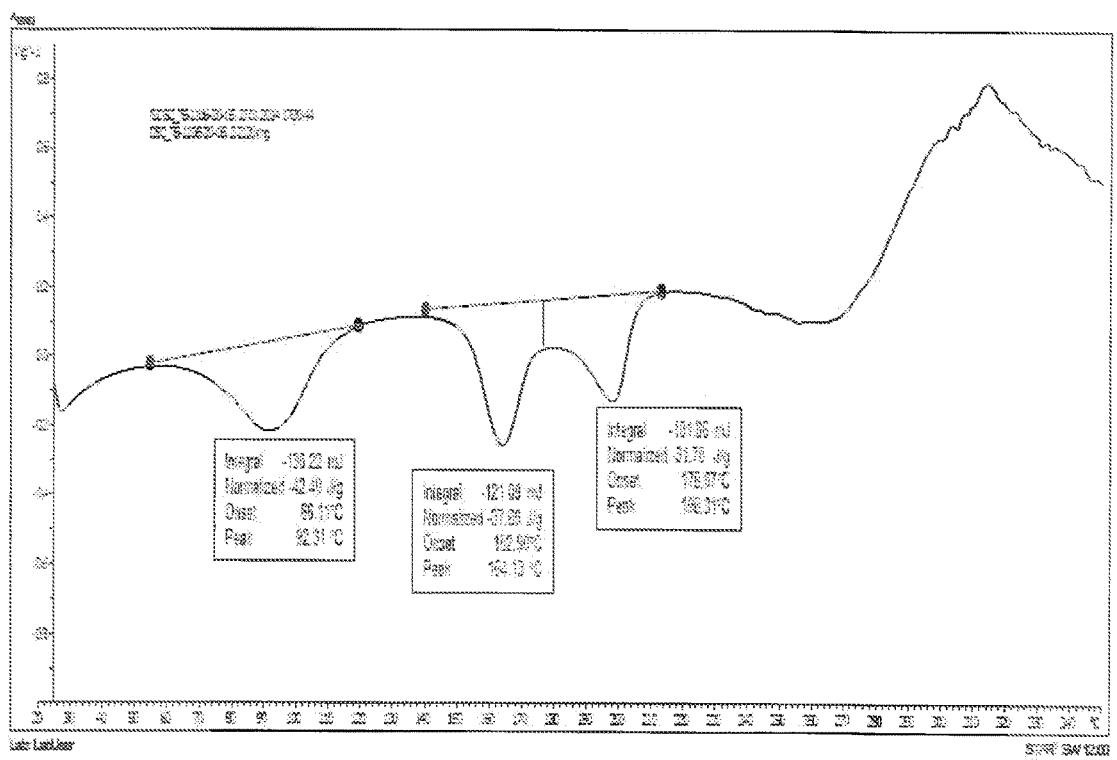
Figure 15C:
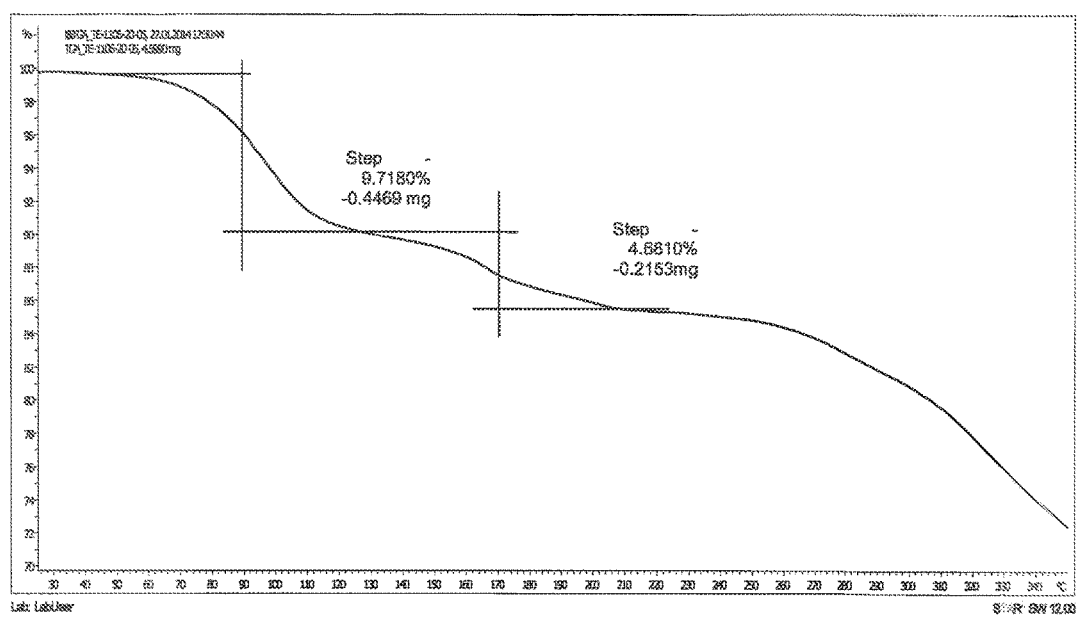

In one aspect, provided is Pattern 2 of the polymorphic Form I of a hydrochloride salt of (S)-2-(1-(9H-purin-6-ylamino)propyl)-5-fluoro-3-phenylquinazolin-4(3H)-one, wherein the polymorph exhibits an X-ray powder diffraction (XRPD) pattern substantially as shown in FIG. 15A. Pattern 2 may exhibit a differential scanning calorimetry (DSC) thermogram substantially as shown in FIG. 15B. Pattern 2 may exhibit a thermographic analysis (TGA) graph substantially as shown in FIG. 15C.

In some embodiments, Pattern 2 is a prepared in the presence of isopropyl acetate. In some embodiments, Pattern 2 corresponds to an isopropyl acetate solvate of the hydrochloride salt of (S)-2-(1-(9H-purin-6-ylamino)propyl)-5-fluoro-3-phenylquinazolin-4(3H)-one.

In some embodiments of Pattern 2, at least one, at least two, at least three, at least four, at least five, or all of the following (a)-(f) apply: (a) Pattern 2 has an XRPD pattern substantially as shown in FIG. 15A; (b) Pattern 2 has a DSC thermogram substantially as shown in FIG. 15B; (c) Pattern 2 has a TGA graph substantially as shown in FIG. 15C; (d) Form 2 has a melting temperature onset as determined by DSC at about 68° C.; (e) Pattern 2 has a second melting temperature onset as determined by DSC at about 153° C.; and (f) Pattern 2 has a third melting temperature onset as determined by DSC at about 179° C.

In some embodiments, Pattern 2 has at least one or both of the following properties:
  (a) an XRPD pattern substantially as shown in FIG. 15A;
  (b) a DSC thermogram substantially as shown in FIG. 15B;

In some embodiments, Pattern 2 has an XRPD pattern displaying at least two, at least three, at least four, at least five, or at least six of the degree 2θ-reflections with the greatest intensity as the XRPD pattern substantially as shown in FIG. 15A. It should be understood that relative intensities can vary depending on a number of factors, including sample preparation, mounting, and the instrument and analytical procedure and settings used to obtain the spectrum. As such, the peak assignments listed herein, including for Pattern 2, are intended to encompass variations of +/−0.2 degrees 2θ.

In certain embodiments, Pattern 2 has an XRPD pattern comprising degree 2θ-reflections (+/−0.2 degrees 2θ) at 7.8, 23.4, 9.2, 25.8, and 16.7. In one embodiment, Pattern 2 has an XRPD pattern comprising degree 2θ-reflections (+/−0.2 degrees 2θ) at 7.8, 23.4, 9.2, 25.8, and 16.7 and one or more of the degree 2θ-reflections (+/−0.2 degrees 2θ) at 22.8, 25.0, 18.6, 13.3, and 28.1. In one embodiment, Pattern 2 has an XRPD pattern comprising degree 2θ-reflections (+/−0.2 degrees 2θ) at 7.8, 23.4, 9.2, 25.8, and 16.7 and one of the degree 2θ-reflections (+/−0.2 degrees 2θ) at 22.8, 25.0, 18.6, 13.3, and 28.1. In one embodiment, Pattern 2 has an XRPD pattern comprising degree 2θ-reflections (+/−0.2 degrees 2θ) at 7.8, 23.4, 9.2, 25.8, and 16.7 and two of the degree 2θ-reflections (+/−0.2 degrees 2θ) at 22.8, 25.0, 18.6, 13.3, and 28.1. In one embodiment, Pattern 2 has an XRPD pattern comprising degree 2θ-reflections (+/−0.2 degrees 2θ) at 7.8, 23.4, 9.2, 25.8, and 16.7 and three of the degree 2θ-reflections (+/−0.2 degrees 2θ) at 22.8, 25.0, 18.6, 13.3, and 28.1. In one embodiment, Pattern 2 has an XRPD pattern comprising degree 2θ-reflections (+/−0.2 degrees 2θ) at 7.8, 23.4, 9.2, 25.8, 16.7, 22.8, 25.0, 18.6, 13.3, and 28.1. Table 3 shows the full XRPD peak list for Pattern 2.

TABLE 3

XRPD Peak List for Pattern 2

| Angle (2-Theta °) | Intensity (%) |
|---|---|
| 6.8 | 5.2 |
| 7.8 | 100.0 |
| 9.2 | 31.0 |
| 11.6 | 8.2 |
| 13.3 | 10.5 |
| 14.1 | 5.4 |
| 15.6 | 4.7 |
| 16.7 | 18.4 |
| 18.1 | 9.9 |
| 18.6 | 12.4 |
| 20.1 | 8.3 |
| 21.1 | 7.5 |
| 22.8 | 18.3 |
| 23.4 | 52.1 |
| 25.0 | 17.8 |
| 25.8 | 20.6 |
| 28.1 | 10.2 |

Pattern 3

Figure 16A:
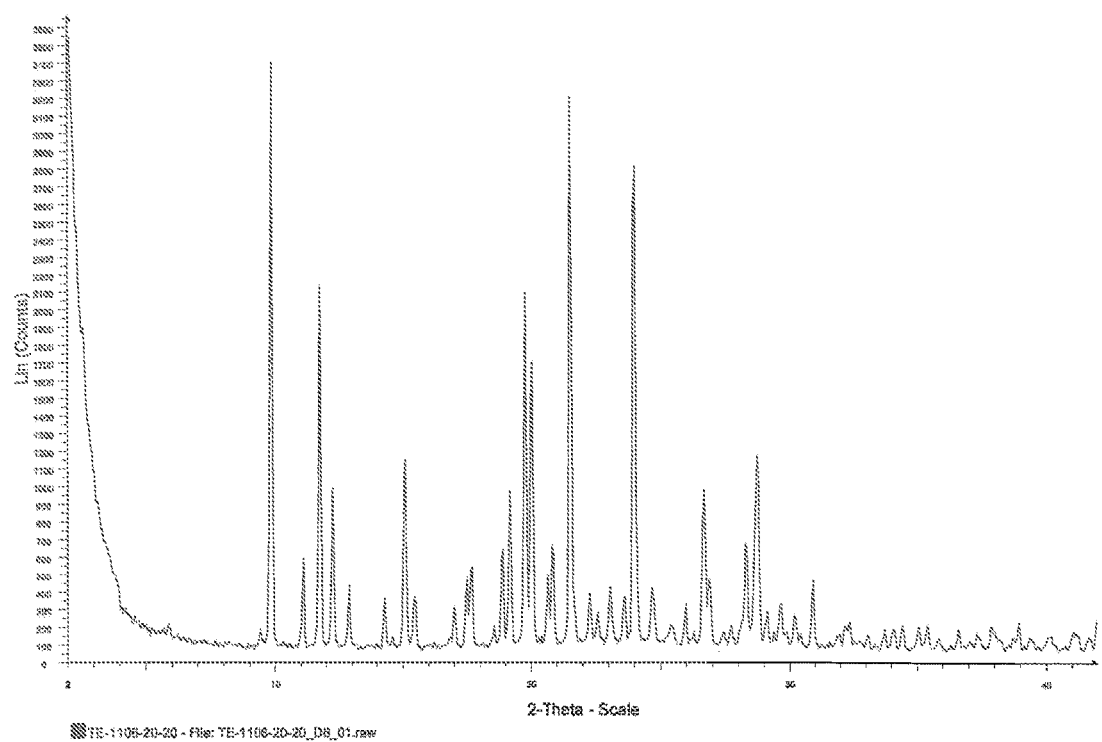
FIGS. 16A-16C show an X-ray powder diffraction pattern (XRPD) pattern, a differential scanning calorimetry (DSC) graph, and a thermographic analysis (TGA) graph of Pattern 3, a solvate of a hydrochloride salt of (S)-2-(1-(9H-purin-6-ylamino)propyl)-5-fluoro-3-phenylquinazolin-4(3H)-one.
Figure 16B:
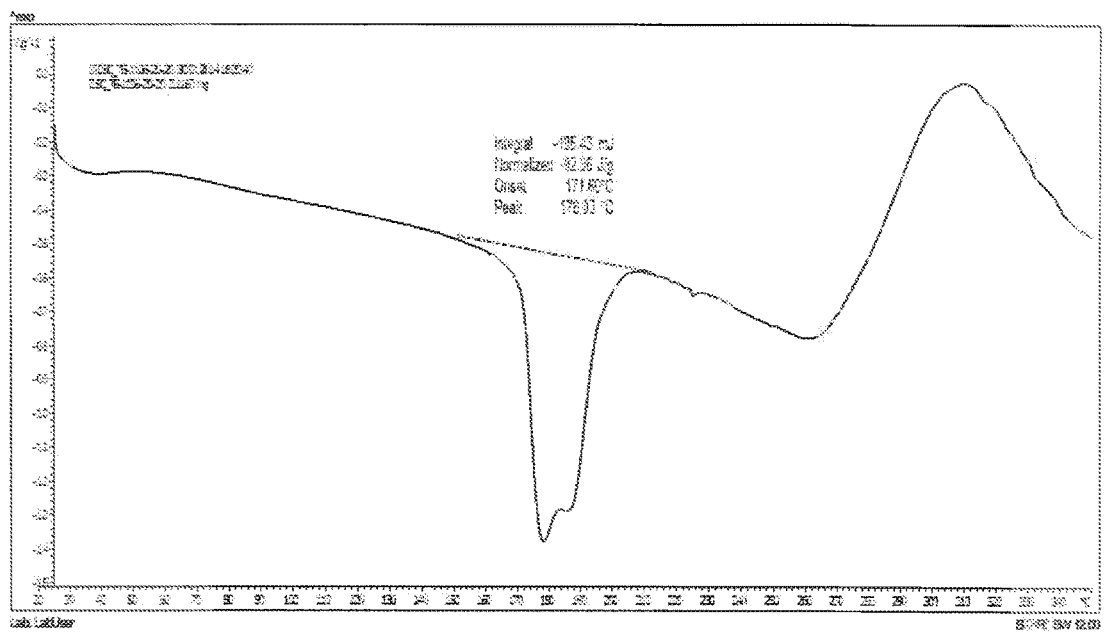
Figure 16C:
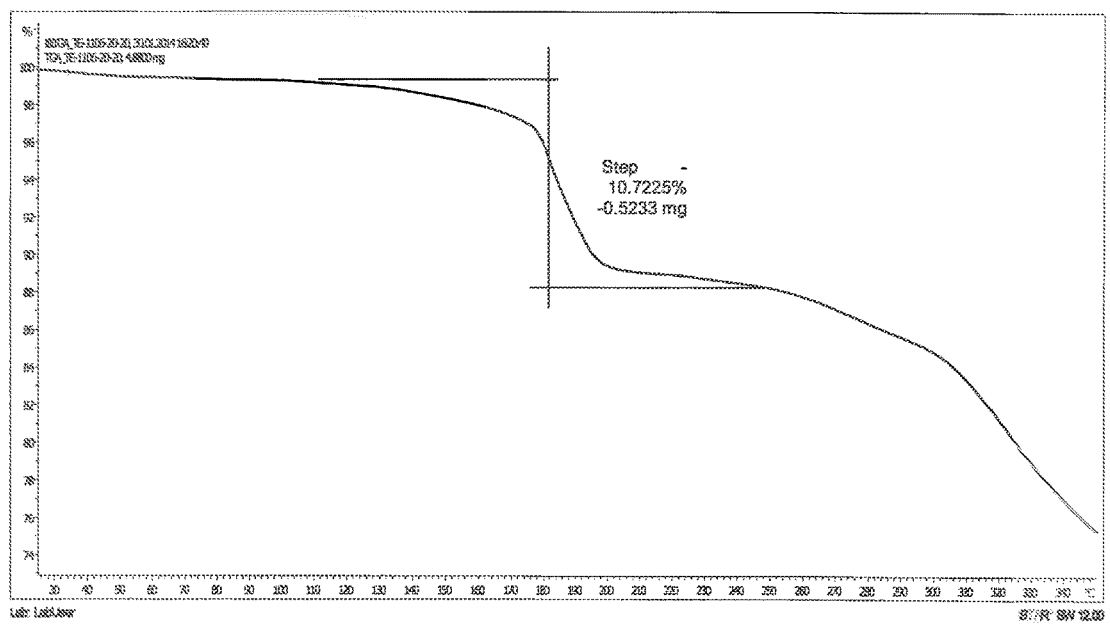

In one aspect, provided is Pattern 3 of the polymorphic Form I of a hydrochloride salt of (S)-2-(1-(9H-purin-6-ylamino)propyl)-5-fluo-3-phenylquinazolin-4(3H)-one, wherein the polymorph exhibits an X-ray powder diffraction (XRPD) pattern substantially as shown in FIG. 16A. Pattern 3 may exhibit a differential scanning calorimetry (DSC) thermogram substantially as shown in FIG. 16B. Pattern 3 may exhibit a thermographic analysis (TGA) graph substantially as shown in FIG. 16C.

In some embodiments, Pattern 3 is a prepared in the presence of 1,2-dimethoxyethane. In some embodiments, Pattern 3 corresponds to an 1,2-dimethoxyethane solvate of the hydrochloride salt of (S)-2-(1-(9H-purin-6-ylamino)propyl)-5-fluoro-3-phenylquinazolin-4(3H)-one.

In some embodiments of Pattern 3, at least one, at least two, at least three, or all of the following (a)-(d) apply: (a) Pattern 3 has an XRPD pattern substantially as shown in FIG. 16A; (b) Pattern 3 has a DSC thermogram substantially as shown in FIG. 16B; (c) Pattern 3 has a TGA graph substantially as shown in FIG. 16C; and (d) Pattern 3 has a melting temperature onset as determined by DSC at about 172° C.

In some embodiments, Pattern 3 has at least one or both of the following properties:
  (a) an XRPD pattern substantially as shown in FIG. 16A;
  (b) a DSC thermogram substantially as shown in FIG. 16B;

In some embodiments, Pattern 3 has an XRPD pattern displaying at least two, at least three, at least four, at least five, or at least six of the degree 2θ-reflections with the greatest intensity as the XRPD pattern substantially as shown in FIG. 16A. It should be understood that relative intensities can vary depending on a number of factors, including sample preparation, mounting, and the instrument and analytical procedure and settings used to obtain the spectrum. As such, the peak assignments listed herein, including for Pattern 3, are intended to encompass variations of +/−0.2 degrees 2θ.

In certain embodiments, Pattern 3 has an XRPD pattern comprising degree 2θ-reflections (+/−0.2 degrees 2θ) at 9.8, 21.5, 24.0, 11.7, and 19.7. In one embodiment, Pattern 3 has an XRPD pattern comprising degree 2θ-reflections (+/−0.2 degrees 2θ) at 9.8, 21.5, 24.0, 11.7, and 19.7 and one or more of the degree 2θ-reflections (+/−0.2 degrees 2θ) at 20.0, 28.7, 15.1, 12.2, and 26.7. In one embodiment, Pattern 3 has an XRPD pattern comprising degree 2θ-reflections (+/−0.2 degrees 2θ) at 9.8, 21.5, 24.0, 11.7, and 19.7 and one of the degree 2θ-reflections (+/−0.2 degrees 2θ) at 20.0, 28.7, 15.1, 12.2, and 26.7. In one embodiment, Pattern 3 has an XRPD pattern comprising degree 2θ-reflections (+/−0.2 degrees 2θ) at 9.8, 21.5, 24.0, 11.7, and 19.7 and two of the degree 2θ-reflections (+/−0.2 degrees 2θ) at 20.0, 28.7, 15.1, 12.2, and 26.7. In one embodiment, Pattern 3 has an XRPD pattern comprising degree 2θ-reflections (+/−0.2 degrees 2θ) at 9.8, 21.5, 24.0, 11.7, and 19.7 and three of the degree 2θ-reflections (+/−0.2 degrees 2θ) at 20.0, 28.7, 15.1, 12.2, and 26.7. In one embodiment, Pattern 3 has an XRPD pattern comprising degree 2θ-reflections (+/−0.2 degrees 2θ) at 9.8, 21.5, 24.0, 11.7, 19.7, 20.0, 28.7, 15.1, 12.2, and 26.7. Table 4 shows the full XRPD peak list for Pattern 3.

TABLE 4

XRPD Peak List for Pattern 3

| Angle (2-Theta °) | Intensity (%) |
|---|---|
| 9.4 | 5.3 |
| 9.8 | 100.0 |
| 11.1 | 17.6 |
| 11.7 | 62.8 |
| 12.2 | 28.9 |
| 12.9 | 12.6 |

TABLE 4-continued

XRPD Peak List for Pattern 3

| Angle (2-Theta °) | Intensity (%) |
|---|---|
| 14.3 | 10.8 |
| 14.6 | 4.1 |
| 15.1 | 33.6 |
| 15.4 | 10.7 |
| 17.0 | 9.1 |
| 17.4 | 14.1 |
| 17.7 | 15.7 |
| 18.5 | 5.9 |
| 18.9 | 18.7 |
| 19.1 | 28.6 |
| 19.7 | 61.5 |
| 20.0 | 50.1 |
| 20.6 | 14.4 |
| 20.9 | 19.5 |
| 21.5 | 94.2 |
| 22.3 | 11.6 |
| 22.6 | 8.1 |
| 23.0 | 12.6 |
| 23.6 | 10.8 |
| 24.0 | 82.7 |
| 24.7 | 12.2 |
| 25.4 | 6.1 |
| 26.0 | 9.6 |
| 26.3 | 5.0 |
| 26.7 | 28.7 |
| 27.4 | 5.0 |
| 27.7 | 6.1 |
| 28.3 | 19.9 |
| 28.7 | 34.5 |
| 29.1 | 8.5 |
| 29.7 | 9.6 |

Pattern 4

Figure 17A:
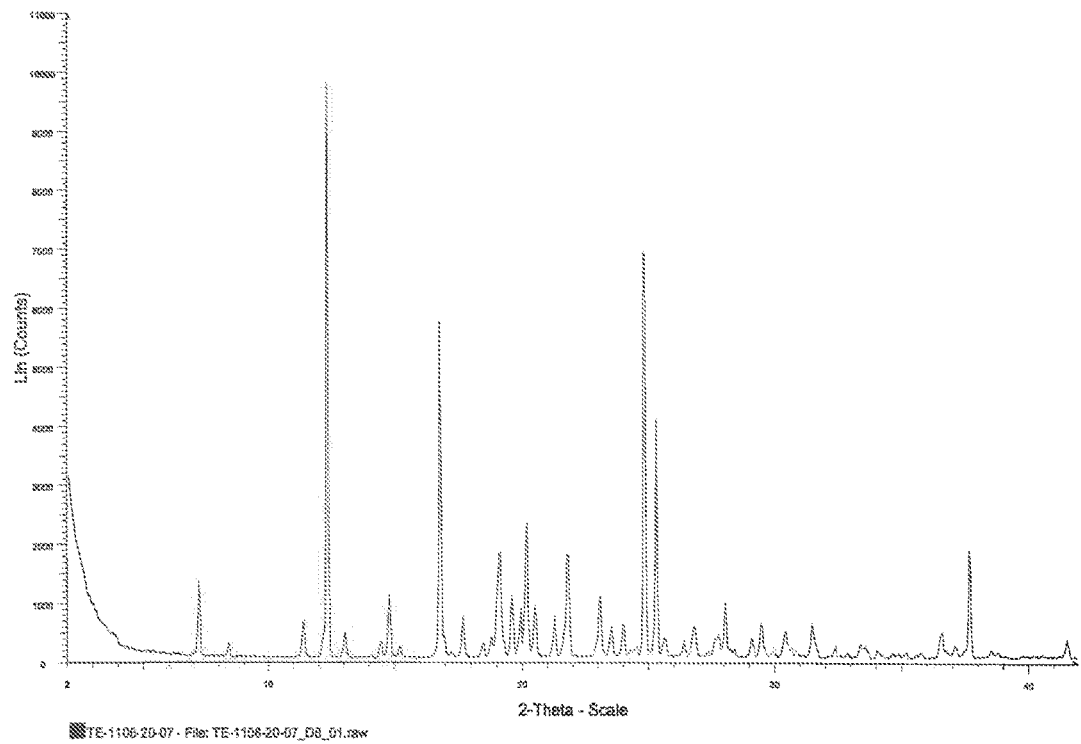
FIGS. 17A-17C show an X-ray powder diffraction pattern (XRPD) pattern, a differential scanning calorimetry (DSC) graph, and a thermographic analysis (TGA) graph of Pattern 4, a solvate of a hydrochloride salt of (S)-2-(1-(9H-purin-6-ylamino)propyl)-5-fluoro-3-phenylquinazolin-4(3H)-one.

In one aspect, provided is Pattern 4 of the polymorphic Form I of a hydrochloride salt of (S)-2-(1-(9H-purin-6-ylamino)propyl)-5-fluoro-3-phenylquinazolin-4(3H)-one, wherein the polymorph exhibits an X-ray powder diffraction (XRPD) pattern substantially as shown in FIG. 17A.

Figure 17B:
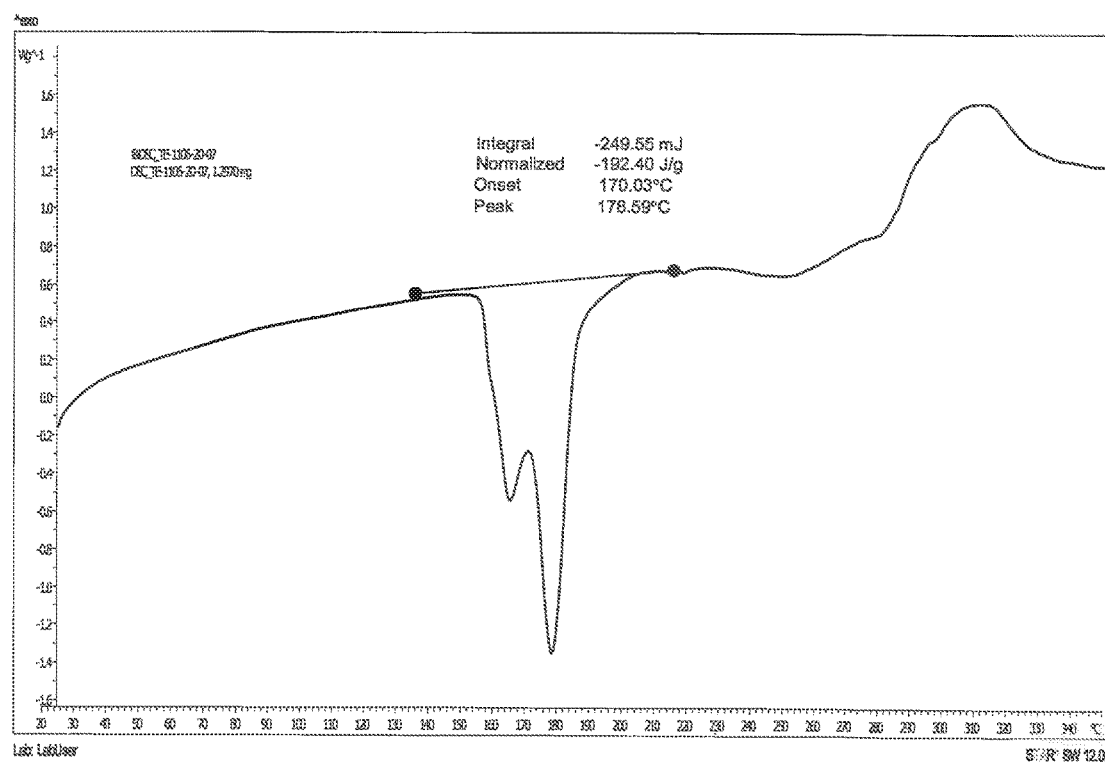
Figure 17C:
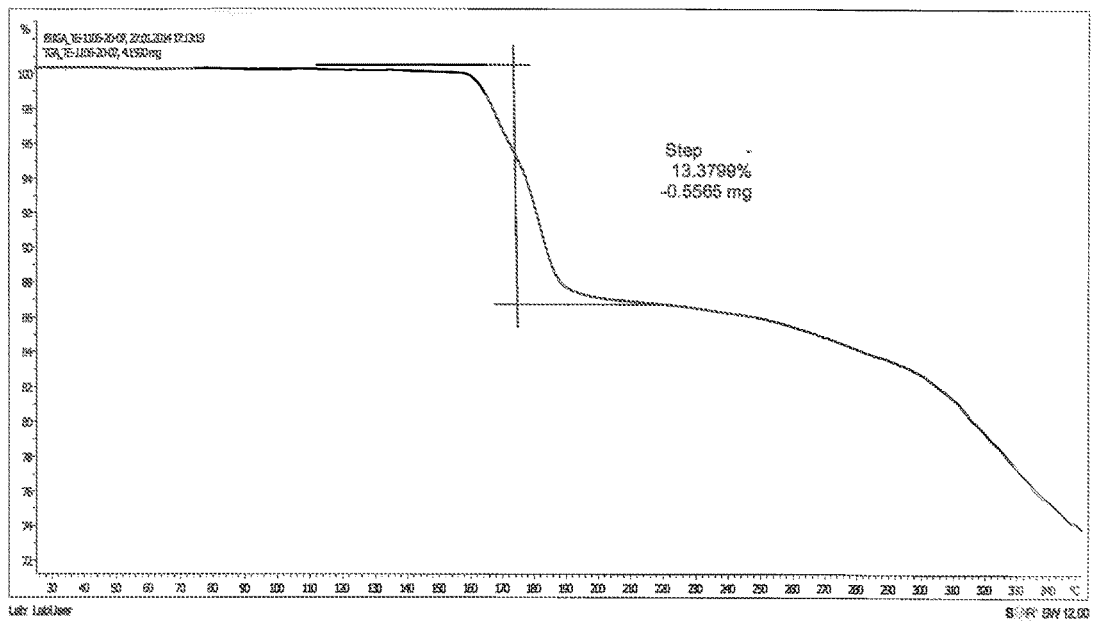

Pattern 4 may exhibit a differential scanning calorimetry (DSC) thermogram substantially as shown in FIG. 17B. Pattern 4 may exhibit a thermographic analysis (TGA) graph substantially as shown in FIG. 17C.

In some embodiments, Pattern 4 is a prepared in the presence of isopropyl alcohol. In some embodiments, Pattern 4 corresponds to an isopropyl alcohol solvate of the hydrochloride salt of (S)-2-(1-(9H-purin-6-ylamino)propyl)-5-fluoro-3-phenylquinazolin-4(3H)-one.

In some embodiments of Pattern 4, at least one, at least two, at least three, or all of the following (a)-(d) apply: (a) Pattern 4 has an XRPD pattern substantially as shown in FIG. 17A; (b) Pattern 4 has a DSC thermogram substantially as shown in FIG. 17B; (c) Pattern 4 has a TGA graph substantially as shown in FIG. 17C; and (d) Pattern 4 has a melting temperature onset as determined by DSC at about 170° C.

In some embodiments, Pattern 4 has at least one or both of the following properties:
 (a) an XRPD pattern substantially as shown in FIG. 17A;
 (b) a DSC thermogram substantially as shown in FIG. 17B;

In some embodiments, Pattern 4 has an XRPD pattern displaying at least two, at least three, at least four, at least five, or at least six of the degree 2θ-reflections with the greatest intensity as the XRPD pattern substantially as shown in FIG. 17A. It should be understood that relative intensities can vary depending on a number of factors, including sample preparation, mounting, and the instrument and analytical procedure and settings used to obtain the spectrum. As such, the peak assignments listed herein, including for Pattern 4, are intended to encompass variations of +/−0.2 degrees 2θ.

In certain embodiments, Pattern 4 has an XRPD pattern comprising degree 2θ-reflections (+/−0.2 degrees 2θ) at 12.3, 24.9, 16.8, 25.3, and 20.2. In one embodiment, Pattern 4 has an XRPD pattern comprising degree 2θ-reflections (+/−0.2 degrees 2θ) at 12.3, 24.9, 16.8, 25.3, and 20.2 and one or more of the degree 2θ-reflections (+/−0.2 degrees 2θ) at 19.1, 21.8, 7.2, 14.8, and 19.6. In one embodiment, Pattern 4 has an XRPD pattern comprising degree 2θ-reflections (+/−0.2 degrees 2θ) at 12.3, 24.9, 16.8, 25.3, and 20.2 and one of the degree 2θ-reflections (+/−0.2 degrees 2θ) at 19.1, 21.8, 7.2, 14.8, and 19.6. In one embodiment, Pattern 4 has an XRPD pattern comprising degree 2θ-reflections (+/−0.2 degrees 2θ) at 12.3, 24.9, 16.8, 25.3, and 20.2 and two of the degree 2θ-reflections (+/−0.2 degrees 2θ) at 19.1, 21.8, 7.2, 14.8, and 19.6. In one embodiment, Pattern 4 has an XRPD pattern comprising degree 2θ-reflections (+/−0.2 degrees 2θ) at 12.3, 24.9, 16.8, 25.3, and 20.2 and three of the degree 2θ-reflections (+/−0.2 degrees 2θ) at 19.1, 21.8, 7.2, 14.8, and 19.6. In one embodiment, Pattern 4 has an XRPD pattern comprising degree 2θ-reflections (+/−0.2 degrees 2θ) at 12.3, 24.9, 16.8, 25.3, 20.2, 19.1, 21.8, 7.2, 14.8, and 19.6. Table 5 shows the full XRPD peak list for Pattern 4.

TABLE 5

XRPD Peak List for Pattern 4

| Angle (2-Theta °) | Intensity (%) |
|---|---|
| 7.2 | 13.8 |
| 8.4 | 3.1 |
| 11.4 | 7.0 |
| 12.3 | 100.0 |
| 13.0 | 5.1 |
| 14.5 | 3.4 |
| 14.8 | 11.3 |
| 15.2 | 2.6 |
| 16.8 | 58.7 |
| 17.3 | 1.8 |
| 17.7 | 7.9 |
| 18.5 | 3.2 |
| 18.8 | 4.4 |
| 19.1 | 18.9 |
| 19.6 | 11.3 |
| 19.9 | 9.1 |
| 20.2 | 24.2 |
| 20.5 | 9.7 |
| 21.3 | 7.7 |
| 21.8 | 18.5 |
| 23.0 | 11.3 |
| 23.5 | 6.0 |
| 24.0 | 6.3 |
| 24.5 | 2.8 |
| 24.9 | 70.9 |
| 25.3 | 42.0 |
| 25.7 | 4.2 |
| 26.4 | 3.6 |
| 26.8 | 6.1 |
| 27.4 | 1.8 |
| 27.8 | 4.7 |
| 28.0 | 10.3 |
| 28.3 | 2.2 |
| 29.1 | 4.2 |
| 29.5 | 6.6 |

2-Methyl-1-propanol Solvate

Figure 18A:
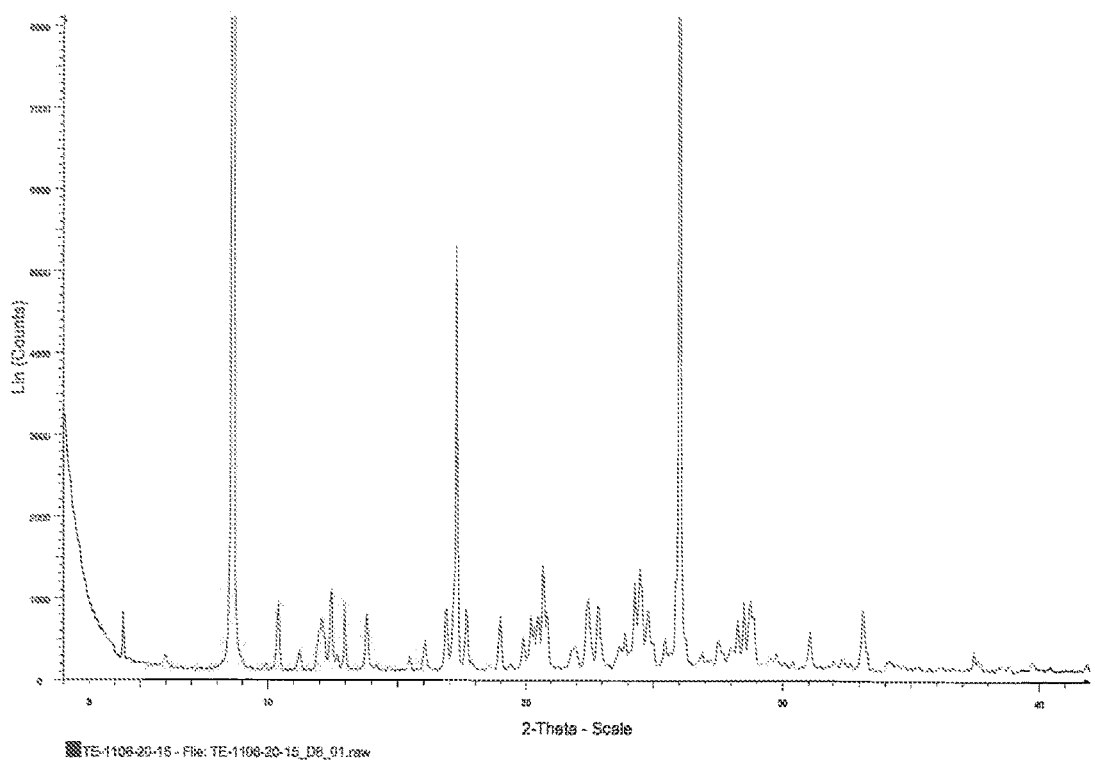
FIGS. 18A-18D show an X-ray powder diffraction pattern (XRPD) pattern, a differential scanning calorimetry (DSC) graph, a thermographic analysis (TGA) graph, and an X-ray powder diffraction pattern (XRPD) pattern of a 2-methyl-1-propanol solvate of a hydrochloride salt of (S)-2-(1-(9H-purin-6-ylamino)propyl)-5-fluoro-3-phenylquinazolin-4(3H)-one.
Figure 18B:
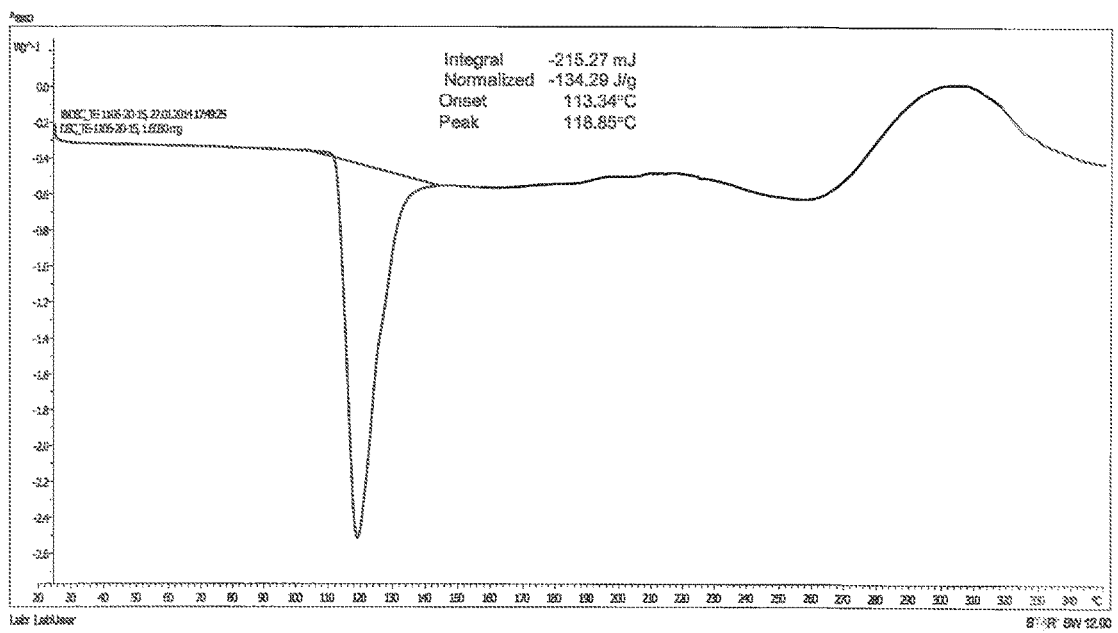
Figure 18C:
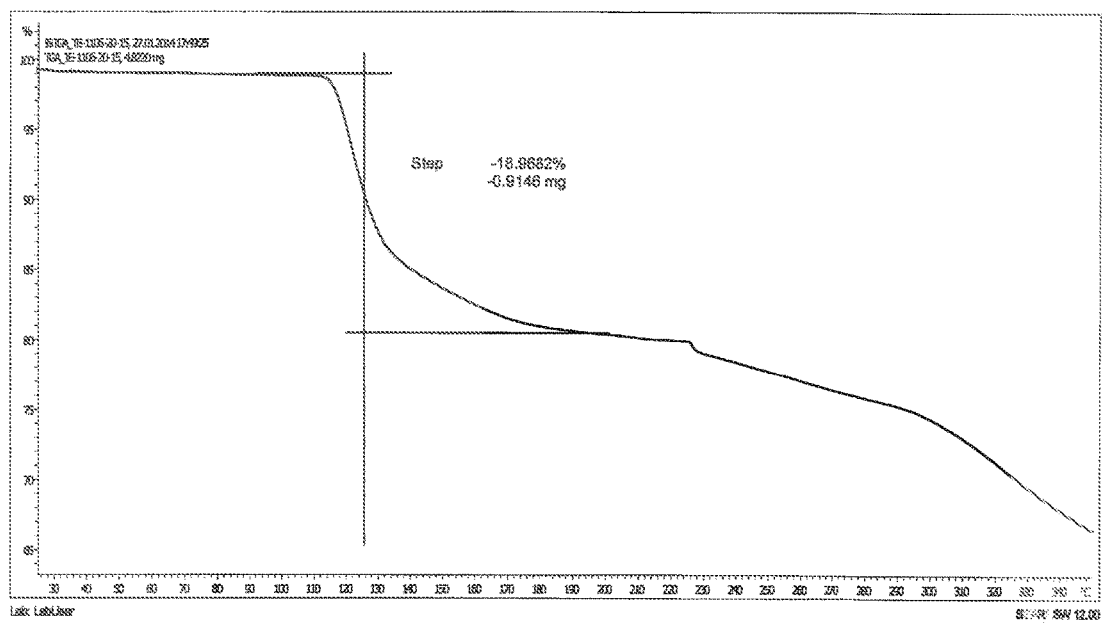

In one aspect, provided is the 2-methyl-1-propanol solvate form of a hydrochloride salt of (S)-2-(1-(9H-purin-6- ylamino)propyl)-5-fluoro-3-phenylquinazolin-4(3H)-one, wherein the polymorph exhibits an X-ray powder diffraction (XRPD) pattern substantially as shown in FIG. 18A. The 2-methyl-1-propanol solvate may exhibit a differential scanning calorimetry (DSC) thermogram substantially as shown in FIG. 18B. The 2-methyl-1-propanol solvate may exhibit a thermographic analysis (TGA) graph substantially as shown in FIG. 18C.

In some embodiments of the 2-methyl-1-propanol solvate, at least one, at least two, at least three, or all of the following (a)-(d) apply: (a) 2-methyl-1-propanol solvate has an XRPD pattern substantially as shown in FIG. 18A; (b) 2-methyl-1-propanol solvate has a DSC thermogram substantially as shown in FIG. 18B; (c) 2-methyl-1-propanol solvate has a TGA graph substantially as shown in FIG. 18C; and (d) 2-methyl-1-propanol solvate has a melting temperature onset as determined by DSC at about 113° C.

In some embodiments, the 2-methyl-1-propanol solvate has at least one or both of the following properties:
 (a) an XRPD pattern substantially as shown in FIG. 18A;
 (b) a DSC thermogram substantially as shown in FIG. 18B;

In some embodiments, the 2-methyl-1-propanol solvate has an XRPD pattern displaying at least two, at least three, at least four, at least five, or at least six of the degree 2θ-reflections with the greatest intensity as the XRPD pattern substantially as shown in FIG. 18A. It should be understood that relative intensities can vary depending on a number of factors, including sample preparation, mounting, and the instrument and analytical procedure and settings used to obtain the spectrum. As such, the peak assignments listed herein, including for the 2-methyl-1-propanol solvate, are intended to encompass variations of +/−0.2 degrees 2θ.

In certain embodiments, the 2-methyl-1-propanol solvate has an XRPD pattern comprising degree 2θ-reflections (+/−0.2 degrees 2θ) at 8.6, 26.0, 17.3, 20.7, and 24.5. In one embodiment, the 2-methyl-1-propanol solvate has an XRPD pattern comprising degree 2θ-reflections (+/−0.2 degrees 2θ) at 8.6, 26.0, 17.3, 20.7, and 24.5 and one or more of the degree 2θ-reflections (+/−0.2 degrees 2θ) at 24.3, 12.4, 22.5, 12.9, and 28.5. In one embodiment, the 2-methyl-1-propanol solvate has an XRPD pattern comprising degree 2θ-reflections (+/−0.2 degrees 2θ) at 8.6, 26.0, 17.3, 20.7, and 24.5 and one of the degree 2θ-reflections (+/−0.2 degrees 2θ) at 24.3, 12.4, 22.5, 12.9, and 28.5. In one embodiment, the 2-methyl-1-propanol solvate has an XRPD pattern comprising degree 2θ-reflections (+/−0.2 degrees 2θ) at 8.6, 26.0, 17.3, 20.7, and 24.5 and two of the degree 2θ-reflections (+/−0.2 degrees 2θ) at 24.3, 12.4, 22.5, 12.9, and 28.5. In one embodiment, the 2-methyl-1-propanol solvate has an XRPD pattern comprising degree 2θ-reflections (+/−0.2 degrees 2θ) at 8.6, 26.0, 17.3, 20.7, and 24.5 and three of the degree 2θ-reflections (+/−0.2 degrees 2θ) at 24.3, 12.4, 22.5, 12.9, and 28.5. In one embodiment, the 2-methyl-1-propanol solvate has an XRPD pattern comprising degree 2θ-reflections (+/−0.2 degrees 2θ) at 8.6, 26.0, 17.3, 20.7, 24.5, 24.3, 12.4, 22.5, 12.9, and 28.5. Table 6 shows the full XRPD peak list for the 2-methyl-1-propanol solvate.

TABLE 6

XRPD Peak List for 2-Methyl-1-propanol Solvate Form

| Angle (2-Theta °) | Intensity (%) |
| --- | --- |
| 4.3 | 2.9 |
| 5.9 | 1.0 |
| 8.6 | 100.0 |
| 9.9 | 0.7 |
| 10.3 | 3.2 |
| 11.2 | 1.2 |
| 12.1 | 2.6 |
| 12.4 | 3.8 |
| 12.7 | 1.1 |
| 12.9 | 3.3 |
| 13.8 | 2.8 |
| 14.1 | 0.6 |
| 14.6 | 0.5 |
| 15.4 | 0.9 |
| 16.0 | 1.6 |
| 16.9 | 3.0 |
| 17.3 | 18.5 |
| 17.7 | 3.0 |
| 17.9 | 0.9 |
| 18.5 | 0.7 |
| 18.9 | 2.7 |
| 19.4 | 0.6 |
| 19.9 | 1.8 |
| 20.2 | 2.7 |
| 20.5 | 2.8 |
| 20.7 | 4.8 |
| 20.9 | 2.9 |
| 21.9 | 1.4 |
| 22.5 | 3.4 |
| 22.8 | 3.2 |
| 23.7 | 1.4 |
| 23.9 | 1.9 |
| 24.3 | 4.1 |
| 24.5 | 4.7 |
| 24.8 | 2.9 |
| 25.4 | 1.7 |
| 26.0 | 60.2 |
| 26.9 | 1.2 |
| 27.6 | 1.7 |
| 28.0 | 1.4 |
| 28.3 | 2.6 |
| 28.5 | 3.3 |
| 28.8 | 3.3 |
| 29.6 | 1.0 |
| 29.8 | 1.1 |

1,4-Dioxane Solvate

Figure 19A:
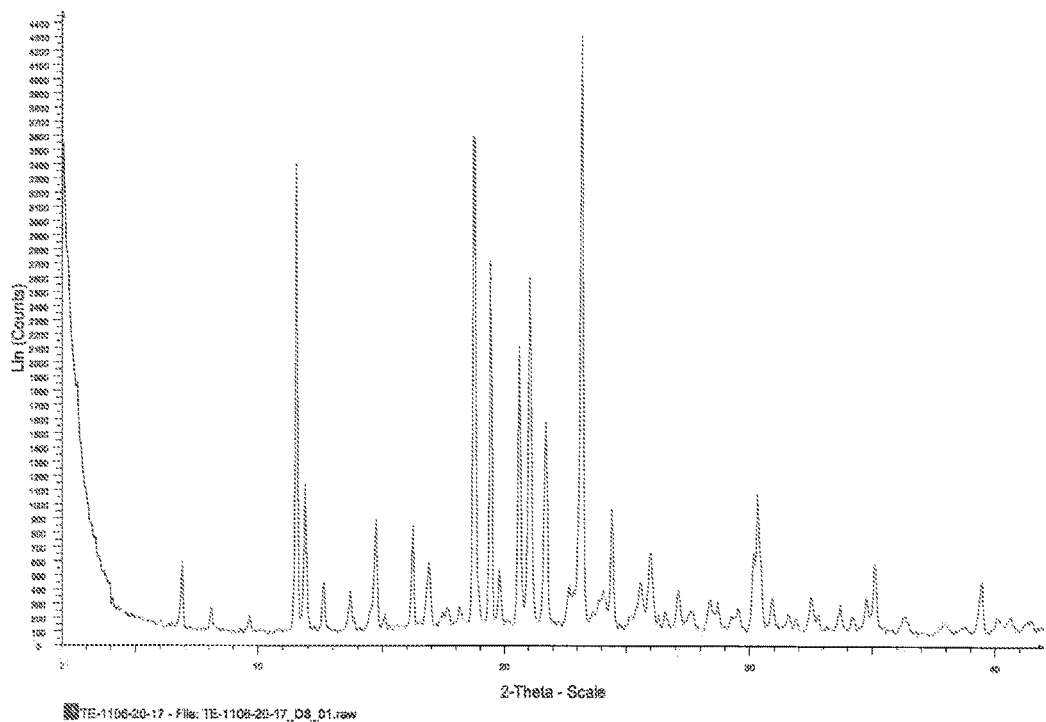
FIGS. 19A-19C show an X-ray powder diffraction pattern (XRPD) pattern, a differential scanning calorimetry (DSC) graph, and a thermographic analysis (TGA) graph of a 1,4-dioxane solvate of a hydrochloride salt of (S)-2-(1-(9H-purin-6-ylamino)propyl)-5-fluoro-3-phenylquinazolin-4(3H)-one.
Figure 19B:
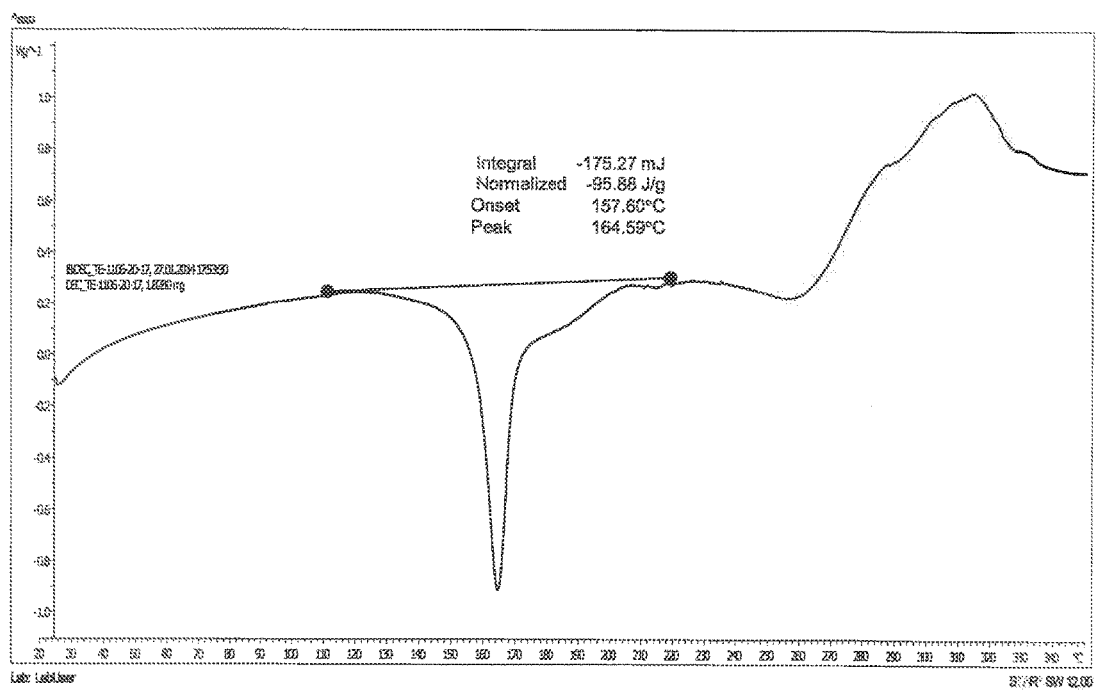
Figure 19C:
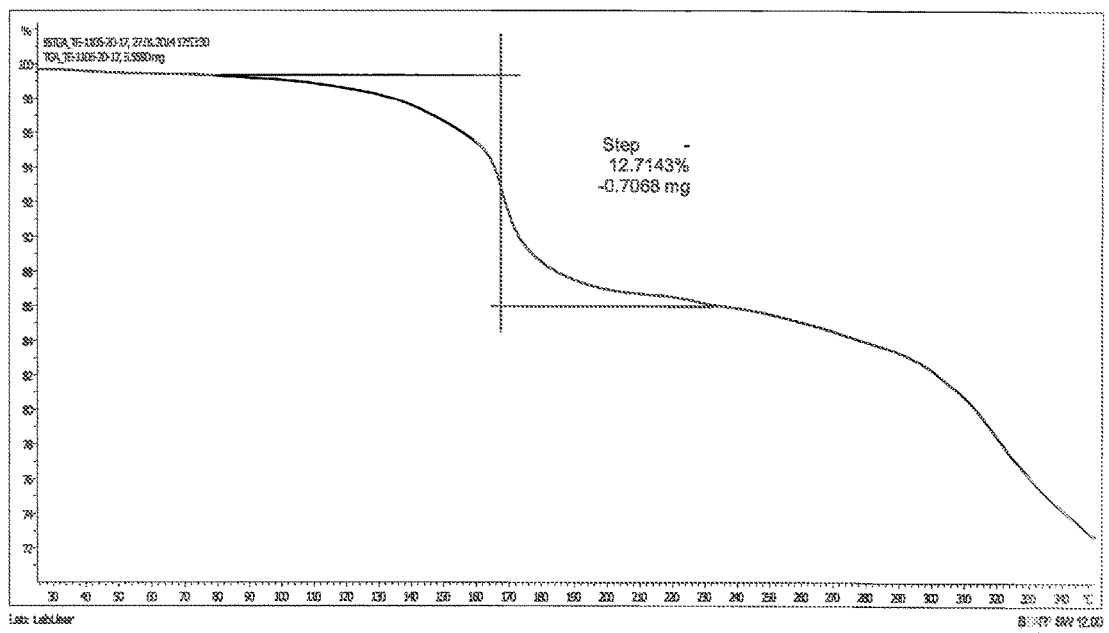

In one aspect, provided is the 1,4-dioxane solvate form of a hydrochloride salt of (S)-2-(1-(9H-purin-6-ylamino)propyl)-5-fluoro-3-phenylquinazolin-4(3H)-one, wherein the polymorph exhibits an X-ray powder diffraction (XRPD) pattern substantially as shown in FIG. 19A. The 1,4-dioxane solvate may exhibit a differential scanning calorimetry (DSC) thermogram substantially as shown in FIG. 19B. The 1,4-dioxane solvate may exhibit a thermographic analysis (TGA) graph substantially as shown in FIG. 19C.

In some embodiments of the 1,4-dioxane solvate, at least one, at least two, at least three, or all of the following (a)-(d) apply: (a) 1,4-dioxane solvate has an XRPD pattern substantially as shown in FIG. 19A; (b) 1,4-dioxane solvate has a DSC thermogram substantially as shown in FIG. 19B; (c) 1,4-dioxane solvate has a TGA graph substantially as shown in FIG. 19C; and (d) 1,4-dioxane solvate has a melting temperature onset as determined by DSC at about 158° C.

In some embodiments, the 1,4-dioxane solvate has at least one or both of the following properties:
 (a) an XRPD pattern substantially as shown in FIG. 19A;
 (b) a DSC thermogram substantially as shown in FIG. 19B;

In some embodiments, the 1,4-dioxane solvate has an XRPD pattern displaying at least two, at least three, at least four, at least five, or at least six of the degree 2θ-reflections with the greatest intensity as the XRPD pattern substantially as shown in FIG. 19A. It should be understood that relative intensities can vary depending on a number of factors, including sample preparation, mounting, and the instrument and analytical procedure and settings used to obtain the spectrum. As such, the peak assignments listed herein, including for the 1,4-dioxane solvate, are intended to encompass variations of +/−0.2 degrees 2θ.

In certain embodiments, the 1,4-dioxane solvate has an XRPD pattern comprising degree 2θ-reflections (+/−0.2 degrees 2θ) at 23.2, 18.8, 11.5, 19.4, and 21.1. In one embodiment, the 1,4-dioxane solvate has an XRPD pattern comprising degree 2θ-reflections (+/−0.2 degrees 2θ) at 23.2, 18.8, 11.5, 19.4, and 21.1 and one or more of the degree 2θ-reflections (+/−0.2 degrees 2θ) at 20.6, 21.7, 11.9, 24.5, and 14.7. In one embodiment, the 1,4-dioxane solvate has an XRPD pattern comprising degree 2θ-reflections (+/−0.2 degrees 2θ) at 23.2, 18.8, 11.5, 19.4, and 21.1 and one of the degree 2θ-reflections (+/−0.2 degrees 2θ) at 20.6, 21.7, 11.9, 24.5, and 14.7. In one embodiment, the 1,4-dioxane solvate has an XRPD pattern comprising degree 2θ-reflections (+/−0.2 degrees 2θ) at 23.2, 18.8, 11.5, 19.4, and 21.1 and two of the degree 2θ-reflections (+/−0.2 degrees 2θ) at 20.6, 21.7, 11.9, 24.5, and 14.7. In one embodiment, the 1,4-dioxane solvate has an XRPD pattern comprising degree 2θ-reflections (+/−0.2 degrees 2θ) at 23.2, 18.8, 11.5, 19.4, and 21.1 and three of the degree 2θ-reflections (+/−0.2 degrees 2θ) at 20.6, 21.7, 11.9, 24.5, and 14.7. In one embodiment, the 1,4-dioxane solvate has an XRPD pattern comprising degree 2θ-reflections (+/−0.2 degrees 2θ) at 23.2, 18.8, 11.5, 19.4, 21.1, 20.6, 21.7, 11.9, 24.5, and 14.7. Table 7 shows the full XRPD peak list for the 1,4-dioxane solvate.

TABLE 7

XRPD Peak List for 1,4-Dioxane Solvate Form

| Angle (2-Theta °) | Intensity (%) |
|---|---|
| 6.9 | 13.6 |
| 8.0 | 6.1 |
| 9.6 | 4.9 |
| 11.5 | 78.6 |
| 11.9 | 26.1 |
| 12.7 | 10.2 |
| 13.7 | 8.7 |
| 14.7 | 20.5 |
| 15.1 | 4.9 |
| 16.2 | 19.4 |
| 16.9 | 13.5 |
| 17.5 | 5.4 |
| 17.7 | 6.2 |
| 18.1 | 6.4 |
| 18.8 | 83.1 |
| 19.4 | 62.8 |
| 19.8 | 12.5 |
| 20.6 | 49.0 |
| 21.1 | 60.0 |
| 21.7 | 36.3 |
| 22.7 | 9.8 |
| 23.2 | 100.0 |
| 24.1 | 9.1 |
| 24.5 | 22.2 |
| 25.2 | 4.8 |
| 25.6 | 10.4 |
| 26.0 | 15.0 |
| 26.3 | 5.2 |
| 26.6 | 5.5 |
| 27.2 | 8.9 |

TABLE 7-continued

XRPD Peak List for 1,4-Dioxane Solvate Form

| Angle (2-Theta °) | Intensity (%) |
|---|---|
| 27.7 | 5.6 |
| 28.4 | 7.4 |
| 28.7 | 7.1 |
| 29.3 | 4.7 |
| 29.6 | 6.1 |

Toluene Solvate

Figure 20:
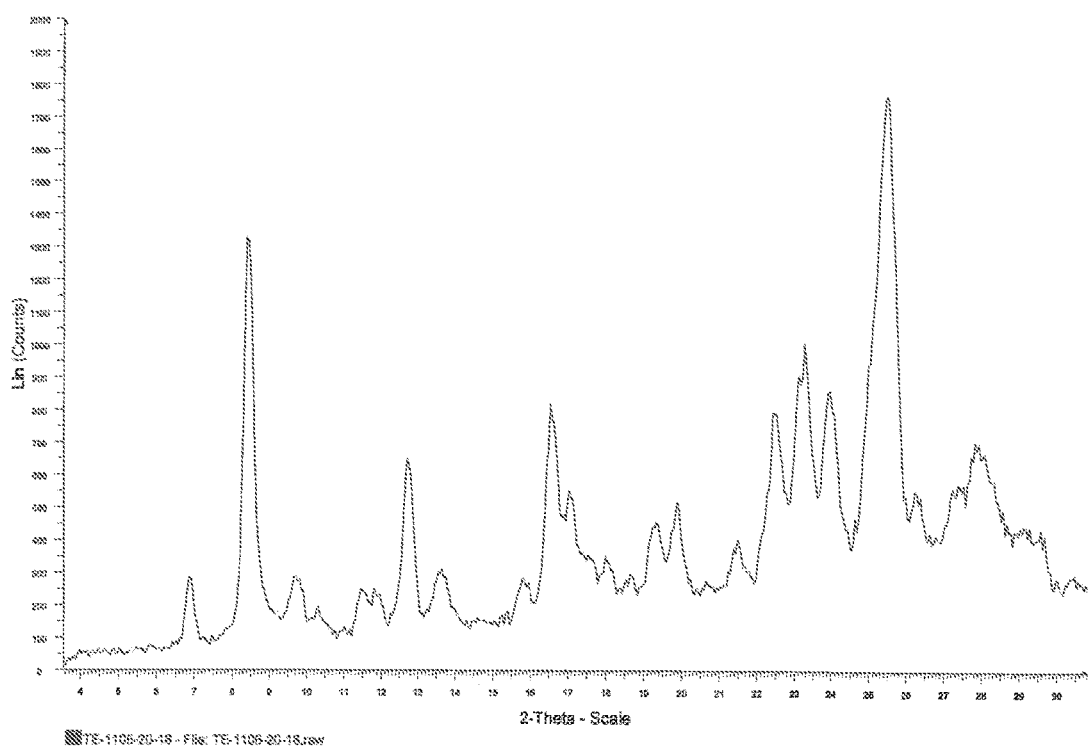
FIG. 20 shows an X-ray powder diffraction pattern (XRPD) pattern of a toluene solvate of a hydrochloride salt of (S)-2-(1-(9H-purin-6-ylamino)propyl)-5-fluoro-3-phenylquinazolin-4(3H)-one.

In one aspect, provided is a toluene solvent form of a hydrochloride salt of (S)-2-(1-(9H-purin-6-ylamino)propyl)-5-fluoro-3-phenylquinazolin-4(3H)-one, wherein the polymorph exhibits an X-ray powder diffraction (XRPD) pattern substantially as shown in FIG. 20.

In some embodiments of the toluene solvent form, the toluene solvent form has an XRPD pattern substantially as shown in FIG. 20.

In some embodiments, the toluene solvent form has an XRPD pattern displaying at least two, at least three, at least four, at least five, or at least six of the degree 2θ-reflections with the greatest intensity as the XRPD pattern substantially as shown in FIG. 20. It should be understood that relative intensities can vary depending on a number of factors, including sample preparation, mounting, and the instrument and analytical procedure and settings used to obtain the spectrum. As such, the peak assignments listed herein, including for the toluene solvent form, are intended to encompass variations of +/−0.2 degrees 2θ.

In certain embodiments the toluene solvent form has an XRPD pattern comprising degree 2θ-reflections (+/−0.2 degrees 2θ) at 25.5, 8.4, 23.3, 23.1, and 24.0. In one embodiment, the toluene solvent form has an XRPD pattern comprising degree 2θ-reflections (+/−0.2 degrees 2θ) at 25.5, 8.4, 23.3, 23.1, and 24.0 and one or more of the degree 2θ-reflections (+/−0.2 degrees 2θ) at 16.6, 22.5, 27.9, 12.7, and 27.5. In one embodiment, the toluene solvent form has an XRPD pattern comprising degree 2θ-reflections (+/−0.2 degrees 2θ) at 25.5, 8.4, 23.3, 23.1, and 24.0 and one of the degree 2θ-reflections (+/−0.2 degrees 2θ) at 16.6, 22.5, 27.9, 12.7, and 27.5. In one embodiment the toluene solvent form has an XRPD pattern comprising degree 2θ-reflections (+/−0.2 degrees 2θ) at 25.5, 8.4, 23.3, 23.1, and 24.0 and two of the degree 2θ-reflections (+/−0.2 degrees 2θ) at 16.6, 22.5, 27.9, 12.7, and 27.5. In one embodiment, the toluene solvent form has an XRPD pattern comprising degree 2θ-reflections (+/−0.2 degrees 2θ) at 25.5, 8.4, 23.3, 23.1, and 24.0 and three of the degree 2θ-reflections (+/−0.2 degrees 2θ) at 16.6, 22.5, 27.9, 12.7, and 27.5. In one embodiment, the toluene solvent form has an XRPD pattern comprising degree 2θ-reflections (+/−0.2 degrees 2θ) at 25.5, 8.4, 23.3, 23.1, 24.0, 16.6, 22.5, 27.9, 12.7, and 27.5. Table 8 shows the full XRPD peak list for the toluene solvent form.

TABLE 8

XRPD Peak List for Toluene Solvent Form

| Angle (2-Theta °) | Intensity (%) |
|---|---|
| 6.9 | 15.9 |
| 8.4 | 75.1 |
| 9.7 | 16.1 |
| 10.3 | 10.7 |
| 11.5 | 13.9 |
| 11.9 | 13.3 |

TABLE 8-continued

XRPD Peak List for Toluene Solvent Form

| Angle (2-Theta °) | Intensity (%) |
|---|---|
| 12.7 | 36.6 |
| 13.6 | 17.4 |
| 15.8 | 15.9 |
| 16.6 | 46.2 |
| 17.1 | 31.0 |
| 18.0 | 19.8 |
| 19.3 | 25.8 |
| 19.9 | 29.2 |
| 21.5 | 22.6 |
| 22.5 | 44.8 |
| 23.1 | 51.3 |
| 23.3 | 56.7 |
| 24.0 | 48.5 |
| 25.5 | 100.0 |
| 26.3 | 31.3 |
| 27.5 | 32.2 |
| 27.9 | 39.7 |
| 29.6 | 24.7 |

Compositions Thereof

Provided are also compositions comprising at least one, at least two, at least three, at least four, at least five, at least six, at least seven, at least eight, at least nine, at least ten, at least eleven, at least twelve, or all of polymorphs (e.g., any one or more of polymorphic Forms I, II, III, IV, V, VI, VII, VIII, IX, XI, XII and XIII) as described herein. In a particular embodiment, a composition comprising one of polymorphic Forms I, II, III, IV, V, VI, VII, VIII, IX, X, XI, XII and XIII described herein is provided. In a particular embodiment, a composition comprising two of polymorphic Forms I, II, III, IV, V, VI, VII, VIII, IX, X, XI, XII and XIII described herein is provided. In a particular embodiment, a composition comprising three of polymorphic Forms I, II, III, IV, V, VI, VII, VIII, IX, X, XI, XII and XIII described herein is provided. In a particular embodiment, a composition comprising four of polymorphic Forms I, II, m, IV, V, VI, VII, VIII, IX, X, XI, XII and XIII described herein is provided. In a particular embodiment, a composition comprising five of polymorphic Forms I, II, III, IV, V, VI, VII, VIII, IX, X, XI, XII and XIII described herein is provided. In a particular embodiment, a composition comprising six of polymorphic Forms I, II, III, IV, V, VI, VII, VIII, IX, X, XI, XII and XIII described herein is provided. In a particular embodiment, a composition comprising seven of polymorphic Forms I, II, III, IV, V, VI, VII, VIII, IX, X, XI, XII and XIII described herein is provided. In a particular embodiment, a composition comprising eight of polymorphic Forms I, II, III, IV, V, VI, VII, VIII, IX, X, XI, XII and XIII described herein is provided. In a particular embodiment, a composition comprising nine of polymorphic Forms I, II, III, IV, V, VI, VII, VIII, IX, X, XI, XII and XIII described herein is provided. In a particular embodiment, a composition comprising ten of polymorphic Forms I, II, III, IV, V, VI, VII, VIII, IX, X, XI, XII and XIII described herein is provided. In a particular embodiment, a composition comprising eleven of polymorphic Forms I, II, III, IV, V, VI, VII, VIII, IX, X, XI, XII and XIII described herein is provided. In a particular embodiment, a composition comprising twelve of polymorphic Forms I, II, III, IV, V, VI, VII, VIII, IX, X, XI, XII and XIII described herein is provided. In other embodiments, the compositions described herein may comprise substantially pure polymorphic forms, or may be substantially free of other polymorphs and/or impurities.

In some embodiments, the term "substantially pure" or "substantially free" with respect to a particular polymorphic form of a compound means that the composition comprising the polymorphic form contains less than 95%, less than 90%, less than 80%, less than 70%, less than 65%, less than 60%, less than 55%, less than 50%, less than 40%, less than 30%, less than 20%, less than 15%, less than 10%, less than 5%, or less than 1% by weight of other substances, including other polymorphic forms and/or impurities. In certain embodiments, "substantially pure" or "substantially free of" refers to a substance free of other substances, including other polymorphic forms and/or impurities. Impurities may, for example, include by-products or left over reagents from chemical reactions, contaminants, degradation products, other polymorphic forms, water, and solvents.

Form I

In some embodiments, the composition comprises polymorphic Form I of a hydrochloride salt of (S)-2-(1-(9H-purin-6-ylamino)propyl)-5-fluoro-3-phenylquinazolin-4(3H)-one. In certain embodiments are provided compositions comprising polymorphic Form I as described herein, wherein the hydrochloride salt of (S)-2-(1-(9H-purin-6-ylamino)propyl)-5-fluoro-3-phenylquinazolin-4(3H)-one within the composition is a substantially pure polymorphic Form I. In particular embodiments of compositions comprising polymorphic Form I, at least about 50%, at least about 60%, at least about 70%, at least about 80%, at least about 85%, at least about 90%, at least about 95%, at least about 96%, at least about 97%, at least about 98%, or at least about 99% of the hydrochloride salt of (S)-2-(1-(9H-purin-6-ylamino)propyl)-5-fluoro-3-phenylquinazolin-4(3H)-one present in the composition is polymorphic Form I. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of Form I of the hydrochloride salt of (S)-2-(1-(9H-purin-6-ylamino)propyl)-5-fluoro-3-phenylquinazolin-4(3H)-one.

In other embodiments of compositions comprising the polymorphic Form I, less than about 50%, less than about 40%, less than about 30%, less than about 20%, less than about 10%, less than about 5%, less than about 4%, less than about 3%, less than about 2% or less than about 1% of the hydrochloride salt of (S)-2-(1-(9H-purin-6-ylamino)propyl)-5-fluoro-3-phenylquinazolin-4(3H)-one present in the composition are other polymorphs of the hydrochloride salt of (S)-2-(1-(9H-purin-6-ylamino)propyl)-5-fluoro-3-phenylquinazolin-4(3H)-one (including, for example, polymorphic Forms II-XIII) and/or impurities.

In yet other embodiments of compositions comprising the polymorphic Form I, impurities make up less than about 5%, less than about 4%, less than about 3%, less than about 2% or less than about 1% of the total mass relative to the mass of the polymorphic Form I present. Impurities may, for example, include by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, and solvents. In certain embodiments, impurities include by-products from the process of synthesizing the hydrochloride salt of (S)-2-(1-(9H-purin-6-ylamino)propyl)-5-fluoro-3-phenylquinazolin-4(3H)-one. In certain embodiments, impurities include contaminants from the process of synthesizing the hydrochloride salt of (S)-2-(1-(9H-purin-6-ylamino)propyl)-5-fluoro-3-phenylquinazolin-4(3H)-one. In certain embodiments, impurities include degradation products of the hydrochloride salt of (S)-2-(1-(9H-purin-6-ylamino)propyl)-5-fluoro-3-phenylquinazolin-4(3H)-one. In certain embodiments, impurities include other polymorphic forms of the hydrochloride salt of (S)-2-(1-(9H-purin-6-ylamino)propyl)-5-fluoro-3-phenylquinazolin-4(3H)-one. In certain embodiments, impurities include water or solvent. In certain embodiments of compositions comprising the polymorphic Form I, impurities are selected from the group consisting of by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, solvents and combinations thereof.

In yet other embodiments, the composition comprising the polymorphic Form I has less than about 5%, less than about 4%, less than about 3%, less than about 2%, or less than about 1% by weight of amorphous or non-crystalline hydrochloride salt of (S)-2-(1-(9H-purin-6-ylamino)propyl)-5-fluoro-3-phenylquinazolin-4(3H)-one.

In yet other embodiments, the composition comprising the polymorphic Form I has less than about 5%, less than about 4%, less than about 3%, less than about 2%, or less than about 1% by weight of (S)-2-(1-(9H-purin-6-ylamino)propyl)-5-fluoro-3-phenylquinazolin-4(3H)-one (e.g., in its free form).

Form II

In some embodiments, the composition comprises polymorphic Form II of a hydrochloride salt of (S)-2-(1-(9H-purin-6-ylamino)propyl)-5-fluoro-3-phenylquinazolin-4(3H)-one. In certain embodiments are provided compositions comprising polymorphic Form II as described herein, wherein the hydrochloride salt of(S)-2-(1-(9H-purin-6-ylamino)propyl)-5-fluoro-3-phenylquinazolin-4(3H)-one within the composition is a substantially pure polymorphic Form II. In particular embodiments of compositions comprising polymorphic Form II, at least about 50%, at least about 60%, at least about 70%, at least about 80%, at least about 85%, at least about 90%, at least about 95%, at least about 96%, at least about 97%, at least about 98%, or at least about 99% of the hydrochloride salt of (S)-2-(1-(9H-purin-6-ylamino)propyl)-5-fluoro-3-phenylquinazolin-4(3H)-one present in the composition is polymorphic Form II. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of Form II of the hydrochloride salt of(S)-2-(1-(9H-purin-6-ylamino)propyl)-5-fluoro-3-phenylquinazolin-4(3H)-one.

In other embodiments of compositions comprising the polymorphic Form II, less than about 50%, less than about 40%, less than about 30%, less than about 20%, less than about 10%, less than about 5%, less than about 4%, less than about 3%, less than about 2% or less than about 1% of the hydrochloride salt of (S)-2-(1-(9H-purin-6-ylamino)propyl)-5-fluoro-3-phenylquinazolin-4(3H)-one present in the composition are other polymorphs of the hydrochloride salt of (S)-2-(1-(9H-purin-6-ylamino)propyl)-5-fluoro-3-phenylquinazolin-4(3H)-one (including, for example, polymorphic Forms I, III-XIII) and/or impurities.

In yet other embodiments of compositions comprising the polymorphic Form II, impurities make up less than about 5%, less than about 4%, less than about 3%, less than about 2% or less than about 1% of the total mass relative to the mass of the polymorphic Form II present. Impurities may, for example, include by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, and solvents. In certain embodiments, impurities include by-products from the process of synthesizing the hydrochloride salt of (S)-2-(1-(9H-purin-6-ylamino)propyl)-5-fluoro-3-phenylquinazolin-4(3H)-one. In certain embodiments, impurities include contaminants from the process of synthesizing the hydrochloride salt of (S)-2-(1-(9H-purin-6-ylamino)propyl)-5-fluoro-3-phenylquinazolin-4(3H)-one. In certain embodiments, impurities include degradation products of the hydrochloride salt of (S)-2-(1-(9H-purin-6-ylamino)propyl)-5-fluoro-3-phenylquinazolin-4(3H)-one. In certain embodiments, impurities include other polymorphic forms of the hydrochloride salt of (S)-2-(1-(9H-purin-6-ylamino)propyl)-5-fluoro-3-phenylquinazolin-4(3H)-one. In certain embodiments, impurities include water or solvent. In certain embodiments of compositions comprising the polymorphic Form II, impurities are selected from the group consisting of by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, solvents and combinations thereof.

In certain embodiments of compositions comprising the polymorphic Form II, the compositions further comprise polymorphic Form X of the hydrochloride salt of (S)-2-(1-(9H-purin-6-ylamino)propyl)-5-fluoro-3-phenylquinazolin-4(3H)-one. In other words, the compositions may comprise a mixture of polymorphic forms. In particular embodiments of compositions comprising a mixture of polymorphic Forms II and X, at least about 50%, at least about 60%, at least about 70%, at least about 80%, at least about 85%, at least about 90%, at least about 95%, at least about 96%, at least about 97%, at least about 98%, or at least about 99% of the hydrochloride salt of (S)-2-(1-(9H-purin-6-ylamino)propyl)-5-fluoro-3-phenylquinazolin-4(3H)-one present in the composition are polymorphic Forms II and X. It should be understood that the relative ratio of polymorphic Form II to polymorphic Form X present in the composition may vary.

In yet other embodiments, the composition comprising the polymorphic Form II has less than about 5%, less than about 4%, less than about 3%, less than about 2%, or less than about 1% by weight of amorphous or non-crystalline hydrochloride salt of (S)-2-(1-(9H-purin-6-ylamino)propyl)-5-fluoro-3-phenylquinazolin-4(3H)-one.

In yet other embodiments, the composition comprising the polymorphic Form II has less than about 5%, less than about 4%, less than about 3%, less than about 2%, or less than about 1% by weight of (S)-2-(1-(9H-purin-6-ylamino)propyl)-5-fluoro-3-phenylquinazolin-4(3H)-one (e.g., in its free form).

Form III

In some embodiments, the composition comprises polymorphic Form III of a hydrochloride salt of (S)-2-(1-(9H-purin-6-ylamino)propyl)-5-fluoro-3-phenylquinazolin-4(3H)-one. In certain embodiments are provided compositions comprising polymorphic Form III as described herein, wherein the hydrochloride salt of(S)-2-(1-(9H-purin-6-ylamino)propyl)-5-fluoro-3-phenylquinazolin-4(3H)-one within the composition is a substantially pure polymorphic Form III. In particular embodiments of compositions comprising polymorphic Form III, at least about 50%, at least about 60%, at least about 70%, at least about 80%, at least about 85%, at least about 90%, at least about 95%, at least about 96%, at least about 97%, at least about 98%, or at least about 99% of the hydrochloride salt of (S)-2-(1-(9H-purin-6-ylamino)propyl)-5-fluoro-3-phenylquinazolin-4(3H)-one present in the composition is polymorphic Form III. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of Form III of the hydrochloride salt of (S)-2-(1-(9H-purin-6-ylamino)propyl)-5-fluoro-3-phenylquinazolin-4(3H)-one.

In other embodiments of compositions comprising the polymorphic Form III, less than about 50%, less than about 40%, less than about 30%, less than about 20%, less than about 10%, less than about 5%, less than about 4%, less than about 3%, less than about 2% or less than about 1% of the hydrochloride salt of (S)-2-(1-(9H-purin-6-ylamino)propyl)-5-fluoro-3-phenylquinazolin-4(3H)-one present in the composition are other polymorphs of the hydrochloride salt of (S)-2-(1-(9H-purin-6-ylamino)propyl)-5-fluoro-3-phenylquinazolin-4(3H)-one (including, for example, polymorphic Forms I-II, IV-XIII) and/or impurities.

In yet other embodiments of compositions comprising the polymorphic Form III, impurities make up less than about 5%, less than about 4%, less than about 3%, less than about 2% or less than about 1% of the total mass relative to the mass of the polymorphic Form II present. Impurities may, for example, include by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, and solvents. In certain embodiments, impurities include by-products from the process of synthesizing the hydrochloride salt of (S)-2-(1-(9H-purin-6-ylamino)propyl)-5-fluoro-3-phenylquinazolin-4(3H)-one. In certain embodiments, impurities include contaminants from the process of synthesizing the hydrochloride salt of (S)-2-(1-(9H-purin-6-ylamino)propyl)-5-fluoro-3-phenylquinazolin-4(3H)-one. In certain embodiments, impurities include degradation products of the hydrochloride salt of (S)-2-(1-(9H-purin-6-ylamino)propyl)-5-fluoro-3-phenylquinazolin-4(3H)-one. In certain embodiments, impurities include other polymorphic forms of the hydrochloride salt of (S)-2-(1-(9H-purin-6-ylamino)propyl)-5-fluoro-3-phenylquinazolin-4(3H)-one. In certain embodiments, impurities include water or solvent. In certain embodiments of compositions comprising the polymorphic Form II, impurities are selected from the group consisting of by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, solvents and combinations thereof.

In certain embodiments of compositions comprising the polymorphic Form III, the compositions further comprise polymorphic Form V of the hydrochloride salt of (S)-2-(1-(9H-purin-6-ylamino)propyl)-5-fluoro-3-phenylquinazolin-4(3H)-one. In other words, the compositions may comprise a mixture of polymorphic forms. In particular embodiments of compositions comprising a mixture of polymorphic Forms III and V, at least about 50%, at least about 60%, at least about 70%, at least about 80%, at least about 85%, at least about 90%, at least about 95%, at least about 96%, at least about 97%, at least about 98%, or at least about 99% of the hydrochloride salt of (S)-2-(1-(9H-purin-6-ylamino)propyl)-5-fluoro-3-phenylquinazolin-4(3H)-one present in the composition are polymorphic Forms III and V. It should be understood that the relative ratio of polymorphic Form III to polymorphic Form V present in the composition may vary.

In yet other embodiments, the composition comprising the polymorphic Form III has less than about 5%, less than about 4%, less than about 3%, less than about 2%, or less than about 1% by weight of amorphous or non-crystalline hydrochloride salt of (S)-2-(1-(9H-purin-6-ylamino)propyl)-5-fluoro-3-phenylquinazolin-4(3H)-one.

In yet other embodiments, the composition comprising the polymorphic Form III has less than about 5%, less than about 4%, less than about 3%, less than about 2%, or less than about 1% by weight of (S)-2-(1-(9H-purin-6-ylamino)propyl)-5-fluoro-3-phenylquinazolin-4(3H)-one (e.g., in its free form).

Form IV

In some embodiments, the composition comprises polymorphic Form IV of a hydrochloride salt of (S)-2-(1-(9H-purin-6-ylamino)propyl)-5-fluoro-3-phenylquinazolin-4(3H)-one. In certain embodiments are provided compositions comprising polymorphic Form IV as described herein, wherein the hydrochloride salt of (S)-2-(1-(9H-purin-6-ylamino)propyl)-5-fluoro-3-phenylquinazolin-4(3H)-one within the composition is a substantially pure polymorphic Form IV. In particular embodiments of compositions comprising polymorphic Form IV, at least about 50%, at least about 60%, at least about 70%, at least about 80%, at least about 85%, at least about 90%, at least about 95%, at least about 96%, at least about 97%, at least about 98%, or at least about 99% of the hydrochloride salt of (S)-2-(1-(9H-purin-6-ylamino)propyl)-5-fluoro-3-phenylquinazolin-4(3H)-one present in the composition is polymorphic Form IV. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of Form IV of the hydrochloride salt of (S)-2-(1-(9H-purin-6-ylamino)propyl)-5-fluoro-3-phenylquinazolin-4(3H)-one.

In other embodiments of compositions comprising the polymorphic Form IV, less than about 50%, less than about 40%, less than about 30%, less than about 20%, less than about 10%, less than about 5%, less than about 4%, less than about 3%, less than about 2% or less than about 1% of the hydrochloride salt of (S)-2-(1-(9H-purin-6-ylamino)propyl)-5-fluoro-3-phenylquinazolin-4(3H)-one present in the composition are other polymorphs of the hydrochloride salt of (S)-2-(1-(9H-purin-6-ylamino)propyl)-5-fluoro-3-phenylquinazolin-4(3H)-one (including, for example, polymorphic Forms I-III, V-XIII) and/or impurities.

In yet other embodiments of compositions comprising the polymorphic Form IV, impurities make up less than about 5%, less than about 4%, less than about 3%, less than about 2% or less than about 1% of the total mass relative to the mass of the polymorphic Form IV present. Impurities may, for example, include by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, and solvents. In certain embodiments, impurities include by-products from the process of synthesizing the hydrochloride salt of(S)-2-(1-(9H-purin-6-ylamino)propyl)-5-fluoro-3-phenylquinazolin-4(3H)-one. In certain embodiments, impurities include contaminants from the process of synthesizing the hydrochloride salt of (S)-2-(1-(9H-purin-6-ylamino)propyl)-5-fluoro-3-phenylquinazolin-4(3H)-one. In certain embodiments, impurities include degradation products of the hydrochloride salt of (S)-2-(1-(9H-purin-6-ylamino)propyl)-5-fluoro-3-phenylquinazolin-4(3H)-one. In certain embodiments, impurities include other polymorphic forms of the hydrochloride salt of (S)-2-(1-(9H-purin-6-ylamino)propyl)-5-fluoro-3-phenylquinazolin-4(3H)-one. In certain embodiments, impurities include water or solvent. In certain embodiments of compositions comprising the polymorphic Form IV, impurities are selected from the group consisting of by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, solvents and combinations thereof.

In certain embodiments of compositions comprising the polymorphic Form IV, the compositions further comprise polymorphic Form IX of the hydrochloride salt of (S)-2-(1-(9H-purin-6-ylamino)propyl)-5-fluoro-3-phenylquinazolin-4(3H)-one. In other words, the compositions may comprise a mixture of polymorphic forms. In particular embodiments of compositions comprising a mixture of polymorphic Forms IV and IX, at least about 50%, at least about 60%, at least about 70%, at least about 80%, at least about 85%, at least about 90%, at least about 95%, at least about 96%, at least about 97%, at least about 98%, or at least about 99% of the hydrochloride salt of (S)-2-(1-(9H-purin-6-ylamino)propyl)-5-fluoro-3-phenylquinazolin-4(3H)-one present in the composition are polymorphic Forms IV and IX. It should be understood that the relative ratio of polymorphic Form IV to polymorphic Form IX present in the composition may vary.

In yet other embodiments, the composition comprising the polymorphic Form IV has less than about 5%, less than about 4%, less than about 3%, less than about 2%, or less than about 1% by weight of amorphous or non-crystalline hydrochloride salt of (S)-2-(1-(9H-purin-6-ylamino)propyl)-5-fluoro-3-phenylquinazolin-4(3H)-one.

In yet other embodiments, the composition comprising the polymorphic Form IV has less than about 5%, less than about 4%, less than about 3%, less than about 2%, or less than about 1% by weight of (S)-2-(1-(9H-purin-6-ylamino)propyl)-5-fluoro-3-phenylquinazolin-4(3H)-one (e.g., in its free form).

Form V

In some embodiments, the composition comprises polymorphic Form V of a hydrochloride salt of (S)-2-(1-(9H-purin-6-ylamino)propyl)-5-fluoro-3-phenylquinazolin-4(3H)-one. In certain embodiments are provided compositions comprising polymorphic Form V as described herein, wherein the hydrochloride salt of (S)-2-(1-(9H-purin-6-ylamino)propyl)-5-fluoro-3-phenylquinazolin-4(3H)-one within the composition is a substantially pure polymorphic Form V. In particular embodiments of compositions comprising polymorphic Form V, at least about 50%, at least about 60%, at least about 70%, at least about 80%, at least about 85%, at least about 90%, at least about 95%, at least about 96%, at least about 97%, at least about 98%, or at least about 99% of the hydrochloride salt of (S)-2-(1-(9H-purin-6-ylamino)propyl)-5-fluoro-3-phenylquinazolin-4(3H)-one present in the composition is polymorphic Form V. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of Form V of the hydrochloride salt of (S)-2-(1-(9H-purin-6-ylamino)propyl)-5-fluoro-3-phenylquinazolin-4(3H)-one.

In other embodiments of compositions comprising the polymorphic Form V, less than about 50%, less than about 40%, less than about 30%, less than about 20%, less than about 10%, less than about 5%, less than about 4%, less than about 3%, less than about 2% or less than about 1% of the hydrochloride salt of (S)-2-(1-(9H-purin-6-ylamino)propyl)-5-fluoro-3-phenylquinazolin-4(3H)-one present in the composition are other polymorphs of the hydrochloride salt of (S)-2-(1-(9H-purin-6-ylamino)propyl)-5-fluoro-3-phenylquinazolin-4(3H)-one (including, for example, polymorphic Forms I-IV, VI-XIII) and/or impurities.

In yet other embodiments of compositions comprising the polymorphic Form V, impurities make up less than about 5%, less than about 4%, less than about 3%, less than about 2% or less than about 1% of the total mass relative to the mass of the polymorphic Form V present. Impurities may, for example, include by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, and solvents. In certain embodiments, impurities include by-products from the process of synthesizing the hydrochloride salt of (S)-2-(1-(9H-purin-6-ylamino)propyl)-5-fluoro-3-phenylquinazolin-4(3H)-one. In certain embodiments, impurities include contaminants from the process of synthesizing the hydrochloride salt of (S)-2-(1-(9H-purin-6-ylamino)propyl)-5-fluoro-3-phenylquinazolin-4(3H)-one. In certain embodiments, impurities include degradation products of the hydrochloride salt of (S)-2-(1-(9H-purin-6-ylamino)propyl)-5-fluoro-3-phenylquinazolin-4(3H)-one. In certain embodiments, impurities include other polymorphic forms of the hydrochloride salt of (S)-2-(1-(9H-purin-6-ylamino)propyl)-5-fluoro-3-phenylquinazolin-4(3H)-one. In certain embodiments, impurities include water or solvent. In certain embodiments of compositions comprising the polymorphic Form V, impurities are selected from the group consisting of by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, solvents and combinations thereof.

In certain embodiments of compositions comprising the polymorphic Form V, the compositions further comprise polymorphic Form II of the hydrochloride salt of (S)-2-(1-(9H-purin-6-ylamino)propyl)-5-fluoro-3-phenylquinazolin-4(3H)-one. In other words, the compositions may comprise a mixture of polymorphic forms. In particular embodiments of compositions comprising a mixture of polymorphic Forms III and V, at least about 50%, at least about 60%, at least about 70%, at least about 80%, at least about 85%, at least about 90%, at least about 95%, at least about 96%, at least about 97%, at least about 98%, or at least about 99% of the hydrochloride salt of (S)-2-(1-(9H-purin-6-ylamino)propyl)-5-fluoro-3-phenylquinazolin-4(3H)-one present in the composition are polymorphic Forms III and V. It should be understood that the relative ratio of polymorphic Form III to polymorphic Form V present in the composition may vary.

In yet other embodiments, the composition comprising the polymorphic Form V has less than about 5%, less than about 4%, less than about 3%, less than about 2%, or less than about 1% by weight of amorphous or non-crystalline hydrochloride salt of (S)-2-(1-(9H-purin-6-ylamino)propyl)-5-fluoro-3-phenylquinazolin-4(3H)-one.

In yet other embodiments, the composition comprising the polymorphic Form V has less than about 5%, less than about 4%, less than about 3%, less than about 2%, or less than about 1% by weight of (S)-2-(1-(9H-purin-6-ylamino)propyl)-5-fluoro-3-phenylquinazolin-4(3H)-one (e.g., in its free form).

Form VI

In some embodiments, the composition comprises polymorphic Form VI of a hydrochloride salt of (S)-2-(1-(9H- purin-6-ylamino)propyl)-5-fluoro-3-phenylquinazolin-4 (3H)-one. In certain embodiments are provided compositions comprising polymorphic Form VI as described herein, wherein the hydrochloride salt of (S)-2-(1-(9H-purin-6-ylamino)propyl)-5-fluoro-3-phenylquinazolin-4(3H)-one within the composition is a substantially pure polymorphic Form VI. In particular embodiments of compositions comprising polymorphic Form VI, at least about 50%, at least about 60%, at least about 70%, at least about 80%, at least about 85%, at least about 90%, at least about 95%, at least about 96%, at least about 97%, at least about 98%, or at least about 99% of the hydrochloride salt of (S)-2-(1-(9H-purin-6-ylamino)propyl)-5-fluoro-3-phenylquinazolin-4(3H)-one present in the composition is polymorphic Form VI. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of Form VI of the hydrochloride salt of (S)-2-(1-(9H-purin-6-ylamino)propyl)-5-fluoro-3-phenylquinazolin-4(3H)-one.

In other embodiments of compositions comprising the polymorphic Form VI, less than about 50%, less than about 40%, less than about 30%, less than about 20%, less than about 10%, less than about 5%, less than about 4%, less than about 3%, less than about 2% or less than about 1% of the hydrochloride salt of (S)-2-(1-(9H-purin-6-ylamino)propyl)-5-fluoro-3-phenylquinazolin-4(3H)-one present in the composition are other polymorphs of the hydrochloride salt of (S)-2-(1-(9H-purin-6-ylamino)propyl)-5-fluoro-3-phenylquinazolin-4(3H)-one (including, for example, polymorphic Forms I-V, VII-XIII) and/or impurities.

In yet other embodiments of compositions comprising the polymorphic Form VI, impurities make up less than about 5%, less than about 4%, less than about 3%, less than about 2% or less than about 1% of the total mass relative to the mass of the polymorphic Form VI present. Impurities may, for example, include by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, and solvents. In certain embodiments, impurities include by-products from the process of synthesizing the hydrochloride salt of (S)-2-(1-(9H-purin-6-ylamino)propyl)-5-fluoro-3-phenylquinazolin-4(3H)-one. In certain embodiments, impurities include contaminants from the process of synthesizing the hydrochloride salt of (S)-2-(1-(9H-purin-6-ylamino)propyl)-5-fluoro-3-phenylquinazolin-4(3H)-one. In certain embodiments, impurities include degradation products of the hydrochloride salt of (S)-2-(1-(9H-purin-6-ylamino)propyl)-5-fluoro-3-phenylquinazolin-4(3H)-one. In certain embodiments, impurities include other polymorphic forms of the hydrochloride salt of (S)-2-(1-(9H-purin-6-ylamino)propyl)-5-fluoro-3-phenylquinazolin-4(3H)-one. In certain embodiments, impurities include water or solvent. In certain embodiments of compositions comprising the polymorphic Form VI, impurities are selected from the group consisting of by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, solvents and combinations thereof.

In yet other embodiments, the composition comprising the polymorphic Form VI has less than about 5%, less than about 4%, less than about 3%, less than about 2%, or less than about 1% by weight of amorphous or non-crystalline hydrochloride salt of (S)-2-(1-(9H-purin-6-ylamino)propyl)-5-fluoro-3-phenylquinazolin-4(3H)-one.

In yet other embodiments, the composition comprising the polymorphic Form VI has less than about 5%, less than about 4%, less than about 3%, less than about 2%, or less than about 1% by weight of (S)-2-(1-(9H-purin-6-ylamino)propyl)-5-fluoro-3-phenylquinazolin-4(3H)-one (e.g., in its free form).

Form VII

In some embodiments, the composition comprises polymorphic Form VII of a hydrochloride salt of (S)-2-(1-(9H-purin-6-ylamino)propyl)-5-fluoro-3-phenylquinazolin-4(3H)-one. In certain embodiments are provided compositions comprising polymorphic Form VII as described herein, wherein the hydrochloride salt of(S)-2-(1-(9H-purin-6-ylamino)propyl)-5-fluoro-3-phenylquinazolin-4(3H)-one within the composition is a substantially pure polymorphic Form VII. In particular embodiments of compositions comprising polymorphic Form VII, at least about 50%, at least about 60%, at least about 70%, at least about 80%, at least about 85%, at least about 90%, at least about 95%, at least about 96%, at least about 97%, at least about 98%, or at least about 99% of the hydrochloride salt of (S)-2-(1-(9H-purin-6-ylamino)propyl)-5-fluoro-3-phenylquinazolin-4(3H)-one present in the composition is polymorphic Form VII. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of Form VII of the hydrochloride salt of (S)-2-(1-(9H-purin-6-ylamino)propyl)-5-fluoro-3-phenylquinazolin-4(3H)-one.

In other embodiments of compositions comprising the polymorphic Form VII, less than about 50%, less than about 40%, less than about 30%, less than about 20%, less than about 10%, less than about 5%, less than about 4%, less than about 3%, less than about 2% or less than about 1% of the hydrochloride salt of (S)-2-(1-(9H-purin-6-ylamino)propyl)-5-fluoro-3-phenylquinazolin-4(3H)-one present in the composition are other polymorphs of the hydrochloride salt of (S)-2-(1-(9H-purin-6-ylamino)propyl)-5-fluoro-3-phenylquinazolin-4(3H)-one (including, for example, polymorphic Forms I-VI, VIII-XIII) and/or impurities.

In yet other embodiments of compositions comprising the polymorphic Form VII, impurities make up less than about 5%, less than about 4%, less than about 3%, less than about 2% or less than about 1% of the total mass relative to the mass of the polymorphic Form VII present. Impurities may, for example, include by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, and solvents. In certain embodiments, impurities include by-products from the process of synthesizing the hydrochloride salt of (S)-2-(1-(9H-purin-6-ylamino)propyl)-5-fluoro-3-phenylquinazolin-4(3H)-one. In certain embodiments, impurities include contaminants from the process of synthesizing the hydrochloride salt of (S)-2-(1-(9H-purin-6-ylamino)propyl)-5-fluoro-3-phenylquinazolin-4(3H)-one. In certain embodiments, impurities include degradation products of the hydrochloride salt of (S)-2-(1-(9H-purin-6-ylamino)propyl)-5-fluoro-3-phenylquinazolin-4(3H)-one. In certain embodiments, impurities include other polymorphic forms of the hydrochloride salt of (S)-2-(1-(9H-purin-6-ylamino)propyl)-5-fluoro-3-phenylquinazolin-4(3H)-one. In certain embodiments, impurities include water or solvent. In certain embodiments of compositions comprising the polymorphic Form VII, impurities are selected from the group consisting of by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, solvents and combinations thereof.

In yet other embodiments, the composition comprising the polymorphic Form VII has less than about 5%, less than about 4%, less than about 3%, less than about 2%, or less than about 1% by weight of amorphous or non-crystalline hydrochloride salt of (S)-2-(1-(9H-purin-6-ylamino)propyl)-5-fluoro-3-phenylquinazolin-4(3H)-one.

In yet other embodiments, the composition comprising the polymorphic Form VII has less than about 5%, less than about 4%, less than about 3%, less than about 2%, or less than about 1% by weight of (S)-2-(1-(9H-purin-6-ylamino)propyl)-5-fluoro-3-phenylquinazolin-4(3H)-one (e.g., in its free form).

Form VIII

In some embodiments, the composition comprises polymorphic Form VIII of a hydrochloride salt of (S)-2-(1-(9H-purin-6-ylamino)propyl)-5-fluoro-3-phenylquinazolin-4(3H)-one. In certain embodiments are provided compositions comprising polymorphic Form VIII as described herein, wherein the hydrochloride salt of (S)-2-(1-(9H-purin-6-ylamino)propyl)-5-fluoro-3-phenylquinazolin-4(3H)-one within the composition is a substantially pure polymorphic Form VIII. In particular embodiments of compositions comprising polymorphic Form VIII, at least about 50%, at least about 60%, at least about 70%, at least about 80%, at least about 85%, at least about 90%, at least about 95%, at least about 96%, at least about 97%, at least about 98%, or at least about 99% of the hydrochloride salt of (S)-2-(1-(9H-purin-6-ylamino)propyl)-5-fluoro-3-phenylquinazolin-4(3H)-one present in the composition is polymorphic Form VIII. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of Form VIII of the hydrochloride salt of (S)-2-(1-(9H-purin-6-ylamino)propyl)-5-fluoro-3-phenylquinazolin-4(3H)-one.

In other embodiments of compositions comprising the polymorphic Form VIII, less than about 50%, less than about 40%, less than about 30%, less than about 20%, less than about 10%, less than about 5%, less than about 4%, less than about 3%, less than about 2% or less than about 1% of the hydrochloride salt of (S)-2-(1-(9H-purin-6-ylamino)propyl)-5-fluoro-3-phenylquinazolin-4(3H)-one present in the composition are other polymorphs of the hydrochloride salt of (S)-2-(1-(9H-purin-6-ylamino)propyl)-5-fluoro-3-phenylquinazolin-4(3H)-one (including, for example, polymorphic Forms I-VII, IX-XIII) and/or impurities.

In yet other embodiments of compositions comprising the polymorphic Form VIII, impurities make up less than about 5%, less than about 4%, less than about 3%, less than about 2% or less than about 1% of the total mass relative to the mass of the polymorphic Form VIII present. Impurities may, for example, include by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, and solvents. In certain embodiments, impurities include by-products from the process of synthesizing the hydrochloride salt of (S)-2-(1-(9H-purin-6-ylamino)propyl)-5-fluoro-3-phenylquinazolin-4(3H)-one. In certain embodiments, impurities include contaminants from the process of synthesizing the hydrochloride salt of (S)-2-(1-(9H-purin-6-ylamino)propyl)-5-fluoro-3-phenylquinazolin-4(3H) one. In certain embodiments, impurities include degradation products of the hydrochloride salt of (S)-2-(1-(9H-purin-6-ylamino)propyl)-5-fluoro-3-phenylquinazolin-4(3H)-one. In certain embodiments, impurities include other polymorphic forms of the hydrochloride salt of (S)-2-(1-(9H-purin-6-ylamino)propyl)-5-fluoro-3-phenylquinazolin-4(3H)-one. In certain embodiments, impurities include water or solvent. In certain embodiments of compositions comprising the polymorphic Form VIII, impurities are selected from the group consisting of by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, solvents and combinations thereof.

In yet other embodiments, the composition comprising the polymorphic Form VIII has less than about 5%, less than about 4%, less than about 3%, less than about 2%, or less than about 1% by weight of amorphous or non-crystalline hydrochloride salt of (S)-2-(1-(9H-purin-6-ylamino)propyl)-5-fluoro-3-phenylquinazolin-4(3H)-one.

In yet other embodiments, the composition comprising the polymorphic Form VIII has less than about 5%, less than about 4%, less than about 3%, less than about 2%, or less than about 1% by weight of (S)-2-(1-(9H-purin-6-ylamino)propyl)-5-fluoro-3-phenylquinazolin-4(3H)-one (e.g., in its free form).

Form IX

In some embodiments, the composition comprises polymorphic Form IX of a hydrochloride salt of (S)-2-(1-(9H-purin-6-ylamino)propyl)-5-fluoro-3-phenylquinazolin-4(3H)-one. In certain embodiments are provided compositions comprising polymorphic Form IX as described herein, wherein the hydrochloride salt of (S)-2-(1-(9H-purin-6-ylamino)propyl)-5-fluoro-3-phenylquinazolin-4(3H)-one within the composition is a substantially pure polymorphic Form IX. In particular embodiments of compositions comprising polymorphic Form IX, at least about 50%, at least about 60%, at least about 70%, at least about 80%, at least about 85%, at least about 90%, at least about 95%, at least about 96%, at least about 97%, at least about 98%, or at least about 99% of the hydrochloride salt of (S)-2-(1-(9H-purin-6-ylamino)propyl)-5-fluoro-3-phenylquinazolin-4(3H)-one present in the composition is polymorphic Form IX. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of Form IX of the hydrochloride salt of (S)-2-(1-(9H-purin-6-ylamino)propyl)-5-fluoro-3-phenylquinazolin-4(3H)-one.

In other embodiments of compositions comprising the polymorphic Form IX, less than about 50%, less than about 40%, less than about 30%, less than about 20%, less than about 10%, less than about 5%, less than about 4%, less than about 3%, less than about 2% or less than about 1% of the hydrochloride salt of (S)-2-(1-(9H-purin-6-ylamino)propyl)-5-fluoro-3-phenylquinazolin-4(3H)-one present in the composition are other polymorphs of the hydrochloride salt of (S)-2-(1-(9H-purin-6-ylamino)propyl)-5-fluoro-3-phenylquinazolin-4(3H)-one (including, for example, polymorphic Forms I-VIII, X-XIII) and/or impurities.

In yet other embodiments of compositions comprising the polymorphic Form IX, impurities make up less than about 5%, less than about 4%, less than about 3%, less than about 2% or less than about 1% of the total mass relative to the mass of the polymorphic Form IX present. Impurities may, for example, include by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, and solvents. In certain embodiments, impurities include by-products from the process of synthesizing the hydrochloride salt of (S)-2-(1-(9H-purin-6-ylamino)propyl)-5-fluoro-3-phenylquinazolin-4(3H)-one. In certain embodiments, impurities include contaminants from the process of synthesizing the hydrochloride salt of (S)-2-(1-(9H-purin-6-ylamino)propyl)-5-fluoro-3-phenylquinazolin-4(3H)-one. In certain embodiments, impurities include degradation products of the hydrochloride salt of (S)-2-(1-(9H-purin-6-ylamino)propyl)-5-fluoro-3-phenylquinazolin-4(3H)-one. In certain embodiments, impurities include other polymorphic forms of the hydrochloride salt of (S)-2-(1-(9H-purin-6-ylamino)propyl)-5-fluoro-3-phenylquinazolin-4(3H)-one. In certain embodiments, impurities include water or solvent. In certain embodiments of compositions comprising the polymorphic Form IX, impurities are selected from the group consisting of by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, solvents and combinations thereof.

In certain embodiments of compositions comprising the polymorphic Form IX, the compositions further comprise polymorphic Form IV of the hydrochloride salt of (S)-2-(1-(9H-purin-6-ylamino)propyl)-5-fluoro-3-phenylquinazolin-4(3H)-one. In other words, the compositions may comprise a mixture of polymorphic forms. In particular embodiments of compositions comprising a mixture of polymorphic Forms IV and IX, at least about 50%, at least about 60%, at least about 70%, at least about 80%, at least about 85%, at least about 90%, at least about 95%, at least about 96%, at least about 97%, at least about 98%, or at least about 99% of the hydrochloride salt of (S)-2-(1-(9H-purin-6-ylamino)propyl)-5-fluoro-3-phenylquinazolin-4(3H) one present in the composition are polymorphic Forms IV and IX. It should be understood that the relative ratio of polymorphic Form IV to polymorphic Form IX present in the composition may vary.

In yet other embodiments, the composition comprising the polymorphic Form IX has less than about 5%, less than about 40, less than about 3%, less than about 2%, or less than about 1% by weight of amorphous or non-crystalline hydrochloride salt of (S)-2-(1-(9H-purin-6-ylamino)propyl)-5-fluoro-3-phenylquinazolin-4(3H)-one.

In yet other embodiments, the composition comprising the polymorphic Form IX has less than about 5%, less than about 4%, less than about 3%, less than about 2%, or less than about 1% by weight of (S)-2-(1-(9H-purin-6-ylamino)propyl)-5-fluoro-3-phenylquinazolin-4(3H)-one (e.g., in its free form).

Form X

In some embodiments, the composition comprises polymorphic Form X of a hydrochloride salt of (S)-2-(1-(9H-purin-6-ylamino)propyl)-5-fluoro-3-phenylquinazolin-4(3H)-one. In certain embodiments are provided compositions comprising polymorphic Form X as described herein, wherein the hydrochloride salt of (S)-2-(1-(9H-purin-6-ylamino)propyl)-5-fluoro-3-phenylquinazolin-4(3H)-one within the composition is a substantially pure polymorphic Form X. In particular embodiments of compositions comprising polymorphic Form X, at least about 50%, at least about 60%, at least about 70%, at least about 80%, at least about 85%, at least about 90%, at least about 95%, at least about 96%, at least about 97%, at least about 98%, or at least about 99% of the hydrochloride salt of (S)-2-(1-(9H-purin-6-ylamino)propyl)-5-fluoro-3-phenylquinazolin-4(3H)-one present in the composition is polymorphic Form X. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of Form X of the hydrochloride salt of (S)-2-(1-(9H-purin-6-ylamino)propyl)-5-fluoro-3-phenylquinazolin-4(3H)-one.

In other embodiments of compositions comprising the polymorphic Form X, less than about 50%, less than about 40%, less than about 30%, less than about 20%, less than about 10%, less than about 5%, less than about 4%, less than about 3%, less than about 2% or less than about 1% of the hydrochloride salt of (S)-2-(1-(9H-purin-6-ylamino)propyl)-5-fluoro-3-phenylquinazolin-4(3H)-one present in the composition are other polymorphs of the hydrochloride salt of (S)-2-(1-(9H-purin-6-ylamino)propyl)-5-fluoro-3-phenylquinazolin-4(3H)-one (including, for example, polymorphic Forms I-IX, XI-XII) and/or impurities.

In yet other embodiments of compositions comprising the polymorphic Form X, impurities make up less than about 5%, less than about 4%, less than about 3%, less than about 2% or less than about 1% of the total mass relative to the mass of the polymorphic Form X present. Impurities may, for example, include by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, and solvents. In certain embodiments, impurities include by-products from the process of synthesizing the hydrochloride salt of (S)-2-(1-(9H-purin-6-ylamino)propyl)-5-fluoro-3-phenylquinazolin-4(3H)-one. In certain embodiments, impurities include contaminants from the process of synthesizing the hydrochloride salt of (S)-2-(1-(9H-purin-6-ylamino)propyl)-5-fluoro-3-phenylquinazolin-4(3H)-one. In certain embodiments, impurities include degradation products of the hydrochloride salt of (S)-2-(1-(9H-purin-6-ylamino)propyl)-5-fluoro-3-phenylquinazolin-4(3H)-one. In certain embodiments, impurities include other polymorphic forms of the hydrochloride salt of (S)-2-(1-(9H-purin-6-ylamino)propyl)-5-fluoro-3-phenylquinazolin-4(3H)-one. In certain embodiments, impurities include water or solvent. In certain embodiments of compositions comprising the polymorphic Form X, impurities are selected from the group consisting of by-products from synthesizing the hydrochloride salt of (8)-2-(1-(9H-purin-6-ylamino)propyl)-5-fluoro-3-phenylquinazolin-4(3H)-one, contaminants, degradation products, other polymorphic forms, water, solvents and combinations thereof.

In certain embodiments of compositions comprising the polymorphic Form X, the compositions further comprise polymorphic Form II of the hydrochloride salt of (S)-2-(1-(9H-purin-6-ylamino)propyl)-5-fluoro-3-phenylquinazolin-4(3H)-one. In other words, the compositions may comprise a mixture of polymorphic forms. In particular embodiments of compositions comprising a mixture of polymorphic Forms II and X, at least about 50%, at least about 60%, at least about 70%, at least about 80%, at least about 85%, at least about 90%, at least about 95%, at least about 96%, at least about 97%, at least about 98%, or at least about 99% of the hydrochloride salt of (S)-2-(1-(9H-purin-6-ylamino)propyl)-5-fluoro-3-phenylquinazolin-4(3H)-one present in the composition are polymorphic Forms II and X. It should be understood that the relative ratio of polymorphic Form II to polymorphic Form X present in the composition may vary.

In yet other embodiments, the composition comprising the polymorphic Form X has less than about 5%, less than about 4%, less than about 3%, less than about 2%, or less than about 1% by weight of amorphous or non-crystalline hydrochloride salt of (S)-2-(1-(9H-purin-6-ylamino)propyl)-5-fluoro-3-phenylquinazolin-4(3H)-one.

In yet other embodiments, the composition comprising the polymorphic Form X has less than about 5%, less than about 4%, less than about 3%, less than about 2%, or less than about 1% by weight of (S)-2-(1-(9H-purin-6-ylamino)propyl)-5-fluoro-3-phenylquinazolin-4(3H)-one (e.g., in its free form).

Form XI

In some embodiments, the composition comprises polymorphic Form XI of a hydrochloride salt of (S)-2-(1-(9H-purin-6-ylamino)propyl)-5-fluoro-3-phenylquinazolin-4(3H)-one. In certain embodiments are provided compositions comprising polymorphic Form XI as described herein, wherein the hydrochloride salt of (S)-2-(1-(9H-purin-6-ylamino)propyl)-5-fluoro-3-phenylquinazolin-4(3H)-one within the composition is a substantially pure polymorphic Form XI. In particular embodiments of compositions comprising polymorphic Form XI, at least about 50%, at least about 60%, at least about 70%, at least about 80%, at least about 85%, at least about 90%, at least about 95%, at least about 96%, at least about 97%, at least about 98%, or at least about 99% of the hydrochloride salt of (S)-2-(1-(9H-purin-6-ylamino)propyl)-5-fluoro-3-phenylquinazolin-4(3H)-one present in the composition is polymorphic Form XI. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of Form XI of the hydrochloride salt of (S)-2-(1-(9H-purin-6-ylamino)propyl)-5-fluoro-3-phenylquinazolin-4(3H) one.

In other embodiments of compositions comprising the polymorphic Form XI, less than about 50%, less than about 40%, less than about 30%, less than about 20%, less than about 10%, less than about 5%, less than about 4%, less than about 3%, less than about 2% or less than about 1% of the hydrochloride salt of (S)-2-(1-(9H-purin-6-ylamino)propyl)-5-fluoro-3-phenylquinazolin-4(3H)-one present in the composition are other polymorphs of the hydrochloride salt of (S)-2-(1-(9H-purin-6-ylamino)propyl)-5-fluoro-3-phenylquinazolin-4(3H)-one (including, for example, polymorphic Forms I-X, XII-XIII) and/or impurities.

In yet other embodiments of compositions comprising the polymorphic Form XI, impurities make up less than about 5%, less than about 4%, less than about 3%, less than about 2% or less than about 1% of the total mass relative to the mass of the polymorphic Form XI present. Impurities may, for example, include by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, and solvents. In certain embodiments, impurities include by-products from the process of synthesizing the hydrochloride salt of (S)-2-(1-(9H-purin-6-ylamino)propyl)-5-fluoro-3-phenylquinazolin-4(3H)-one. In certain embodiments, impurities include contaminants from the process of synthesizing the hydrochloride salt of (S)-2-(1-(9H-purin-6-ylamino)propyl)-5-fluoro-3-phenylquinazolin-4(3H)-one. In certain embodiments, impurities include degradation products of the hydrochloride salt of (S)-2-(1-(9H-purin-6-ylamino)propyl)-5-fluoro-3-phenylquinazolin-4(3H)-one. In certain embodiments, impurities include other polymorphic forms of the hydrochloride salt of (S)-2-(1-(9H-purin-6-ylamino)propyl)-5-fluoro-3-phenylquinazolin-4(3H)-one. In certain embodiments, impurities include water or solvent. In certain embodiments of compositions comprising the polymorphic Form XI, impurities are selected from the group consisting of by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, solvents and combinations thereof.

In yet other embodiments, the composition comprising the polymorphic Form XI has less than about 5%, less than about 4%, less than about 3%, less than about 2%, or less than about 1% by weight of amorphous or non-crystalline hydrochloride salt of (S)-2-(1-(9H-purin-6-ylamino)propyl)-5-fluoro-3-phenylquinazolin-4(3H)-one.

In yet other embodiments, the composition comprising the polymorphic Form XI has less than about 5%, less than about 4%, less than about 3%, less than about 2%, or less than about 1% by weight of (S)-2-(1-(9H-purin-6-ylamino)propyl)-5-fluoro-3-phenylquinazolin-4(3H)-one (e.g., in its free form).

Form XII

In some embodiments, the composition comprises polymorphic Form XII of a hydrochloride salt of (S)-2-(1-(9H-purin-6-ylamino)propyl)-5-fluoro-3-phenylquinazolin-4(3H)-one. In certain embodiments are provided compositions comprising polymorphic Form XII as described herein, wherein the hydrochloride salt of (S)-2-(1-(9H-purin-6-ylamino)propyl)-5-fluoro-3-phenylquinazolin-4(3H)-one within the composition is a substantially pure polymorphic Form XII. In particular embodiments of compositions comprising polymorphic Form XII, at least about 50%, at least about 60%, at least about 70%, at least about 80%, at least about 85%, at least about 90%, at least about 95%, at least about 96%, at least about 97%, at least about 98%, or at least about 99% of the hydrochloride salt of (S)-2-(1-(9H-purin-6-ylamino)propyl)-5-fluoro-3-phenylquinazolin-4(3H)-one present in the composition is polymorphic Form XII. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of Form XII of the hydrochloride salt of (S)-2-(1-(9H-purin-6-ylamino)propyl)-5-fluo-3-phenylquinazolin-4(3H)-one.

In other embodiments of compositions comprising the polymorphic Form XII, less than about 50%, less than about 40%, less than about 30%, less than about 20%, less than about 10%, less than about 5%, less than about 4%, less than about 3%, less than about 2% or less than about 1% of the hydrochloride salt of (S)-2-(1-(9H-purin-6-ylamino)propyl)-5-fluoro-3-phenylquinazolin-4(3H)-one present in the composition are other polymorphs of the hydrochloride salt of (S)-2-(1-(9H-purin-6-ylamino)propyl)-5-fluoro-3-phenylquinazolin-4(3H)-one (including, for example, polymorphic Forms I-XI, XIII) and/or impurities.

In yet other embodiments of compositions comprising the polymorphic Form XII, impurities make up less than about 5%, less than about 4%, less than about 3%, less than about 2% or less than about 1% of the total mass relative to the mass of the polymorphic Form XII present. Impurities may, for example, include by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, and solvents. In certain embodiments, impurities include by-products from the process of synthesizing the hydrochloride salt of (S)-2-(1-(9H-purin-6-ylamino)propyl)-5-fluoro-3-phenylquinazolin-4(3H)-one. In certain embodiments, impurities include contaminants from the process of synthesizing the hydrochloride salt of (S)-2-(1-(9H-purin-6-ylamino)propyl)-5-fluoro-3-phenylquinazolin-4(3H)-one. In certain embodiments, impurities include degradation products of the hydrochloride salt of (S)-2-(1-(9H-purin-6-ylamino)propyl)-5-fluoro-3-phenylquinazolin-4(3H)-one. In certain embodiments, impurities include other polymorphic forms of the hydrochloride salt of (S)-2-(1-(9H-purin-6-ylamino)propyl)-5-fluoro-3-phenylquinazolin-4(3H)-one. In certain embodiments, impurities include water or solvent. In certain embodiments of compositions comprising the polymorphic Form XII, impurities are selected from the group consisting of by-products from synthesizing the hydrochloride salt of(S)-2-(1-(9H-purin-6-ylamino)propyl)-5-fluoro-3-phenylquinazolin-4(3H)-one, contaminants, degradation products, other polymorphic forms, water, solvents and combinations thereof.

In yet other embodiments, the composition comprising the polymorphic Form XII has less than about 5%, less than about 4%, less than about 3%, less than about 2%, or less than about 1% by weight of amorphous or non-crystalline hydrochloride salt of (S)-2-(1-(9H-purin-6-ylamino)propyl)-5-fluoro-3-phenylquinazolin-4(3H)-one.

In yet other embodiments, the composition comprising the polymorphic Form XII has less than about 5%, less than about 4%, less than about 3%, less than about 2%, or less than about 1% by weight of (S)-2-(1-(9H-purin-6-ylamino)propyl)-5-fluoro-3-phenylquinazolin-4(3H)-one (e.g., in its free form).

Form XII

In some embodiments, the composition comprises polymorphic Form XIII of a hydrochloride salt of (S)-2-(1-(9H-purin-6-ylamino)propyl)-5-fluoro-3-phenylquinazolin-4(3H)-one. In certain embodiments are provided compositions comprising polymorphic Form XIII as described herein, wherein the hydrochloride salt of(S)-2-(1-(9H-purin-6-ylamino)propyl)-5-fluoro-3-phenylquinazolin-4(3H)-one within the composition is a substantially pure polymorphic Form XIII. In particular embodiments of compositions comprising polymorphic Form XIII, at least about 50%, at least about 60%, at least about 70%, at least about 80%, at least about 85%, at least about 90%, at least about 95%, at least about 96%, at least about 97%, at least about 98%, or at least about 99% of the hydrochloride salt of (S)-2-(1-(9H-purin-6-ylamino)propyl)-5-fluoro-3-phenylquinazolin-4(3H)-one present in the composition is polymorphic Form XIII. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of Form XIII of the hydrochloride salt of (S)-2-(1-(9H-purin-6-ylamino)propyl)-5-fluoro-3-phenylquinazolin-4(3H)-one.

In other embodiments of compositions comprising the polymorphic Form XIII, less than about 50%, less than about 40%, less than about 30%, less than about 20%, less than about 10%, less than about 5%, less than about 4%, less than about 3%, less than about 2% or less than about 1% of the hydrochloride salt of (S)-2-(1-(9H-purin-6-ylamino)propyl)-5-fluoro-3-phenylquinazolin-4(3H)-one present in the composition are other polymorphs of the hydrochloride salt of (S)-2-(1-(9H-purin-6-ylamino)propyl)-5-fluoro-3-phenylquinazolin-(3)-one (including, for example, polymorphic Forms I-XII) and/or impurities.

In yet other embodiments of compositions comprising the polymorphic Form XIII, impurities make up less than about 5%, less than about 4%, less than about 3%, less than about 2% or less than about 1% of the total mass relative to the mass of the polymorphic Form XIII present. Impurities may, for example, include by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, and solvents. In certain embodiments, impurities include by-products from the process of synthesizing the hydrochloride salt of (S)-2-(1-(9H-purin-6-ylamino)propyl)-5-fluoro-3-phenylquinazolin-4(3H)-one. In certain embodiments, impurities include contaminants from the process of synthesizing the hydrochloride salt of (S)-2-(1-(9H-purin-6-ylamino)propyl)-5-fluoro-3-phenylquinazolin-4(3H)-one. In certain embodiments, impurities include degradation products of the hydrochloride salt of (S)-2-(1-(9H-purin-6-ylamino)propyl)-5-fluoro-3-phenylquinazolin-4(3H)-one. In certain embodiments, impurities include other polymorphic forms of the hydrochloride salt of (S)-2-(1-(9H-purin-6-ylamino)propyl)-5-fluoro-3-phenylquinazolin-4(3H)-one. In certain embodiments, impurities include water or solvent. In certain embodiments of compositions comprising the polymorphic Form XIII, impurities are selected from the group consisting of by-products from synthesizing the hydrochloride salt of (S)-2-(1-(9H-purin-6-ylamino)propyl)-5-fluoro-3-phenylquinazolin-4(3H)-one, contaminants, degradation products, other polymorphic forms, water, solvents and combinations thereof.

In yet other embodiments, the composition comprising the polymorphic Form XIII has less than about 5%, less than about 4%, less than about 3%, less than about 2%, or less than about 1% by weight of amorphous or non-crystalline hydrochloride salt of (S)-2-(1-(9H-purin-6-ylamino)propyl)-5-fluoro-3-phenylquinazolin-4(3H)-one.

In yet other embodiments, the composition comprising the polymorphic Form XIII has less than about 5%, less than about 4%, less than about 3%, less than about 2%, or less than about 1% by weight of (S)-2-(1-(9H-purin-6-ylamino)propyl)-5-fluoro-3-phenylquinazolin-4(3H)-one (e.g., in its free form).

Preparation of the Polymorphs

One method of synthesizing (S)-2-(1-(9H-purin-6-ylamino)propyl)-5-fluoro-3-phenylquinazolin-4(3H)-one has been previously described in U.S. Pat. No. 7,932,260. This reference is hereby incorporated herein by reference in its entirety, and specifically with respect to the synthesis of (S)-2-(1-(9H-purin-6-ylamino)propyl)-5-fluoro-3-phenylquinazolin-4(3H)-one. One or more polymorphic forms of the hydrochloride salt of (S)-2-(1-(9H-purin-6-ylamino)propyl)-5-fluoro-3-phenylquinazolin-4(3H)-one may be prepared from (S)-2-(1-(9H-purin-6-ylamino)propyl)-5-fluoro-3-phenylquinazolin-4(3H)-one or from its hydrochloride salt.

For example, in one aspect, provided is a method of producing a composition comprising one or more polymorphs of a hydrochloride salt of (S)-2-(1-(9H-purin-6-ylamino)propyl)-5-fluoro-3-phenylquinazolin-4(3H)-one, wherein the method comprises combining a compound of Formula (I) with hydrochloric acid and a suitable solvent or a mixture of suitable solvents to produce a composition comprising one or more polymorphs of the hydrochloride salt of the compound of Formula (I). In another aspect, provided is another method of producing a composition comprising one or more polymorphs of a hydrochloride salt of (S)-2-(1-(9H-purin-6-ylamino)propyl)-5-fluoro-3-phenylquinazolin-4(3H)-one, wherein the method comprises combining a hydrochloride salt of (S)-2-(1-(9H-purin-6-ylamino)propyl)-5-fluoro-3-phenylquinazolin-4(3H)-one with a suitable solvent or a mixture of suitable solvents.

The choice of a particular solvent or combination of solvents affects the formation favoring one polymorphic form of a hydrochloride salt (S)-2-(1-(9H-purin-6-ylamino)propyl)-5-fluoro-3-phenylquinazolin-4(3H)-one over another. Solvents suitable for polymorph formation may include, for example, methanol, ethanol, water, isopropyl acetate, ethyl acetate, methyl tert-butyl ether, n-heptane, acetonitrile, acetone, 2-methyltetrahydrofuran, tetrahydrofuran, methyl isobutyl ketone, methyl ethyl ketone, dichloromethane, 2-propanol, 1-propanol, 1-butanol, and any mixtures thereof.

In another aspect, provided is also one or more polymorphs of a hydrochloride salt of (S)-2-(1-(9H-purin-6-ylamino)propyl)-5-fluoro-3-phenylquinazolin-4(3H)-one produced according to any of the methods described herein.

It should be understood that the methods for preparing the polymorphs described herein (including any one or more of polymorphic Forms I to XIII) may yield quantity and quality differences compared to the methods for preparing the hydrochloride salt of (S)-2-(1-(9H-purin-6-ylamino)propyl)-5-fluoro-3-phenylquinazolin-4(3H)-one produced on laboratory scale.

Form I

In one embodiment, provided is a method of producing a composition comprising polymorphic Form I of a hydrochloride salt of (S)-2-(1-(9H-purin-6-ylamino)propyl)-5-fluoro-3-phenylquinazolin-4(3H)-one, wherein the method comprises combining (S)-2-(1-(9H-purin-6-ylamino)propyl)-5-fluoro-3-phenylquinazolin-4(3H)-one with hydrochloric acid and a solvent to produce a composition comprising polymorphic Form I of the hydrochloride salt of (S)-2-(1-(9H-purin-6-ylamino)propyl)-5-fluoro-3-phenylquinazolin-4(3H)-one, wherein the solvent is selected from the group consisting of methanol, ethanol, water, isopropyl acetate, ethyl acetate, methyl tert-butyl ether, n-heptane, acetonitrile, and any mixtures thereof.

In another embodiment, provided is a method of producing a composition comprising polymorphic Form I of a hydrochloride salt of (S)-2-(1-(9H-purin-6-ylamino)propyl)-5-fluoro-3-phenylquinazolin-4(3H)-one, wherein the method comprises combining a hydrochloride salt of (S)-2-(1-(9H-purin-6-ylamino)propyl)-5-fluoro-3-phenylquinazolin-4(3H)-one with a solvent to produce a composition comprising polymorphic Form I of the hydrochloride salt of (S)-2-(1-(9H-purin-6-ylamino)propyl)-5-fluoro-3-phenylquinazolin-4(3H)-one, wherein the solvent is selected from the group consisting of methanol, ethanol, water, isopropyl acetate, ethyl acetate, methyl tert-butyl ether, n-heptane, acetonitrile, and any mixtures thereof.

Provided is a polymorphic Form I of a hydrochloride salt of (S)-2-(1-(9H-purin-6-ylamino)propyl)-5-fluoro-3-phenylquinazolin-4(3H)-one produced by combining (S)-2-(1-(9H-purin-6-ylamino)propyl)-5-fluoro-3-phenylquinazolin-4(3H)-one with hydrochloric acid and a solvent, wherein the solvent is selected from the group consisting of methanol, ethanol, water, isopropyl acetate, ethyl acetate, methyl tert-butyl ether, n-heptane, acetonitrile, and any mixtures thereof.

Provided is also a polymorphic Form I of a hydrochloride salt of (S)-2-(1-(9H-purin-6-ylamino)propyl)-5-fluoro-3-phenylquinazolin-4(3H)-one produced by combining a hydrochloride salt of (S)-2-(1-(9H-purin-6-ylamino)propyl)-5-fluoro-3-phenylquinazolin-4(3H)-one with a solvent, wherein the solvent is selected from the group consisting of methanol, ethanol, water, isopropyl acetate, ethyl acetate, methyl tert-butyl ether, n-heptane, acetonitrile, and any mixtures thereof.

In certain embodiments of the polymorphic Form I produced according to the methods described above, the hydrochloride salt of (S)-2-(1-(9H-purin-6-ylamino)propyl)-5-fluoro-3-phenylquinazolin-4(3H)-one is a monohydrochloride salt of (S)-2-(1-(9H-purin-6-ylamino)propyl)-5-fluoro-3-phenylquinazolin-4(3H)-one.

Forms II and X

In one embodiment, provided is a method of producing a composition comprising polymorphic Form II, Form X, or a mixture thereof, of a hydrochloride salt of (S)-2-(1-(9H-purin-6-ylamino)propyl)-5-fluoro-3-phenylquinazolin-4(3H)-one, wherein the method comprises combining (S)-2-(1-(9H-purin-6-ylamino)propyl)-5-fluoro-3-phenylquinazolin-4(3H)-one with hydrochloric acid and a solvent to produce a composition comprising polymorphic Form II, Form X, or a mixture thereof, of the hydrochloride salt of (S)-2-(1-(9H-purin-6-ylamino)propyl)-5-fluoro-3-phenylquinazolin-4(3H)-one, wherein the solvent is acetone.

In another embodiment, provided is a method of producing a composition comprising polymorphic Form II, Form X, or a mixture thereof, of a hydrochloride salt of (S)-2-(1-(9H-purin-6-ylamino)propyl)-5-fluoro-3-phenylquinazolin-4(3H)-one, wherein the method comprises combining a hydrochloride salt of (S)-2-(1-(9H-purin-6-ylamino)propyl)-5-fluoro-3-phenylquinazolin-4(3H)-one with a solvent to produce a composition comprising polymorphic Form II, Form X, or a mixture thereof, of the hydrochloride salt of (S)-2-(1-(9H-purin-6-ylamino)propyl)-5-fluoro-3-phenylquinazolin-4(3H)-one, wherein the solvent is acetone.

Provided is a polymorphic Form II, Form X, or a mixture thereof, of a hydrochloride salt of (S)-2-(1-(9H-purin-6-ylamino)propyl)-5-fluoro-3-phenylquinazolin-4(3H)-one produced by combining (S)-2-(1-(9H-purin-6-ylamino)propyl)-5-fluoro-3-phenylquinazolin-4(3H)-one with hydrochloric acid and a solvent, wherein the solvent is acetone.

Provided is also a polymorphic Form II, Form X, or a mixture thereof, of a hydrochloride salt of (S)-2-(1-(9H-purin-6-ylamino)propyl)-5-fluoro-3-phenylquinazolin-4(3H)-one prepared by combining a hydrochloride salt of (S)-2-(1-(9H-purin-6-ylamino)propyl)-5-fluoro-3-phenylquinazolin-4(3H)-one with a solvent, wherein the solvent is acetone.

In certain embodiments of the polymorphic Form II, Form X, or a mixture thereof produced according to the methods described above, the hydrochloride salt of(S)-2-(1-(9H-purin-6-ylamino)propyl)-5-fluoro-3-phenylquinazolin-4(3H)-one is a monohydrochloride salt of (S)-2-(1-(9H-purin-6-ylamino)propyl)-5-fluoro-3-phenylquinazolin-4(3H)-one.

Forms I and V

In one embodiment, provided is a method of producing a composition comprising polymorphic Form III, Form V, or a mixture thereof, of a hydrochloride salt of (S)-2-(1-(9H-purin-6-ylamino)propyl)-5-fluoro-3-phenylquinazolin-4(3H)-one, wherein the method comprises combining (S)-2-(1-(9H-purin-6-ylamino)propyl)-5-fluoro-3-phenylquinazolin-4(3H)-one with hydrochloric acid and a solvent to produce a composition comprising polymorphic Form III, Form V, or a mixture thereof, of the hydrochloride salt of (S)-2-(1-(9H-purin-6-ylamino)propyl)-5-fluoro-3-phenylquinazolin-4(3H)-one, wherein the solvent is 2-methyltetrahydrofuran.

In another embodiment, provided is a method of producing a composition comprising polymorphic Form III, Form V, or a mixture thereof, of a hydrochloride salt of (S)-2-(1-(9H-purin-6-ylamino)propyl)-5-fluoro-3-phenylquinazolin-4(3H)-one, wherein the method comprises combining a hydrochloride salt of (S)-2-(1-(9H-purin-6-ylamino)propyl)-5-fluoro-3-phenylquinazolin-4(3H)-one with a solvent to produce a composition comprising polymorphic Form III, Form V, or a mixture thereof, of the hydrochloride salt of (S)-2-(1-(9H-purin-6-ylamino)propyl)-5-fluoro-3-phenylquinazolin-4(3H)-one, wherein the solvent is 2-methyltetrahydrofuran.

Provided is a polymorphic Form III, Form V, or a mixture thereof, of a hydrochloride salt of (S)-2-(1-(9H-purin-6-ylamino)propyl)-5-fluoro-3-phenylquinazolin-4(3H)-one produced by combining (S)-2-(1-(9H-purin-6-ylamino)propyl)-5-fluoro-3-phenylquinazolin-4(3H)-one with hydrochloric acid and a solvent, wherein the solvent is 2-methyltetrahydrofuran.

Provided is also a polymorphic Form III, Form V, or a mixture thereof, of a hydrochloride salt of (S)-2-(1-(9H-purin-6-ylamino)propyl)-5-fluoro-3-phenylquinazolin-4(3H)-one produced by combining a hydrochloride salt of (S)-2-(1-(9H-purin-6-ylamino)propyl)-5-fluoro-3-phenylquinazolin-4(3H)-one with a solvent, wherein the solvent is 2-methyltetrahydrofuran.

In certain embodiments of the polymorphic Form III, Form V, or a mixture thereof, produced according to the methods described above, the hydrochloride salt of (S)-2-(1-(9H-purin-6-ylamino)propyl)-5-fluoro-3-phenylquinazolin-4(3H)-one is a monohydrochloride salt of (S)-2-(1-(9H-purin-6-ylamino)propyl)-5-fluoro-3-phenylquinazolin-4(3H)-one.

Forms IV and IX

In one embodiment, provided is a method of producing a composition comprising polymorphic Form IV, Form IX, or a mixture thereof, of a hydrochloride salt of (S)-2-(1-(9H-purin-6-ylamino)propyl)-5-fluoro-3-phenylquinazolin-4(3H)-one, wherein the method comprises combining (S)-2-(1-(9H-purin-6-ylamino)propyl)-5-fluoro-3-phenylquinazolin-4(3H)-one with hydrochloric acid and a solvent to produce a composition comprising polymorphic Form IV, Form IX, or a mixture thereof of the hydrochloride salt of (S)-2-(1-(9H-purin-6-ylamino)propyl)-5-fluoro-3-phenylquinazolin-4(3H)-one, wherein the solvent is tetrahydrofuran.

In another embodiment, provided is a method of producing a composition comprising polymorphic Form IV, Form IX, or a mixture thereof, of a hydrochloride salt of (S)-2-(1-(9H-purin-6-ylamino)propyl)-5-fluoro-3-phenylquinazolin-4(3H)-one, wherein the method comprises combining a hydrochloride salt of (S)-2-(1-(9H-purin-6-ylamino)propyl)-5-fluoro-3-phenylquinazolin-4(3H)-one with a solvent to produce a composition comprising polymorphic Form IV, Form IX, or a mixture thereof, of the hydrochloride salt of (S)-2-(1-(9H-purin-6-ylamino)propyl)-5-fluoro-3-phenylquinazolin-4(3H)-one, wherein the solvent is tetrahydrofuran.

Provided is a polymorphic Form IV, Form IX, or a mixture thereof, of a hydrochloride salt of (S)-2-(1-(9H-purin-6-ylamino)propyl)-5-fluoro-3-phenylquinazolin-4(3H)-one produced by combining (S)-2-(1-(9H-purin-6-ylamino)propyl)-5-fluoro-3-phenylquinazolin-4(3H)-one with hydrochloric acid and a solvent, wherein the solvent is tetrahydrofuran.

Provided is a polymorphic Form IV, Form IX, or a mixture thereof, of a hydrochloride salt of (S)-2-(1-(9H-purin-6-ylamino)propyl)-5-fluoro-3-phenylquinazolin-4(3H)-one produced by combining a hydrochloride salt of(S)-2-(1-(9H-purin-6-ylamino)propyl)-5-fluoro-3-phenylquinazolin-4(3H)-one with a solvent, wherein the solvent is tetrahydrofuran.

In certain embodiments of the polymorphic Form IV, Form IX, or a mixture thereof, produced according to the methods described above, the hydrochloride salt of (S)-2-(1-(9H-purin-6-ylamino)propyl)-5-fluoro-3-phenylquinazolin-4(3H)-one is a monohydrochloride salt of (S)-2-(1-(9H-purin-6-ylamino)propyl)-5-fluoro-3-phenylquinazolin-4(3H)-one.

Form VI

In one embodiment, provided is a method of producing a composition comprising polymorphic Form VI of a hydrochloride salt of (S)-2-(1-(9H-purin-6-ylamino)propyl)-5-fluoro-3-phenylquinazolin-4(3H)-one, wherein the method comprises combining (S)-2-(1-(9H-purin-6-ylamino)propyl)-5-fluoro-3-phenylquinazolin-4(3H)-one with hydrochloric acid and a solvent to produce a composition comprising polymorphic Form VI of the hydrochloride salt of (S)-2-(1-(9H-purin-6-ylamino)propyl)-5-fluoro-3-phenylquinazolin-4(3H)-one, wherein the solvent is methyl isobutyl ketone.

In another embodiment, provided is a method of producing a composition comprising polymorphic Form VI of a hydrochloride salt of (S)-2-(1-(9H-purin-6-ylamino)propyl)-5-fluoro-3-phenylquinazolin-4(3H)-one, wherein the method comprises combining a hydrochloride salt of (S)-2-(1-(9H-purin-6-ylamino)propyl)-5-fluoro-3-phenylquinazolin-4(3H)-one with a solvent to produce a composition comprising polymorphic Form VI of the hydrochloride salt of (S)-2-(1-(9H-purin-6-ylamino)propyl)-5-fluoro-3-phenylquinazolin-4(3H)-one, wherein the solvent is methyl isobutyl ketone.

Provided is a polymorphic Form VI of a hydrochloride salt of (S)-2-(1-(9H-purin-6-ylamino)propyl)-5-fluoro-3-phenylquinazolin-4(3H)-one produced by combining (S)-2-(1-(9H-purin-6-ylamino)propyl)-5-fluoro-3-phenylquinazolin-4(3H)-one with hydrochloric acid and a solvent, wherein the solvent is methyl isobutyl ketone.

Provided is also a polymorphic Form VI of a hydrochloride salt of (S)-2-(1-(9H-purin-6-ylamino)propyl)-5-fluoro-3-phenylquinazolin-4(3H)-one to produce a hydrochloride salt of (S)-2-(1-(9H-purin-6-ylamino)propyl)-5-fluoro-3-phenylquinazolin-4(3H)-one with a solvent, wherein the solvent is methyl isobutyl ketone.

In certain embodiments of the polymorphic Form VI produced according to the methods described above, the hydrochloride salt of (S)-2-(1-(9H-purin-6-ylamino)propyl)-5-fluoro-3-phenylquinazolin-4(3H)-one is a monohydrochloride salt of (S)-2-(1-(9H-purin-6-ylamino)propyl)-5-fluoro-3-phenylquinazolin-4(3H)-one.

Form VII

In one embodiment, provided is a method of producing a composition comprising polymorphic Form VII of a hydrochloride salt of (S)-2-(1-(9H-purin-6-ylamino)propyl)-5-fluoro-3-phenylquinazolin-4(3H)-one, wherein the method comprises combining (S)-2-(1-(9H-purin-6-ylamino)propyl)-5-fluoro-3-phenylquinazolin-4(3H)-one with hydrochloric acid and a solvent to produce a composition comprising polymorphic Form VII of the hydrochloride salt of (S)-2-(1-(9H-purin-6-ylamino)propyl)-5-fluoro-3-phenylquinazolin-4(3H)-one, wherein the solvent is methyl ethyl ketone.

In another embodiment, provided is a method of producing a composition comprising polymorphic Form VII of a hydrochloride salt of (S)-2-(1-(9H-purin-6-ylamino)propyl)-5-fluoro-3-phenylquinazolin-4(3H)-one, wherein the method comprises combining a hydrochloride salt of (S)-2-(1-(9H-purin-6-ylamino)propyl)-5-fluoro-3-phenylquinazolin-4(3H)-one with a solvent to produce a composition comprising polymorphic Form VII of the hydrochloride salt of (S)-2-(1-(9H-purin-6-ylamino)propyl)-5-fluoro-3-phenylquinazolin-4(3H)-one, wherein the solvent is methyl ethyl ketone.

Provided is a polymorphic Form VII of a hydrochloride salt of (S)-2-(1-(9H-purin-6-ylamino)propyl)-5-fluoro-3-phenylquinazolin-4(3H)-one produced by combining (S)-2-(1-(9H-purin-6-ylamino)propyl)-5-fluoro-3-phenylquinazolin-4(3H)-one with hydrochloric acid and a solvent, wherein the solvent is methyl ethyl ketone.

Provided is also a polymorphic Form VII of a hydrochloride salt of (S)-2-(1-(9H-purin-6-ylamino)propyl)-5-fluoro-3-phenylquinazolin-4(3H)-one produced by combining a hydrochloride salt of (S)-2-(1-(9H-purin-6-ylamino)propyl)-5-fluoro-3-phenylquinazolin-4(3H)-one with a solvent, wherein the solvent is methyl ethyl ketone.

In certain embodiments of the polymorphic Form VII produced according to the methods described above, the hydrochloride salt of (S)-2-(1-(9H-purin-6-ylamino)propyl)-5-fluoro-3-phenylquinazolin-4(3H)-one is a monohydrochloride salt of (S)-2-(1-(9H-purin-6-ylamino)propyl)-5-fluoro-3-phenylquinazolin-4(3H)-one.

Form VIII

In one embodiment, provided is a method of producing a composition comprising polymorphic Form VIII of a hydrochloride salt of (S)-2-(1-(9H-purin-6-ylamino)propyl)-5-fluoro-3-phenylquinazolin-4(3H)-one, wherein the method comprises combining (S)-2-(1-(9H-purin-6-ylamino)propyl)-5-fluoro-3-phenylquinazolin-4(3H)-one with hydrochloric acid and a solvent to produce a composition comprising polymorphic Form VIII of the hydrochloride salt of (S)-2-(1-(9H-purin-6-ylamino)propyl)-5-fluoro-3-phenylquinazolin-4(3H)-one, wherein the solvent is dichloromethane.

In another embodiment, provided is a method of producing a composition comprising polymorphic Form VIII of a hydrochloride salt of (S)-2-(1-(9H-purin-6-ylamino)propyl)-5-fluoro-3-phenylquinazolin-4(3H)-one, wherein the method comprises combining a hydrochloride salt of (S)-2-(1-(9H-purin-6-ylamino)propyl)-5-fluoro-3-phenylquinazolin-4(3H)-one with a solvent to produce a composition comprising polymorphic Form VIII of the hydrochloride salt of (S)-2-(1-(9H-purin-6-ylamino)propyl)-5-fluoro-3-phenylquinazolin-4(3H)-one, wherein the solvent is dichloromethane.

Provided is a polymorphic Form VIII of a hydrochloride salt of (S)-2-(1-(9H-purin-6-ylamino)propyl)-5-fluoro-3-phenylquinazolin-4(3H)-one produced by combining (S)-2-(1-(9H-purin-6-ylamino)propyl)-5-fluoro-3-phenylquinazolin-4(3H)-one with hydrochloric acid and a solvent, wherein the solvent is dichloromethane.

Provided is also a polymorphic Form VIII of a hydrochloride salt of (S)-2-(1-(9H-purin-6-ylamino)propyl)-5-fluoro-3-phenylquinazolin-4(3H)-one prepared by combining a hydrochloride salt of (S)-2-(1-(9H-purin-6-ylamino)propyl)-5-fluoro-3-phenylquinazolin-4(3H)-one with a solvent, wherein the solvent is dichloromethane.

In certain embodiments of the polymorphic Form VIII produced according to the methods described above, the hydrochloride salt of (S)-2-(1-(9H-purin-6-ylamino)propyl)-5-fluoro-3-phenylquinazolin-4(3H)-one is a monohydrochloride salt of (S)-2-(1-(9H-purin-6-ylamino)propyl)-5-fluoro-3-phenylquinazolin-4(3H)-one.

Form XI

In one embodiment, provided is a method of producing a composition comprising polymorphic Form XI of a hydrochloride salt of (S)-2-(1-(9H-purin-6-ylamino)propyl)-5-fluoro-3-phenylquinazolin-4(3H)-one, wherein the method comprises combining (S)-2-(1-(9H-purin-6-ylamino)propyl)-5-fluoro-3-phenylquinazolin-4(3H)-one with hydrochloric acid and a solvent to produce a composition comprising polymorphic Form XI of the hydrochloride salt of (S)-2-(1-(9H-purin-6-ylamino)propyl)-5-fluoro-3-phenylquinazolin-4(3H)-one, wherein the solvent is 2-propanol.

In another embodiment, provided is a method of producing a composition comprising polymorphic Form XI of a hydrochloride salt of (S)-2-(1-(9H-purin-6-ylamino)propyl)-5-fluoro-3-phenylquinazolin-4(3H)-one, wherein the method comprises combining a hydrochloride salt of (S)-2-(1-(9H-purin-6-ylamino)propyl)-5-fluoro-3-phenylquinazolin-4(3H)-one with a solvent to produce a composition comprising polymorphic Form XI of the hydrochloride salt of (S)-2-(1-(9H-purin-6-ylamino)propyl)-5-fluoro-3-phenylquinazolin-4(3H)-one, wherein the solvent is 2-propanol.

Provided is a polymorphic Form XI of a hydrochloride salt of (S)-2-(1-(9H-purin-6-ylamino)propyl)-5-fluoro-3-phenylquinazolin-4(3H)-one produced by combining (S)-2-(1-(9H-purin-6-ylamino)propyl)-5-fluoro-3-phenylquinazolin-4(3H)-one with hydrochloric acid and a solvent, wherein the solvent is 2-propanol.

Provided is also a polymorphic Form XI of a hydrochloride salt of (S)-2-(1-(9H-purin-6-ylamino)propyl)-5-fluoro-3-phenylquinazolin-4(3H)-one produced by combining a hydrochloride salt of (S)-2-(1-(9H-purin-6-ylamino)propyl)-5-fluoro-3-phenylquinazolin-4(3H)-one with a solvent, wherein the solvent is 2-propanol.

In certain embodiments of the polymorphic Form XI produced according to the methods described above, the hydrochloride salt of (S)-2-(1-(9H-purin-6-ylamino)propyl)-5-fluoro-3-phenylquinazolin-4(3H)-one is a monohydrochloride salt of (S)-2-(1-(9H-purin-6-ylamino)propyl)-5-fluoro-3-phenylquinazolin-4(3H)-one.

Form XII

In one embodiment, provided is a method of producing a composition comprising polymorphic Form XII of a hydrochloride salt of (S)-2-(1-(9H-purin-6-ylamino)propyl)-5-fluoro-3-phenylquinazolin-4(3H)-one, wherein the method comprises combining (S)-2-(1-(9H-purin-6-ylamino)propyl)-5-fluoro-3-phenylquinazolin-4(3H)-one with hydrochloric acid and a solvent to produce a composition comprising polymorphic Form XII of the hydrochloride salt of (S)-2-(1-(9H-purin-6-ylamino)propyl)-5-fluoro-3-phenylquinazolin-4(3H)-one, wherein the solvent is 1-propanol.

In another embodiment, provided is a method of producing a composition comprising polymorphic Form XII of a hydrochloride salt of (S)-2-(1-(9H-purin-6-ylamino)propyl)-5-fluoro-3-phenylquinazolin-4(3H)-one, wherein the method comprises combining a hydrochloride salt of (S)-2-(1-(9H-purin-6-ylamino)propyl)-5-fluoro-3-phenylquinazolin-4(3H)-one with a solvent to produce a composition comprising polymorphic Form XII of the hydrochloride salt of (S)-2-(1-(9H-purin-6-ylamino)propyl)-5-fluoro-3-phenylquinazolin-4(3H)-one, wherein the solvent is 1-propanol.

Provided is a polymorphic Form XII of a hydrochloride salt of (S)-2-(1-(9H-purin-6-ylamino)propyl)-5-fluoro-3-phenylquinazolin-4(3H)-one produced by combining (S)-2-(1-(9H-purin-6-ylamino)propyl)-5-fluoro-3-phenylquinazolin-4(3H)-one with hydrochloric acid and a solvent, wherein the solvent is 1-propanol.

Provided is also a polymorphic Form XII of a hydrochloride salt of (S)-2-(1-(9H-purin-6-ylamino)propyl)-5-fluoro-3-phenylquinazolin-4(3H)-one produced by combining a hydrochloride salt of (S)-2-(1-(9H-purin-6-ylamino)propyl)-5-fluoro-3-phenylquinazolin-4(3H)-one with a solvent, wherein the solvent is 1-propanol.

In certain embodiments of the polymorphic Form XII produced according to the methods described above, the hydrochloride salt of (S)-2-(1-(9H-purin-6-ylamino)propyl)-5-fluoro-3-phenylquinazolin-4(3H)-one is a monohydrochloride salt of (S)-2-(1-(9H-purin-6-ylamino)propyl)-5-fluoro-3-phenylquinazolin-4(3H)-one.

Form XIII

In one embodiment, provided is a method of producing a composition comprising polymorphic Form XIII of a hydrochloride salt of (S)-2-(1-(9H-purin-6-ylamino)propyl)-5-fluoro-3-phenylquinazolin-4(3H)-one, wherein the method comprises combining (S)-2-(1-(9H-purin-6-ylamino)propyl)-5-fluoro-3-phenylquinazolin-4(3H)-one with hydrochloric acid and a solvent to produce a composition comprising polymorphic Form XIII of the hydrochloride salt of (S)-2-(1-(9H-purin-6-ylamino)propyl)-5-fluoro-3-phenylquinazolin-4(3H)-one, wherein the solvent is 1-butanol.

In another embodiment, provided is a method of producing a composition comprising polymorphic Form XIII of a hydrochloride salt of (S)-2-(1-(9H-purin-6-ylamino)propyl)-5-fluoro-3-phenylquinazolin-4(3H)-one, wherein the method comprises combining a hydrochloride salt of (S)-2-(1-(9H-purin-6-ylamino)propyl)-5-fluoro-3-phenylquinazolin-4(3H)-one with a solvent to produce a composition comprising polymorphic Form XIII of the hydrochloride salt of (S)-2-(1-(9H-purin-6-ylamino)propyl)-5-fluoro-3-phenylquinazolin-4(3H)-one, wherein the solvent is 1-butanol.

Provided is a polymorphic Form XIII of a hydrochloride salt of (S)-2-(1-(9H-purin-6-ylamino)propyl)-5-fluoro-3-phenylquinazolin-4(3H)-one produced by combining (S)-2-(1-(9H-purin-6-ylamino)propyl)-5-fluoro-3-phenylquinazolin-4(3H)-one with hydrochloric acid and a solvent, wherein the solvent is 1-butanol.

Provided is also a polymorphic Form XIII of a hydrochloride salt of (S)-2-(1-(9H-purin-6-ylamino)propyl)-5-fluoro-3-phenylquinazolin-4(3H)-one produced by combining a hydrochloride salt of (S)-2-(1-(9H-purin-6-ylamino)propyl)-5-fluoro-3-phenylquinazolin-4(3H)-one with a solvent, wherein the solvent is 1-butanol.

In certain embodiments of the polymorphic Form XIII produced according to the methods described above, the hydrochloride salt of (S)-2-(1-(9H-purin-6-ylamino)propyl)-5-fluoro-3-phenylquinazolin-4(3H)-one is a monohydrochloride salt of (S)-2-(1-(9H-purin-6-ylamino)propyl)-5-fluoro-3-phenylquinazolin-4(3H)-one.

The combination of the hydrochloride salt of (S)-2-(1-(9H-purin-6-ylamino)propyl)-5-fluoro-3-phenylquinazolin-4(3H)-one with one or more suitable solvents, as described above, yields a composition or mixture comprising the solvent and the one or more polymorphic forms produced. In some instances where only a portion of the hydrochloride salt of (S)-2-(1-(9H-purin-6-ylamino)propyl)-5-fluoro-3-phenylquinazolin-4(3H)-one is converted into one or more polymorphic forms, the composition further comprises the hydrochloride salt. In some embodiments of the methods described above to produce the one or more polymorphic forms, the method further comprises isolating the one or more polymorphic forms from the resulting composition. Any suitable techniques or methods known in the art to isolate the one or more polymorphic forms from the composition may be employed. For example, the solvent or mixture of solvents used in the methods described above may be removed by known methods, such as filtration and/or evaporation, to isolate the one or more polymorphic forms produced from the composition.

Pharmaceutical Compositions

The polymorphic forms described herein can be administered as the neat chemical, but it is typical, and preferable, to administer the compound in the form of a pharmaceutical composition or formulation. Accordingly, provided are pharmaceutical compositions comprising one or more of the polymorphic forms described herein (e.g., one or more of polymorphic Forms I to XIII of a hydrochloride salt of (S)-2-(1-(9H-purin-6-ylamino)propyl)-5-fluoro-3-phenylquinazolin-4(3H)-one, and any combinations thereof) and one or more pharmaceutically acceptable carriers, excipients, or other ingredients (including inert solid diluents and fillers, diluents, including sterile aqueous solution and various organic solvents, permeation enhancers, solubilizers and adjuvants). In certain embodiments, pharmaceutical compositions comprising one or more of the polymorphic forms described herein (e.g., one or more of polymorphic Forms I to XIII of a hydrochloride salt of (S)-2-(1-(9H-purin-6-ylamino)propyl)-5-fluoro-3-phenylquinazolin-4(3H)-one) and one or more pharmaceutically acceptable excipients is provided. In certain embodiments, pharmaceutical compositions comprising one or more of the polymorphic forms described herein (e.g., one or more of polymorphic Forms I to XIII of a hydrochloride salt of (S)-2-(1-(9H-purin-6-ylamino)propyl)-5-fluoro-3-phenylquinazolin-4(3H)-one) also include one or more additional therapeutic agents, as well as one or more pharmaceutically acceptable excipients. The composition can include the polymorphic forms described herein either as the sole active agent or in combination with other agents, such as oligo- or polynucleotides, oligo- or polypeptides, drugs, or hormones mixed with one or more pharmaceutically acceptable carriers, excipients, or other ingredients. Carriers, excipients, and other ingredients can be deemed pharmaceutically acceptable insofar as they are compatible with other ingredients of the formulation and not deleterious to the recipient thereof.

Provided herein is a pharmaceutical composition comprising one or more polymorphic forms of a hydrochloride salt of (S)-2-(1-(9H-purin-6-ylamino)propyl)-5-fluoro-3-phenylquinazolin-4(3H)-one described herein (e.g., one or more of polymorphic Forms I to XIII), and a pharmaceutical acceptable carrier or excipient.

Also provided herein is a pharmaceutical composition comprising one or more polymorphic forms of a hydrochloride salt of (S)-2-(1-(9H-purin-6-ylamino)propyl)-5-fluoro-3-phenylquinazolin-4(3H)-one described herein (e.g., one or more of polymorphic Forms I to XIII), and a pharmaceutical acceptable excipient.

In one embodiment, the pharmaceutical composition comprises polymorphic Form I of a hydrochloride salt of (S)-2-(1-(9H-purin-6-ylamino)propyl)-5-fluoro-3-phenylquinazolin-4(3H)-one, and a pharmaceutical acceptable carrier or excipient. In a further embodiment, the pharmaceutical composition comprises polymorphic Form I of a hydrochloride salt of (S)-2-(1-(9H-purin-6-ylamino)propyl)-5-fluoro-3-phenylquinazolin-4(3H)-one, and a pharmaceutical acceptable excipient.

In another embodiment, the pharmaceutical composition comprises polymorphic Form II of a hydrochloride salt of (S)-2-(1-(9H-purin-6-ylamino)propyl)-5-fluoro-3-phenylquinazolin-4(3H)-one, and a pharmaceutical acceptable carrier or excipient. In another embodiment, the pharmaceutical composition comprises polymorphic Form II of a hydrochloride salt of (S)-2-(1-(9H-purin-6-ylamino)propyl)-5-fluoro-3-phenylquinazolin-4(3H)-one, and a pharmaceutical acceptable excipient.

In another embodiment, the pharmaceutical composition comprises polymorphic Form II of a hydrochloride salt of (S)-2-(1-(9H-purin-6-ylamino)propyl)-5-fluoro-3-phenylquinazolin-4(3H)-one, and a pharmaceutical acceptable carrier or excipient. In another embodiment, the pharmaceutical composition comprises polymorphic Form III of a hydrochloride salt of (S)-2-(1-(9H-purin-6-ylamino)propyl)-5-fluoro-3-phenylquinazolin-4(3H)-one, and a pharmaceutical acceptable excipient.

In another embodiment, the pharmaceutical composition comprises polymorphic Form IV of a hydrochloride salt of (S)-2-(1-(9H-purin-6-ylamino)propyl)-5-fluoro-3-phenylquinazolin-4(3H)-one, and a pharmaceutical acceptable carrier or excipient. In another embodiment, the pharmaceutical composition comprises polymorphic Form IV of a hydrochloride salt of (S)-2-(1-(9H-purin-6-ylamino)propyl)-5-fluoro-3-phenylquinazolin-4(3H)-one, and a pharmaceutical acceptable excipient.

In yet another embodiment, the pharmaceutical composition comprises polymorphic Form V of a hydrochloride salt of (S)-2-(1-(9H-purin-6-ylamino)propyl)-5-fluoro-3-phenylquinazolin-4(3H)-one, and a pharmaceutical acceptable carrier or excipient. In yet another embodiment, the pharmaceutical composition comprises polymorphic Form V of a hydrochloride salt of (S)-2-(1-(9H-purin-6-ylamino)propyl)-5-fluoro-3-phenylquinazolin-4(3H)-one, and a pharmaceutical acceptable excipient.

In yet another embodiment, the pharmaceutical composition comprises polymorphic Form VI of a hydrochloride salt of (S)-2-(1-(9H-purin-6-ylamino)propyl)-5-fluoro-3-phenylquinazolin-4(3H)-one, and a pharmaceutical acceptable carrier or excipient. In yet another embodiment, the pharmaceutical composition comprises polymorphic Form VI of a hydrochloride salt of (S)-2-(1-(9H-purin-6-ylamino)propyl)-5-fluoro-3-phenylquinazolin-4(3H)-one, and a pharmaceutical acceptable excipient.

In yet another embodiment, the pharmaceutical composition comprises polymorphic Form VII of a hydrochloride salt of (S)-2-(1-(9H-purin-6-ylamino)propyl)-5-fluoro-3-phenylquinazolin-4(3H)-one, and a pharmaceutical acceptable carrier or excipient. In yet another embodiment, the pharmaceutical composition comprises polymorphic Form VII of a hydrochloride salt of (S)-2-(1-(9H-purin-6-ylamino)propyl)-5-fluoro-3-phenylquinazolin-4(3H)-one, and a pharmaceutical acceptable excipient.

In yet another embodiment, the pharmaceutical composition comprises polymorphic Form VIII of a hydrochloride salt of (S)-2-(1-(9H-purin-6-ylamino)propyl)-5-fluoro-3-phenylquinazolin-4(3H)-one, and a pharmaceutical acceptable carrier or excipient. In yet another embodiment, the pharmaceutical composition comprises polymorphic Form VIII of a hydrochloride salt of (S)-2-(1-(9H-purin-6-ylamino)propyl)-5-fluoro-3-phenylquinazolin-4(3H)-one, and a pharmaceutical acceptable excipient.

In yet another embodiment, the pharmaceutical composition comprises polymorphic Form IX of a hydrochloride salt of (S)-2-(1-(9H-purin-6-ylamino)propyl)-5-fluoro-3-phenylquinazolin-4(3H)-one, and a pharmaceutical acceptable carrier or excipient. In yet another embodiment, the pharmaceutical composition comprises polymorphic Form IX of a hydrochloride salt of (S)-2-(1-(9H-purin-6-ylamino)propyl)-5-fluoro-3-phenylquinazolin-4(3H)-one, and a pharmaceutical acceptable excipient.

In yet another embodiment, the pharmaceutical composition comprises polymorphic Form X of a hydrochloride salt of (S)-2-(1-(9H-purin-6-ylamino)propyl)-5-fluoro-3-phenylquinazolin-4(3H)-one, and a pharmaceutical acceptable carrier or excipient. In yet another embodiment, the pharmaceutical composition comprises polymorphic Form X of a hydrochloride salt of (S)-2-(1-(9H-purin-6-ylamino)propyl)-5-fluoro-3-phenylquinazolin-4(3H)-one, and a pharmaceutical acceptable excipient.

In yet another embodiment, the pharmaceutical composition comprises polymorphic Form XI of a hydrochloride salt of (S)-2-(1-(9H-purin-6-ylamino)propyl)-5-fluoro-3-phenylquinazolin-4(3H)-one, and a pharmaceutical acceptable carrier or excipient. In yet another embodiment, the pharmaceutical composition comprises polymorphic Form XI of a hydrochloride salt of (S)-2-(1-(9H-purin-6-ylamino)propyl)-5-fluoro-3-phenylquinazolin-4(3H)-one, and a pharmaceutical acceptable excipient.

In yet another embodiment, the pharmaceutical composition comprises polymorphic Form XII of a hydrochloride salt of (S)-2-(1-(9H-purin-6-ylamino)propyl)-5-fluoro-3-phenylquinazolin-4(3H)-one, and a pharmaceutical acceptable carrier or excipient. In yet another embodiment, the pharmaceutical composition comprises polymorphic Form XII of a hydrochloride salt of (S)-2-(1-(9H-purin-6-ylamino)propyl)-5-fluoro-3-phenylquinazolin-4(3H)-one, and a pharmaceutical acceptable excipient.

In yet another embodiment, the pharmaceutical composition comprises polymorphic Form XIII of a hydrochloride salt of (S)-2-(1-(9H-purin-6-ylamino)propyl)-5-fluoro-3-phenylquinazolin-4(3H)-one, and a pharmaceutical acceptable carrier or excipient. In yet another embodiment, the pharmaceutical composition comprises polymorphic Form XIII of a hydrochloride salt of (S)-2-(1-(9H-purin-6-ylamino)propyl)-5-fluoro-3-phenylquinazolin-4(3H)-one, and a pharmaceutical acceptable excipient.

Techniques for formulation and administration of pharmaceutical compositions can be found in *Remington's Pharmaceutical Sciences,* 18th Ed., Mack Publishing Co, Easton, Pa., 1990. The pharmaceutical compositions described herein can be manufactured using any conventional method, e.g., mixing, dissolving, granulating, dragee-making, levigating, emulsifying, encapsulating, entrapping, melt-spinning, spray-drying, or lyophilizing processes. An optimal pharmaceutical formulation can be determined by one of skill in the art depending on the route of administration and the desired dosage. Such formulations can influence the physical state, stability, rate of in vivo release, and rate of in vivo clearance of the administered agent. Depending on the condition being treated, these pharmaceutical compositions can be formulated and administered systemically or locally.

The pharmaceutical compositions can be formulated to contain suitable pharmaceutically acceptable carriers, and optionally can comprise excipients and auxiliaries that facilitate processing of the polymorphic forms described herein into preparations that can be used pharmaceutically. The mode of administration generally determines the nature of the carrier. For example, formulations for parenteral administration can include aqueous solutions of the active compounds in water-soluble form. Carriers suitable for parenteral administration can be selected from among saline, buffered saline, dextrose, water, and other physiologically compatible solutions. Preferred carriers for parenteral administration are physiologically compatible buffers such as Hanks's solution, Ringer's solution, or physiologically buffered saline. For tissue or cellular administration, penetrants appropriate to the particular barrier to be permeated are used in the formulation. Such penetrants are generally known in the art. For preparations including proteins, the formulation can include stabilizing materials, such as polyols (e.g., sucrose) and/or surfactants (e.g., nonionic surfactants), and the like.

Alternatively, formulations for parenteral use can include dispersions or suspensions of polymorphic forms described herein prepared as appropriate oily injection suspensions. Suitable lipophilic solvents or vehicles include fatty oils, such as sesame oil, and synthetic fatty acid esters, such as ethyl oleate or triglycerides, or liposomes. Aqueous injection suspensions can contain substances that increase the viscosity of the suspension, such as sodium carboxymethylcellulose, sorbitol, dextran, and mixtures thereof. Optionally, the suspension also can contain suitable stabilizers or agents that increase the solubility of the compounds to allow for the preparation of highly concentrated solutions. Aqueous polymers that provide pH-sensitive solubilization and/or sustained release of the active agent also can be used as coatings or matrix structures, e.g., methacrylic polymers, such as the EUDRAGIT™ series available from Rohm America Inc. (Piscataway, N.J.). Emulsions, e.g., oil-in-water and water-in-oil dispersions, also can be used, optionally stabilized by an emulsifying agent or dispersant (surface active materials; surfactants). Suspensions can contain suspending agents such as ethoxylated isostearyl alcohols, polyoxyethylene sorbitol and sorbitan esters, microcrystalline cellulose, aluminum metahydroxide, bentonite, agar-agar, gum tragacanth, and mixtures thereof.

Liposomes containing the polymorphic forms described herein also can be employed for parenteral administration. Liposomes generally are derived from phospholipids or other lipid substances. The compositions in liposome form also can contain other ingredients, such as stabilizers, preservatives, excipients, and the like. Preferred lipids include phospholipids and phosphatidyl cholines (lecithins), both natural and synthetic. Methods of forming liposomes are known in the art. See, e.g., Prescott (Ed.), Methods in Cell Biology, Vol. XIV, p. 33, Academic Press, New York (1976).

In some embodiments, the polymorph or composition thereof disclosed herein is formulated for oral administration using pharmaceutically acceptable carriers, excipients or other ingredients well known in the art. Preparations formulated for oral administration can be in the form of tablets, pills, capsules, cachets, dragees, lozenges, liquids, gels, syrups, slurries, elixirs, suspensions, or powders. To illustrate, pharmaceutical preparations for oral use can be obtained by combining the active compounds with a solid excipient, optionally grinding the resulting mixture, and processing the mixture of granules, after adding suitable auxiliaries if desired, to obtain tablets or dragee cores. Oral formulations can employ liquid carriers similar in type to those described for parenteral use, e.g., buffered aqueous solutions, suspensions, and the like.

In certain embodiments, the pharmaceutical compositions described herein are in the form of tablets, pills or capsules. In a particular embodiment, the pharmaceutical compositions described herein are in the form of a tablet. Preferred oral formulations include tablets, dragees, and gelatin capsules. These preparations can contain one or more excipients, which include, without limitation:

a) diluents, such as microcrystalline cellulose and sugars, including lactose, dextrose, sucrose, mannitol, or sorbitol;

b) binders, such as sodium starch glycolate, croscarmellose sodium, magnesium aluminum silicate, starch from corn, wheat, rice, potato, etc.;

c) cellulose materials, such as methylcellulose, hydroxypropylmethyl cellulose, and sodium carboxymethylcellulose, polyvinylpyrrolidone, gums, such as gum arabic and gum tragacanth, and proteins, such as gelatin and collagen;

d) disintegrating or solubilizing agents such as cross-linked polyvinyl pyrrolidone, starches, agar, alginic acid or a salt thereof, such as sodium alginate, or effervescent compositions;

e) lubricants, such as silica, talc, stearic acid or its magnesium or calcium salt, and polyethylene glycol;

f) flavorants and sweeteners;

g) colorants or pigments, e.g., to identify the product or to characterize the quantity (dosage) of active compound; and h) other ingredients, such as preservatives, stabilizers, swelling agents, emulsifying agents, solution promoters, salts for regulating osmotic pressure, and buffers.

For example, provided is a tablet comprising one or more of the polymorphic forms described herein (e.g., one or more of polymorphic Forms I to XIII of a hydrochloride salt of (S)-2-(1-(9H-purin-6-ylamino)propyl)-5-fluoro-3-phenylquinazolin-4(3H)-one, and any combinations thereof) and one or more pharmaceutically acceptable carriers or excipients. Also provided is a tablet comprising one or more of the polymorphic forms described herein (e.g., one or more of polymorphic Forms I to XIII of a hydrochloride salt of (S)-2-(1-(9H-purin-6-ylamino)propyl)-5-fluoro-3-phenylquinazolin-4(3H)-one, and any combinations thereof) and one or more pharmaceutically acceptable excipients.

In one embodiment, the tablet comprises substantially pure polymorphic Form I of a hydrochloride salt of (S)-2-(1-(9H-purin-6-ylamino)propyl)-5-fluoro-3-phenylquinazolin-4(3H)-one, and one or more pharmaceutically acceptable carriers or excipients. In one embodiment, the tablet comprises substantially pure polymorphic Form I of a hydrochloride salt of (S)-2-(1-(9H-purin-6-ylamino)propyl)-5-fluoro-3-phenylquinazolin-4(3H)-one, and a pharmaceutically acceptable excipient.

In another embodiment, the tablet comprises substantially pure polymorphic Form II of a hydrochloride salt of (S)-2-(1-(9H-purin-6-ylamino)propyl)-5-fluoro-3-phenylquinazolin-4(3H)-one, and a pharmaceutical acceptable carrier or excipient. In one embodiment, the tablet comprises substantially pure polymorphic Form II of a hydrochloride salt of (S)-2-(1-(9H-purin-6-ylamino)propyl)-5-fluoro-3-phenylquinazolin-4(3H)-one, and a pharmaceutical acceptable excipient.

In another embodiment, the tablet comprises substantially pure polymorphic Form III of a hydrochloride salt of (S)-2-(1-(9H-purin-6-ylamino)propyl)-5-fluoro-3-phenylquinazolin-4(3H)-one, and a pharmaceutical acceptable carrier or excipient. In one embodiment, the tablet comprises substantially pure polymorphic Form III of a hydrochloride salt of (S)-2-(1-(9H-purin-6-ylamino)propyl)-5-fluoro-3-phenylquinazolin-4(3H)-one, and a pharmaceutical acceptable excipient.

In another embodiment, the tablet comprises substantially pure polymorphic Form IV of a hydrochloride salt of (S)-2-(1-(9H-purin-6-ylamino)propyl)-5-fluoro-3-phenylquinazolin-4(3H)-one, and a pharmaceutical acceptable carrier or excipient. In one embodiment, the tablet comprises substantially pure polymorphic Form IV of a hydrochloride salt of (S)-2-(1-(9H-purin-6-ylamino)propyl)-5-fluoro-3-phenylquinazolin-4(3H)-one, and a pharmaceutical acceptable excipient.

In yet another embodiment, the tablet comprises substantially pure polymorphic Form V of a hydrochloride salt of (S)-2-(1-(9H-purin-6-ylamino)propyl)-5-fluoro-3-phenylquinazolin-4(3H)-one, and a pharmaceutical acceptable carrier or excipient. In one embodiment, the tablet comprises substantially pure polymorphic Form V of a hydrochloride salt of (S)-2-(1-(9H-purin-6-ylamino)propyl)-5-fluoro-3-phenylquinazolin-4(3H)-one, and a pharmaceutical acceptable excipient.

In yet another embodiment, the tablet comprises substantially pure polymorphic Form VI of a hydrochloride salt of (S)-2-(1-(9H-purin-6-ylamino)propyl)-5-fluoro-3-phenylquinazolin-4(3H)-one, and a pharmaceutical acceptable carrier or excipient. In one embodiment, the tablet comprises substantially pure polymorphic Form VI of a hydrochloride salt of (S)-2-(1-(9H-purin-6-ylamino)propyl)-5-fluoro-3-phenylquinazolin-4(3H)-one, and a pharmaceutical acceptable excipient.

In yet another embodiment, the tablet comprises substantially pure polymorphic Form VII of a hydrochloride salt of (S)-2-(1-(9H-purin-6-ylamino)propyl)-5-fluoro-3-phenylquinazolin-4(3H)-one, and a pharmaceutical acceptable carrier or excipient. In one embodiment, the tablet comprises substantially pure polymorphic Form VII of a hydrochloride salt of (S)-2-(1-(9H-purin-6-ylamino)propyl)-5-fluoro-3-phenylquinazolin-4(3H)-one, and a pharmaceutical acceptable excipient.

In yet another embodiment, the tablet comprises substantially pure polymorphic Form VIII of a hydrochloride salt of (S)-2-(1-(9H-purin-6-ylamino)propyl)-5-fluoro-3-phenylquinazolin-4(3H)-one, and a pharmaceutical acceptable carrier or excipient. In one embodiment, the tablet comprises substantially pure polymorphic Form VIII of a hydrochloride salt of (S)-2-(1-(9H-purin-6-ylamino)propyl)-5-fluoro-3-phenylquinazolin-4(3H)-one, and a pharmaceutical acceptable excipient.

In yet another embodiment, the tablet comprises substantially pure polymorphic Form IX of a hydrochloride salt of (S)-2-(1-(9H-purin-6-ylamino)propyl)-5-fluoro-3-phenylquinazolin-4(3H)-one, and a pharmaceutical acceptable carrier or excipient. In one embodiment, the tablet comprises substantially pure polymorphic Form IX of a hydrochloride salt of (S)-2-(1-(9H-purin-6-ylamino)propyl)-5-fluoro-3-phenylquinazolin-4(3H)-one, and a pharmaceutical acceptable excipient.

In yet another embodiment, the tablet comprises substantially pure polymorphic Form X of a hydrochloride salt of (S)-2-(1-(9H-purin-6-ylamino)propyl)-5-fluoro-3-phenylquinazolin-4(3H)-one, and a pharmaceutical acceptable carrier or excipient. In one embodiment, the tablet comprises substantially pure polymorphic Form X of a hydrochloride salt of (S)-2-(1-(9H-purin-6-ylamino)propyl)-5-fluoro-3-phenylquinazolin-4(3H)-one, and a pharmaceutical acceptable excipient.

In yet another embodiment, the tablet comprises substantially pure polymorphic Form XI of a hydrochloride salt of (S)-2-(1-(9H-purin-6-ylamino)propyl)-5-fluoro-3-phenylquinazolin-4(3H)-one, and a pharmaceutical acceptable carrier or excipient. In one embodiment, the tablet comprises substantially pure polymorphic Form XI of a hydrochloride salt of (S)-2-(1-(9H-purin-6-ylamino)propyl)-5-fluoro-3-phenylquinazolin-4(3H)-one, and a pharmaceutical acceptable excipient.

In yet another embodiment, the tablet comprises substantially pure polymorphic Form XII of a hydrochloride salt of (S)-2-(1-(9H-purin-6-ylamino)propyl)-5-fluoro-3-phenylquinazolin-4(3H)-one, and a pharmaceutical acceptable carrier or excipient. In one embodiment, the tablet comprises substantially pure polymorphic Form XII of a hydrochloride salt of (S)-2-(1-(9H-purin-6-ylamino)propyl)-5-fluoro-3-phenylquinazolin-4(3H)-one, and a pharmaceutical acceptable excipient.

In yet another embodiment, the tablet comprises substantially pure polymorphic Form XIII of a hydrochloride salt of (S)-2-(1-(9H-purin-6-ylamino)propyl)-5-fluoro-3-phenylquinazolin-4(3H)-one, and a pharmaceutical acceptable carrier or excipient. In one embodiment, the tablet comprises substantially pure polymorphic Form XIII of a hydrochloride salt of (S)-2-(1-(9H-purin-6-ylamino)propyl)-5-fluoro-3-phenylquinazolin-4(3H)-one, and a pharmaceutical acceptable excipient.

In any of the foregoing tablets, in one variation, the tablet is substantially free of amorphous or non-crystalline hydrochloride salt of (S)-2-(1-(9H-purin-6-ylamino)propyl)-5-fluoro-3-phenylquinazolin-4(3H)-one. In another embodiment, in any of the foregoing tablets, the tablet is free of amorphous or non-crystalline hydrochloride salt of (S)-2-(1-(9H-purin-6-ylamino)propyl)-5-fluoro-3-phenylquinazolin-4(3H)-one.

Gelatin capsules include push-fit capsules made of gelatin, as well as soft, sealed capsules made of gelatin and a coating such as glycerol or sorbitol. Push-fit capsules can contain the active ingredient(s) mixed with fillers, binders, lubricants, and/or stabilizers, etc. In soft capsules, the active compounds can be dissolved or suspended in suitable fluids, such as fatty oils, liquid paraffin, or liquid polyethylene glycol with or without stabilizers.

Dragee cores can be provided with suitable coatings such as concentrated sugar solutions, which also can contain gum arabic, talc, polyvinyl pyrrolidone, carbopol gel, polyethylene glycol, and/or titanium dioxide, lacquer solutions, and suitable organic solvents or solvent mixtures.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The polymorphs described herein are effective over a wide dosage range and are generally administered in a pharmaceutically effective amount. It will be understood, however, that the amount of the polymorph actually administered will be determined by a physician, in the light of the relevant circumstances, including the condition to be treated, the chosen route of administration, the age, weight, and response of the subject receiving such treatment, the severity of the subject's symptoms, and the like.

The tablets or pills described herein may be coated or otherwise compounded to provide a dosage form affording the advantage of prolonged action, or to protect from the acid conditions of the stomach. For example, the tablet or pill can comprise an inner dosage and an outer dosage element, the latter being in the form of an envelope over the former. The two elements can be separated by an enteric layer that serves to resist disintegration in the stomach and permit the inner element to pass intact into the duodenum or to be delayed in release. A variety of materials can be used for such enteric layers or coatings, such materials including a number of polymorphic acids and mixtures of polymorphic acids with such materials as shellac, cetyl alcohol, and cellulose acetate.

For example, provided is a unit dosage comprising one or more of the polymorphic forms described herein (e.g., one or more of polymorphic Forms I to XIII of a hydrochloride salt of (S)-2-(1-(9H-purin-6-ylamino)propyl)-5-fluoro-3-phenylquinazolin-4(3H)-one. In one embodiment, the unit dosage comprises polymorphic Form I of a hydrochloride salt of (S)-2-(1-(9H-purin-6-ylamino)propyl)-5-fluoro-3-phenylquinazolin-4(3H)-one. In another embodiment, the unit dosage comprises polymorphic Form II of a hydrochloride salt of (S)-2-(1-(9H-purin-6-ylamino)propyl)-5-fluoro-3-phenylquinazolin-4(3H)-one. In another embodiment, the unit dosage comprises polymorphic Form III of a hydrochloride salt of (S)-2-(1-(9H-purin-6-ylamino)propyl)-5-fluoro-3-phenylquinazolin-4(3H)-one. In another embodiment, the unit dosage comprises polymorphic Form IV of a hydrochloride salt of (S)-2-(1-(9H-purin-6-ylamino)propyl)-5-fluoro-3-phenylquinazolin-4(3H)-one. In yet another embodiment, the unit dosage comprises polymorphic Form V of a hydrochloride salt of (S)-2-(1-(9H-purin-6-ylamino)propyl)-5-fluoro-3-phenylquinazolin-4(3H)-one. In yet another embodiment, the unit dosage comprises polymorphic Form VI of a hydrochloride salt of (S)-2-(1-(9H-purin-6-ylamino)propyl)-5-fluoro-3-phenylquinazolin-4(3H)-one. In yet another embodiment, the unit dosage comprises polymorphic Form VII of a hydrochloride salt of (S)-2-(1-(9H-purin-6-ylamino)propyl)-5-fluoro-3-phenylquinazolin-4(3H)-one. In yet another embodiment, the unit dosage comprises polymorphic Form VIII of a hydrochloride salt of (S)-2-(1-(9H-purin-6-ylamino)propyl)-5-fluoro-3-phenylquinazolin-4(3H)-one. In yet another embodiment, the unit dosage comprises polymorphic Form IX of a hydrochloride salt of (S)-2-(1-(9H-purin-6-ylamino)propyl)-5-fluoro-3-phenylquinazolin-4(3H)-one. In yet another embodiment, the unit dosage comprises polymorphic Form X of a hydrochloride salt of (S)-2-(1-(9H-purin-6-ylamino)propyl)-5-fluoro-3-phenylquinazolin-4(3H)-one. In yet another embodiment, the unit dosage comprises polymorphic Form XI of a hydrochloride salt of (S)-2-(1-(9H-purin-6-ylamino)propyl)-5-fluoro-3-phenylquinazolin-4(3H)-one. In yet another embodiment, the unit dosage comprises polymorphic Form XII of a hydrochloride salt of (S)-2-(1-(9H-purin-6-ylamino)propyl)-5-fluoro-3-phenylquinazolin-4(3H)-one. In yet another embodiment, the unit dosage comprises polymorphic Form XIII of a hydrochloride salt of (S)-2-(1-(9H-purin-6-ylamino)propyl)-5-fluoro-3-phenylquinazolin-4(3H)-one.

In any of the foregoing unit dosage forms, in certain embodiments, the hydrochloride salt is a monohydrochloride salt of (S)-2-(1-(9H-purin-6-ylamino)propyl)-5-fluoro-3-phenylquinazolin-4(3H)-one.

In any of the foregoing unit dosage forms, in one variation, the unit dosage form is substantially free of amorphous or non-crystalline hydrochloride salt of (S)-2-(1-(9H-purin-6-ylamino)propyl)-5-fluoro-3-phenylquinazolin-4(3H)-one.

In certain embodiments, in any of the foregoing unit dosage forms, the tablet further includes one or more excipients.

In certain embodiments, the unit dosage forms described herein include 75-300 mg of the polymorphic forms described herein. In certain embodiments, the unit dosage forms described herein include 75-200 mg of the polymorphic forms described herein. In certain embodiments, the unit dosage forms described herein include 75-150 mg of the polymorphic forms described herein. In certain embodiments, the unit dosage forms described herein include 75 mg, 100 mg, 125 mg, 150 mg, 175 mg, 200 mg, 250 mg, or 300 mg of the polymorphic forms described herein. In certain embodiments, the unit dosage forms described herein include 75 mg, 100 mg, 150 mg, or 200 mg of the polymorphic forms described herein. In certain embodiments, the unit dosage forms described herein include 100 mg or 150 mg 200 mg of the polymorphic forms described herein.

Modes of Administration and Dosages

Pharmaceutical compositions including the polymorphic forms described herein can be administered to the subject by any conventional method, including parenteral and enteral techniques. Parenteral administration modalities include those in which the composition is administered by a route other than through the gastrointestinal tract, for example, intravenous, intraarterial, intraperitoneal, intramedullary, intramuscular, intraarticular, intrathecal, and intraventricular injections. Enteral administration modalities include, for example, oral, buccal, sublingual, and rectal administration. Transepithelial administration modalities include, for example, transmucosal administration and transdermal administration. Transmucosal administration includes, for example, enteral administration as well as nasal, inhalation, and deep lung administration; vaginal administration; and buccal and sublingual administration. Transdermal administration includes passive or active transdermal or transcutaneous modalities, including, for example, patches and iontophoresis devices, as well as topical application of pastes, salves, or ointments. Parenteral administration also can be accomplished using a high-pressure technique, e.g., POWDERJECT™.

Moreover, the therapeutic index of the compound having the polymorphic forms described herein can be enhanced by modifying or derivatizing the compound for targeted delivery to cancer cells expressing a marker that identifies the cells as such. For example, the compound can be linked to an antibody that recognizes a marker that is selective or specific for cancer cells, so that the compounds are brought into the vicinity of the cells to exert their effects locally, as previously described. See e.g., Pietersz et al., Immunol. Rev., 129:57 (1992); Trail et al., Science, 261:212 (1993); and Rowlinson-Busza et al., Curr. Opin. Oncol., 4:1142 (1992). Tumor-directed delivery of the compound can enhance the therapeutic benefit by, inter alia, minimizing potential nonspecific toxicities that can result from radiation treatment or chemotherapy. In some embodiments, the compound having a polymorphic form described herein, and radioisotopes or chemotherapeutic agents can be conjugated to the same anti-tumor antibody.

Pharmacokinetic and pharmacodynamic information about the polymorphic forms described herein and the formulation of the compound having a polymorphic form described herein can be collected through preclinical in vitro and in vivo studies, later confirmed in humans during the course of clinical trials. Thus, for the compound having a polymorphic form described herein used in the methods described herein, a therapeutically effective dose can be estimated initially from biochemical and/or cell-based assays. Then, dosage can be formulated in animal models to achieve a desirable circulating concentration range that modulates PI3Kδ expression or activity. As human studies are conducted further information will emerge regarding the appropriate dosage levels and duration of treatment for various diseases and conditions.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the "therapeutic index", which typically is expressed as the ratio $LD_{50}/ED_{50}$. Compounds that exhibit large therapeutic indices, i.e., the toxic dose is substantially higher than the effective dose, are preferred. The data obtained from such cell culture assays and additional animal studies can be used in formulating a range of dosage for human use. The dosage of such compounds lies preferably within a range of circulating concentrations that include the ED.sub.50 with little or no toxicity.

It should be understood that any effective administration regimen regulating the timing and sequence of doses can be used. A compound having a polymorphic form described herein and pharmaceutical compositions thereof may include those wherein the active ingredient is administered in an effective amount to achieve its intended purpose.

In some embodiments, a "therapeutically effective amount" means an amount sufficient to modulate PI3K expression or activity, including PI3Kδ expression or activity, and thereby treat a subject (e.g., a human) suffering an indication, or to alleviate the existing symptoms of the indication.

Exemplary dosage levels for a human subject may be of the order of from about 0.001 milligram of active agent per kilogram body weight (mg/kg) to about 1000 mg/kg. Dosage units of the active agent may comprise from about 0.01 mg to about 1000 mg, or from about 0.1 mg to about 100 mg, depending upon the indication, route of administration, and severity of the condition, for example. Depending on the route of administration, a suitable dose can be calculated according to body weight, body surface area, or organ size. For example, when administered orally, the total daily dosage for a human subject may be between 1 mg and 1,000 mg, between about 10-500 mg/day, between about 50-300 mg/day, between about 75-200 mg/day, or between about 100-150 mg/day. In certain embodiments, the total daily dosage for a human subject is about 150-300 mg/day. In certain embodiments, the total daily dosage for a human subject is about 200-300 mg/day. In certain embodiments, the total daily dosage for a human subject is 75 mg, 100 mg, 125 mg, 150 mg, 175 mg, 200 mg, 250 mg, or 300 mg. In certain embodiments, the total daily dosage for a human subject is 75 mg, 100 mg, 150 mg, 200 mg, or 300 mg. In certain embodiments, the total daily dosage for a human subject is 150 mg, 200 mg, or 300 mg. In certain embodiments, the total daily dosage for a human subject is 200 mg or 300 mg. In certain embodiments, the total daily dosage for a human subject is 100 mg or 150 mg. The final dosage regimen is determined by the attending physician in view of good medical practice, considering various factors that modify the action of drugs, e.g., the specific activity of the compound, the identity and severity of the disease state, the responsiveness of the subject, the age, condition, body weight, sex, and diet of the subject, and the severity of any infection. Additional factors that can be taken into account include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in human clinical trials. Appropriate dosages can be ascertained through use of established assays for determining concentration of the agent in a body fluid or other sample together with dose response data.

The frequency of dosing depends on the pharmacokinetic parameters of the agent and the route of administration. Dosage and administration are adjusted to provide sufficient levels of the active moiety or to maintain the desired effect. Accordingly, the pharmaceutical compositions can be administered in a single dose, multiple discrete doses, continuous infusion, sustained release depots, or combinations thereof; as required to maintain desired minimum level of the agent. Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks.

In certain embodiments, the pharmaceutical composition disclosed herein are administered once, twice, or three times daily. In certain embodiments, the pharmaceutical composition disclosed herein are administered once or twice daily. In certain embodiments, the pharmaceutical composition disclosed herein are administered once daily.

Bioequivalents of the Polymorphs

Also provided herein are polymorphs that are bioequivalent to any one or more of polymorphic Forms I to XIII of a hydrochloride salt of (S)-2-(1-(9H-purin-6-ylamino)propyl)-5-fluoro-3-phenylquinazolin-4(3H)-one described herein.

In certain embodiments, bioequivalence between two polymorphs refers to polymorphs having substantially similar bioavailability, substantially similar efficacy, substantially similar safety profiles, or a combination thereof.

In yet other embodiments, bioequivalence refers to polymorphs that exhibit substantially similar pharmacokinetic profiles or therapeutic effects. Bioequivalence may be demonstrated through several in vivo and in vitro methods. These methods may include, for example, pharmacokinetic, pharmacodynamic, clinical and in vitro studies. In some embodiments, bioequivalence can be demonstrated using any suitable pharmacokinetic measures or combination of pharmacokinetic measures known in the art, including loading dose, steady-state dose, initial or steady-state concentration of drug, biological half-life, elimination rate, area under the curve (AUC), clearance, the peak blood or plasma concentration ($C_{max}$), time to peak concentration ($T_{max}$), bioavailability and potency. In some embodiments, bioequivalence is achieved with similar dosing amounts. In alternative embodiments, bioequivalence is achieved with different dosing amounts.

Uses of the Polymorphs and Compositions Thereof

Therapeutic Uses

Provided are also a use of the polymorphs or compositions thereof described herein to selectively or specifically inhibit PI3Kδ activity therapeutically or prophylactically. The method comprises administering the polymorphs or compositions thereof to a subject (e.g., a human) in need thereof in an amount sufficient to inhibit PI3Kδ activity. The method can be employed to treat humans or animals suffering from, or subject to, a condition whose symptoms or pathology is mediated by PI3Kδ expression or activity.

"Treatment" or "treating" is an approach for obtaining beneficial or desired results including clinical results. Beneficial or desired clinical results may include one or more of the following:
  (i) decreasing one more symptoms resulting from the disease;
  (ii) diminishing the extent of the disease and/or stabilizing the disease (e.g., delaying the worsening of the disease);
  (iii) delaying the spread (e.g., metastasis) of the disease;

(iv) delaying or slowing the recurrence of the disease and/or the progression of the disease;
(v) ameliorating the disease state and/or providing a remission (whether partial or total) of the disease and/or decreasing the dose of one or more other medications required to treat the disease;
(vi) increasing the quality of life; and/or
(vii) prolonging survival.

In some embodiments, "disorder" is intended to encompass medical disorders, diseases, conditions, syndromes, and the like, without limitation.

The methods disclosed in the application embrace various modes of treating an animal subject, preferably a mammal, more preferably a primate, and still more preferably a human. Among the mammalian animals that can be treated are, for example, humans; companion animals (pets), including dogs and cats; farm animals, including cattle, horses, sheep, pigs, and goats; laboratory animals, including rats, mice, rabbits, guinea pigs, and nonhuman primates; and zoo specimens. Among the non-mammalian animals that can be treated include, for example, birds, fish, reptiles, and amphibians.

In one aspect, the polymorphs and compositions thereof described herein can be employed in methods of inhibiting the growth or proliferation of cancer cells of hematopoietic origin, such as cancer cells. In some embodiments, the cancer cells are of lymphoid origin, and in specific embodiments, the cancer cells are related to or derived from B lymphocytes or B lymphocyte progenitors. In another aspect, the polymorphs and compositions thereof described herein can be employed in methods of treating a human with a cancer.

Cancers amenable to treatment using the method disclosed in the application include, for example, lymphomas (e.g., malignant neoplasms of lymphoid and reticuloendothelial tissues, such as Burkitt's lymphoma, Hodgkins' lymphoma, non-Hodgkins' lymphomas, lymphocytic lymphomas); multiple myelomas; leukemias (e.g., lymphocytic leukemias, chronic myeloid (myelogenous) leukemias), and solid tumor (e.g., pancreatic). Other cancer cells, of hematopoietic origin or otherwise, that express p110δ also can be treated by administration of the polymorphs and compositions thereof described herein.

In other embodiments, the forms described herein may be used to treat cancers that are mediated by, dependent on or associated with PI3K activity, such as PI3Kδ activity. In certain embodiments, the cancer is a hematologic malignancy. In certain embodiments, the cancer is lymphoma, multiple myeloma, or leukemia. In certain embodiments, the cancer is a solid tumor cancer. In particular embodiments, the hematologic malignancy is leukemia or lymphoma. In specific embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), juvenile myelomonocytic leukemia (JMML), multiple myeloma (MM), Hodgkin lymphoma, non-Hodgkin's lymphoma (NHL), indolent non-Hodgkin's lymphoma (iNHL), refractory iNHL, mantle cell lymphoma (MCL), follicular lymphoma, Waldestrom's macroglobulinemia (WM), minimal residual disease (MRD), T-cell lymphoma, B-cell lymphoma, diffuse large B-cell lymphoma (DLBCL), T-cell acute lymphoblastic leukemia (T-ALL), B-cell acute lymphoblastic leukemia (B-ALL), lymphoplasmacytic lymphoma, marginal zone lymphoma, Burkitt lymphoma, or follicular B-cell non-Hodgkin lymphoma (FL). In one embodiment, the cancer is T-cell acute lymphoblastic leukemia (T-ALL), or B-cell acute lymphoblastic leukemia (B-ALL). In one embodiment, the cancer is indolent non-Hodgkin's lymphoma (iNHL). It should be understood that non-Hodgkin's lymphoma may, in certain embodiments, encompass the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt lymphoma, diffuse large B-cell lymphoma (DLBCL) and mantle cell lymphoma (MCL). In certain embodiments, the forms described herein may be used to treat chronic lymphocytic leukemia (CLL), follicular B-cell non-Hodgkin lymphoma (FL), or small lymphocytic lymphoma (SLL). In certain embodiments, the forms described herein may be used to treat relapsed chronic lymphocytic leukemia (CLL), relapsed follicular B-cell non-Hodgkin lymphoma (FL), or relapsed small lymphocytic lymphoma (SLL). In certain embodiments, the forms described herein may be used to treat non-Hodgkin's lymphoma (NHL) or indolent non-Hodgkin's lymphoma (iNHL). In certain embodiments, the forms described herein may be used to treat relapsed non-Hodgkin's lymphoma (NHL) or relapsed indolent non-Hodgkin's lymphoma (iNHL).

In another aspect, the polymorphs and compositions thereof described herein can be employed in methods of treating an autoimmune disease. In some embodiments, the autoimmune disease is systemic lupus erythematosus (SLE), myestenia gravis, rheumatoid arthritis (RA), acute disseminated encephalomyelitis, idiopathic thrombocytopenic purpura, multiple sclerosis (MS), Sjoegren's syndrome, psoriasis, autoimmune hemolytic anemia, asthma, or chronic obstructive pulmonary disease (COPD). In particular embodiments, the autoimmune disease is asthma, rheumatoid arthritis, multiple sclerosis, or lupus.

In yet another aspect, provided are methods of treating a human having a PI3K-mediated disorder by administering one or more of the polymorphic forms described herein (e.g., one or more of polymorphic Forms I, II, III, IV, V, VI, VII, VIII, IX, X, XI, XII and XIII) to the human. In another aspect, provided are methods of treating a human having a PI3K-mediated disorder by administering one or more of the polymorphic forms described herein (e.g., one or more of the solvate forms corresponding to Pattern 1, 2, 3, 4, or the 2-methyl-1-propanol solvate, or the 1,4-dioxane solvate, or the toluene solvate) to the human. Provided are also methods of modulating PI3K an individual by administering one or more of the polymorphic forms described herein (e.g., one or more of polymorphic Forms I to XIII a hydrochloride salt of (S)-2-(1-(9H-purin-6-ylamino)propyl)-5-fluoro-3-phenylquinazolin-4(3H)-one. In one variation, the human has cancer, such as leukemia or lymphoma. In another variation, the human has an autoimmune disease, such as asthma, rheumatoid arthritis, multiple sclerosis, or lupus.

In any of the foregoing methods, one or more polymorphic forms may be administered to the individual as unit dosage, for example in the form of a tablet, as described herein. Exemplary unit dosage levels of polymorphic Forms I, II, III, IV, V, VI, VII, VIII, IX, X, XI, XII and XIII, for a human subject may, in certain variations, be between about 0.01 mg to about 1000 mg, between about 1 mg to about 15 mg, or between about 50 mg to about 200 mg, or about 5 mg, about 10 mg, about 15 mg, about 25 mg, about 50 mg, about 75 mg, about 100 mg, about 125 mg, or about 150 mg, or about 175 mg, about 200 mg, or about 250 mg.

In another aspect, polymorphic forms described herein (e.g., polymorphic Forms I, II, III, IV, V, VI, VII, VIII, IX, X, XI, XII and XIII) may be used in combination with one or more additional therapeutic agent that are being used and/or developed to treat cancers or inflammatory disorders. The one or more additional therapeutic agent may be an inhibitor to PI3K such as PI3Kγ, PI3Kβ, and/or PI3Kα, Janus kinase (JAK) such as JAK1, JAK2 and/or JAK3, spleen tyrosine kinase (SYK), Bruton's tyrosine kinase (BTK), bromodomain containing protein inhibitor (BRD) such as BRD4, a lysyl oxidase protein (LOX), lysyl oxidase-like protein (LOXL) such as LOXL1-5, matrix metalloprotease (MMP) such as MMP 1-10, adenosine A2B receptor (A2B), isocitrate dehydrogenase (IDH) such as IDH1, apoptosis signal-regulating kinase (ASK) such as ASK1, serine/threonine kinase TPL2, discoidin domain receptor (DDR) such as DDR1 and DDR2, histone deacetylase (HDAC), protein kinase C (PKC), or monoclonal antibody (such as an anti-CD20 monoclonal antibody or an anti-CD39 monoclonal antibody) or any combination thereof.

One, two, three, or more of the therapeutic agents (e.g. a PI3K inhibitor, a JAK inhibitor, a SYK inhibitor, a BTK inhibitor, a BRD4 inhibitor, a LOXL2 inhibitor, a MMP9 inhibitor, a A2B inhibitor, an IDH inhibitor, an ASK inhibitor, a TPL2 inhibitor, a DDR1 inhibitor, a TBK inhibitor, a HDAC inhibitor, a PKC inhibitor, or a monoclonal antibody) may be further used or combined with a chemotherapeutic agent, an immunotherapeutic agent, a radiotherapeutic agent, an anti-neoplastic agent, an anti-cancer agent, an anti-fibrotic agent, an anti-angiogenic agent, a therapeutic antibody, or any combination thereof.

Chemotherapeutic agents may be categorized by their mechanism of action into, for example, the following groups: anti-metabolites/anti-cancer agents, such as pyrimidine analogs (floxuridine, capecitabine, and cytarabine); purine analogs, folate antagonists and related inhibitors antiproliferative/antimitotic agents including natural products such as vinca alkaloid (vinblastine, vincristine) and microtubule such as taxane (paclitaxel, docetaxel), vinblastin, nocodazole, epothilones and navelbine, epidipodophyllotoxins (etoposide, teniposide); DNA damaging agents (actinomycin, amsacrine, busulfan, carboplatin, chlorambucil, cisplatin, cyclophosphamide, Cytoxan, dactinomycin, daunorubicin, doxorubicin, epirubicin, iphosphamide, melphalan, merchlorehtamine, mitomycin, mitoxantrone, nitrosourea, procarbazine, taxol, taxotere, teniposide, etoposide, triethylenethiophosphoramide); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards cyclophosphamide and analogs (bendamustine, melphalan, chlorambucil), and (hexamethylmelamine and thiotepa), alkyl nitrosoureas (BCNU) and analogs, streptozocin), trazenes-dacarbazinine (DTIC); antiproliferative/antimitotic antimetabolites such as folic acid analogs (methotrexate); platinum coordination complexes (cisplatin, oxiloplatinim, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel; antimigratory agents; antisecretory agents (breveldin); immunosuppressives tacrolimus sirolimus azathioprine, mycophenolate; compounds (TNP-470, genistein) and growth factor inhibitors (vascular endothelial growth factor inhibitors, fibroblast growth factor inhibitors); angiotensin receptor blocker, nitric oxide donors; anti-sense oligonucleotides; antibodies (trastuzumab, rituximab); cell cycle inhibitors and differentiation inducers (tretinoin); inhibitors, topoisomerase inhibitors (doxorubicin (adriamycin), daunorubicin, dactinomycin, eniposide, epirubicin, etoposide, idarubicin, irinotecan and mitoxantrone, topotecan, irinotecan, camptothesin), corticosteroids (cortisone, dexamethasone, hydrocortisone, methylpednisolone, prednisone, and prenisolone); growth factor signal transduction kinase inhibitors; dysfunction inducers, toxins such as Cholera toxin, ricin, *Pseudomonas exotoxin, Bordetella pertussis* adenylate cyclase toxin, or diphtheria toxin, and caspase activators; and chromatin.

As used herein the term "chemotherapeutic agent" or "chemotherapeutic" (or "chemotherapy", in the case of treatment with a chemotherapeutic agent) may encompass any non-proteinaceous (e.g., non-peptidic) chemical compound useful in the treatment of cancer. Examples of chemotherapeutic agents include alkylating agents such as bendamustine, thiotepa and cyclophosphamide (CYTOXAN™); alkyl sulfonates such as busulfan, improsulfan and piposulfan; aziridines such as benzodopa, carboquone, meturedopa, and uredopa; emylerumines and memylamelamines including alfretamine, triemylenemelamine, triethylenephosphoramide, triethylenethiophosphoramide and trimemylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (articularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g., calicheamicin, especially calicheamicin gammaII and calicheamicin phiI1, see, e.g., Agnew, Chem. Intl. Ed. Engl, 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubanimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replinisher such as frolinic acid; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; PSK®; razoxane; rhizoxin; sizofiran; spirogermanium; tenuazonic acid; triaziquone; 2,2',2''-tricUorotriemylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiopeta; taxoids, e.g., paclitaxel (TAXOL®, Bristol Meyers Squibb Oncology, Princeton, N.J.) and docetaxel (TAXOTERE®, Rhone-Poulenc Rorer, Antony, France); chlorambucil; gemcitabine (Gemzar®); 6-thioguanine; mercaptopurine; methotrexate; platinum analogs such as cisplatin and carboplatin; vinblastine; platinum; etoposide (VP-16); ifosfamide; mitroxantrone; vancristine; vinorelbine (Navelbine®); novantrone; teniposide; edatrexate; daunomycin; aminopterin; xeoloda; ibandronate; CPT-1; topoisomerase inhibitor RFS 2000; difluoromethylornithine (DMFO); retinoids such as retinoic acid; capecitabine; FOLFIRI (fluorouracil, leucovorin, and irinotecan) and pharmaceutically acceptable salts, acids or derivatives of any of the above. One or more chemotherapeutic agent are used or included in the present application. For example, gemcitabine, nab-paclitaxel, and gemcitabine/nab-paclitaxel are used with the JAK inhibitor and/or PI3Kδ inhibitor for treating hyperproliferative disorders.

Chemotherapeutic agents may also include, for example, anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston®); inhibitors of the enzyme aromatase, which regulates estrogen production in the adrenal glands, such as, for example, 4(5)-imidazoles, aminoglutethimide, megestrol acetate (Megace®), exemestane, formestane, fadrozole, vorozole (Rivisor®), letrozole (Femara®), and anastrozole (Arimidex®); and anti-androgens such as flutamide, nilutamide, bicalutamide, leuprohde, and goserelin; and pharmaceutically acceptable salts, acids or derivatives of any of the above.

The anti-angiogenic agents include, but are not limited to, retinoid acid and derivatives thereof; 2-methoxyestradiol, ANGIOSTATIN, ENDOSTATIN, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,I-3,4-dehydroproline, thiaproline, .alpha.-dipyridyl, beta-aminopropionitrile fumarate, 4-propyl-5-(4-pyridinyl)-2 (3h)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpha-2-antiplasmin, bisantrene, lobenzarit disodium, n-2-carboxyphenyl-4-chloroanthronilic acid disodium or "CCA", thalidomide; angiostatic steroid, cargboxynaminolmidazole; metalloproteinase inhibitors such as BB94. Other anti-angiogenesis agents include antibodies, preferably monoclonal antibodies against these angiogenic growth factors: beta-FGF, alpha-FGF, FGF-5, VEGF isoforms, VEGF-C, HGF/SF and Ang-1/Ang-2. See Ferrara N. and Alitalo, K. "Clinical application of angiogenic growth factors and their inhibitors" (1999) Nature Medicine 5:1359-1364.

The anti-fibrotic agents include, but are not limited to, the compounds such as beta-aminoproprionitrile (BAPN), as well as the compounds disclosed in U.S. Pat. No. 4,965,288 to Palfreyman, et al., issued Oct. 23, 1990, entitled "Inhibitors of lysyl oxidase," relating to inhibitors of lysyl oxidase and their use in the treatment of diseases and conditions associated with the abnormal deposition of collagen; U.S. Pat. No. 4,997,854 to Kagan, et al., issued Mar. 5, 1991, entitled "Anti-fibrotic agents and methods for inhibiting the activity of lysyl oxidase in situ using adjacently positioned diamine analogue substrate," relating to compounds which inhibit LOX for the treatment of various pathological fibrotic states, which are herein incorporated by reference. Further exemplary inhibitors are described in U.S. Pat. No. 4,943,593 to Palfreyman, et al., issued Jul. 24, 1990, entitled "Inhibitors of lysyl oxidase," relating to compounds such as 2-isobutyl-3-fluoro-, chloro-, or bromo-allylamine; as well as, e.g., U.S. Pat. No. 5,021,456; U.S. Pat. No. 5,5059,714; U.S. Pat. No. 5,120,764; U.S. Pat. No. 5,182,297; U.S. Pat. No. 5,252,608 (relating to 2-(1-naphthyloxymemyl)-3-fluoroallylamine); and U.S. Patent Application No. 2004/0248871, which are herein incorporated by reference in their entirety. Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives, semicarbazide, and urea derivatives, aminonitriles, such as beta-aminopropionitrile (BAPN), or 2-nitroethylamine, unsaturated or saturated haloamines, such as 2-bromo-ethylamine, 2-chloroethylamine, 2-trifluoroethylamine, 3-bromopropylamine, p-halobenzylamines, selenohomocysteine lactone. Also, the anti-fibrotic agents are copper chelating agents, penetrating or not penetrating the cells. Exemplary compounds include indirect inhibitors such compounds blocking the aldehyde derivatives originating from the oxidative deamination of the lysyl and hydroxylysyl residues by the lysyl oxidases, such as the thiolamines, in particular D-penicillamine, or its analogues such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio) butane sulphurate, 2-acetamidoethyl-2-acetamidoethanethiol sulphanate, sodium-4-mercaptobutanesulphinate trihydrate.

The immunotherapeutic agents include and are not limited to therapeutic antibodies suitable for treating patients; such as abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minrctumomab, mitumomab, moxetumomab, narnatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8. The exemplified therapeutic antibodies may be further labeled or combined with a radioisotope particle, such as indium In 111, yttrium Y 90, iodine I-131.

The application also provides a method for treating a subject who is undergoing one or more standard therapies, such as chemotherapy, radiotherapy, immunotherapy, surgery, or combination thereof. Accordingly, one or more therapeutic agent or inhibitors may be administered before, during, or after administration of chemotherapy, radiotherapy, immunotherapy, surgery or combination thereof.

In certain embodiments, the subject may be a human who is (i) substantially refractory to at least one chemotherapy treatment, or (ii) in relapse after treatment with chemotherapy, or both (i) and (ii). In some of embodiments, the subject is refractory to at least two, at least three, or at least four chemotherapy treatments (including standard or experimental chemotherapies).

In certain embodiments, the subject is refractory to at least one, at least two, at least three, or at least four chemotherapy treatment (including standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, Adriamycin®, cyclophosphamide, etoposide).

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CLL" *Hematology* 2006, p. 285-294. Lymphoma incidence patterns in the United States is profiled in Morton, L. M., et al. "Lymphoma Incidence Patterns by WHO Subtype in the United States, 1992-2001" *Blood* 2006, 107(1), p. 265-276.

Examples of immunotherapeutic agents treating lymphoma or leukemia include, but are not limited to, rituximab (such as Rituxan), alemtuzumab (such as Campath, Mab-Campath), anti-CD19 antibodies, anti-CD20 antibodies, anti-CD39 antibodies, anti-MN-14 antibodies, anti-TRAIL, Anti-TRAIL DR4 and DR5 antibodies, anti-CD74 antibodies, apolizumab, bevacizumab, CHIR-12.12, epratuzumab (hLL2-anti-CD22 humanized antibody), galiximab, ha20, ibritumomab tiuxetan, lumiliximab, milatuzumab, ofaturmumab, PRO131921, SGN-40, WT-1 analog peptide vaccine, WT1 126-134 peptide vaccine, tositumomab, autologous human tumor-derived HSPPC-96, and veltuzumab. Additional immunotherapy agents includes using cancer vaccines based upon the genetic makeup of an individual patient's tumor, such as lymphoma vaccine example is GTOP-99 (MyVax®).

Examples of chemotherapy agents for treating lymphoma or leukemia include aldesleukin, alvocidib, antineoplaston AS2-1, antineoplaston A10, anti-thymocyte globulin, amifostine trihydrate, aminocamptothecin, arsenic trioxide, beta alethine, Bcl-2 family protein inhibitor ABT-263, BMS-345541, bortezomib (Velcade®), bryostatin 1, busulfan, carboplatin, campath-1H, CC-5103, carmustine, caspofungin acetate, clofarabine, cisplatin, Cladribine (Leustarin), Chlorambucil (Leukeran), Curcumin, cyclosporine, Cyclophosphamide (Cyloxan, Endoxan, Endoxana, Cyclostin), cytarabine, denileukin diftitox, dexamethasone, DT PACE, docetaxel, dolastatin 10, Doxorubicin (Adriamycin®, Adriblastine), doxorubicin hydrochloride, enzastaurin, epoetin alfa, etoposide, Everolimus (RAD001), fenretinide, filgrastim, melphalan, mesna, Flavopiridol, Fludarabine (Fludara), Geldanamycin (17-AAG), ifosfamide, irinotecan hydrochloride, ixabepilone, Lenalidomide (Revlimid®, CC-5013), lymphokine-activated killer cells, melphalan, methotrexate, mitoxantrone hydrochloride, motexafin gadolinium, mycophenolate mofetil, nelarabine, oblimersen (Genasnnse) Obatoclax (GXI 5-070), oblimersen, octreotide acetate, omega-3 fatty acids, oxaliplatin, paclitaxel, PD0332991, PEGylated liposomal doxorubicin hydrochloride, pegfilgrastim, Pentstatin (Nipent), perifosine, Prednisolone, Prednisone, R-roscovitine (Selicilib, CYC202), recombinant interferon alfa, recombinant interleukin-12, recombinant interleukin-11, recombinant flt3 ligand, recombinant human thrombopoietin, rituximab, sargramostim, sildenafil citrate, simvastatin, sirolimus, Styryl sulphones, tacrolimus, tanespimycin, Temsirolimus (CC1-779), Thalidomide, therapeutic allogeneic lymphocytes, thiotepa, tipifarnib, Velcade® (bortezomib or PS-341), Vincristine (Oncovin), vincristine sulfate, vinorelbine ditartrate, Vorinostat (SAHA), vorinostat, and FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R-CHOP (rituximab plus CHOP), R-CVP (rituximab plus CVP), R-FCM (rituximab plus FCM), R-ICE (rituximab-ICE), and R-MCP (R-MCP).

The therapeutic treatments can be supplemented or combined with any of the abovementioned therapies with stem cell transplantation or treatment. One example of modified approach is radioimmunotherapy, wherein a monoclonal antibody is combined with a radioisotope particle, such as indium In 111, yttrium Y 90, iodine I-131. Examples of combination therapies include, but are not limited to, Iodine-131 tositumomab (Bexxar®), Yttrium-90 ibritumomab tiuxetan (Zevalin®), Bexxar® with CHOP.

Other therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

Uses in Manufacturing of Drug Product

Provided are also a use of the polymorphs described herein in the manufacture of a drug product. The one or more of the polymorphic forms described herein (e.g., one or more of polymorphic Forms I, II, III, IV, V, VI, VII, VIII, IX, X, XI, XII and XIII) may be used as an intermediate in the manufacturing process to produce the drug product.

In certain embodiments, Forms I to XIII of a hydrochloride salt of (S)-2-(1-(9H-purin-6-ylamino)propyl)-5-fluoro-3-phenylquinazolin-4(3H)-one are used in the manufacture of an active pharmaceutical ingredient. In certain embodiments, Form I of a hydrochloride salt of (S)-2-(1-(9H-purin-6-ylamino)propyl)-5-fluoro-3-phenylquinazolin-4(3H)-one is used in the manufacture of an active pharmaceutical ingredient. In certain embodiments, Form II of a hydrochloride salt of (S)-2-(1-(9H-purin-6-ylamino)propyl)-5-fluoro-3-phenylquinazolin-4(3H)-one is used in the manufacture of an active pharmaceutical ingredient. In certain embodiments, Form III of a hydrochloride salt of (S)-2-(1-(9H-purin-6-ylamino)propyl)-5-fluoro-3-phenylquinazolin-4(3H)-one is used in the manufacture of an active pharmaceutical ingredient. In certain embodiments, Form IV of a hydrochloride salt of (S)-2-(1-(9H-purin-6-ylamino)propyl)-5-fluoro-3-phenylquinazolin-4(3H)-one is used in the manufacture of an active pharmaceutical ingredient. In certain embodiments, Form V of a hydrochloride salt of (S)-2-(1-(9H-purin-6-ylamino)propyl)-5-fluoro-3-phenylquinazolin-4(3H)-one is used in the manufacture of an active pharmaceutical ingredient. In certain embodiments, Form VI of a hydrochloride salt of (S)-2-(1-(9H-purin-6-ylamino)propyl)-5-fluoro-3-phenylquinazolin-4(3H)-one is used in the manufacture of an active pharmaceutical ingredient. In certain embodiments, Form VII of a hydrochloride salt of (S)-2-(1-(9H-purin-6-ylamino)propyl)-5-fluoro-3-phenylquinazolin-4(3H)-one is used in the manufacture of an active pharmaceutical ingredient. In certain embodiments, Form VIII of a hydrochloride salt of (S)-2-(1-(9H-purin-6-ylamino)propyl)-5-fluoro-3-phenylquinazolin-4(3H)-one is used in the manufacture of an active pharmaceutical ingredient. In certain embodiments, Form IX of a hydrochloride salt of (S)-2-(1-(9H-purin-6-ylamino)propyl)-5-fluoro-3-phenylquinazolin-4(3H)-one is used in the manufacture of an active pharmaceutical ingredient. In certain embodiments, Form X of a hydrochloride salt of (S)-2-(1-(9H-purin-6-ylamino)propyl)-5-fluoro-3-phenylquinazolin-4(3H)-one is used in the manufacture of an active pharmaceutical ingredient. In certain embodiments, Form XI of a hydrochloride salt of (S)-2-(1-(9H-purin-6-ylamino)propyl)-5-fluoro-3-phenylquinazolin-4(3H)-one is used in the manufacture of an active pharmaceutical ingredient. In certain embodiments, Form XII of a hydrochloride salt of (S)-2-(1-(9H-purin-6-ylamino)propyl)-5-fluoro-3-phenylquinazolin-4(3H)-one is used in the manufacture of an active pharmaceutical ingredient. In certain embodiments, Form XIII of a hydrochloride salt of (S)-2-(1-(9H-purin-6-ylamino)propyl)-5-fluoro-3-phenylquinazolin-4(3H)-one is used in the manufacture of an active pharmaceutical ingredient. In certain embodiments, the active pharmaceutical ingredient is Idelalisib.

Articles of Manufacture and Kits

Compositions comprising one or more of the polymorphic forms described herein (e.g., one or more of polymorphic Forms I to XIII of a hydrochloride salt of (S)-2-(1-(9H-purin-6-ylamino)propyl)-5-fluoro-3-phenylquinazolin-4(3H)-one and formulated in one or more pharmaceutically acceptable carriers, excipients or other ingredients can be prepared, placed in an appropriate container, and labeled for treatment of an indicated condition. Accordingly, there also is contemplated an article of manufacture, such as a container comprising a dosage form of one or more of the polymorphic forms described herein (e.g., one or more of polymorphic Forms I to XIII of a hydrochloride salt of (S)-2-(1-(9H-purin-6-ylamino)propyl)-5-fluoro-3-phenylquinazolin-4(3H)-one, and a label containing instructions for use of the compound(S).

In some embodiments, the article of manufacture is a container comprising a dosage form of one or more of the polymorphic forms described herein (e.g., one or more of polymorphic Forms I to XIII of a hydrochloride salt of (S)-2-(1-(9H-purin-6-ylamino)propyl)-5-fluoro-3-phenylquinazolin-4(3H)-one, and one or more pharmaceutically acceptable carriers, excipients or other ingredients. In one embodiment of the articles of manufacture described herein, the dosage form is a tablet.

Kits also are contemplated. For example, a kit can comprise a dosage form of a pharmaceutical composition and a package insert containing instructions for use of the composition in treatment of a medical condition. The instructions for use in the kit may be for treating a PI3K-mediated disorder, including, for example, a hematologic malignancy. In certain embodiments, the instructions for use in the kit may be for treating leukemia. In one embodiment, the instructions for use in the kit may be for treating non-Hodgkin's lymphoma (NHL) or chronic lymphocytic leukemia (CLL).

In certain embodiments, conditions indicated on the label can include, for example, treatment of cancer. Conditions indicated on the label can include non-Hodgkin's lymphoma (NHL). In one embodiment, the condition may be indolent non-Hodgkin's lymphoma (iNHL). In another embodiment, the condition may be chronic lymphocytic leukemia (CLL). Other conditions that may be indicated on the label include, for example, follicular lymphoma (FL); lymphoplastic lymphoma (LPL); Waldenström macroglobulinemia (WM); marginal zone lymphoma (MZL); and small cell lymphocytic lymphoma (SLL).

In certain embodiments, the polymorphic and solvate forms described herein may potentially exhibit improved properties. For example, in certain embodiments, the polymorphic and solvate forms described herein may potentially exhibit improved stability. Such improved stability could have a potentially beneficial impact on the manufacture of the Compound of Formula I, such as for example offering the ability to store process intermediate for extended periods of time. Improved stability could also potentially benefit a composition or pharmaceutical composition of the Compound of Formula I. In certain embodiments, the polymorphic and solvate forms described herein may also potentially result in improved yield of the Compound of Formula I, or potentially result in an improvement of the quality of the Compound of Formula I. In certain embodiments, the polymorphic and solvate forms described herein may also exhibit improved pharmacokinetic properties and/or potentially improved bioavailability.

EXAMPLES

The following examples are provided to further aid in understanding the embodiments disclosed in the application, and presuppose an understanding of conventional methods well known to those persons having ordinary skill in the art to which the examples pertain. The particular materials and conditions described hereunder are intended to exemplify particular aspects of embodiments disclosed herein and should not be construed to limit the reasonable scope thereof.

The polymorphic forms of a hydrochloride salt of (S)-2-(1-(9H-purin-6-ylamino)propyl)-5-fluoro-3-phenylquinazolin-4(3H)-one were characterized by various analytical techniques, including X-ray powder diffraction pattern (XPPD), differential scanning calorimetry (DSC), and thermographic analysis (TGA) using the procedures described below.

X-Ray Powder Diffraction:

XRPD patterns were collected at room temperature, using a PANalytical X'Pert MPD Pro Powder X-Ray Diffractometer configured with reflectance stage with spinning, data acquisition range: 2-40 degrees 2θ, Copper (Cu) anode; Kα1/Kα2 radiation; tube current 40 mA; tube tension 45 kV; automatic divergence and anti-scatter slits. Samples were prepared for analysis by distributing solid material as a thin layer on a silicon holder. Each holder was mounted on a reflectance/transmittance stage and rotated during data acquisition.

Differential Scanning Calorimetry:

DSC was performed using a TA Instruments Q2000 DSC instrument. The sample was placed into an aluminum DSC pan, and the weight accurately recorded. The pan was covered with a lid, and then either crimped or hermetically sealed. The same cell was heated under a nitrogen purge at a rate of 10° C./min, up to a final temperature of 300° C. Indium was used as the calibration standard.

Thermogravimetric Analysis:

TGA was performed using a TA Instruments Q5000 TGA instrument. Each sample was placed in an aluminum sample pan and inserted into the TG furnace. The furnace was heated under nitrogen at a rate of 10° C./min, up to a final temperature of 300° C. The TGA furnace was calibrated using the magnetic Curie point method.

Example 1

Preparation of Form I of the HCl Salt of the Compound of Formula (I)

This Example demonstrates exemplary methods to synthesize a hydrochloride salt of (S)-2-(1-(9H-purin-6-ylamino)propyl)-5-fluoro-3-phenylquinazolin-4(3H)-one (the compound of Formula (I)).

Method A

In a vessel was charged 10.0 grams (S)-2-(1-(9H-purin-6-ylamino)propyl)-5-fluoro-3-phenylquinazolin-4(3H)-one and 50 mL absolute ethanol. In a separate vessel 1 mL of 12 M HCl (0.5 equiv.) was diluted in 20 mL absolute ethanol. The acidified ethanol was added to the vessel containing the (S)-2-(1-(9H-purin-6-ylamino)propyl)-5-fluoro-3-phenylquinazolin-4(3H)-one suspension while stirring. After a few minutes the suspension was seeded with <1 mL of polymorphic Form I of a hydrochloride salt of (S)-2-(1-(9H-purin-6-ylamino)propyl)-5-fluoro-3-phenylquinazolin-4 (3H)-one suspension. The seeds were prepared by adding ethanol to amorphous solids, thereby allowing the conversion of amorphous solids to crystalline solid. The crystalline solids were then air dried. XRPD was used to monitor progress in converting to the HCl salt. Additional 1 mL of 12 M HCl (0.5 equiv.) was charged after about 24 hours. After 14 days, the XRPD confirmed full conversion to the HCl salt. The suspension was stored at ambient temperature for 30 days and solids were isolated by filtration. The solids were washed one time with about 50 mL water and allowed to air dry at room temperature.

KF of the resulting hydrochloride salt of (S)-2-(1-(9H-purin-6-ylamino)propyl)-5-fluoro-3-phenylquinazolin-4 (3H)-one was observed to be about 13% and about 16% (avg. about 15%). DSC of the resulting hydrochloride salt (as seen in FIG. 1B) shows two broad endothermic events, one beginning at about 48° C. and the other at about 184° C. No exothermic events were observed to be present. TGA of the resulting hydrochloride salt (as seen in FIG. 1C) shows two mass loss events, one beginning at about 25° C. and ending at about 50° C., the other beginning at about 125° C. and ending (for the most part) at about 200° C. DVS of the resulting hydrochloride salt (as seen in FIGS. 1D and 1E) showed minor mass increase as a function of RH at 25° C. A single crystal X-ray of crystals grown from the resulting hydrochloride salt filtrate was taken, and the data is summarized in Table 9 below. The Single Crystal X-Ray Crystallography data showed that the crystals are a channel solvate and a mono-HCl salt. Data from further characterization of the crystals are summarized in Table 10 below.

TABLE 9

Single Crystal X-Ray Crystallography Data for the Compound of Formula (I)

| Form and Composition | | | | Unit Cell Dimensions | | | | | |
|---|---|---|---|---|---|---|---|---|---|
| | | | | Distance (Å) | | | Angle (°) | | |
| Form | water | solvent | API:water:solvent | a | b | c | α | β | γ |
| Form I | N | Methanol | 1:1:0.5 | 31.102 (15) | 9.166 (5) | 19.738 (10) | 90 | 125.948 (17) | 90 |

TABLE 10

Crystal Data and Structure Refinement for the Compound of Formula (I)

| Property | Value |
| --- | --- |
| Empirical formula | C22.50 H18 Cl F N7 O1.50 |
| Formula weight | 464.89 |
| Temperature | 100(2) K |
| Wavelength | 0.71073 Å |
| Crystal system | Monoclinic |
| Space group | C2 |
| Volume | 4555(4) Å$^3$ |
| Z | 8 |
| Density (calculated) | 1.356 g/cm$^3$ |

Method B

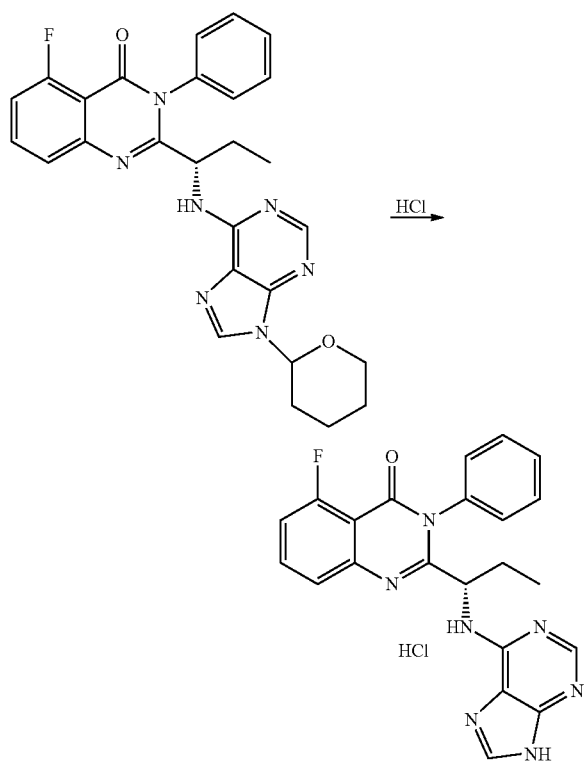

To a slurry of 5-fluoro-3-phenyl-2-((1S)-1-((9-(tetrahydro-2H-pyran-2-yl)-9H-purin-6-yl)amino)propyl)quinazolin-4(3H)-one (18 g contains about 30% TEA HCl) in ethanol (30 g), concentrated hydrochloric acid (5.0 g, 1.6 mole eq.) was added maintaining temperature ≤30° C. Immediately upon addition completion, high purity water (15.0 g) was added to the solution. After adjusting the contents to about 19 to 25° C. and checking the pH (targeting a value of ≤2.0, adding more concentrated hydrochloric acid if needed), the solution was agitated for about 1 h at about 19 to 25° C. To slightly increase the substrate concentration, (S)-2-(1-(9H-purin-6-ylamino)propyl)-5-fluoro-3-phenylquinazolin-4(3H)-one (in free form) (0.4 g) was charged portion-wise at about 19 to 25° C. A cloudy mixture was observed, which turned into a suspension after 30 min. The resulting slurry was agitated at about 19 to 25° C. for about 5 h and filtered. The wet cake was washed with cold EtOH (8.0 g, about 9° C.) and dried under vacuum at about 50° C. (S)-2-(1-(9H-Purin-6-ylamino)propyl)-5-fluoro-3-phenylquinazolin-4(3H)-one hydrochloride was obtained as a solid. $^1$H NMR (400 MHz, DMSO-d$_6$): δ 8.62 (d, 2H), 7.85 (m, 1H), 7.70-7.40 (m, 6H), 7.30 (m, 1H), 4.67 (br, 1H), 2.10 (m, 1H), 1.90 (m, 1H), 0.85 (t, 3H).

Example 2

Hydrate Screen on the HCl Salt of the Compound of Formula (I)

This Example demonstrates the effect of water on the stability of polymorphic Form I of the hydrochloride salt of (S)-2-(1-(9H-purin-6-ylamino)propyl)-5-fluoro-3-phenylquinazolin-4(3H)-one.

Polymorphic Form I of a hydrochloride salt of (S)-2-(1-(9H-purin-6-ylamino)propyl)-5-fluoro-3-phenylquinazolin-4(3H)-one, i.e., Compound of Formula (I), prepared according to the protocols described in Example 1 above was mixed with ethanol and water. The amount of hydrochloride salt (Form I) and the ethanol/water ratio summarized in Table 11 below. XRPDs were taken on Days 5 and 21. Results from this Example are summarized in Table 11 below.

TABLE 11

Results from hydrate screen on the HCl salt of the Compound of Formula I

| Form I HCl salt of Compound of Formula (I) (mg) | Ethanol/water a$_w$ | solubility (mg/mL) | XRPD after 5 days | solubility (mg/mL) | XRPD after 21 days |
| --- | --- | --- | --- | --- | --- |
| 98 | 0.2 | 26 | Form I | 60 | Form I |
| 114 | 0.3 | 47 | Form I | 33 | Form I |
| 112 | 0.4 | 57 | Form I | 66 | Form I |
| 112 | 0.5 | 72 | Form I | 93 | Form I |
| 107 | 0.6 | NA | Form I | 183 | Form I |
| 127 | 0.7 | NA | Form I | 223 | Form I |
| 118 | 0.8 | NA | Form I | 174 | Form I |
| 113 | 0.9 | NA | Form I & Form I of the free form of Compound of Formula (I) | 44 | Form I & Form I of the free form of Compound of Formula (I) |

The hydrate screen in the water/ethanol system showed no changes in XRPD except in the case of water activity 0.9, which converted some of the hydrochloride salt to polymorphic Form I of the free form of (S)-2-(1-(9H-purin-6-ylamino)propyl)-5-fluoro-3-phenylquinazolin-4(3H)-one, i.e., Compound of Formula (I).

Example 3

Form Screen on the HCl Salt of the Compound of Formula (I)

This Example demonstrates the conversion of polymorphic Form I of the hydrochloride salt of (S)-2-(1-(9H-purin-6-ylamino)propyl)-5-fluoro-3-phenylquinazolin-4(3H)-one, i.e., the Compound of Formula (I), into other polymorphic forms based on particular solvents used.

Polymorphic Form I of a hydrochloride salt of (S)-2-(1-(9H-purin-6-ylamino)propyl)-5-fluoro-3-phenylquinazolin-4(3H)-one, i.e., Compound of Formula (I), prepared according to the protocols described in Example 1 above was mixed with the solvent (as listed in Table 12 below) in a vial/flask, resulting in a suspension. The amount of hydrochloride salt (Form I) is also listed in Table 12 below.

After 7 days, a sample of the suspension was removed from the vial/flask, and the sample was centrifuged and filtered to separate the solids from the liquid in the sample. The isolated solids were characterized by XRPD (collected at room temperature). The filtrate was retained.

For several experiments, including the experiments involving THF, acetone and 2-MeTHF, crystals large enough for Single Crystal X-Ray Crystallography were observed in the vial/flask. A sample of the crystals taken in suspension was removed and analyzed by Single Crystal X-Ray Crystallography (data acquired at 100K).

After about 25 days, another sample was removed from the vial/flask, and the sample was centrifuged and filtered to separate the solids from the liquid in the sample. The isolated solids were characterized by XRPD (collected at room temperature). Results from this Example are summarized in Table 12 below.

TABLE 12

Results from form screen on the HCl salt of the Compound of Formula I

| Form I HCl salt of Compound of Formula (I) | Solvent | XRPD after 7 days | XRPD after about 25 | Single Crystal X-Ray of crystals from suspension |
|---|---|---|---|---|
| 119 mg | water | Form I | Form I | NA |
| 117 mg | isopropyl acetate (IPAc) | Form I | Form I | NA |
| 150 mg | methyl t-butyl ether (MTBE) | Form I | Form I | NA |
| 132 mg | 2-propanol | Form I | mixture | NA |
| 160 mg | dichloromethane (DCM) | new | Form VIII | NA |
| 163 mg | n-heptane | Form I | Form I | NA |
| 114 mg | tetrahydrofuran (THF) | new | Form IX | IV |
| 125 mg | acetone | new | Form X | II |
| 155 mg | methanol | Form I | Form I | NA |
| 120 mg | acetonitrile (ACN) | Form I | Form I | NA |
| 157 mg | Ethanol | Form I | Form I | NA |
| 140 mg | ethyl acetate (EtOAc) | Form I | Form I | NA |
| 154 mg | 2-methyltetrahydrofuran (2-MeTHF) | Form V | Form V | III |
| 149 mg | methyl ethyl ketone (MEK) | new | Form VII | NA |
| 176 mg | methyl isobutyl ketone (MIBK) | Form I | Form VI | NA |
| 10 g | 1-propanol | 1-propanol solvate | Form XII | NA |
| 10 g | 2-propanol | 1-propanol solvate | Form XI | NA |
| 10 g | 1-butanol | 1-butanol solvate | Form XIII | NA |

The XRPDs taken for polymorphic Forms II-XIII are provided in FIGS. 2-13, respectively. Single Crystal X-Ray Crystallography data were collected from polymorphic Forms II-IV and XII prepared in this Example, and such data is summarized in Table 13 below.

TABLE 13

Single Crystal X-Ray Crystallography Data

| Form and Composition | | | Unit Cell Dimensions | | | | | |
|---|---|---|---|---|---|---|---|---|
| | | | Distance (Å) | | | Angle (°) | | |
| Form | solvent | API:water:solvent | a | b | c | α | β | γ |
| II | acetone | 1:0:3 | 13.266 (3) | 13.858 (3) | 31.012 (6) | 90 | 90 | 90 |
| III | 2MeTHF | 1:1:1.5 | 25.077 (3) | 9.1485 (10) | 14.2476 (14) | 90 | 110.967 (3) | 90 |
| IV | THF | 1:0:3 | 13.4685 (6) | 13.8415 (6) | 31.7543 (14) | 90 | 90 | 90 |
| XII | 1-propanol | 1:0:1 | 10.717 (3) | 10.161 (3) | 12.409 (4) | 90 | 104.021 (4) | 90 |

Example 4

Solvent Screen on Form I of the HCl Salt of the Compound of Formula (I)

This Example demonstrates the preparation of solvated forms of polymorphic Form I of the hydrochloride salt of (S)-2-(1-(9H-purin-6-ylamino)propyl)-5-fluoro-3-phenylquinazolin-4(3H)-one, i.e., the Compound of Formula (I).

Polymorphic Form I of a hydrochloride salt of (S)-2-(1-(9H-purin-6-ylamino)propyl)-5-fluoro-3-phenylquinazolin-4(3H)-one, i.e., Compound of Formula (I) was prepared by suspending 5 g of the free base Form I of (S)-2-(1-(9H-purin-6-ylamino)propyl)-5-fluoro-3-phenylquinazolin-4(3H)-one in 25 mL absolute ethanol. The sample was agitated at 200 rpm and about 23° C. 1.05 mL of 12M HCl (1.1 eq.) was diluted in 10 mL absolute ethanol, then added to the suspension of the Compound of Formula (I) in ethanol, forming a slurry. The slurry suspension was stirred at about 23° C. for about 24 hours, filtered and washed with 10 mL absolute ethanol and dried under vacuum for three days. Formation of the polymorphic Form I of a hydrochloride salt of the Compound of Formula (I) was confirmed by x-ray powder diffraction.

50 mg of the polymorphic Form I of a hydrochloride salt of the Compound of Formula (I) prepared according to the protocols described above was mixed with increasing amounts of each solvent listed in Table 14 below (10 vol, 20 vol, 30 vol, 40 vol, 50 vol, 60 vol, 70 vol, 70 vol (at about 50° C.)) until the material dissolved or reached the maximum amount of solvent. The mixtures were then evaluated for identification of the solid form using the following screening procedures:

Maturation: The suspensions were cycled in a platform shaker incubator between about 50° C. and room temperature (8 hours per cycle, for three days);

Slurry at 5° C.: 50 mg of the polymorphic Form I of a hydrochloride salt of the Compound of Formula (I) was suspended in 40 vol of the solvent. The suspensions were left stirring at about 5° C. for about 7 days;

Slurry at 50° C.: 50 mg of the polymorphic Form I of a hydrochloride salt of the Compound of Formula (I) was suspended in 40 vol of the solvent. The suspensions were left stirring at about 50° C. for about 2 days;

Salt formation: 50 mg of the polymorphic Form I of a hydrochloride salt of the Compound of Formula (I) was dissolved or suspended in 10 vol of solvent and held at about 50° C. for 15 minutes, after which 1.1 eq of HCl (11.6 μL of 12M HCl) were added and the sample was slowly cooled to about 5° C. at about 0.1° C. per minute;

Solvent deposition: 25 mg of the polymorphic Form I of a hydrochloride salt of the Compound of Formula (I) was transferred to a 2 mL vial, which was then placed into a larger sealed vial with 3 mL of the corresponding solvent, then held at about 40° C. for about 13 days.

Any solids obtained from the above screening procedures were analyzed wet/damp by XRPD as described below. The solids were isolated by decanting and/or filtration, then dried under vacuum. Solid form samples obtained after maturation experiments were dried under vacuum and analyzed by NMR to determine if the solvating ethanol was replaced by the suspending solvent. As shown in Table 14, the screening experiments identified new solvated forms of the HC salt of the Compound of Formula I. For Patterns 1, 2, 3, and 4, each of the four of the identified solvated forms are a family of solvates, which are observed from more than one solvent.

TABLE 14

Results from solvent screen on Form I of the HCl salt of the Compound of Formula I

| Form | Solvent | Representative XRPD |
|---|---|---|
| Pattern 1 | Ethyl Acetate | FIG. 14A (damp) |
|  | Propyl acetate | FIG. 14B (dry) |
| Pattern 2 | 1-Methyl-1-propanol | FIG. 15A |
|  | Isopropyl acetate |  |
| Pattern 3 | 1,2-Dimethyoxyethane | FIG. 16A |
|  | 1,4-Dioxane |  |
|  | Acetone |  |
|  | Acetone:Water |  |
|  | Acetonitrile |  |
|  | Chloroform |  |
|  | Dicholoromethane |  |
|  | Diethyl ether |  |
|  | Ethyl acetate |  |
|  | MEK |  |
|  | MIBK |  |
|  | Nitromethane |  |
|  | Propyl acetate |  |
|  | Tetrahydrofuran |  |
|  | Toluene |  |
| Pattern 4 | 1-Propanol | FIG. 17A |
|  | 2-Propanol |  |
|  | IPA:Water (5%) |  |
| 2-Methyl-1-propanol solvate | 2-Methyl-1-propanol | FIG. 18A |
| 1,4-Dioxane solvate | 1,4-Dioxane | FIG. 19A |
| Toluene solvate | Toluene | FIG. 20 |

Representative samples of the solvate forms listed in Table 14 obtained from the crystallization screening were dried under vacuum and further characterized. The data from these further characterization experiments is summarized in Table 15.

TABLE 15

Results from solvent screen on Form I of the HCl salt of the Compound of Formula I

| Form | Solvent | NMR of dry | DSC | TGA |
|---|---|---|---|---|
| Pattern 1 | Propylacetate | n/t | n/t | n/t |
| Pattern 2 | Isopropyl acetate | 0.56eq iPrOAc | 68° C. (−42 J/g) | 9.7% (40° C.-130° C.) |
|  |  |  | 153° C. (−38 J/g) | 4.7% (130° C.-230° C.) |
|  |  |  | 179° C. (−32 J/g) |  |
| Pattern 3 | 1,2-Dimethyoxyethane | 0.93eq DME | 172° C. (−92 J/g) | 10.7% (110° C.-245°C.) |
| Pattern 4 | Isopropyl alcohol | 0.98eq IPA | 170° C. (−192 J/g) | 13.4% (130° C.-215° C.) |
| 2-Methyl-1-propanol solvate | 2-Methyl-1-propanol | 1.34eq 2-Methyl-1-propanol | 113° C. (−134 J/g) | 19.0% (90° C.-225° C.) |
| 1,4-Dioxane solvate | 1,4-Dioxane | 0.65eq 1.4-Dioxane | 158° C. (−96 J/g) | 12.7% (80° C.-225° C.) |
| Toluene solvate | Toluene | n/t | n/t | n/t | n/t: not tested

X-Ray Powder Diffraction (XRPD)

Two methods were used to collect XRPD on the samples described above.

Bruker AXS C2 GADDS

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm.

The beam divergence, i.e. the effective size of the X-ray beam on the sample, was approximately 4 mm. A θ-θ continuous scan mode was employed with a sample-detector distance of 20 cm which gives an effective 2θ range of 3.2°-29.7°. Typically the sample would be exposed to the X-ray beam for 120 seconds. The software used for data collection was GADDS for XP/2000 4.1.43 and the data were analysed and presented using Diffrac Plus EVA v13.0.0.2 or v15.0.0.0.

Ambient conditions: Samples run under ambient conditions were prepared as flat plate specimens using powder as received without grinding. Approximately 1-2 mg of the sample was lightly pressed on a glass slide to obtain a flat surface.

Non-ambient conditions: Samples run under non-ambient conditions were mounted on a silicon wafer with heat-conducting compound. The sample was then heated to the appropriate temperature at 50° C./min and subsequently held isothermally for up to 4 minutes before data collection was initiated.

Bruker AXS D8 Advance

X-Ray Powder Diffraction patterns were collected on a Bruker D8 diffractometer using Cu Kα radiation (40 kV, 40 mA), 0-2θ goniometer, and divergence of V4 and receiving slits, a Ge monochromator and a Lynxeye detector. The software used for data collection was Diffrac Plus XRD Commander v2.6.1 and the data were analysed and presented using Diffrac Plus EVA v13.0.0.2 or v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are: angular range: 2 to 42°2θ, step size: 0.05°2θ, collection time: 0.5 s/step.

Nuclear Magnetic Resonance (NMR)

$^1$H-NMR spectra were collected on a Bruker 400 MHz instrument equipped with an autosampler and controlled by a DRX400 console. Automated experiments were acquired using ICON-NMR v4.0.7 running with Topspin v1.3 using the standard Bruker loaded experiments. For non-routine spectroscopy, data were acquired through the use of Topspin alone.

Samples were prepared in DMSO-d6, unless otherwise stated. Off-line analysis was carried out using ACD Labs 2012 release (build 61851).

Differential Scanning Calorimetry (DSC)

DSC data were collected on a Mettler DSC 823E equipped with a 34 position auto-sampler. The instrument was calibrated for energy and temperature using certified indium. Typically 0.5-4 mg of each sample, in a pin-holed aluminium pan, was heated at 10° C./min from 25° C. to 350° C. A nitrogen purge at 50 ml/min was maintained over the sample.

The instrument control and data analysis software was STARe v9.20.

Thermo-Gravimetric Analysis (TGA) TGA data were collected on a Mettler TGA/SDTA 851e equipped with a 34 position autosampler. The instrument was temperature calibrated using certified indium. Typically 2-13 mg of each sample was loaded onto a pre-weighed aluminium crucible and was heated at 10° C./min from ambient temperature to 350° C. A nitrogen purge at 50 ml/min was maintained over the sample.

The instrument control and data analysis software was STARe v9.20.

The XRPDs taken for the solvate forms identified in Table 14 are provided in FIGS. 14A, 14B, 15A, 16A, 17A, 18A, 29A, and 20 respectively.

Figure 14C:
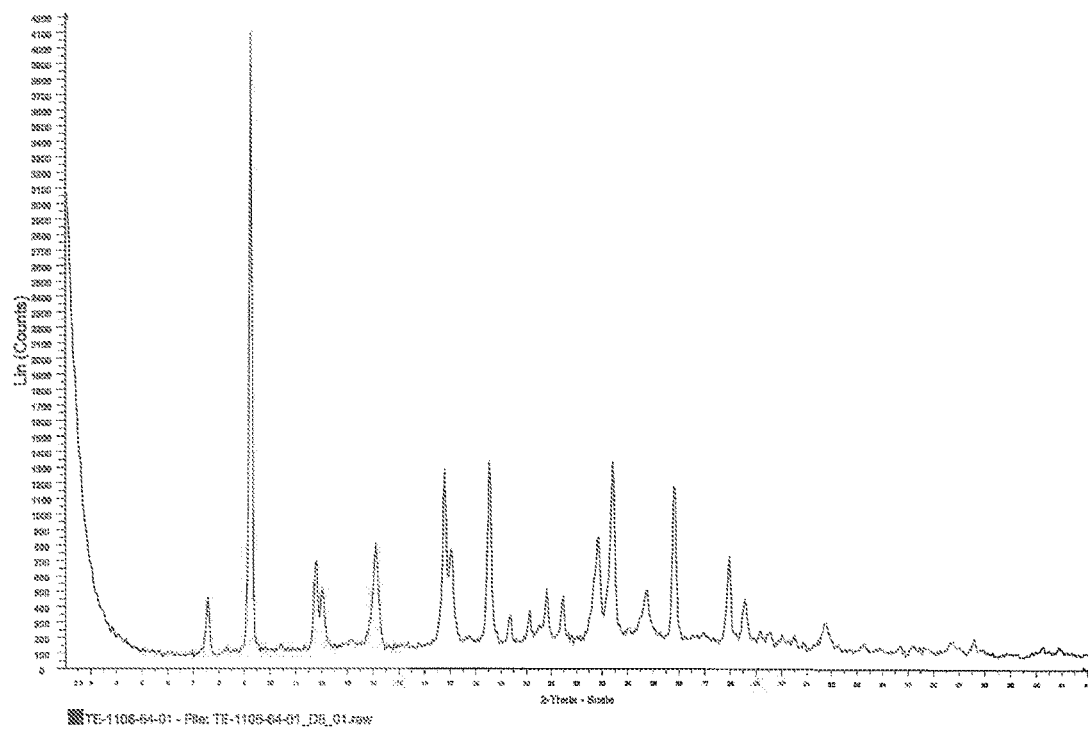
FIG. 14C shows XRPD Pattern 9' of a solvate form of a hydrochloride salt of (S)-2-(1-(9H-purin-6-ylamino)propyl)-5-fluoro-3-phenylquinazolin-4(3H)-one.
Figure 14D:
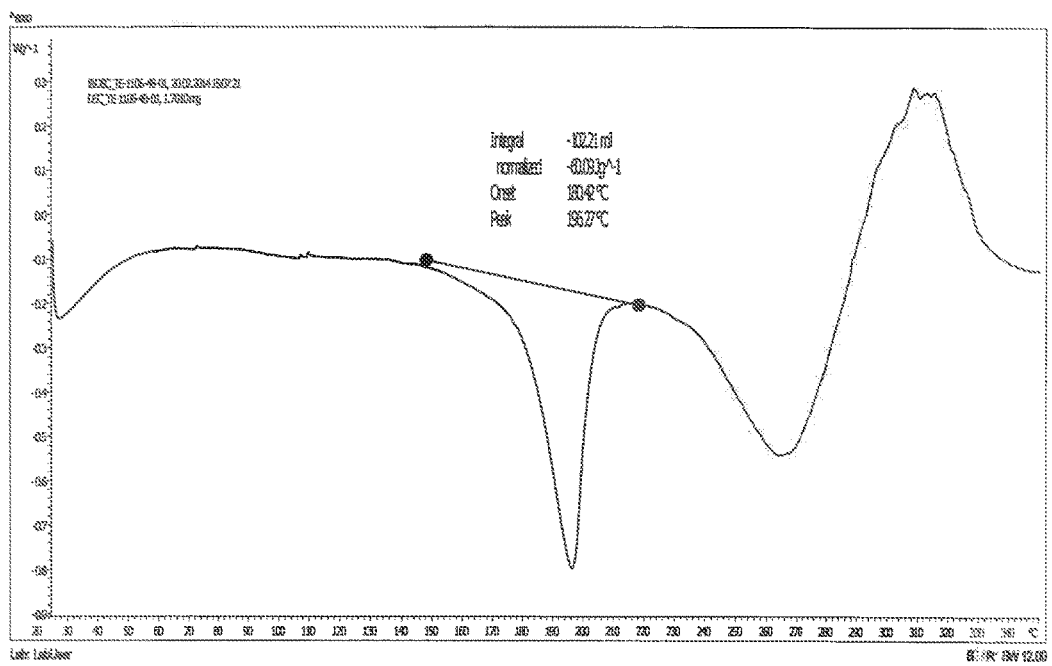
FIG. 14D shows a differential scanning calorimetry (DSC) graph of a hydrochloride salt of (S)-2-(1-(9H-purin-6-ylamino)propyl)-5-fluoro-3-phenylquinazolin-4(3H)-one represented as Pattern 9.
Figure 14E:
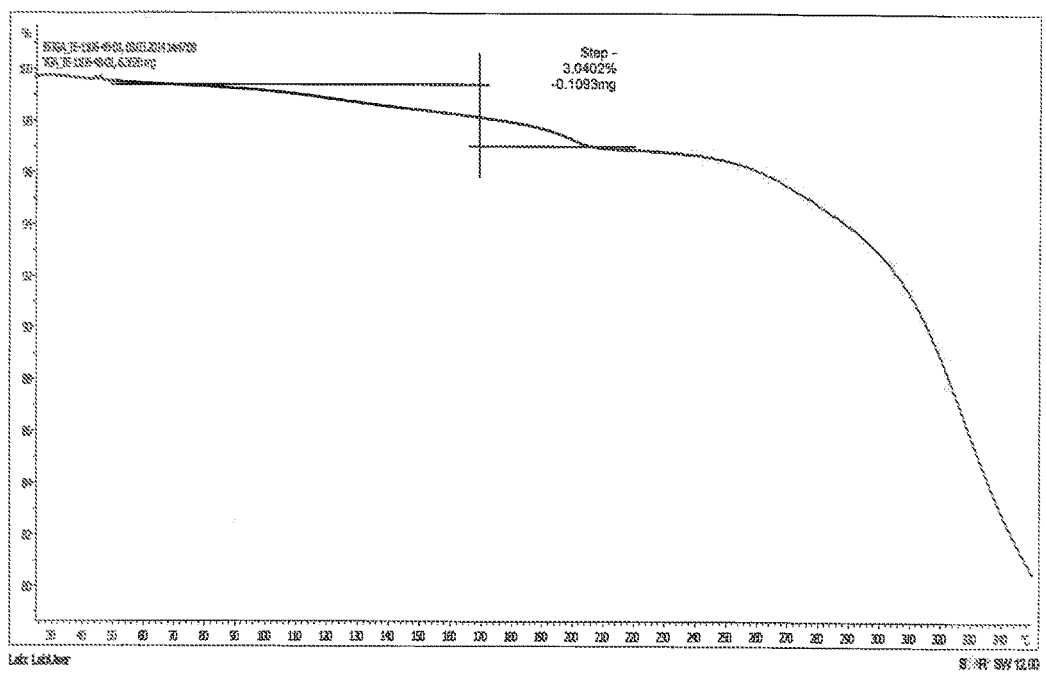
FIG. 14E shows a thermographic analysis (TGA) graph of a hydrochloride salt of (S)-2-(1-(9H-purin-6-ylamino)propyl)-5-fluoro-3-phenylquinazolin-4(3H)-one represented as Pattern 9.

For Pattern 1, shown in FIGS. 14A and 15B, 50 mg of the hydrochloride salt of the Compound of Formula (I) was suspended in propyl acetate (3.5 mL, 70 vol) and held at 50° C. for 15 minutes, after which 1.1 eq of 12M HCl (11.6 μL) was added and the sample slowly cooled from 50° C. to 5° C. at 0.1° C. per minute. The XRPD pattern shown in FIG. 14A was observed while the sample was wet. On drying in a vacuum oven at about 25° C. for 6 days, the sample was converted to the XRPD pattern shown in FIG. 14B (Pattern 9). NMR data confirm the presence of propyl acetate in the crystallized from. FIG. 14C depicts the XRPD pattern after further heating at about 145° C. for about 16 hours (Pattern 9'). Table 16 lists the XRPD peaks for Pattern 9'

TABLE 16

| XRPD Peak List for Pattern 9' Form | |
|---|---|
| Angle (2-Theta °) | Intensity (%) |
| 7.5 | 11.1 |
| 9.2 | 100.0 |
| 11.8 | 16.8 |
| 12.0 | 12.4 |
| 14.1 | 19.5 |
| 16.8 | 31.3 |
| 17.1 | 18.8 |
| 18.5 | 32.6 |
| 19.4 | 8.2 |
| 20.1 | 9.0 |
| 20.8 | 12.4 |
| 21.5 | 11.2 |
| 22.9 | 20.7 |
| 23.4 | 32.5 |
| 24.7 | 12.2 |
| 25.9 | 28.7 |
| 28.0 | 17.7 |
| 28.6 | 10.9 |
| 29.2 | 5.9 |
| 29.5 | 5.6 |

For Pattern 2, shown in FIG. 15A, 50 mg of the polymorphic Form I of a hydrochloride salt of the Compound of Formula (I) was treated with isopropyl acetate (3.5 mL, 70 vols) producing a suspension at 50° C. This suspension was matured between 50° C. and room temperature (8 hours per cycle) for three days. $^1$H NMR data confirm the presence of isopropyl acetate in the crystallized from.

For Pattern 3, shown in FIG. 16A, 50 mg of the polymorphic Form I of a hydrochloride salt of the Compound of Formula (I) was treated with 1,2-dimethoxyethane (3.5 mL, 70 vols) producing a suspension at 50° C. This suspension was matured between 50° C. and room temperature (8 hours per cycle) for three days. $^1$H NMR data confirm the presence of 1,2-dimethoxyethane in the crystallized from.

For Pattern 4, shown in FIG. 17A, 50 mg of the polymorphic Form I of a hydrochloride salt of the Compound of Formula (I) was treated with 2-propanol (3.5 mL, 70 vols), producing a suspension at 50° C. This suspension was matured between 50° C. and room temperature (8 hours per cycle) for three days. ¹H NMR data confirm the presence of 2-propanol in the crystallized from.

Figure 18D:
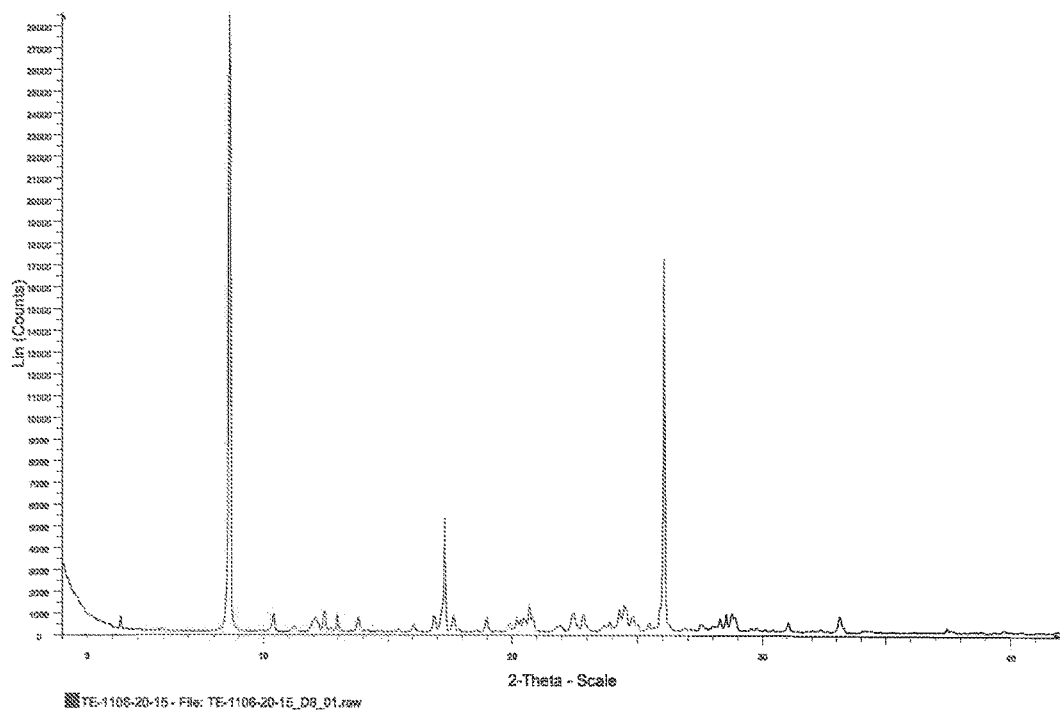

For the 2-Methyl-1-propanol solvate, shown in FIG. 18A, 50 mg of the polymorphic Form I of a hydrochloride salt of the Compound of Formula (I) was treated with 2-methyl-1-propanol (3.5 mL, 70 vols), producing a suspension at 50° C. This suspension was matured between 50° C. and room temperature (8 hours per cycle) for three days. FIG. 18D depicts the same XRPD diffractogram, showing the entire Y axis (i.e., not truncated). ¹H NMR data confirm the presence of 2-methyl-1-propanol in the crystallized from.

For the 1,4-Dioxane solvate, shown in FIG. 19A, 50 mg of the polymorphic Form I of a hydrochloride salt of the Compound of Formula (I) was treated with 1,4-dioxane (3.5 mL, 70 vols), producing a suspension at 50° C. This suspension was matured between 50° C. and room temperature (8 hours per cycle) for three days. The XRPD pattern is shown in FIG. 20. ¹H NMR data confirm the presence of 1,4-dioxane in the crystallized from.

For the toluene solvate, shown in FIG. 20 (wet), 50 mg of the polymorphic Form I of a hydrochloride salt of the Compound of Formula (I) was treated with toluene (3.5 mL, 70 vols), producing a suspension at 50° C. This suspension was matured between 50° C. and room temperature (8 hours per cycle) for three days. Upon drying, the XRPD of the toluene solvent is a mixture of Pattern 1 and Pattern 9'.

DSC plots for Pattern 9, Pattern 2, Pattern 3, Pattern 4, the 2-Methyl-1-propanol solvate form, and the 1,4-dioxane solvate form identified in Table 14 are provided in FIGS. 14D, 15B, 16B, 17B, 18B, and 19B respectively. TGA plots for Pattern 9, Pattern 2, Pattern 3, Pattern 4, the 2-Methyl-1-propanol solvate form, and the 1,4-dioxane solvate form identified in Table 14 are provided in FIGS. 14E, 15C, 16C, 17C, 18C, and 19C, respectively.

What is claimed is:

1. A polymorph of a hydrochloride salt of a compound of Formula (I):

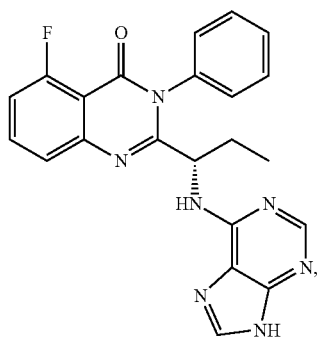

(I)

wherein the polymorph is selected from the group consisting of Form I, Form V, Form VI, Form VII, Form VIII, Form IX, Form X, Form XI, Form XII, and Form XIII; and wherein:

Form I has an X-ray diffraction pattern comprising degree 2θ-reflections, plus or minus 0.2 degrees 2θ, at 11.6, 16.6, 18.2, 23.2 and 25.1;

Form V has an X-ray diffraction pattern comprising degree 2θ-reflections, plus or minus 0.2 degrees 2θ, at 15.9, 24.0, 25.6 and 28.1;

Form VI has an X-ray diffraction pattern comprising degree 2θ-reflections, plus or minus 0.2 degrees 2θ, at 11.8, 17.0, 23.2 and 25.1;

Form VII has an X-ray diffraction pattern comprising degree 2θ-reflections, plus or minus 0.2 degrees 2θ, at 9.8, 17.8, 21.7 and 24.0;

Form VIII has an X-ray diffraction pattern comprising degree 2θ-reflections, plus or minus 0.2 degrees 2θ, at 10.0, 19.9, 21.7 and 24.1;

Form IX has an X-ray diffraction pattern comprising degree 2θ-reflections, plus or minus 0.2 degrees 2θ, at 9.8, 19.6, 21.8 and 24.0;

Form X has an X-ray diffraction pattern comprising degree 2θ-reflections, plus or minus 0.2 degrees 2θ, at 9.9, 21.8, and 24.2;

Form XI has an X-ray diffraction pattern comprising degree 2θ-reflections, plus or minus 0.2 degrees 2θ, at 12.5, 17.0, 19.3, 20.3, 22.0 and 25.5;

Form XII has an X-ray diffraction pattern comprising degree 2θ-reflections, plus or minus 0.2 degrees 2θ, at 7.4, 12.4, 16.9 and 25.4; and Form XIII has an X-ray diffraction pattern comprising degree 2θ-reflections, plus or minus 0.2 degrees 2θ, at 6.9, 16.8, 18.5 and 23.9.

2. The polymorph of claim 1, wherein the polymorph is selected from the group consisting of Form I, Form V, Form VI, Form VII, Form VIII, Form IX, Form X, Form XI, Form XII, and Form XIII; and wherein:

Form I has an X-ray diffraction pattern comprising degree 2θ-reflections, plus or minus 0.2 degrees 2θ, at 8.9, 11.6, 13.8, 16.6, 18.2, 19.4, 22.5, 23.2 and 25.1;

Form V has an X-ray diffraction pattern comprising degree 2θ-reflections, plus or minus 0.2 degrees 2θ, at 8.0, 15.9, 18.9, 20.3, 24.0, 25.6, 28.1 and 36.3;

Form VI has an X-ray diffraction pattern comprising degree 2θ-reflections, plus or minus 0.2 degrees 2θ, at 11.8, 13.9, 16.7, 17.0, 19.9, 22.3, 22.5, 23.2 and 25.1;

Form VII has an X-ray diffraction pattern comprising degree 2θ-reflections, plus or minus 0.2 degrees 2θ, at 6.0, 9.8, 11.9, 15.3, 19.7, 20.1, 21.7, 24.0, 28.4 and 28.9;

Form VIII has an X-ray diffraction pattern comprising degree 2θ-reflections, plus or minus 0.2 degrees 2θ, at 10.0, 12.4, 15.3, 19.0, 19.9, 20.3, 21.7, 24.1 and 28.9;

Form IX has an X-ray diffraction pattern comprising degree 2θ-reflections, plus or minus 0.2 degrees 2θ, at 9.5, 9.8, 12.5, 19.6, 20.8, 21.8, 24.0 and 29.0;

Form X has an X-ray diffraction pattern comprising degree 2θ-reflections, plus or minus 0.2 degrees 2θ, at 9.9, 11.9, 15.5, 19.4, 19.8, 20.3, 21.8, 24.2, 28.6 and 29.0;

Form XI has an X-ray diffraction pattern comprising degree 2θ-reflections, plus or minus 0.2 degrees 2θ, at 7.4, 12.5, 15.0, 17.0, 19.3, 20.3, 22.0, 25.5 and 31.7;

Form XII has an X-ray diffraction pattern comprising degree 2θ-reflections, plus or minus 0.2 degrees 2θ, at 7.4, 12.4, 16.9, 19.1, 19.6, 23.3, 24.9, 25.4 and 29.4; and Form XIII has an X-ray diffraction pattern comprising degree 2θ-reflections, plus or minus 0.2 degrees 2θ, at 6.9, 8.0, 8.1, 9.7, 11.7, 13.6, 16.8, 18.5, 23.5, 23.9 and 25.7.

3. A polymorph of a hydrochloride salt of a compound of Formula (I):

(I)

[Structure of Formula (I): 5-fluoro-3-phenyl-2-[(1S)-1-(9H-purin-6-ylamino)propyl]quinazolin-4(3H)-one]

wherein the polymorph is selected from the group consisting of Form I, Form II, Form III, Form IV, Form V, Form VI, Form VII, Form VIII, Form IX, Form X, Form XI, Form XII, and Form XIII; and wherein:

Form I has an X-ray diffraction pattern as shown in FIG. 1;

Form II has a calculated X-ray diffraction pattern as shown in FIG. 2;

Form III has a calculated X-ray diffraction pattern as shown in FIG. 3;

Form IV has a calculated X-ray diffraction pattern as shown in FIG. 4;

Form V has an X-ray diffraction pattern as shown in FIG. 5;

Form VI has an X-ray diffraction pattern as shown in FIG. 6;

Form VII has an X-ray diffraction pattern as shown in FIG. 7;

Form VIII has an X-ray diffraction pattern as shown in FIG. 8;

Form IX has an X-ray diffraction pattern as shown in FIG. 9;

Form X has an X-ray diffraction pattern as shown in FIG. 10;

Form XI has an X-ray diffraction pattern as shown in FIG. 11;

Form XII has an X-ray diffraction pattern as shown in FIG. 12; and

Form XIII has an X-ray diffraction pattern as shown in FIG. 13.

4. A polymorph of a hydrochloride salt of a compound of Formula (I):

(I)

[Structure of Formula (I)]

wherein the polymorph is selected from the group consisting of Form I, Form II, Form III, Form IV and Form XII; and wherein:

Form I has a unit cell, as determined by crystal X-ray crystallography, of the following dimensions: a=31.102 (15) Å; b=9.166 (5) Å; c=19.738 (10) Å; α=90°; β=125.948(17°); and γ=90°;

Form II has a unit cell, as determined by crystal X-ray crystallography, of the following dimensions: a=13.266 (3) Å; b=13.858 (3) Å; c=31.012 (6) Å; α=90°; β=90°; and γ=90°;

Form III has a unit cell, as determined by crystal X-ray crystallography, of the following dimensions: a=25.077 (3) Å; b=9.149 (10) Å; c=14.248 (14) Å; α=90°; β=110.967 (3°); and γ=90°;

Form IV has a unit cell, as determined by crystal X-ray crystallography, of the following dimensions: a=13.469 (6) Å; b=13.842 (6) Å; c=31.754 (14) Å; α=90°; β=90°; and γ=90°; and Form XII has a unit cell, as determined by crystal X-ray crystallography, of the following dimensions: a=10.717 (3); b=10.161 (3); c=12.409 (4); α=90; β=104.021 (4); and γ=90.

5. The polymorph of claim 1, wherein the polymorph is Form I.

6. The polymorph of claim 3, wherein the polymorph is Form II.

7. The polymorph of claim 3, wherein the polymorph is Form III.

8. The polymorph of claim 3, wherein the polymorph is Form IV.

9. The polymorph of claim 1, wherein the polymorph is Form V.

10. The polymorph of claim 1, wherein the polymorph is Form VI.

11. The polymorph of claim 1, wherein the polymorph is Form VII.

12. The polymorph of claim 1, wherein the polymorph is Form VIII.

13. The polymorph of claim 1, wherein the polymorph is Form IX.

14. The polymorph of claim 1, wherein the polymorph is Form X.

15. The polymorph of claim 1, wherein the polymorph is Form XI.

16. The polymorph of claim 1, wherein the polymorph is Form XII.

17. The polymorph of claim 1, wherein the polymorph is Form XIII.

18. A composition produced by:

combining a compound of Formula (I):

(I)

[Structure of Formula (I)]

with hydrochloric acid and a solvent to produce the composition comprising one or more polymorphs of a hydrochloride salt of the compound of Formula (I); or
combining a hydrochloride salt of the compound of Formula (I) with a solvent to produce the composition comprising one or more polymorphs of a hydrochloride salt of the compound of Formula (I),
wherein the solvent is selected from the group consisting of methanol, ethanol, water, isopropyl acetate, ethyl acetate, methyl tert-butyl ether, n-heptane, acetonitrile, acetone, 2-methyltetrahydrofuran, tetrahydrofuran, methyl isobutyl ketone, methyl ethyl ketone, dichloromethane, 2-propanol, 1-propanol, 1-butanol, and any mixtures thereof, and
wherein the one or more polymorphs are selected from the group consisting of Form I, Form V, Form VI, Form VII, Form VIII, Form IX, Form X, Form XI, Form XII, and Form XIII; and wherein:
Form I has an X-ray diffraction pattern comprising degree 2θ-reflections, plus or minus 0.2 degrees 2θ, at 11.6, 16.6, 18.2, 23.2 and 25.1;
Form V has an X-ray diffraction pattern comprising degree 2θ-reflections, plus or minus 0.2 degrees 2θ, at 15.9, 24.0, 25.6 and 28.1;
Form VI has an X-ray diffraction pattern comprising degree 2θ-reflections, plus or minus 0.2 degrees 2θ, at 11.8, 17.0, 23.2 and 25.1;
Form VII has an X-ray diffraction pattern comprising degree 2θ-reflections, plus or minus 0.2 degrees 2θ, at 9.8, 17.8, 21.7 and 24.0;
Form VIII has an X-ray diffraction pattern comprising degree 2θ-reflections, plus or minus 0.2 degrees 2θ, at 10.0, 19.9, 21.7 and 24.1;
Form IX has an X-ray diffraction pattern comprising degree 2θ-reflections, plus or minus 0.2 degrees 2θ, at 9.8, 19.6, 21.8 and 24.0;
Form X has an X-ray diffraction pattern comprising degree 2θ-reflections, plus or minus 0.2 degrees 2θ, at 9.9, 21.8, and 24.2;
Form XI has an X-ray diffraction pattern comprising degree 2θ-reflections, plus or minus 0.2 degrees 2θ, at 12.5, 17.0, 19.3, 20.3, 22.0 and 25.5;
Form XII has an X-ray diffraction pattern comprising degree 2θ-reflections, plus or minus 0.2 degrees 2θ, at 7.4, 12.4, 16.9 and 25.4; and
Form XIII has an X-ray diffraction pattern comprising degree 2θ-reflections, plus or minus 0.2 degrees 2θ, at 6.9, 16.8, 18.5 and 23.9.

19. The composition of claim 18, wherein:
the one or more polymorphs is Form I; and
the solvent is selected from the group consisting of methanol, ethanol, water, isopropyl acetate, ethyl acetate, methyl tert-butyl ether, n-heptane, acetonitrile, and any mixtures thereof.

20. The composition of claim 18, wherein:
the one or more polymorphs is Form II or Form X, or a mixture thereof; and
the solvent is acetone.

21. The composition of claim 18, wherein:
the one or more polymorphs is Form III or Form V, or a mixture thereof; and
the solvent is 2-methyltetrahydrofuran.

22. The composition of claim 18, wherein:
the one or more polymorphs is Form IV or Form IX, or a mixture thereof; and
the solvent is tetrahydrofuran.

23. The composition of claim 18, wherein:
the one or more polymorphs is Form VI; and
the solvent is methyl isobutyl ketone.

24. The composition of claim 18, wherein:
the one or more polymorphs is Form VII; and
the solvent is methyl ethyl ketone.

25. The composition of claim 18, wherein:
the one or more polymorphs is Form VIII; and
the solvent is dichloromethane.

26. The composition of claim 18, wherein:
the one or more polymorphs is Form XI; and
the solvent is 2-propanol.

27. The composition of claim 18, wherein:
the one or more polymorphs is Form XII; and
the solvent is 1-propanol.

28. The composition of claim 18, wherein:
the one or more polymorphs is Form XIII; and
the solvent is 1-butanol.

29. The polymorph of claim 1, wherein the hydrochloride salt is a monohydrochloride salt.

30. A composition comprising one or more polymorphs of claim 1.

31. The composition of claim 30, wherein the one or more polymorphs are a mixture of at least two polymorphs.

32. The composition of claim 30, wherein the composition contains less than 95% by weight of substances other than the one or more polymorphs.

33. A pharmaceutical composition comprising the polymorph of claim 1, and one or more pharmaceutically acceptable carriers or excipients.

34. The pharmaceutical composition of claim 33, wherein the pharmaceutical composition is a tablet.

35. A method of treating a human in need of a treatment for cancer, comprising administering to the human a polymorph of claim 1, wherein the cancer is selected from the group consisting of chronic lymphocytic leukemia (CLL), indolent non-Hodgkin's lymphoma (iNHL), and refractory iNHL.

36. The method of claim 35, wherein the cancer is selected from small lymphocytic lymphoma (SLL), and follicular B-cell non-Hodgin Lymphoma (FL).

37. A method of producing a composition comprising one or more polymorphs of a hydrochloride salt of a compound of Formula (I):

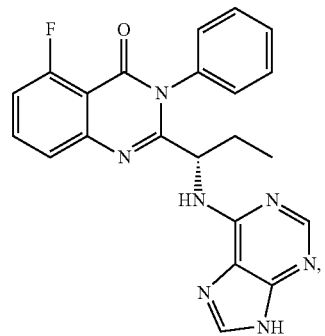

(I)

comprising:
combining the compound of Formula (I) with hydrochloric acid and a solvent to produce the composition; or
combining a hydrochloride salt of the compound of Formula (I) with a solvent to produce the composition, wherein the solvent is selected from the group consisting of methanol, ethanol, water, isopropyl acetate, ethyl acetate, methyl tert-butyl ether, n-heptane, acetonitrile, acetone, 2-methyltetrahydrofuran, tetrahydrofuran, methyl isobutyl ketone, methyl ethyl ketone, dichloromethane, 2-propanol, 1-propanol, 1-butanol, and any mixtures thereof, and wherein the one or more polymorphs are selected from the group consisting of Form I, Form V, Form VI, Form VII, Form VIII, Form IX, Form X, Form XI, Form XII, and Form XIII; and wherein:

Form I has an X-ray diffraction pattern comprising degree 2θ-reflections, plus or minus 0.2 degrees 2θ, at 11.6, 16.6, 18.2, 23.2 and 25.1;

Form V has an X-ray diffraction pattern comprising degree 2θ-reflections, plus or minus 0.2 degrees 2θ, at 15.9, 24.0, 25.6 and 28.1;

Form VI has an X-ray diffraction pattern comprising degree 2θ-reflections, plus or minus 0.2 degrees 2θ, at 11.8, 17.0, 23.2 and 25.1;

Form VII has an X-ray diffraction pattern comprising degree 2θ-reflections, plus or minus 0.2 degrees 2θ, at 9.8, 17.8, 21.7 and 24.0;

Form VIII has an X-ray diffraction pattern comprising degree 2θ-reflections, plus or minus 0.2 degrees 2θ, at 10.0, 19.9, 21.7 and 24.1;

Form IX has an X-ray diffraction pattern comprising degree 2θ-reflections, plus or minus 0.2 degrees 2θ, at 9.8, 19.6, 21.8 and 24.0;

Form X has an X-ray diffraction pattern comprising degree 2θ-reflections, plus or minus 0.2 degrees 2θ, at 9.9, 21.8, and 24.2;

Form XI has an X-ray diffraction pattern comprising degree 2θ-reflections, plus or minus 0.2 degrees 2θ, at 12.5, 17.0, 19.3, 20.3, 22.0 and 25.5;

Form XII has an X-ray diffraction pattern comprising degree 2θ-reflections, plus or minus 0.2 degrees 2θ, at 7.4, 12.4, 16.9 and 25.4; and Form XIII has an X-ray diffraction pattern comprising degree 2θ-reflections, plus or minus 0.2 degrees 2θ, at 6.9, 16.8, 18.5 and 23.9.

38. The method of claim 37, wherein:
the one or more polymorphs is Form I; and
the solvent is selected from the group consisting of methanol, ethanol, water, isopropyl acetate, ethyl acetate, methyl tert-butyl ether, n-heptane, acetonitrile, and any mixtures thereof.

39. The method of claim 37, wherein:
the one or more polymorphs is Form II or Form X, or a mixture thereof; and
the solvent is acetone.

40. The method of claim 37, wherein:
the one or more polymorphs is Form III or Form V, or a mixture thereof; and
the solvent is 2-methyltetrahydrofuran.

41. The method of claim 37, wherein:
the one or more polymorphs is Form IV or Form IX, or a mixture thereof; and
the solvent is tetrahydrofuran.

42. The method of claim 37, wherein:
the one or more polymorphs is Form VI; and
the solvent is methyl isobutyl ketone.

43. The method of claim 37, wherein:
the one or more polymorphs is Form VII; and
the solvent is methyl ethyl ketone.

44. The method of claim 37, wherein:
the one or more polymorphs is Form VIII; and
the solvent is dichloromethane.

45. The method of claim 37, wherein:
the one or more polymorphs is Form XI; and
the solvent is 2-propanol.

46. The method of claim 37, wherein:
the one or more polymorphs is Form XII; and
the solvent is 1-propanol.

47. The method of claim 37, wherein:
the one or more polymorphs is Form XIII; and
the solvent is 1-butanol.

* * * * *